United States Patent
Guiducci et al.

(10) Patent No.: US 9,868,955 B2
(45) Date of Patent: Jan. 16, 2018

(54) HUMAN TOLL-LIKE RECEPTOR INHIBITORS AND METHODS OF USE THEREOF

(71) Applicant: Dynavax Technologies Corporation, Berkeley, CA (US)

(72) Inventors: Cristiana Guiducci, Albany, CA (US); Karen L. Fearon, Lafayette, CA (US); Franck Barrat, New York, NY (US)

(73) Assignee: Dynavax Technologies Corporation, Berkeley, CA (US)

( * ) Notice: Subject to any disclaimer, the term of this patent is extended or adjusted under 35 U.S.C. 154(b) by 108 days.

(21) Appl. No.: 14/430,876

(22) PCT Filed: Sep. 27, 2013

(86) PCT No.: PCT/US2013/062479
§ 371 (c)(1),
(2) Date: Mar. 24, 2015

(87) PCT Pub. No.: WO2014/052931
PCT Pub. Date: Apr. 3, 2014

(65) Prior Publication Data
US 2015/0252363 A1    Sep. 10, 2015

Related U.S. Application Data

(63) Continuation-in-part of application No. 13/842,861, filed on Mar. 15, 2013, now Pat. No. 9,228,184.
(Continued)

(51) Int. Cl.
*C12N 15/117* (2010.01)
*A61K 31/7125* (2006.01)
(Continued)

(52) U.S. Cl.
CPC ........ *C12N 15/117* (2013.01); *C12N 2310/17* (2013.01); *C12N 2310/331* (2013.01); *C12N 2310/344* (2013.01)

(58) Field of Classification Search
USPC ...................................... 536/23.1, 24.3, 24.5
See application file for complete search history.

(56) References Cited

U.S. PATENT DOCUMENTS 6,225,292 B1    5/2001  Raz et al.
7,375,180 B2    5/2008  Gorden et al.
(Continued)

FOREIGN PATENT DOCUMENTS

WO    WO-2004/047734 A2    6/2004
WO    WO-2006/028742 A2    3/2006
(Continued)

OTHER PUBLICATIONS

Robbins et al. (2007). "2'-O-methyl-modified RNAs Act as TLR7 Antagonists," Molecular Therapy. 15(9):1663-1669.
(Continued)

*Primary Examiner* — Terra C Gibbs
(74) *Attorney, Agent, or Firm* — Morrison & Foerster LLP

(57) ABSTRACT

Provided herein are human Toll-like receptor (TLR)-inhibitors and methods for use in individuals having an autoimmune disease or an inflammatory disorder. The TLR inhibitors of the present disclosure are polynucleotides comprising an inhibitory motif for one or more of TLR7, TLR8 and TLR9.

20 Claims, 39 Drawing Sheets

TLR7-mediated IFN-α

Related U.S. Application Data

(60) Provisional application No. 61/761,214, filed on Feb. 5, 2013, provisional application No. 61/707,887, filed on Sep. 29, 2012.

(51) Int. Cl.
*A61K 31/712* (2006.01)
*A61K 31/7115* (2006.01)
*A61K 31/711* (2006.01)
*A61K 31/713* (2006.01)

(56) References Cited

U.S. PATENT DOCUMENTS

| | | |
|---|---|---|
| 7,410,975 B2 | 8/2008 | Lipford et al. |
| 7,498,409 B2 | 3/2009 | Vlach et al. |
| 7,560,436 B2 | 7/2009 | Raz et al. |
| 8,729,039 B2 | 5/2014 | Raz et al. |
| 8,759,305 B2 | 6/2014 | Barrat et al. |
| 8,940,310 B2 | 1/2015 | Barrat et al. |
| 8,962,579 B2 | 2/2015 | Barrat et al. |
| 9,063,123 B2 | 6/2015 | Barrat et al. |
| 2003/0133988 A1 | 7/2003 | Fearon et al. |
| 2003/0232074 A1 | 12/2003 | Lipford et al. |
| 2004/0162309 A1 | 8/2004 | Gorden et al. |
| 2004/0171086 A1 | 9/2004 | Fink et al. |
| 2005/0119273 A1 | 6/2005 | Lipford et al. |
| 2005/0226878 A1 | 10/2005 | Tomai et al. |
| 2005/0239733 A1 | 10/2005 | Jurk et al. |
| 2005/0256073 A1 | 11/2005 | Lipford et al. |
| 2006/0172966 A1 | 8/2006 | Lipford et al. |
| 2007/0142315 A1 | 6/2007 | Forsbach et al. |
| 2007/0232622 A1 | 10/2007 | Lipford et al. |
| 2007/0238678 A1 | 10/2007 | Barrat et al. |
| 2008/0026986 A1 | 1/2008 | Wang et al. |
| 2008/0171712 A1 | 7/2008 | Kandimalla et al. |
| 2008/0171716 A1 | 7/2008 | MacLachlan et al. |
| 2008/0234251 A1 | 9/2008 | Doherty et al. |
| 2008/0306050 A1 | 12/2008 | Doherty et al. |
| 2009/0053205 A1 | 2/2009 | Kandimalla et al. |
| 2009/0169472 A1 | 7/2009 | Diebold et al. |
| 2009/0169529 A1 | 7/2009 | Hartmann et al. |
| 2010/0047188 A1 | 2/2010 | Kandimalla et al. |
| 2010/0113565 A1 | 5/2010 | Gorden et al. |
| 2011/0003885 A1 | 1/2011 | Barrat et al. |
| 2012/0252051 A1 | 10/2012 | Barrat et al. |
| 2013/0156814 A1 | 6/2013 | Barrat et al. |
| 2014/0094504 A1 | 4/2014 | Guiducci et al. |
| 2015/0050296 A1 | 2/2015 | Barrat et al. |
| 2015/0203850 A1 | 7/2015 | Barrat et al. |

FOREIGN PATENT DOCUMENTS

| | | |
|---|---|---|
| WO | WO-2006/066003 A2 | 6/2006 |
| WO | WO-2009/055076 A2 | 4/2009 |
| WO | WO-2009/154610 A1 | 12/2009 |
| WO | WO-2011/159328 A1 | 12/2011 |
| WO | WO-2011/159958 A2 | 12/2011 |
| WO | WO-2012/135549 A2 | 10/2012 |
| WO | WO-2014/052931 A1 | 4/2014 |

OTHER PUBLICATIONS

Akira (2001). "Toll-Like Receptors and Innate Immunity," *Adv. Immunol.* 78:1-56.

Akira et al. (2003). "Recognition of Pathogen-Associated Molecular Patterns by TLR Family," *Immunol. Lett.* 85:85-95.

Barrat et al. (2005). "Nucleic Acids of Mammalian Origin Can Act as Endogenous Ligands for Toll-Like Receptors and May Promote Systemic Lupus Erythematosus," *J. Exp. Med.* 202(8):1131-1139.

Barrat et al. (2007). "Treatment of Lupus-prone Mice with a Dual Inhibitor of TLR7 and TLR9 Leads to Reduction of Autoantibody Production and Amelioration of Disease Symptoms," *Eur. J. Immunol.* 37(12):3582-6.

Barrat et al. (2008). "Development of TLR Inhibitors for the Treatment of Autoimmune Diseases," *Immunol. Rev.* 223:271-283.

Båve et al. (2005). "Activation of the Type I interferon System in Primary Sjögren's Syndrome: A Possible Etiopathogenic Mechanism," *Arthritis Rheum.* 52(4):1185-1195.

Davila et al. (2008). "Genetic Association and Expression Studies Indicate a Role of Toll-Like Receptor 8 in Pulmonary Tuberculosis," *PLoS Genet.* 4(10):e1000218.

Deanne et al. (2007). "Control of Toll-Like Receptor 7 Expression is Essential to Restrict Autoimmunity and Dendritic Cell Proliferation," *Immunity.* 27(5):801-10.

Demaria et al. (2010). "TLR8 Deficiency Leads to Autoimmunity in Mice," *J. Clin. Invest.* 120(10):3651-3662.

Diebold et al. (2004). "Innate Antiviral Responses by Means of TLR7-Mediated Recognition of Single-Stranded RNA," *Science.* 303(5663):1529-1531.

Doring et al. (2010). "Human Antiphospholipid Antibodies Induce TNFα in Monocytes via Toll-Like Receptor 8," *Immunobiology.* 215(3):230-241.

Duramad et al. (2005). "Inhibitors of TLR-9 act on Multiple Cell Subsets in Mouse and Man In Vitro and Prevent Death In Vivo from Systemic Inflammation," *J. Immunol.* 174(9):5193-5200.

Enevold et al. (2010). "Multiplex Screening of 22 Single-Nucleotide Polymorphisms in 7 Toll-Like Receptors: An Association Study in Rheumatoid Arthritis," *J. Rheumatol.* 37(5):905-910.

Ganguly et al. (2009). "Self-RNA-Antimicrobial Peptide Complexes Activate Human Dendritic Cells Through TLR7 and TLR8," *J. Exp. Med.* 206(9):1983-1994.

Gantier et al. (2008). "TLR7 is Involved in Sequence-Specific Sensing of Single-Stranded RNAs in Human Macrophages," *J. Immunol.* 180(4):2117-2124.

Gilliet et al. (2008). "Plasmacytoid Dendritic Cells: Sensing Nucleic Acids in Viral Infection and Autoimmune Diseases," *Nat. Rev. Immunol.* 8(8):594-606.

Gorden et al. (2005). "Synthetic TLR Agonists Reveal Functional Differences Between Human TLR7 and TLR8," *J. Immunol.* 174(3):1259-1268.

Gorden et al. (2006). "Oligodeoxynucleotides Differentially Modulate Activation of TLR7 and TLR8 by Imidazoquinolines," *J. Immunol.* 177(11):8164-8170.

Gottenberg et al. (2006). "Activation of IFN Pathways and Plasmacytoid Dendritic Cell Recruitment in Target Organs of Primary Sjögren's Syndrome," *Proc. Natl. Acad. Sci. USA* 103(8):2770-2775.

Gringhuis et al. (2010). "HIV-1 Exploits Innate Signaling by TLR8 and DC-SIGN for Productive Infection of Dendritic Cells," *Nat. Immunol.* 11(5):419-426.

Guiducci et al. (2009). "Signalling pathways leading to IFN-α production in human plasmacytoid dendritic cell and the possible use of agonists or antagonists of TLR7 and TLR9 in clinical indications." *J. Intern. Med.* 265(1):43-57.

Guiducci et al. (2010). "Autoimmune Skin Inflammation is Dependent on Plasmacytoid Dendritic Cell Activation by Nucleic Acids via TLR7 and TLR9," *J. Exp. Med.* 207(13):2931-2942.

Guiducci et al. (2010). "TLR recognition of self nucleic acids hampers glucocorticoid activity in lupus." *Nature.* 465(7300):937-41.

Guiducci et al. (2013). "RNA Recognition by Human TLR8 can Lead to Autoimmune Inflammation," *J. Exp. Med.* 210(13):2903-2919.

Hansel et al. (2011). "Human Slan (6-Sulfo LacNAc) Dendritic Cells are Inflammatory Dermal Dendritic Cells in Psoriasis and Drive Strong $T_H17/T_H1$ T-Cell Responses," *J. Allergy Clin. Immunol.* 127(3):787-794.

Hansel et al. (2013). "Human 6-Sulfo LacNAc (slan) Dendritic Cells have Molecular and Functional Features of an Important Pro-Inflammatory Cell Type in Lupus Erythematosus," *J. Autoimmun.* 40:1-8.

Heil et al. (2004). "Species-Specific Recognition of Single-Stranded RNA via Toll-Like Receptor 7 and 8," *Science.* 303(5663):1526-1529.

(56) References Cited

OTHER PUBLICATIONS

Hemmi et al. (2002). "Small Anti-Viral Compounds Activate Immune Cells via the TLR7 MyD88-Dependent Signaling Pathway," *Nat. Immunol.* 3(2):196-200.

Hurst et al. (2007). "Toll-like Receptors and Autoimmunity," *Autoimmunity Reviews.* 7(3):204-208.

Hurst et al. (2009). "TLR7 and TLR8 Ligands and Antiphospholipid Antibodies Show Synergistic Effects on the Induction of IL-1β and Caspase-1 in Monocytes," *Immunobiology.* 214:683-691.

International Search Report dated Mar. 20, 2014, for PCT Patent Application No. PCT/US2013/062479, filed on Sep. 27, 2013, 7 pages.

Jurk et al. (2002). "Human TLR7 or TLR8 Independently Confer Responsiveness to the Antiviral Compound R-848," *Nat. Immunol.* 3(6):499.

Kandimalla et al. (2001). "Effect of Chemical Modifications of Cytosine and Guanine in a CpG-Motif of Oligonucleotides: Structure-Immunostimulatory Activity Relationships," *Bioorg. Med. Chem.* 9:807-813.

Kattah et al. (2010). "The U1-snRNP Complex: Structural Properties Relating to Autoimmune Pathogenesis in Rheumatic Diseases," *Immunol. Rev.* 233(1):126-145.

Klinman et al. (2003). "Regulation of CpG-Induced Immune Activation by Suppressive Oligodeoxynucleotides," *Ann. NY Acad. Sci.* 1002:112-123.

Lan et al. (2007). "Stabilized Immune Modulatory RNA Compounds as Agonists of Toll-like Receptors 7 and 8," *Proc. Natl. Acad. Sci. USA* 104(34):13750-13755.

Langer (1990). "New Methods of Drug Delivery," *Science.* 249(4976):1527-1533.

Leadbetter (2002). "Chromatin-IgG Complexes Activate B Cells by Dual Engagement of IgM and Toll-Like Receptors," *Nature.* 416(6881):603-607.

Liu et al. (2010). "A Five-Amino-Acid Motif in the Undefined Region of the TLR8 Ectodomain is Required for Species-Specific Ligand Recognition," *Mol. Immunol.* 47(5):1083-1090.

Lund et al. (2004). "Recognition of Single-Stranded RNA Viruses by Toll-Like Receptor 7," *Proc. Natl. Acad. Sci. USA.* 101(15):5598-5603.

Lund (2003). "Toll-Like Receptor 9-Mediated Recognition of Herpes Simplex Virus-2 by Plasmacytoid Dendritic Cells," *J. Exp. Med.* 198(3):513-520.

Ma (2006). "Toll-Like Receptor 8 Functions as a Negative Regulator of Neurite Outgrowth and Inducer of Neuronal Apoptosis," *J. Cell Biol.* 175(2):209-215.

Marshak-Rothstein (2006). "Toll-Like Receptors in Systemic Autoimmune Disease," *Nat. Rev. Immunol.* 6(11):823-835.

Medzhitov et al. (2000). "Innate Immune Recognition: Mechanisms and Pathways," *Immunol. Rev.* 173:89-97.

Oberste, M.S. et al. (2000). "Comparison of classic and molecular approaches for the identification of untypeable enteroviruses", *J. Clin. Micobiol.* 38(3):1170-1174.

Peng (2005). "Toll-Like Receptor 8-Mediated Reversal of CD4+ Regulatory T Cell Function," *Science.* 309(5739):1380-1384.

Prinz et al. (2011). "Antiphospholipid Antibodies Induce Translocation of TLR7 and TLR8 to the Endosome in Human Monocytes and Plasmacytoid Dendritic Cells," *Blood.* 118:2322-2332.

Sacre et al. (2008). "Inhibitors of TLR8 Reduce TNF Production from Human Rheumatoid Synovial Membrane Cultures," *J. Immunol.* 181(11):8002-8009.

Schakel et al. (2006). "Human 6-Sulfo LacNAc-Expressing Dendritic Cells are Principal Producers of Early Interleukin-12 and are Controlled by Erythrocytes," *Immunity.* 24(6):767-777.

Smits et al. (2008). "The Use of TLR7 and TLR8 Ligands for the Enhancement of Cancer Immunotherapy," *The Oncologist* 13(8):859-875.

Stunz (2002). "Inhibitory Oligonucleotides Specifically Block Effects of Stimulatory CpG Oligonucleotides in B Cells," *Eur. J. Immunol.* 32(5):1212-1222.

Vollmer et al. (2005). "Immune Stimulation Mediated by Autoantigen Binding Sites within Small Nuclear RNAs Involves Toll-Like Receptors 7 and 8," *J. Exp. Med.* 202(11):1575-1585.

Written Opinion of the International Searching Authority dated Mar. 20, 2014, for PCT Patent Application No. PCT/US2013/062479, filed on Sep. 27, 2013, 9 pages.

Yamada (2002). "Effect of Suppressive DNA on CpG-Induced Immune Activation," *J. Immunol.* 169(10):5590-5594.

Yu et al. (2012). "Recognition of Nucleic Acid Ligands by Toll-Like Receptors 7/8: Importance of Chemical Modification," *Current Medicinal Chemistry* 19(9):1365-1377.

High Dosages of Inhibitory Polynucleotides in Rats

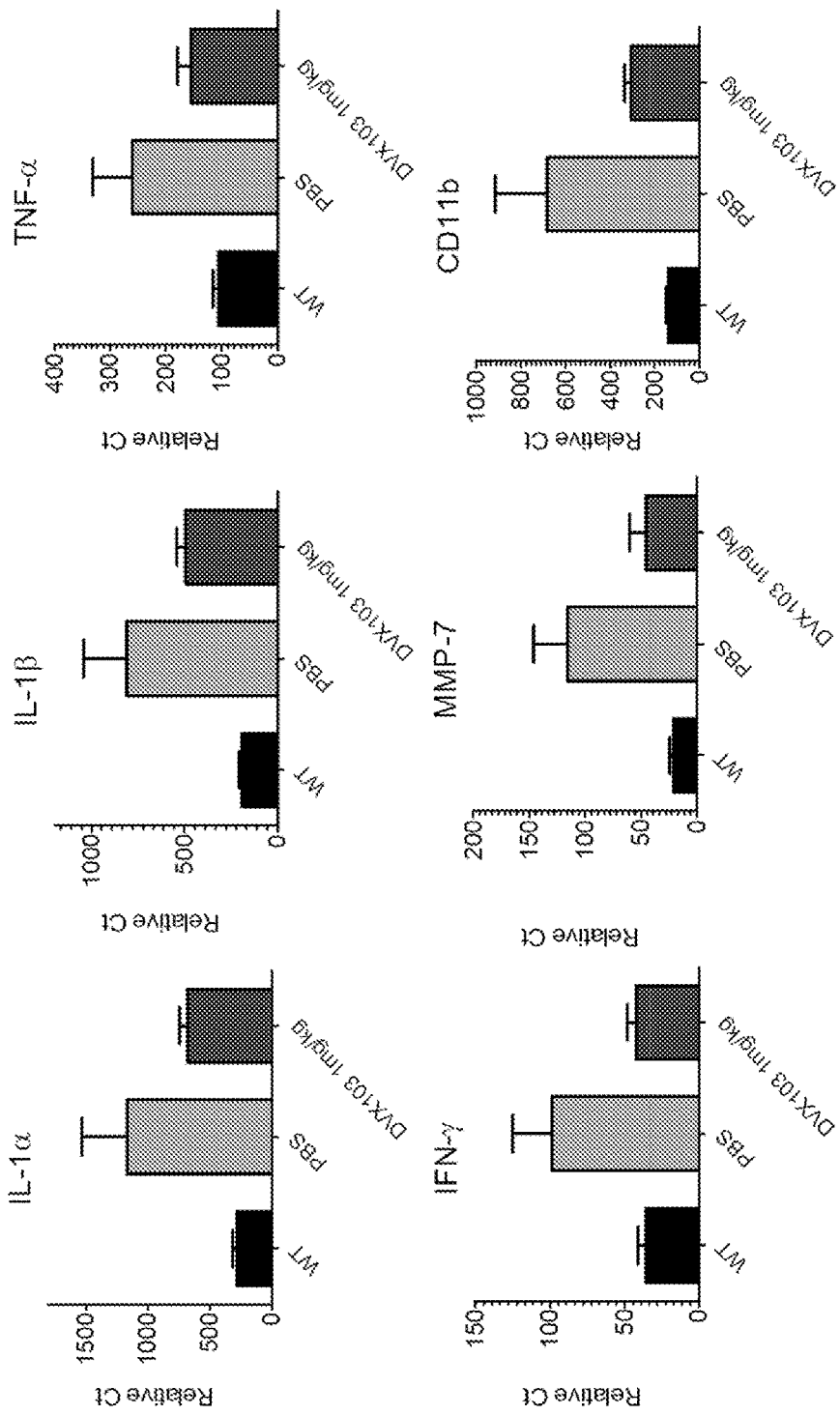

HUMAN TOLL-LIKE RECEPTOR INHIBITORS AND METHODS OF USE THEREOF

CROSS-REFERENCE TO RELATED APPLICATIONS

This application is a U.S. National Stage of PCT/US2013/62479, filed Sep. 27, 2013, which claims benefit of U.S. Provisional Application No. 61/707,887, filed Sep. 29, 2012; U.S. Provisional Application No. 61/761,214, filed Feb. 5, 2013; and is a continuation-in-part of U.S. Utility application Ser. No. 13/842,861, filed Mar. 15, 2013, now U.S. Pat. No. 9,228,184, all of which are incorporated by reference in their entirety.

STATEMENT REGARDING FEDERALLY SPONSORED RESEARCH

This invention was made with government support under Grant No. 1R43AI096641 awarded by the National Institute of Allergy and Infectious Diseases, of the National Institutes of Health. The government has certain rights in the invention.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 377882005430SeqList.txt, date recorded: Mar. 24, 2015, size: 36 KB).

FIELD OF THE INVENTION

This application relates to human Toll-like receptor (TLR) inhibitors, and methods for use in individuals having an autoimmune disease or an inflammatory disorder. The TLR inhibitors of the present disclosure are polynucleotides comprising an inhibitory motif for one or more of TLR7, TLR8 and TLR9.

BACKGROUND OF THE INVENTION

Toll-like receptors (TLRs) are type-I transmembrane proteins that recognize a variety of pathogen-associated molecular patterns (PAMPs) from bacteria, viruses and fungi. In this way PAMPs serve as a first-line of defense against invading pathogens. Human TLRs can elicit overlapping yet distinct biological responses due to differences in cellular expression and activation of downstream signal transduction pathways (Akira et al., Adv Immunol, 78: 1-56, 2001). TLRs are characterized by an ectodomain composed of leucine-rich repeats (LRRs) and a cytoplasmic domain, known as a Toll/interleukin-1 receptor (TIR) domain. The LRR-containing ectodomain is responsible for recognition of PAMPs, while the cytoplasmic domain is required for downstream signaling. Studies have shown that LRR8 is involved in DNA and RNA recognition, whereas LRR17 is involved in nucleic acid binding (Smits et al., Oncologist, 13: 859-875, 2008).

The TLRs located in the plasma membrane recognize bacterial membrane components, whereas the TLRs that detect nucleic acid-based ligands are predominately located within endosomal compartments. The nucleic acid-sensing TLRs include TLR3, TLR7, TLR8, and TLR9. TLR3 recognizes double-stranded RNA, TLR7 and TLR8 recognize single-stranded RNA, and TLR9 recognizes bacterial and viral DNA as well as synthetic oligodeoxynucleotides containing unmethylated CG dinucleotides (Akira and Hemmi, Immunol Lett, 85:85-95, 2003).

TLR8 belongs to the same subfamily as TLR7 and TLR9 and is highly homologous to TLR7 (Liu et al., Mol Immunol, 47:1083-90, 2010). Even so, the specificity of TLR8 for RNA and synthetic small molecules with a structure related to nucleic acids is not identical to that of TLR7 (Medzhitov et al., Immunol Rev, 173:-89-97, 2000). For instance, some ssRNA synthetic sequences containing repetitive A/U motifs are able to specifically activate TLR8 but not TLR7 (Gorden et al., J Immunol, 174:1259-68, 2005). Further, in humans, TLR8 is highly expressed in monocytes, macrophages, myeloid dendritic cells (mDC) and neutrophils, whereas TLR7 in blood cells is principally expressed in plasmacytoid dendritic cells (pDCs), B-cells, and neutrophils. Because of this difference in cellular expression, triggering by RNA through TLR7 in blood leads to a response dominated by Type I interferon (IFN) production, whereas activation through TLR8 induces multiple pro-inflammatory cytokines such as TNF, IL-12, IL-6, IL-8 and IL-1 (Barrat et al., J Exp Med, 202:1131-9, 2005; and Gorden et al., J Immunol, 174:1259-68, 2005).

TLRs have been implicated in various autoimmune and inflammatory diseases, with the clearest example being the role played by TLR9 and TLR7 in the pathogenesis of systemic lupus erythematosus (Barrat and Coffman, Immunol Rev, 223:271-283, 2008). Additionally, a TLR8 polymorphism has been associated with rheumatoid arthritis (Enevold et al., J Rheumatol, 37:905-10, 2010). Although various TLR7, TLR8 and TLR9 inhibitors have been described, additional TLR inhibitors are desirable. In particular, polynucleotides having inhibitory motifs for one or more of TLR7, TLR8 and TLR9 are needed to precisely inhibit an immune response in a subject (e.g., patient having an autoimmune disease or an inflammatory disorder).

Additionally, several polynucleotides have been identified, which inhibit R848-induced cytokine secretion by mouse splenocytes. Mouse TLR8, however, lacks the ability to respond to ssRNA ligands, RNA viruses or small molecules, all of which have been shown to activate human TLR8 (Heil et al., Science, 303:1526-9, 2004; Jurk et al. Nat Immunol, 3:499, 2002; Hemmi et al., Nat. Immunol, 3:196-200, 2002; and Lund et al., PNAS, 101:5598-603, 2004). Further, by comparing amino acid sequences, TLR8 of mice and rats was found to lack a five amino-acid sequence required for ligand recognition in man (Liu et al., Mol Immunol, 47:1083-90, 2010). Thus polynucleotides having inhibitory motifs for human TLR8 are desirable for use in human subjects.

SUMMARY OF THE INVENTION

Provided herein are human Toll-like receptor (TLR)-inhibitors and methods for use in individuals having an autoimmune disease or an inflammatory disorder. The TLR inhibitors of the present disclosure are polynucleotides comprising an inhibitory motif for one or more of TLR7, TLR8 and TLR9. It should be understood, that aspects and embodiments of the present disclosure described with "comprising" language, also include "consisting of" and "consisting essentially of" aspects and embodiments.

The present disclosure provides polynucleotides, and for the use of the polynucleotides in inhibiting a TLR8-dependent immune response in an individual, wherein the polynucleotide consists of a nucleotide sequence of the formula: 5'-$N_xX_1X_2X_3X_4X_5X_6$-$M_y$-3', wherein each of N, $X_1$, $X_2$, $X_3$, $X_4$, and M is a nucleotide or nucleotide analog, x is an integer from 0 to 50, y is 0 or 1, $X_5$ is G or I and $X_6$ is I or A, with the proviso that the polynucleotide does not comprise SEQ ID NO:9 (DV197). In some embodiments, $X_3$ and $X_4$ are independently A, C, G, T or I. In some embodiments, each of $X_1$, $X_2$, $X_3$ and $X_4$ are independently A, C, G, T or I. In some embodiments, $X_3X_4X_5X_6$ is one of the group consisting of GAGI, GAGA, GGGI, TTGA, IAII, GTGI, AAII, IAIA, AIIA, IIII, ICII, IGII, ITII, CAII, TAII, CCII, TTII and GGII. In some embodiments, $X_1X_2X_3X_4X_5X_6$ is one of the group consisting of TTGAGI, TTGAGA, TTGGGI, CCTTGA, TTIAII, TTGTGI, TTAAII, TTIAIA, TTAIIA, AGIAII, TTIIII, TTICII, TTIGII, TTITII, TTCAII, TTTAII, TTCCII, TTTTII, TTGGII, IIIAII, CCIAII, GGI-AII, AAIAII, CIIAII, and IIAIIA. The present disclosure further provides polynucleotides for use in inhibiting a TLR8-dependent immune response in an individual, wherein the polynucleotide consists of a nucleotide sequence of the formula: 5'-$N_xX_1X_2X_3X_4X_5X_6$-3', wherein each of N, $X_1$, $X_2$, $X_3$ and $X_4$, is a nucleotide or nucleotide analog, $X_5$ is G or I, $X_6$ is I or A, x is an integer from 0 to 50, and $X_6$ is at the 3' end of the polynucleotide, with the proviso that when $X_5X_6$ is GI or GA, then each of $X_3$ and $X_4$ is A, T or C. In some embodiments, each of $X_1$ and $X_2$ is A, T, C, G, or I. The present disclosure also provides polynucleotides for use in inhibiting a TLR8-dependent immune response in an individual, wherein the polynucleotide consists of a nucleotide sequence of the formula: 5'-$N_xX_1X_2X_3X_4X_5X_6$-3', wherein N is a nucleotide or nucleotide analog, each of $X_1$ and $X_2$ is A, T, C, G, or I, each of $X_3$ and $X_4$ is A, T or C, $X_5$ is G or I, $X_6$ is I or A, x is an integer from 0 to 50, and $X_6$ is at the 3' end of the polynucleotide. In some embodiments, the polynucleotide does not comprise SEQ ID NO:9 (DV197). In some preferred embodiments, the polynucleotide does not comprise a CG dinucleotide. In some embodiments, polynucleotide does not comprise a C analog or a G analog (e.g., does not comprise 7-deazaguanosine). In some embodiments, the polynucleotide does not comprise a modified base. In some embodiments, the polynucleotide does not comprise a modified sugar. In some preferred embodiments, the polynucleotide is not an antisense sequence or an RNAi molecule. In some embodiments, the polynucleotide does not comprise a TGC or a UGC trinucleotide within 0, 1, 2, 3, 4, 5, 6, 7, 8, 9, or 10 nucleotides from the 5' end of the polynucleotide. In some embodiments, the polynucleotide does not comprise the trinucleotide at 0, 1, or 2 nucleotides from the 5'end of the polynucleotide. In other embodiments, the polynucleotide comprises a TGC or a UGC trinucleotide located at 0, 1, or 2 nucleotides from the 5' end of the polynucleotide. In some embodiments, the polynucleotide does not comprise 5'-GGGG-3' or 5'-GIGG-3'. In some embodiments, the polynucleotide does not comprise 5'-$S_1S_2S_3S_4$-3', wherein $S_1$, $S_2$, $S_3$, and $S_4$ are independently G, deazaG or I (ribonucleotide or deoxyyribonucleotide). In other embodiments, the polynucleotide comprises 5'-GGGG-3' or 5'-GIGG-3' (or comprises 5'-$S_1S_2S_3S_4$-3', wherein $S_1$, $S_2$, $S_3$, and $S_4$ are independently G, deazaG or I). In some embodiments, the polynucleotide comprises a TGC or a UGC trinucleotide located at 0, 1, or 2 nucleotides from the 5' end of the polynucleotide, and comprises 5'-GGGG-3' or 5'-GIGG-3'. In some embodiments, the polynucleotide comprises a TGC or a UGC trinucleotide located at 0, 1, or 2 nucleotides from the 5' end of the polynucleotide, and comprises 5'-$S_1S_2S_3S_4$-3', wherein $S_1$, $S_2$, $S_3$, and $S_4$ are independently G, deazaG or I (ribonucleotide or deoxyyribonucleotide). In some embodiments, $X_5$ is G. In some embodiments, $X_5$ is I. In some embodiments, $X_6$ is I. In some embodiments $X_6$ is A. In some embodiments, $X_5X_6$ is GI. In some embodiments, $X_5X_6$ is GA. In some embodiments, $X_5X_6$ is II. In some embodiments, $X_5X_6$ is IA. In some embodiments, $X_5$ is not G; $X_5$ is not I; $X_6$ is not I; or $X_6$ is not A. In some embodiments, $X_5X_6$ is not GI; $X_5X_6$ is not GA; $X_5X_6$ is not II; or $X_5X_6$ is not IA. In some embodiments, the polynucleotide does not comprise 5'-$S_1S_2S_3S_4$-3', wherein $S_1$, $S_2$, $S_3$, and $S_4$ are independently G or a molecule that is capable of preventing G-tetrad formation and/or preventing Hoogsteen base pairing. In a subset of these embodiments, the molecule that is capable of preventing G-tetrad formation and/or preventing Hoogsteen base-pairing is a ribonucleotide or deoxyyribonucleotide such as inosine, 7-deaza-guanosine, 7-deaza-2'-deoxyxanthosine, 7-deaza-8-aza-2'-deoxyguanosine, 2'-deoxynebularine, isodeoxyguanosine, or 8-oxo-2'-deoxyguanosine. In some embodiments, $X_3X_4X_5X_6$ is one of the group consisting of TTGA, IAII, AAII, IATA, AIIA, IIII, ICII, IGII, ITII, CAII, TAII, CCII, TTII and GGII. In some embodiments, $X_1X_2X_3X_4X_5X_6$ is one of the group consisting of CCTTGA, TTIAII, TTAAII, TTIAIA, TTAIIA, AGIAII, TTIIII, TTICII, TTIGII, TTITII, TTCAII, TTTAII, TTCCII, TTTTII, TTGGII, IIIAII, CCI-AII, GGIAII, AAIAII, CIIAII, and IIAIIA. In some embodiments, the polynucleotide comprises one of the group consisting of SEQ ID NO:10, SEQ ID NO:14, SEQ ID NO:15, SEQ ID NO:16, SEQ ID NO:17, SEQ ID NO:18, SEQ ID NO:24, SEQ ID NO:26, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:44, SEQ ID NO:48, SEQ ID NO:49, SEQ ID NO:50, SEQ ID NO:51, SEQ ID NO:52, SEQ ID NO:53, SEQ ID NO:56, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:77, SEQ ID NO:78, SEQ ID NO:79, SEQ ID NO:80, SEQ ID NO:81, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, and SEQ ID NO:115, provided that the polynucleotide possesses a dinucleotide selected from the group consisting of GI, GA, II, and IA at the 3' end of the polynucleotide. In some preferred embodiments, the polynucleotide comprises one of the group consisting of SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105 and SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, and SEQ ID NO:115, provided that the polynucleotide possesses a dinucleotide selected from the group consisting of GI, GA, II, and IA at the 3' end of the polynucleotide. In some embodiments, the polynucleotide comprises SEQ ID NO:108. In some embodiments, the polynucleotide comprises SEQ ID NO:109. The present disclosure further provides, polynucleotides for use in inhibiting a TLR8-dependent immune response in an individual, wherein the polynucleotide comprises: (a) one of the group consisting of SEQ ID NO:10, SEQ ID NO:14, SEQ ID NO:15, SEQ ID NO:16, SEQ ID NO:17, SEQ ID NO:18, SEQ ID NO:24, SEQ ID NO:26, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:44, SEQ ID NO:48, SEQ ID NO:49, SEQ ID NO:50, SEQ ID NO:51, SEQ ID NO:52, SEQ ID NO:53, SEQ ID NO:56, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:77, SEQ ID NO:78, SEQ ID NO:79, SEQ ID NO:80, SEQ ID NO:81, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, and SEQ ID NO:115, provided that the polynucleotide possesses a dinucleotide selected from the group consisting of GI, GA, II, and IA at the 3' end of the polynucleotide; or (b) an analog of (a) wherein one or two principal bases other than the dinucleotide at the 3' end of the polynucleotide are each replaced with a naturally or a non-naturally occurring modification of the principal bases, again provided that the polynucleotide possesses a dinucleotide selected from the group consisting of GI, GA, II, and IA at the 3' end of the polynucleotide. In some embodiments, the polynucleotide comprises the analog of (a) in which one of the principal bases other than the dinucleotide is replaced with the naturally occurring modification. In some embodiments, the polynucleotide comprises the analog of (a) in which one of the principal bases other than the dinucleotide is replaced with the non-naturally occurring modification. In some preferred embodiments, the polynucleotide is less than 50, 45, 40, 35, 30, 25 or 20 bases or base pairs (nucleotides) in length. In some embodiments, the polynucleotide is single-stranded. In other embodiments, the polynucleotide is double-stranded. In some embodiments, the polynucleotide is DNA; the polynucleotide is RNA, or the polynucleotide is a DNA/RNA hybrid. In some embodiments, the polynucleotide contains phosphate-modified linkages. In some embodiments, the polynucleotide contains only phosphorothioate linkages. In some embodiments, Nx comprises a non-nucleic acid spacer moiety. Or said another way, in some embodiments, an N of Nx is connected to another N of Nx by a non-nucleic acid spacer moiety. In a subset of these embodiments, the non-nucleic acid spacer moiety comprises hexa-(ethylene glycol). Also provided are pharmaceutical compositions comprising a polynucleotide as described above, and a pharmaceutically acceptable excipient. Additionally, the present disclosure provides methods of inhibiting a TLR8-dependent immune response in an individual, comprising: administering to the individual the pharmaceutical composition in an amount effective to inhibit the TLR8-dependent immune response in the individual. In some preferred embodiments, the individual is human.

Moreover, the present disclosure provides polynucleotides, and for the use of the polynucleotides in inhibiting a TLR7-dependent immune response in an individual, wherein the polynucleotide consists of a nucleotide sequence of the formula: 5'-$Q_z$TICN$_x$-3 or 5'-$Q_z$TTCN$_x$-3, wherein each of Q and N is a nucleotide or nucleotide analog, x is an integer from 3 to 50, z is 0, 1 or 2, and wherein the polynucleotide does not comprise a CG dinucleotide. The present disclosure also provides polynucleotides consisting of a nucleotide sequence of the formula: 5'-$Q_z$TICN$_x$-3 or 5'-$Q_z$TTCN$_x$-3, wherein each of Q and N is a nucleotide or nucleotide analog, x is an integer from 3 to 50, z is 0, 1 or 2, and wherein the polynucleotide does not comprise a CG dinucleotide. In some embodiments, the formula is 5'-$Q_z$TICN$_x$-3. In other embodiments, the formula is 5'-$Q_z$TTCN$_x$-3. In some embodiments, the polynucleotide comprises SEQ ID NO:108. In some embodiments, the polynucleotide comprises SEQ ID NO:109. Pharmaceutical compositions comprising the polynucleotide and a pharmaceutically acceptable excipient are further provided. Additionally, the present disclosure provides methods of inhibiting a TLR7-dependent immune response in an individual, comprising: administering to the individual the pharmaceutical composition in an amount effective to inhibit the TLR7-dependent immune response in the individual. In some preferred embodiments, the individual is human.

Moreover, the present disclosure provides polynucleotides, and for the use of the polynucleotides in inhibiting a TLR7-dependent and a TLR8-dependent immune response in an individual, wherein the polynucleotides consists of a nucleotide sequence of the formula: 5'-$Q_z$TGC-$N_xX_1X_2X_3X_4X_5X_6$-$M_y$-3, 5'-$Q_z$ugc-$N_xX_1X_2X_3X_4X_5X_6$-$M_y$-3, 5'-$Q_z$TIC-$N_xX_1X_2X_3X_4X_5X_6$-$M_y$-3, or 5'-$Q_z$TTC-$N_xX_1X_2X_3X_4X_5X_6$-$M_y$-3, wherein each of Q, N, $X_1$, $X_2$, $X_3$, $X_4$, and M is a nucleotide or nucleotide analog, x is an integer from 0 to 50, y is 0 or 1, z is 0, 1 or 2, $X_5$ is G or I, and $X_6$ is I or A, upper case letters denote DNA, lower case letters denote 2'-O-methyl RNA, and wherein the polynucleotide does not comprise a CG dinucleotide. The present disclosure also provides polynucleotides consisting of a nucleotide sequence of the formula: 5'-$Q_z$TGC-$N_xX_1X_2X_3X_4X_5X_6$-$M_y$-3, 5'-$Q_z$ugc-$N_xX_1X_2X_3X_4X_5X_6$-$M_y$-3, 5'-$Q_z$TIC-$N_xX_1X_2X_3X_4X_5X_6$-$M_y$-3, or 5'-$Q_z$TTC-$N_xX_1X_2X_3X_4X_5X_6$-$M_y$-3, wherein each of Q, N, $X_1$, $X_2$, $X_3$, $X_4$, and M is a nucleotide or nucleotide analog, x is an integer from 0 to 50, y is 0 or 1, z is 0, 1 or 2, $X_5$ is G or I, and $X_6$ is I or A, upper case letters denote DNA, lower case letters (other than x and y in the subscripts) denote 2'-O-methyl RNA, and wherein the polynucleotide does not comprise a CG dinucleotide. In some embodiments, the polynucleotide comprises SEQ ID NO:108. In some embodiments, the polynucleotide comprises SEQ ID NO:109. Pharmaceutical composition comprising the polynucleotide and a pharmaceutically acceptable excipient are further provided. Additionally, the present disclosure provides methods of inhibiting a TLR7-dependent and a TLR8-dependent immune response in an individual, comprising: administering to the individual the pharmaceutical composition in an amount effective to inhibit the TLR7-dependent and the TLR8-dependent immune response in the individual. In some preferred embodiments, the individual is human.

Moreover, the present disclosure provides polynucleotides, and for the use of the polynucleotides in inhibiting a TLR7-dependent, a TLR8-dependent, and a TLR9-dependent immune response in an individual, wherein the polynucleotides consists of a nucleotide sequence of the formula: 5'-$Q_z$TGC-$N_x$-$S_1S_2S_3S_4$-Pa-$X_1X_2X_3X_4X_5X_6$-$M_y$-3, 5'-$Q_z$ugc-$N_x$-$S_1S_2S_3S_4$-Pa-$X_1X_2X_3X_4X_5X_6$-$M_y$-3, 5'-$Q_z$TIC-$N_x$-$S_1S_2S_3S_4$-Pa-$X_1X_2X_3X_4X_5X_6$-$M_y$-3, or 5'-$Q_z$TTC-$N_x$-$S_1S_2S_3S_4$-Pa-$X_1X_2X_3X_4X_5X_6$-$M_y$-3, wherein each of Q, N, P, $X_1$, $X_2$, $X_3$, $X_4$, and M is a nucleotide or nucleotide analog, a is an integer from 0 to 20, x is an integer from 0 to 50, y is 0 or 1, z is 0, 1 or 2, each of $S_1$, $S_2$, $S_3$, and $S_4$ are G or I, $X_5$ is G or I, and $X_6$ is I or A, upper case letters denote DNA, lower case letters denote 2'-O-methyl RNA, and wherein the polynucleotide does not comprise a CG dinucleotide. The present disclosure also provides polynucleotides consisting of a nucleotide sequence of the formula: 5'-$Q_z$TGC-$N_x$-$S_1S_2S_3S_4$-Pa-$X_1X_2X_3X_4X_5X_6$-$M_y$-3, 5'-$Q_z$ugc-$N_x$-$S_1S_2S_3S_4$-Pa-$X_1X_2X_3X_4X_5X_6$-$M_y$-3, 5'-$Q_z$TIC-$N_x$-$S_1S_2S_3S_4$-Pa-$X_1X_2X_3X_4X_5X_6$-$M_y$-3, or 5'-$Q_z$TTC-$N_x$-$S_1S_2S_3S_4$-Pa-$X_1X_2X_3X_4X_5X_6$-$M_y$-3, wherein each of Q, N, P, $X_1$, $X_2$, $X_3$, $X_4$, and M is a nucleotide or nucleotide analog, a is an integer from 0 to 20, x is an integer from 0 to 50, y is 0 or 1, z is 0, 1 or 2, each of $S_1$, $S_2$, $S_3$, and $S_4$ are G or I, $X_5$ is G or I, and $X_6$ is I or A, upper case letters denote DNA, lower case letters denote 2'-O-methyl RNA, and wherein the polynucleotide does not comprise a CG dinucleotide. Pharmaceutical compositions comprising the polynucleotide and a pharmaceutically acceptable excipient are further provided. Additionally, the present disclosure provides methods of inhibiting a TLR7-, a TLR8- and a TLR9-dependent immune response in an individual, comprising: administering to the individual the pharmaceutical composition in an amount effective to inhibit the TLR7-, the TLR8- and the TLR9-dependent immune response in the individual. In some preferred embodiments, the individual is human.

Moreover, the present disclosure provides polynucleotides, and for the use of the polynucleotides in inhibiting a TLR8-dependent and a TLR9-dependent immune response in an individual, wherein the polynucleotide consists of a nucleotide sequence of the formula: 5'-$N_x$-$S_1S_2S_3S_4$-Pa-$X_1X_2X_3X_4X_5X_6$-$M_y$-3, wherein each of N, P, $X_1$, $X_2$, $X_3$, $X_4$, and M is a nucleotide or nucleotide analog, a is an integer from 0 to 20, x is an integer from 0 to 50, y is 0 or 1, each of $S_1$, $S_2$, $S_3$, and $S_4$ are G or I, $X_5$ is G or I, and $X_6$ is I or A, and wherein the polynucleotide does not comprise a CG dinucleotide. The present disclosure also provides polynucleotides consisting of a nucleotide sequence of the formula: 5'-$N_x$-$S_1S_2S_3S_4$-Pa-$X_1X_2X_3X_4X_5X_6$-$M_y$-3, wherein each of N, P, $X_1$, $X_2$, $X_3$, $X_4$, and M is a nucleotide or nucleotide analog, a is an integer from 0 to 20, x is an integer from 0 to 50, y is 0 or 1, each of $S_1$, $S_2$, $S_3$, and $S_4$ are G or I, $X_5$ is G or I, and $X_6$ is I or A, and wherein the polynucleotide does not comprise a CG dinucleotide. Pharmaceutical compositions comprising the polynucleotide and a pharmaceutically acceptable excipient are further provided. Additionally, the present disclosure provides methods of inhibiting a TLR8-dependent and a TLR9-dependent immune response in an individual, comprising: administering to the individual the pharmaceutical composition in an amount effective to inhibit the TLR8-dependent and the TLR9-dependent immune response in the individual. In some preferred embodiments, the individual is human.

Furthermore, the present disclosure provides methods of inhibiting an immune response in an individual, comprising: administering to the individual a pharmaceutical composition comprising the polynucleotide of any of the preceding paragraphs in an amount effective to inhibit the immune response in the individual. In some embodiments, the immune response is associated with an autoimmune disease. In some embodiments, inhibiting the immune response ameliorates one or more symptoms of the autoimmune disease. In some preferred embodiments, the autoimmune disease is selected from the group consisting of rheumatoid arthritis, pancreatitis, mixed tissue connective disease, systemic lupus erythematosus, antiphospholipid syndrome, irritable bowel disease, type I diabetes mellitus and Sjogren's syndrome. In some embodiments, the autoimmune disease is Sjogren's syndrome. In some embodiments, the autoimmune disease is associated with RNA-containing immune complexes (or inflammation from RNA bound to peptides such as cationic peptides). In some embodiments, the immune response is associated with an inflammatory disorder. In some embodiments, inhibiting the immune response ameliorates one or more symptoms of the inflammatory disorder. In some embodiments, the inflammatory disorder is associated with elevated expression of TLR8 (or aberrant TLR8 signaling). In some embodiments, inhibiting the immune response treats the autoimmune disease or the inflammatory disorder. In some embodiments, inhibiting the immune response prevents or delays development of the autoimmune disease or the inflammatory disorder. In some preferred embodiments, the individual is human.

The present disclosure also provides polynucleotide of any of the preceding paragraphs for preparation of a medicament for treating or preventing an autoimmune disease or an inflammatory disorder. In some embodiments, the medicament comprises an effective amount of the polynucleotide for ameliorating one or more symptoms of the autoimmune disease. In some preferred embodiments, the autoimmune disease is selected from the group consisting of rheumatoid arthritis, pancreatitis, mixed tissue connective disease, systemic lupus erythematosus, antiphospholipid syndrome, irritable bowel disease, type I diabetes mellitus and Sjogren's syndrome. In some embodiments, the autoimmune disease is Sjogren's syndrome. In some embodiments, the autoimmune disease is associated with RNA-containing immune complexes (or inflammation from RNA bound to peptides such as cationic peptides). In some embodiments, the immune response is associated with an inflammatory disorder. In some embodiments, the medicament comprises an effective amount of the polynucleotide for ameliorating one or more symptoms of the inflammatory disorder. In some embodiments, the inflammatory disorder is associated with elevated expression of TLR8 (or aberrant TLR8 signaling). In some embodiments, the medicament treats the autoimmune disease or the inflammatory disorder. In some embodiments, the medicament prevents or delays development of the autoimmune disease or the inflammatory disorder. In some preferred embodiments, the individual having the autoimmune disease or the inflammatory disorder is human.

BRIEF DESCRIPTION OF THE DRAWINGS

FIG. 34A shows the relative levels of mIL-1α, mIL-1β, mTNF-α, mIFN-γ, mMMP-7, mCD1β.

DETAILED DESCRIPTION

Figure 1:
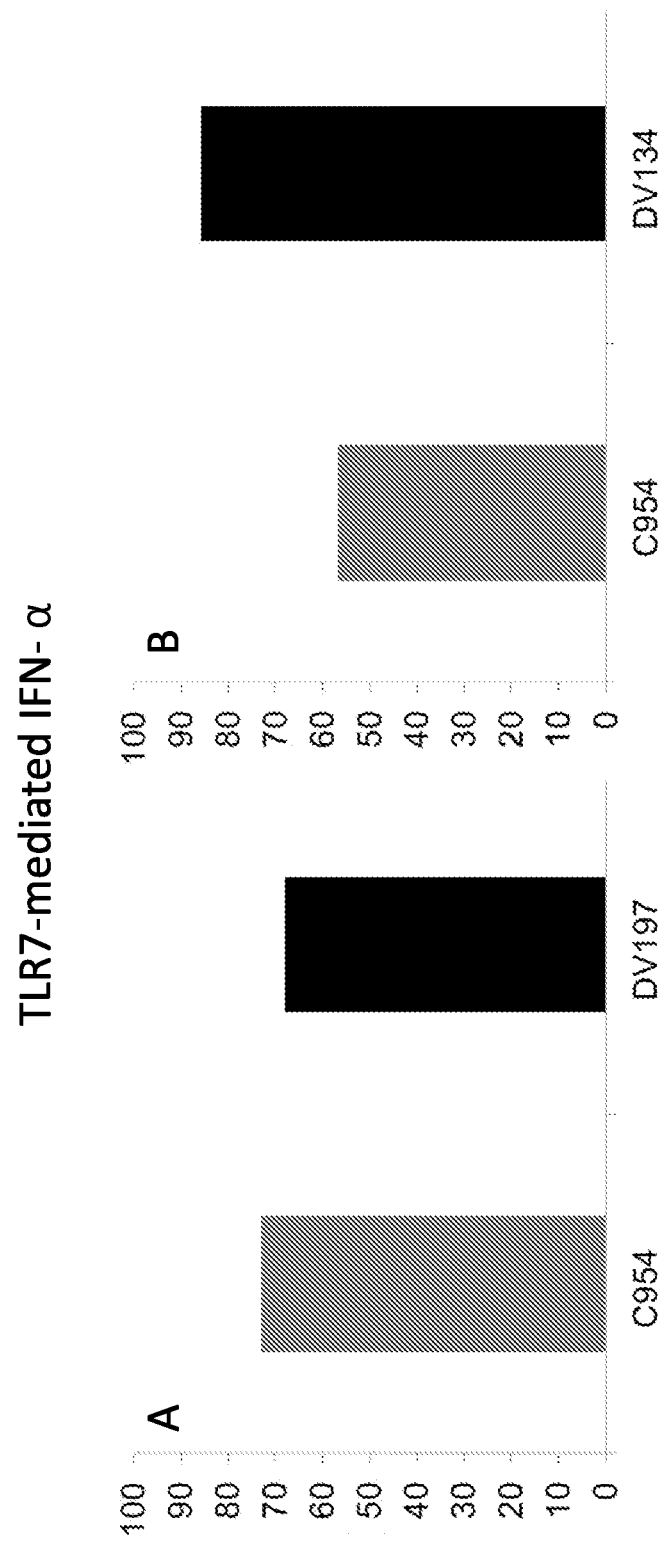
FIGS. 1A and 1B show the percent inhibition of TLR7-mediated IFN-α induction in PDC stimulated with 2 MOI inactivated influenza virus by polynucleotides C954, DV197 and DV134 at a concentration of 30 nM.

Provided herein are human Toll-like receptor (TLR)-inhibitors and methods for use in inhibiting a TLR7-, a TLR8-, and/or a TLR9-dependent immune response in an individual. In some embodiments the individual has an autoimmune disease or an inflammatory disorder. The TLR inhibitors of the present disclosure are polynucleotides comprising an inhibitory motif for one or more of TLR7, TLR8 and TLR9. The following aspects of the present disclosure are described in more detail herein: general techniques; definitions, compositions, methods, and kits.

I. General Techniques

The practice of the present disclosure employs, unless otherwise indicated, conventional techniques of molecular biology (including recombinant techniques), microbiology, cell biology, chemistry, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (Gait, ed., 1984); *Animal Cell Culture* (Freshney, ed., 1987); *Handbook of Experimental Immunology* (Weir & Blackwell, eds.); *Gene Transfer Vectors for Mammalian Cells* (Miller & Calos, eds., 1987); *Current Protocols in Molecular Biology* (Ausubel et al., eds., 1987); *PCR: The Polymerase Chain Reaction* (Mullis et al., eds., 1994); *Current Protocols in Immunology* (Coligan et al., eds., 1991); *The Immunoassay Handbook* (Wild, ed., Stockton Press NY, 1994); *Bioconjugate Techniques* (Hermanson, ed., Academic Press, 1996); and *Methods of Immunological Analysis* (Masseyeff, Albert, and Staines, eds., Weinheim: VCH Verlags gesellschaft mbH, 1993).

II. Definitions

The terms "nucleic acid," "polynucleotide," and "oligonucleotide" are used interchangeably and include single-stranded DNA (ssDNA), double-stranded DNA (dsDNA), single-stranded RNA (ssRNA) and double-stranded RNA (dsRNA), modified polynucleotides and polynucleosides or combinations thereof. The polynucleotide can be linear, branched, or circularly configured, or the polynucleotide can contain one or more linear, branched, and/or circular segments. Polynucleotides are polymers of nucleosides joined, generally, through phosphodiester linkages, although alternate linkages, such as phosphorothioate esters may also be used. A nucleoside consists of a purine (adenine (A) or guanine (G) or derivative thereof) or pyrimidine (thymine (T), cytosine (C) or uracil (U), or derivative thereof) base bonded to a sugar. The four nucleoside units (or bases) in DNA are called deoxyadenosine, deoxyguanosine, thymidine, and deoxycytidine. The four nucleoside units (or bases) in RNA are called adenosine, guanosine, uridine and cytidine. A nucleotide is a phosphate ester of a nucleoside.

The term "agonist" is used in the broadest sense and includes any molecule that activates signaling through a receptor. For instance, a TLR8 agonist binds a TLR8 receptor and activates a TLR8-signaling pathway.

The term "antagonist" is used in the broadest sense, and includes any molecule that blocks a biological activity of an agonist. For instance, a TLR8 antagonist suppresses a TLR8-signaling pathway.

The terms "immunoinhibitory sequence" and "IIS", as used herein, refer to a nucleic acid sequence that inhibits a measurable immune response (e.g., measured in vitro, in vivo, and/or ex vivo).

The terms "immunostimulatory sequence" and "ISS", as used herein, refer to a nucleic acid sequence that stimulates a measurable immune response (e.g., measured in vitro, in vivo, and/or ex vivo). For the purpose of the present disclosure, the term ISS refers to a nucleic acid sequence comprising an unmethylated CG dinucleotide.

The effect of a polynucleotide on a TLR-dependent immune response can be determined in vitro by measuring a response of an immune cell (e.g., leukocytes such as lymphocytes, monocytes, and dendritic cells) contacted with a TLR agonist in the presence and absence of the polynucleotide. Exemplary methods are described in Example 3. As referred to herein, a TLR inhibitor is a polynucleotide that inhibits a TLR-dependent immune response at an IC50 (half maximal inhibitory concentration) of less than 500 nM. Polynucleotides with an IC50 of less than 200 nM are considered to be highly active TLR inhibitors. Polynucleotides with an IC50 of from 201-500 nM are considered to be moderately active TLR inhibitors. Polynucleotides with an IC50 of greater than 500 nM are considered to be essentially inactive (e.g., not a TLR inhibitor).

Examples of measurable immune responses include, but are not limited to, antigen-specific antibody production, cytokine secretion, lymphocyte activation and lymphocyte proliferation.

The terms "antisense" and "antisense sequence" as used herein refer to a non-coding strand of a polynucleotide having a sequence complementary to the coding strand of mRNA. In preferred embodiments, the polynucleotides of the present disclosure are not antisense sequences, or RNAi molecules (miRNA and siRNA). That is in preferred embodiments, the TLR inhibitors of the present disclosure do not have significant homology (or complementarity) to transcripts (or genes) of the mammalian subjects in which they will be used. For instance, a polynucleotide of the present disclosure for inhibiting a TLR-dependent immune response in a human subject is less than 80% identical over its length to nucleic acid sequences of the human genome (e.g., a 20 base human TLR8 inhibitor would share no more than 16 of the 20 bases with a human transcript including but not limited to a tlr8 mRNA). Specifically, TLR inhibitors are less than 80%, 75%, 70%, 65%, 60%, 55%, 50%, 45%, 40%, 35%, 30%, 25% or 20%, identical to nucleic acid sequences of mammalian subjects (e.g., such as humans, nonhuman primates, farm animals, dogs, cats, rabbits, rats, mice, etc.).

The terms "microRNA" and "miRNA" refer to a class of post-transcriptional regulators, in the form of short (~22 nucleotide) RNA sequences that bind to complementary sequences of target mRNAs, typically resulting in their silencing. The terms "small interfering RNA," "short interfering RNA," and "siRNA" refer to a class of double-stranded RNA molecules, 20-25 base pairs in length, that interfere with expression of genes with complementary nucleotide sequences.

"Stimulation" of a response or parameter includes eliciting and/or enhancing that response or parameter when compared to otherwise same conditions except for a parameter of interest, or alternatively, as compared to another condition (e.g., increase in TLR-signaling in the presence of a TLR agonist as compared to the absence of the TLR agonist). For example, "stimulation" of an immune response means an increase in the response, which can arise from eliciting and/or enhancement of a response. Similarly, "stimulation" of production of a cytokine (such as IL-1α, IL-1β, IL-6, and/or TNF-α) or "stimulation" of cell type (such as CTLs) means an increase in the amount or level of cytokine or cell type.

"Suppression" or "inhibition" of a response or parameter includes decreasing that response or parameter when compared to otherwise same conditions except for a parameter of interest, or alternatively, as compared to another condition (e.g., increase in TLR-signaling in the presence of a TLR agonist and a TLR antagonist as compared to the presence of the TLR agonist in the absence of the TLR antagonist).

The term "cells," as used herein, is understood to refer not only to the particular subject cell, but to the progeny or potential progeny of such a cell. Because certain modifications may occur in succeeding generations due to either mutation or environmental influences, such progeny may not, in fact, be identical to the parent cell, but are still included within the scope of the term as used herein.

The term "individual" refers to a mammal, including humans. An individual includes, but is not limited to, human, bovine, equine, feline, canine, rodent, or primate subjects.

A "transgenic animal" is an animal containing one or more cells bearing genetic information received, directly or indirectly, by deliberate genetic manipulation at a subcellular level, such as by microinjection or infection with recombinant virus. This introduced DNA molecule may be integrated within a chromosome, or it may be extrachromosomally replicating DNA.

Administration "in combination with" one or more further therapeutic agents includes simultaneous (concurrent) and consecutive administration in any order.

"Chronic" administration refers to administration of the agent(s) in a continuous mode as opposed to an acute mode, so as to maintain the initial therapeutic effect (activity) for an extended period of time. "Intermittent" administration refers to treatment that is not consecutively and/or continuously done without interruption, but rather is cyclic in nature.

An "effective amount" of an agent disclosed herein is an amount sufficient to carry out a specifically stated purpose. An "effective amount" may be determined empirically and in a routine manner, in relation to the stated purpose.

The term "therapeutically effective amount" refers to an amount of an agent (e.g., TLR inhibitor) effective to "treat" a disease or disorder in a subject (e.g., a mammal such as a human). In the case of autoimmune disease, the therapeutically effective amount of the agent reduces a sign or symptom of the autoimmune disease. For instance in connection with treatment of a rheumatoid arthritis, a therapeutically effect amount of an agent (e.g., TLR inhibitor) reduces a sign or symptom of rheumatoid arthritis in a patient, which may also reduce the rate of damage to bone and cartilage.

The terms "treating" or "treatment" of a disease refer to executing a protocol, which may include administering one or more drugs to an individual (human or otherwise), in an effort to alleviate signs or symptoms of the disease. Thus, "treating" or "treatment" does not require complete alleviation of signs or symptoms, does not require a cure, and specifically includes protocols that have only a marginal effect on the individual.

As used herein, and as well-understood in the art, "treatment" is an approach for obtaining beneficial or desired results, including clinical results. Beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise.

It is understood that aspects and embodiments described herein as "comprising" include "consisting" and/or "consisting essentially of" aspects and embodiments.

III. Compositions

Polynucleotides comprising an inhibitory motif for one or more of TLR7, TLR8 and TLR9 (TLR inhibitors) are provided herein. Also provided are TLR inhibitors for use in any of the methods described herein. Each immunoinhibitory sequence (IIS) described herein comprises at least one inhibitory motif. A TLR inhibitor comprising an inhibitory motif may be single stranded or double stranded DNA, as well as single-stranded or double-stranded RNA or DNA/RNA hybrid. TLR inhibitors comprise one or more ribonucleotides (containing ribose as the only or principal sugar component) and/or deoxyribonucleotides (containing deoxyribose as the principal sugar component). The heterocyclic bases, or nucleic acid bases, which are incorporated in the TLR inhibitors can be the naturally-occurring principal purine and pyrimidine bases, (namely uracil, thymine, cytosine, adenine and guanine). In certain embodiments, the one or two principle bases other than the dinucleotide at the 3' end of the polynucleotide are each replaced with a naturally or a non-naturally occurring modification of the principle bases. In certain embodiments, one or more nucleotides comprise a modification. In certain embodiments, one or more nucleotides comprise a modified base. In certain embodiments, one or more nucleotides comprise a modified sugar. In certain embodiments, one or more nucleotides comprise 2'-deoxyinosine. In certain embodiments, one or more nucleotides do not comprise a C analog or a G analog (e.g., does not comprise 7-deazaguanosine). In certain embodiments, the polynucleotide comprises a modification. In certain embodiments, the polynucleotide does comprise a modified base. In certain embodiments, the polynucleotide does comprise a modified sugar. In certain embodiments, the polynucleotide does not comprise a modified sugar. In certain embodiments, the polynucleotide does not comprise a C analog or a G analog (e.g., does not comprise 7-deazaguanosine). In certain embodiments, the polynucleotide does not comprise a CG dinucleotide. In preferred embodiments, the polynucleotides of the present disclosure, which comprise an IIS, are not antisense sequences, or RNAi molecules (miRNA and siRNA).

In certain embodiments of any of the methods or compositions provided herein, one or more nucleotides comprise a modification. In certain embodiments, the modification is 2'-sugar modification. In certain embodiments, the 2'-sugar modification is a 2'-O-methyl sugar modification or a 2'-O-methoxyethyl sugar modification. In certain embodiments, the polynucleotide is comprised of all 2'-deoxyribo polynucleotides. In certain embodiments, the polynucleotide is a 2'-deoxyribo polynucleotide and a 2'-sugar modification chimeric sequence. In certain embodiments, the polynucleotide is a 2'-deoxyribo polynucleotide and a 2'-O-methyl sugar ribo polynucleotide chimeric sequence. In certain embodiments, the polynucleotide is a 2'-deoxyribo polynucleotide and a 2'-O-methyoxyethyl sugar ribo polynucleotide chimeric sequence. In certain embodiments, the polynucleotide has at least one nucleotide comprising a modified phosphate linkage. In certain embodiments, the polynucleotide comprises only phosphorothioate linkages. In certain embodiments, the polynucleotide comprises only phosphorothioate and phosphodiester linkages. In certain embodiments, one or more nucleotides comprise a modified base. In certain embodiments, one or more nucleotides comprise a modified sugar. In certain embodiments, one or more nucleotides comprise 2'-deoxyinosine. In certain embodiments, one or more nucleotides do not comprise a C analog or a G analog (e.g., does not comprise 7-deazaguanosine). As used herein, the term "nucleotide analog" refers to a compound that essentially retains the identity of the nucleotide from which it was derived. For instance, 7-dG is a G analog and N4-ethyl-dC is a C analog. On the other hand, a nucleotide or base modification refers to a compound that may not retain the identity of the nucleotide or base. That is the term modification encompasses a substitution of a nucleotide or base with a different naturally or non-naturally occurring nucleotide or base. For instance, the term modification encompasses substitution of an A for a G. As is clearly conveyed, it is understood that, with respect to formulae described herein, any and all parameters are independently selected. For example, in a formula that includes variables x and y, if x=0-2, y may be independently selected regardless of the values of x (or any other selectable parameter in a formula).

In some embodiments, the polynucleotide is less than about any of the following nucleotide lengths (in bases or base pairs): 100, 95, 90, 85, 80, 75, 70, 65, 60, 55, 50, 45, 40, 35, 30, 29, 28, 27, 26, 25, 24, 23, 22, 21, 20, 19, 18, 17, 16, 15, 14, 13, 12, 11, 10, 9, 8, or 7. In some embodiments, the polynucleotide is greater than about any of the following nucleotide lengths (in bases or base pairs): 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90 or 95. That is, the polynucleotide can be any of a range of sizes having an upper limit of 100, 95, 90, 85, 80, 75, 70, 65, 60, 55, 50, 45, 40, 35, 30, 29, 28, 27, 26, 25, 24, 23, 22, 21, 20, 19, 18, 17, 16, 15, 14, 13, 12, 11, 10, 9, 8, or 7 and an independently selected lower limit of 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90 or 95, wherein the lower limit is less than the upper limit.

TLR7 Inhibitors

Provided herein are TLR7 inhibitors, for use in any of the methods described herein (e.g., inhibiting or suppressing a TLR7-dependent immune response). The TLR7 inhibitors are polynucleotides comprising at least one TLR7 inhibitory motif.

TLR7 inhibitors of the present disclosure are polynucleotides consisting of a nucleotide sequence of the formula: 5'-$Q_zTICN_x$-3 or 5'-$Q_zTTCN_x$-3, wherein each of Q and N is a nucleotide or nucleotide analog, x is an integer from 3 to 50, z is 0, 1 or 2. Provided herein are polynucleotides for use in inhibiting a TLR7-dependent immune response, wherein the polynucleotide consists of a nucleotide sequence of the formula: 5'-$Q_zTICN_x$-3 or 5'-$Q_zTTCN_x$-3, wherein each of Q and N is a nucleotide or nucleotide analog, x is an integer from 3 to 50, z is 0, 1 or 2. In some embodiments, a polynucleotide consisting of a nucleotide sequence of the formula: 5'-$Q_zTICN_x$-3 or 5'-$Q_zTTCN_x$-3, wherein each of Q and N is a nucleotide or nucleotide analog, x is an integer from 3 to 50, z is 0, 1 or 2, and wherein the polynucleotide does not comprise a CG dinucleotide. This means z is not 3, and $Q_z$ is not TGC or ugc, $Q_zTIC$ is not TGCTIC or ugcTIC, and $Q_zTTC$ is not TGCTTC or ugcTTC, wherein upper case letters denote DNA, lower case letters denote 2'-O-methyl RNA. In some embodiments, the polynucleotide does not comprise a CG dinucleotide. In some embodiments, the polynucleotide does not comprise a modified CG dinucleotide. In certain embodiments, the polynucleotide does not comprise 5'-GGGG-3' or 5'-GIGG-3'. In certain embodiments, the polynucleotide does not comprise 5'-$S_1S_2S_3S_4$-3', wherein $S_1$, $S_2$, $S_3$, and $S_4$ are independently G or a molecule that is capable of preventing G-tetrad formation and/or preventing Hoogsteen base pairing. In further embodiments, the molecule that is capable of preventing G-tetrad formation and/or preventing Hoogsteen base-pairing is a ribonucleotide or deoxyyribonucleotide such as inosine, 7-deazaguanosine, 7-deaza-2'-deoxyxanthosine, 7-deaza-8-aza-2'-deoxyguanosine, 2'-deoxynebularine, isodeoxyguanosine, or 8-oxo-2'-deoxyguanosine. In some embodiments, the polynucleotide comprises 5'-GGGG-3' or 5'-GIGG-3'. In some embodiments, the polynucleotide comprises 5'-$S_1S_2S_3S_4$-3'. In some embodiments, Nx comprises a non-nucleic acid spacer moiety. In further embodiments, the non-nucleic acid spacer moiety comprises hexa-(ethylene glycol).

As described herein, x is an integer between 3 and 50. This means x is 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In some embodiments, x is between 3 to 45, between 3 to 40, between 3 to 35, between 3 to 30, between 3 to 25, between 3 to 20, between 3 to 15, between 3 to 10, or between 3 to 5. In some embodiments, x is greater than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, but no greater than 50. In some embodiments, x is less than 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11 10, 9, 8, 7, 6, 5, or 4, but no less than 3.

As described herein, z is 0, 1, or 2. In some embodiments, z is 0 (the 5'-TIC-3' or 5'-TTC is at the 5' end of the polynucleotide). In some embodiments, z is 1. In some embodiments, z is 2.

Exemplary TLR7 inhibitors are polynucleotides comprising a sequence selected from the group consisting of:

```
5'-TIC TGC TCC TTG AGI-3';         (SEQ ID NO: 36)

5'-TTC TGC TCC TTG AGI-3';         (SEQ ID NO: 38)

5'-TIC TIC TCC TTI AII-3';         (SEQ ID NO: 44)

5'-TTC TTC TCC TTT ATT-3';         (SEQ ID NO: 46)

5'-TIC TCC TTG AGI-3';             (SEQ ID NO: 48)

5'-TTC TCC TTG AGI-3';             (SEQ ID NO: 50)

5'-TIC TCC TTI AAI-3';             (SEQ ID NO: 55)

5'-TIC TCC TTI AIA-3';             (SEQ ID NO: 56)

5'-TIC TCC TTI AAA-3';             (SEQ ID NO: 57)

5'-TIC TCC TTI IAI-3';             (SEQ ID NO: 58)

5'-TIC TCC TTA IIA-3';             (SEQ ID NO: 59)

5'-TIC AGI TTI AII-3';             (SEQ ID NO: 60)

5'-TIC AGI AGI AII-3';             (SEQ ID NO: 61)

5'-TIC TIC TII TTI AII-3';         (SEQ ID NO: 62)

5'-TIC TCC TTI AII-3';             (SEQ ID NO: 63)

5'-TIC TCC TTI III-3';             (SEQ ID NO: 64)

5'-TIC TCC TTI CII-3';             (SEQ ID NO: 65)

5'-TIC TCC TTI GII-3';             (SEQ ID NO: 66)

5'-TIC TCC TTI TII-3';             (SEQ ID NO: 67)

5'-TIC TIC TCC TII TTI CII-3';     (SEQ ID NO: 85)

5'-TIC TIC TCC AGI TTI CII-3';     (SEQ ID NO: 86)

5'-TIC TIC TCC TCC TTI CII-3';     (SEQ ID NO: 87)

5'-TIC TIC TTG AGI TTI CII-3';     (SEQ ID NO: 88)

5'-TIC TIC TCC TCC TTI CII AII-3'; (SEQ ID NO: 90)

5'-TIC TCC TCC TTI CII AII-3';     (SEQ ID NO: 91)

5'-TIC TIC TCC TTI CII-3';         (SEQ ID NO: 95)

5'-TTC TTC TCC TTI CII-3';         (SEQ ID NO: 97)

5'-TIC TCC TCC TTI CII AII A-3';   (SEQ ID NO: 99)

5'-TIC TIC TTG AGI TTI CII AII-3'; (SEQ ID NO: 103)

5'-TIC TTG AGI TTI CII AII-3';     (SEQ ID NO: 104)

5'-TIC TCC TTG AGI AII-3';         (SEQ ID NO: 108)

5'-TIC TCC TCC TTG AGI AII-3';     (SEQ ID NO: 109)

5'-TIC TTC TCC TTG AGI AII-3';     (SEQ ID NO: 110)

5'-TIC TCC TCC TTG IIA II-3';      (SEQ ID NO: 111)

5'-TIC TCC TCC TTG GGI AII-3';     (SEQ ID NO: 114)
and

5'-TIC TTC TCC TTG GGI AII-3';     (SEQ ID NO: 115)
``` wherein I=2'-deoxyinosine and upper case letters denote DNA, provided that the polynucleotide possesses a trinucleotide selected from the group consisting of TIC and TTC, at the 5'end of the polynucleotide. In some embodiments, the polynucleotide comprises SEQ ID NO:108. In some embodiments, the polynucleotide comprises SEQ ID NO:109.

In some embodiments, the polynucleotide comprises:

(a) one of the group consisting of SEQ ID NO:36, SEQ ID NO:38, SEQ ID NO:44, SEQ ID NO:46, SEQ ID NO:48, SEQ ID NO:50, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:85, SEQ ID NO:86, SEQ ID NO:87, SEQ ID NO:88, SEQ ID NO:90, SEQ ID NO:91, SEQ ID NO:95, SEQ ID NO:97, SEQ ID NO:99, SEQ ID NO:103, SEQ ID NO:104, SEQ ID NO:108, SEQ ID NO:109, SEQ ID NO:110; SEQ ID NO:111, SEQ ID NO:114, and SEQ ID NO:115, provided that the polynucleotide possesses a trinucleotide selected from the group consisting of TIC and TTC, at the 5'end of the polynucleotide; or (b) an analog of (a) wherein one or two principal bases other than the dinucleotide at the 3' end of the polynucleotide are each replaced with a with a naturally or a non-naturally occurring modification of the principal bases, provided that the polynucleotide possesses a trinucleotide selected from the group consisting of TIC and TTC, at the 5'end of the polynucleotide. In further embodiments, the polynucleotide comprises the analog of (a) in which one of the principal bases other than the dinucleotide is replaced with the naturally occurring modification. In further embodiments, the polynucleotide comprises the analog of (a) in which one of the principal bases other than the trinucleotide is replaced with the non-naturally occurring modification. In some embodiments, the polynucleotide is less than 50, 45, 40, 35, 30, 25 or 20 bases or base pairs (nucleotides) in length. In some embodiments, the polynucleotide is single-stranded. In some embodiments, the polynucleotide is double-stranded. In some embodiments, the polynucleotide is single-stranded DNA. In some embodiments, the polynucleotide is double-stranded DNA. In some embodiments, the polynucleotide is single-stranded RNA. In some embodiments, the polynucleotide is double-stranded RNA. In some embodiments, the polynucleotide contains phosphate-modified linkages. In some embodiments, the polynucleotide contains only phosphorothioate linkages. In some embodiments, the polynucleotide contains one or more phosphorothioate linkages. In some embodiments, the polynucleotide contains only phosphorothioate and phosphodiester linkages. In some embodiments, Nx comprises a non-nucleic acid spacer moiety. Or said another way, in some embodiments, an N of Nx is connected to another N of Nx by a non-nucleic acid spacer moiety. In further embodiments, the non-nucleic acid spacer moiety comprises hexa-(ethylene glycol).

TLR8 Inhibitors

Provided herein are TLR8 inhibitors, for use in any of the methods described herein (e.g., inhibiting or suppressing a TLR8-dependent immune response). The TLR8 inhibitors are polynucleotides comprising at least one TLR8 inhibitory motif.

TLR8 inhibitors of the present disclosure are polynucleotides consisting of a nucleotide sequence of the formula: 5'-$N_xX_1X_2X_3X_4X_5X_6$-$M_y$-3', wherein each of N, $X_1$, $X_2$, $X_3$, $X_4$, and M is a nucleotide or nucleotide analog, x is an integer from 0 to 50, y is 0 or 1, $X_5$ is G or I and $X_6$ is I or A. That is $M_y$ is at the 3'-end of the polynucleotide. Also provided are TLR8 inhibitors, wherein the TLR8 inhibitor is a polynucleotide consisting of a nucleotide sequence of the formula 5'-$N_xX_1X_2X_3X_4X_5X_6$-3', wherein each of N, $X_1$, $X_2$, $X_3$, and $X_4$ is a nucleotide or nucleotide analog, $X_5$ is G or I, $X_6$ is I or A, x is an integer from 0 to 50, and $X_6$ is at the 3' end of the polynucleotide, with the proviso that when $X_5X_6$ is GI or GA, then each of $X_3$ and $X_4$ is A, T or C. Additionally, provided herein are TLR8 inhibitors, wherein the TLR8 inhibitor is a polynucleotide consisting of a nucleotide sequence of the formula 5'-$N_xX_1X_2X_3X_4X_5X_6$-3', wherein N is a nucleotide or nucleotide analog, each of $X_1$ and $X_2$ is A, T, C, G, or I, each of $X_3$ and $X_4$ is A, T or C, $X_5$ is G or I, $X_6$ is I or A, x is an integer from 0 to 50, and $X_6$ is at the 3'end of the polynucleotide. Provided herein are polynucleotides for use in inhibiting a TLR8-dependent immune response, wherein the polynucleotide consists of a nucleotide sequence of the formula: 5'-$N_xX_1X_2X_3X_4X_5X_6$-$M_y$-3', wherein each of N, $X_1$, $X_2$, $X_3$, $X_4$, and M is a nucleotide or nucleotide analog, x is an integer from 0 to 50, y is 0 or 1, $X_5$ is G or I and $X_6$ is I or A. Further provided herein are polynucleotides for use in inhibiting a TLR8-dependent immune response, wherein the polynucleotide consists of a nucleotide sequence of the formula 5'-$N_xX_1X_2X_3X_4X_5X_6$-3', wherein each of N, $X_1$, $X_2$, $X_3$, and $X_4$ is a nucleotide or nucleotide analog, $X_5$ is G or I, $X_6$ is I or A, x is an integer from 0 to 50, and $X_6$ is at the 3' end of the polynucleotide, with the proviso that when $X_5X_6$ is GI or GA, then each of $X_3$ and $X_4$ is A, T or C. Additionally provided herein are polynucleotides for use in inhibiting a TLR8-dependent immune response, wherein the polynucleotide consists of a nucleotide sequence of the formula 5'-$N_xX_1X_2X_3X_4X_5X_6$-3', wherein N is a nucleotide or nucleotide analog, each of $X_1$ and $X_2$ is A, T, C, G, or I, each of $X_3$ and $X_4$ is A, T or C, $X_5$ is G or I, $X_6$ is I or A, x is an integer from 0 to 50, and $X_6$ is at the 3'end of the polynucleotide. In some embodiments, the polynucleotide does not comprise a CG dinucleotide. In some embodiments, the polynucleotide does not comprise a C analog or G analog (e.g., does not comprise 7-deazaguanosine). In some embodiments, the polynucleotide does not comprise a modified base. In some embodiments, the polynucleotide does not comprise a modified sugar. In some embodiments, the polynucleotide does not comprise a TGC or an ugc trinucleotide located 0, 1, or 2 nucleotides from the 5' end of the polynucleotide. In certain embodiments, the polynucleotide comprises a TGC or an ugc trinucleotide located at 0, 1, or 2 nucleotides from the 5' end of the polynucleotide. In some embodiments, the polynucleotide does not comprise 5'-GGGG-3' or 5'-GIGG-3'. In certain embodiments, the polynucleotide does not comprise 5'-$S_1S_2S_3S_4$-3', wherein $S_1$, $S_2$, $S_3$, and $S_4$ are independently G or a molecule that is capable of preventing G-tetrad formation and/or preventing Hoogsteen base pairing. In further embodiments, the molecule that is capable of preventing G-tetrad formation and/or preventing Hoogsteen base-pairing is a ribonucleotide or deoxyyribonucleotide such as inosine, 7-deaza-guanosine, 7-deaza-2'-deoxyxanthosine, 7-deaza-8-aza-2'-deoxyguanosine, 2'-deoxynebularine, isodeoxyguanosine, or 8-oxo-2'-deoxyguanosine. In some embodiments, the polynucleotide does not comprise SEQ ID NO:9. In some embodiments, the polynucleotide comprises 5'-GGGG-3' or 5'-GIGG-3'. In certain embodiments, the polynucleotide comprises 5'-$S_1S_2S_3S_4$-3', wherein $S_1$, $S_2$, $S_3$, and $S_4$ are independently G or a molecule that is capable of preventing G-tetrad formation and/or preventing Hoogsteen base pairing. In further embodiments, the molecule that is capable of preventing G-tetrad formation and/or preventing Hoogsteen base-pairing is a ribonucleotide or deoxyyribonucleotide such as inosine, 7-deaza-guanosine, 7-deaza-2'-deoxyxanthosine, 7-deaza-8-aza-2'-deoxyguanosine, 2'-deoxynebularine, isodeoxyguanosine, or 8-oxo-2'-deoxyguanosine. In some embodiments, the polynucleotide comprises a TGC or a UGC trinucleotide located 0, 1, or 2 nucleotides from the 5' end of the polynucleotide, and comprises 5'-GGGG-3' or 5'-GIGG-3'. In some embodiments, the polynucleotide does not comprise a GT, GU or GG dinucleotide at the 3-end of the polynucleotide. In some embodiments, the polynucleotide is not an antisense sequence or RNAi sequence. In some embodiments, $X_3$, and $X_4$ are independently A, C, G, T or I. In some embodiments, each of $X_1$, $X_2$, $X_3$, and $X_4$ are independently A, C, G, T or I. In some embodiments, $X_5$ is G. In some embodiments, $X_5$ is I. In some embodiments, $X_6$ is I. In some embodiments, $X_6$ is A. In some embodiments, $X_5X_6$ is GI. In some embodiments, $X_5X_6$ is GA. In some embodiments, $X_5X_6$ is II. In some embodiments, $X_5X_6$ is IA. In some embodiments, $X_5$ is not G. In some embodiments, $X_5$ is not I. In some embodiments, $X_6$ is not I. In some embodiments, $X_6$ is not A. In some embodiments, $X_5X_6$ is not GI. In some embodiments, $X_5X_6$ is not GA. In some embodiments, $X_5X_6$ is not II. In some embodiments, $X_5X_6$ is not IA. In some embodiments, wherein y is 0. In some embodiments, $X_3X_4X_5X_6$ is one of the group consisting of GAGI, GAGA, GGGI, TTGA, TAII, GTGI, AAII, IAIA, AIIA, IIII, ICII, IGII, ITII, CAII, TAII, CCII, TTII and GGII. In some embodiments, $X_3X_4X_5X_6$ is one of the group consisting of TTGA, TAII, AAII, IAIA, AIIA, IIII, ICII, IGII, ITII, CAII, TAII, CCII, TTII and GGII. In some embodiments, $X_1X_2X_3X_4X_5X_6$ is one of the group consisting of TTGAGI, TTGAGA, TTGGGI, CCTTGA, TTIAII, TTGTGI, TTAAII, TTIAIA, TTAIIA, AGIAII, TTIIII, TTICII, TTIGII, TTITII, TTCAII, TTTAII, TTCCII, TTTTII, TTGGII, IIIAII, CCIAII, GGIAII, AAIAII, CIIAII, and IIAIIA. In some embodiments, $X_1X_2X_3X_4X_5X_6$ is one of the group consisting of CCTTGA, TTIAII, TTAAII, TTIAIA, TTAIIA, AGIAII, TTIIII, TTICII, TTIGII, TTITII, TTCAII, TTTAII, TTCCII, TTTTII, TTGGII, IIIAII, CCIAII, GGIAII, AAIAII, CIIAII, and IIAIIA.

As described herein, x is an integer between 0 and 50. This means x is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In some embodiments, x is between 3 to 45, between 3 to 40, between 3 to 35, between 3 to 30, between 3 to 25, between 3 to 20, between 3 to 15, between 3 to 10, or between 3 to 5. In some embodiments, x is greater than 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, but no greater than 50. In some embodiments, x is less than 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11 10, 9, 8, 7, 6, 5, 4, 3, 2, but no less than 1. In some embodiments, x is 0.

As described herein, y is 0 or 1. In some embodiments, y is 0 (the $X_5X_6$ is at the 3' end of the polynucleotide). In some embodiments, y is 1.

In exemplary embodiments, the polynucleotide comprises one of the group consisting of SEQ ID NO:10, SEQ ID NO:14, SEQ ID NO:15, SEQ ID NO:16, SEQ ID NO:17, SEQ ID NO:18, SEQ ID NO:24, SEQ ID NO:26, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:44, SEQ ID NO:48, SEQ ID NO:49, SEQ ID NO:50, SEQ ID NO:51, SEQ ID NO:52, SEQ ID NO:53, SEQ ID NO:56, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:77, SEQ ID NO:78, SEQ ID NO:79, SEQ ID NO:80, SEQ ID NO:81, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, and SEQ ID NO:115, provided that GI, GA, II or IA is 0 or 1 nucleotides from the 3' end of the polynucleotide. In some embodiments, the polynucleotide comprises one of the group consisting of SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, and SEQ ID NO:115, provided that GI, GA, II or IA is 0 or 1 nucleotides from the 3' end of the polynucleotide. In some embodiments, the polynucleotide comprises SEQ ID NO:108. In some embodiments, the polynucleotide comprises SEQ ID NO:109.

In some embodiments, the polynucleotide comprises:

(a) one of the group consisting of SEQ ID NO:10, SEQ ID NO:14, SEQ ID NO:15, SEQ ID NO:16, SEQ ID NO:17, SEQ ID NO:18, SEQ ID NO:24, SEQ ID NO:26, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:44, SEQ ID NO:48, SEQ ID NO:49, SEQ ID NO:50, SEQ ID NO:51, SEQ ID NO:52, SEQ ID NO:53, SEQ ID NO:56, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:77, SEQ ID NO:78, SEQ ID NO:79, SEQ ID NO:80, SEQ ID NO:81, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, and SEQ ID NO:115, provided that the polynucleotide possesses a dinucleotide selected from the group consisting of GI, GA, II, IA 0 or 1 nucleotides from the 3'end of the polynucleotide; or (b) an analog of (a) wherein one or two principal bases other than the dinucleotide at the 3' end of the polynucleotide are each replaced with a with a naturally or a non-naturally occurring modification of the principal bases, provided that the polynucleotide possesses a dinucleotide selected from the group consisting of GI, GA, II, IA 0 or 1 nucleotides from the 3'end of the polynucleotide. In further embodiments, the polynucleotide comprises the analog of (a) in which one of the principal bases other than the dinucleotide is replaced with the naturally occurring modification. In further embodiments, the polynucleotide comprises the analog of (a) in which one of the principal bases other than the dinucleotide is replaced with the non-naturally occurring modification. In some embodiments, the polynucleotide is less than 50, 45, 40, 35, 30, 25 or 20 bases or base pairs (nucleotides) in length. In some embodiments, the polynucleotide is single-stranded. In some embodiments, the polynucleotide is double-stranded. In some embodiments, the polynucleotide is single-stranded DNA. In some embodiments, the polynucleotide is double-stranded DNA. In some embodiments, the polynucleotide is single-stranded RNA. In some embodiments, the polynucleotide is double-stranded RNA. In some embodiments, the polynucleotide contains phosphate-modified linkages. In some embodiments, the polynucleotide contains only phosphorothioate linkages. In some embodiments, the polynucleotide contains one or more phosphorothioate linkages. In some embodiments, the polynucleotide contains only phosphorothioate and phosphodiester linkages. In some embodiments, Nx comprises a non-nucleic acid spacer moiety. In further embodiments, the non-nucleic acid spacer moiety comprises hexa-(ethylene glycol).

TLR7/8 Combination Inhibitors

Provided herein polynucleotides comprising a TLR7 inhibitory motif and a TLR8 inhibitory motif (hereinafter "TRL7/8 combination inhibitors") for use in any of the methods described herein (e.g., inhibiting or suppressing a TLR7-dependent and a TLR8-dependent immune response).

Provided herein are TLR7/8 combination inhibitors, wherein the TLR7/8 combination inhibitors are polynucleotides consisting of a nucleotide sequence of the formula: 5'-$Q_z$TGC-$N_xX_1X_2X_3X_4X_5X_6$-$M_y$-3, 5'-$Q_z$ugc-$N_xX_1X_2X_3X_4X_5X_6$-$M_y$-3, 5'-$Q_z$TIC-$N_xX_1X_2X_3X_4X_5X_6$-$M_y$-3, or 5'-$Q_z$TTC-$N_xX_1X_2X_3X_4X_5X_6$-$M_y$-3, wherein each of Q, N, $X_1$, $X_2$, $X_3$, $X_4$, and M is a nucleotide or nucleotide analog, x is an integer from 0 to 50, y is 0 or 1, z is 0, 1 or 2, $X_5$ is G or I, and $X_6$ is I or A, upper case letters denote DNA, lower case letters denote 2'-O-methyl RNA, and wherein the polynucleotide does not comprise a CG dinucleotide. Provided herein are polynucleotides for use in inhibiting a TLR7-dependent and TL8-dependent immune response, wherein the polynucleotide consists of a nucleotide sequence of the formula: 5'-$Q_z$TGC-$N_xX_1X_2X_3X_4X_5X_6$-$M_y$-3, 5'-$Q_z$ugc-$N_xX_1X_2X_3X_4X_5X_6$-$M_y$-3, 5'-$Q_z$TIC-$N_xX_1X_2X_3X_4X_5X_6$-$M_y$-3, or 5'-$Q_z$TTC-$N_xX_1X_2X_3X_4X_5X_6$-$M_y$-3, wherein each of Q, N, $X_1$, $X_2$, $X_3$, $X_4$, and M is a nucleotide or nucleotide analog, x is an integer from 0 to 50, y is 0 or 1, z is 0, 1 or 2, $X_5$ is G or I, and $X_6$ is I or A, upper case letters denote DNA, lower case letters denote 2'-O-methyl RNA, and wherein the polynucleotide does not comprise a CG dinucleotide. In some embodiments, the polynucleotide does not comprise a modified CG dinucleotide. In some embodiments, a polynucleotide consisting of a nucleotide sequence of the formula: 5'-$Q_z$TGC-$N_xX_1X_2X_3X_4X_5X_6$-$M_y$-3, 5'-$Q_z$ugc-$N_xX_1X_2X_3X_4X_5X_6$-$M_y$-3, 5'-$Q_z$TIC-$N_xX_1X_2X_3X_4X_5X_6$-$M_y$-3, or 5'-$Q_z$TTC-$N_xX_1X_2X_3X_4X_5X_6$-$M_y$-3, wherein each of Q, N, $X_1$, $X_2$, $X_3$, $X_4$, and M is a nucleotide or nucleotide analog, x is an integer from 0 to 50, y is 0 or 1, z is 0, 1 or 2, $X_5$ is G or I, and $X_6$ is I or A, upper case letters denote DNA, lower case letters denote 2'-O-methyl RNA. In some embodiments, wherein the polynucleotide does not comprise a CG dinucleotide.

As described herein, x is an integer between 0 and 50. This means x is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In some embodiments, x is between 3 to 45, between 3 to 40, between 3 to 35, between 3 to 30, between 3 to 25, between 3 to 20, between 3 to 15, between 3 to 10, or between 3 to 5. In some embodiments, x is greater than 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, but no greater than 50. In some embodiments, x is less than 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11 10, 9, 8, 7, 6, 5, 4, 3, 2, but no less than 1. In some embodiments, x is 0.

As described herein, y is 0 or 1. In some embodiments, y is 0 (e.g., the $X_5X_6$ is a nucleotide sequence at the 3'-end of the polynucleotide). In some embodiments, y is 1.

As described herein, z is 0, 1, or 2. In some embodiments, z is 0 (e.g., the 5'-TIC-3' or 5'-TTC is a nucleotide sequence at the 5' end of the polynucleotide). In some embodiments, z is 1. In some embodiments, z is 2.

Exemplary TLR7/8 combination inhibitors, which have TLR7 and TLR8 but not TLR9 inhibitory motifs, are polynucleotides consisting of one of the following sequences:

```
5'-ugcTGCTCCTTGAGA-3';      (SEQ ID NO: 10)
5'-ugcTGCTCCTTGAGI-3';      (SEQ ID NO: 15)
5'-uGCTGCTCCTTGAGI-3';      (SEQ ID NO: 16)
5'-TGCTGCTCCTTGAGI-3';      (SEQ ID NO: 17)
5'-ugcugcTCCTTGAGI-3';      (SEQ ID NO: 18)
5'-ugcTGCTCCTTGAGIT-3';     (SEQ ID NO: 20)
5'-ugcTGCTCCTTGA-3';        (SEQ ID NO: 24)
5'-ugcTICTCCTTIAII-3';      (SEQ ID NO: 26)
5'-TGCTGCTGGTTGTGI-3';      (SEQ ID NO: 30)
5'-ugcugcuccuugagI-3';      (SEQ ID NO: 34)
5'-TGCTCCTTGAGI-3';         (SEQ ID NO: 35)
5'-TICTGCTCCTTGAGI-3';      (SEQ ID NO: 36)
5'-TTCTGCTCCTTGAGI-3';      (SEQ ID NO: 38)
5'-TGCTICTCCTTIAII-3';      (SEQ ID NO: 40)
5'-TICTICTCCTTIAII-3';      (SEQ ID NO: 44)
5'-TICTCCTTGAGI-3';         (SEQ ID NO: 48)
5'-TTCTCCTTGAGI-3';         (SEQ ID NO: 50)
5'-TICTCCTTIAIA-3';         (SEQ ID NO: 56)
5'-TICTCCTTAIIA-3';         (SEQ ID NO: 59)
5'-TICAGITTIAII-3';         (SEQ ID NO: 60)
5'-TICAGIAGIAII-3';         (SEQ ID NO: 61)
5'-TICTICTIITTIAII-3';      (SEQ ID NO: 62)
5'-TICTCCTTIAII-3';         (SEQ ID NO: 63)
5'-TICTCCTTICII-3';         (SEQ ID NO: 65)
5'-TICTCCTTITII-3';         (SEQ ID NO: 67)
5'-TICTICTCCTIITTICII-3';   (SEQ ID NO: 85)
5'-TICTICTCCAGITTICII-3';   (SEQ ID NO: 86)
5'-TICTICTCCTCCTTICII-3';   (SEQ ID NO: 87)
5'-TICTICTTGAGITTICII-3';   (SEQ ID NO: 88)
5'-TICTICTCCTCCTTICIIAII-3'; (SEQ ID NO: 90)
5'-TICTCCTCCTTICIIAII-3';   (SEQ ID NO: 91)
5'-TGCTCCTCCTTICIIAII-3';   (SEQ ID NO: 92)
5'-TGCTTGTCCTCCTTICII-3';   (SEQ ID NO: 93)
5'-TGCTGCTCCTTICII-3';      (SEQ ID NO: 94)
5'-TICTICTCCTTICII-3';      (SEQ ID NO: 95)
5'-TTCTTCTCCTTICII-3';      (SEQ ID NO: 97)
5'-TICTCCTCCTTICIIAIIA-3';  (SEQ ID NO: 99)
5'-TGCTCCTGGAGGTTICII-3';   (SEQ ID NO: 100)
5'-TGCTCCTGGAGGTTICIIAII-3'; (SEQ ID NO: 101)
5'-TGCTCCTGGATTICIIAII-3';  (SEQ ID NO: 102)
5'-TICTICTTGAGITTICIIAII-3'; (SEQ ID NO: 103)
5'-TICTTGAGITTICIIAII-3';   (SEQ ID NO: 104)
5'-TGCTICTTGAGITTICIIAII-3'; (SEQ ID NO: 105)
5'-TGCTTGAGITTICIIAII-3';   (SEQ ID NO: 106)
5'-TICTCCTTGAGIAII-3';      (SEQ ID NO: 108)
5'-TICTCCTCCTTGAGIAII-3';   (SEQ ID NO: 109)
5'-TICTTCTCCTTGAGIAII-3';   (SEQ ID NO: 110)
and
5'-TICTCCTCCTTGIIAII-3';    (SEQ ID NO: 111)
``` wherein I=2'-deoxyinosine, upper case letters denote DNA, and lower case letters denote 2'-O-methyl RNA. In some embodiments, the polynucleotide comprises SEQ ID NO:108. In some embodiments, the polynucleotide comprises SEQ ID NO:109.

TLR8/9 Combination Inhibitors

Also provided herein polynucleotides comprising a TLR8 inhibitory motif and a TLR9 inhibitory motif (hereinafter "TLR8/9 combination inhibitors") for use in any of the methods described herein (e.g., inhibiting or suppressing a TLR8-dependent and a TLR9-dependent immune response).

Provided herein are TLR8/9 combination inhibitors, wherein the TLR8/9 combination inhibitors are polynucleotides consisting of a nucleotide sequence of the formula: 5'-$N_x$-$S_1S_2S_3S_4$-$P_a$-$X_1X_2X_3X_4X_5X_6$-$M_y$-3, wherein each of N, P, $X_1$, $X_2$, $X_3$, $X_4$, and M is a nucleotide or nucleotide analog, a is an integer from 0 to 20, x is an integer from 0 to 50, y is 0 or 1, each of $S_1$, $S_2$, $S_3$, and $S_4$ are G or I, $X_5$ is G or I, and $X_6$ is I or A, and wherein the polynucleotide does not comprise a CG dinucleotide. Provided also herein are polynucleotides for use in inhibiting a TLR8-dependent and TL9-dependent immune response, wherein the polynucleotide consists of a nucleotide sequence of the formula: 5'-$N_x$-$S_1S_2S_3S_4$-Pa-$X_1X_2X_3X_4X_5X_6$-$M_y$-3, wherein each of N, P, $X_1$, $X_2$, $X_3$, $X_4$, and M is a nucleotide or nucleotide analog, a is an integer from 0 to 20, x is an integer from 0 to 50, y is 0 or 1, each of $S_1$, $S_2$, $S_3$, and $S_4$ are G or I, $X_5$ is G or I, and $X_6$ is I or A, and wherein the polynucleotide does not comprise a CG dinucleotide. In some embodiments, a polynucleotide consisting of a nucleotide sequence of the formula: 5'-$N_x$-$S_1S_2S_3S_4$-Pa-$X_1X_2X_3X_4X_5X_6$-$M_y$-3, wherein each of N, P, $X_1$, $X_2$, $X_3$, $X_4$, and M is a nucleotide or nucleotide analog, a is an integer from 0 to 20, x is an integer from 0 to 50, y is 0 or 1, each of $S_1$, $S_2$, $S_3$, and $S_4$ are G or I, $X_5$ is G or I, and $X_6$ is I or A. In some embodiments, wherein the polynucleotide does not comprise a CG dinucleotide.

As described herein, a is an integer between 0 and 20. This means that a is 0, 1, 2, 3, 4, 5, 6, 7, 8, 9, 10, 11, 12, 13, 14, 15, 16, 17, 18, 19 or 20. In some embodiments, a is greater than 0, 1, 2, 3, 4, 5, 6, 7, 8, 9, 10, 11, 12, 13, 14, 15, 16, 17, 18 or 19, but no greater than 20. In some embodiments, a is less than 21, 20, 19, 18, 17, 16, 15, 14, 13, 12, 11 10, 9, 8, 7, 6, 5, 4, 3, 2, but no less than 1. In some embodiments, a is 0.

As described herein, x is an integer between 0 and 50. This means x is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In some embodiments, x is between 3 to 45, between 3 to 40, between 3 to 35, between 3 to 30, between 3 to 25, between 3 to 20, between 3 to 15, between 3 to 10, or between 3 to 5. In some embodiments, x is greater than 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, but no greater than 50. In some embodiments, x is less than 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11 10, 9, 8, 7, 6, 5, 4, 3, 2, but no less than 1. In some embodiments, x is 0.

In some embodiments, y is 0 or 1. In some embodiments, y is 0 (e.g., the $X_5X_6$ is a nucleotide sequence at the 3'-end of the polynucleotide). In some embodiments, y is 1.

Exemplary TLR8/9 combination inhibitors, which have TLR8 and TLR9 but not TLR7 inhibitory motifs, are polynucleotides consisting of one of the following sequences:

```
5'-TAC TCC TTG GII-3';        (SEQ ID NO: 81)
and

5'-TCC TGG AGG GGT TIA II-3'; (SEQ ID NO: 112)
``` wherein I=2'-deoxyinosine and upper case letters denote DNA.

TLR7/8/9 Combination Inhibitors

Provided herein polynucleotides comprising a TLR7 inhibitory motif, a TLR8 inhibitory motif, and a TLR9 inhibitory motif (hereinafter "TRL7/8/9 combination inhibitors") for use in any of the methods described herein (e.g., inhibiting or suppressing a TLR7-dependent, a TLR8-dependent and a TLR9-dependent immune response).

Provided herein are TLR7/8/9 combination inhibitors, wherein the TLR7/8/9 combination inhibitors are polynucleotides consisting of a nucleotide sequence of the formula: 5'-$Q_z$TGC-$N_x$-$S_1S_2S_3S_4$-Pa-$X_1X_2X_3X_4X_5X_6$-$M_y$-3, 5'-$Q_z$ugc-$N_x$-$S_1S_2S_3S_4$-Pa-$X_1X_2X_3X_4X_5X_6$-$M_y$-3, 5'-$Q_z$TIC-$N_x$-$S_1S_2S_3S_4$-Pa-$X_1X_2X_3X_4X_5X_6$-$M_y$-3, or 5'-$Q_z$TTC-$N_x$-$S_1S_2S_3S_4$-Pa-$X_1X_2X_3X_4X_5X_6$-$M_y$-3, wherein each of Q, N, P, $X_1$, $X_2$, $X_3$, $X_4$, and M is a nucleotide or nucleotide analog, a is an integer from 0 to 20, x is an integer from 0 to 50, y is 0 or 1, z is 0, 1 or 2, each of $S_1$, $S_2$, $S_3$, and $S_4$ are G or I, $X_5$ is G or I, and $X_6$ is I or A, upper case letters denote DNA, lower case letters denote 2'-O-methyl RNA, and wherein the polynucleotide does not comprise a CG dinucleotide. Provided also herein are polynucleotides for use in inhibiting a TLR7-dependent, TLR8-dependent and TL9-dependent immune response, wherein the polynucleotide consists of a nucleotide sequence of the formula: 5'-$Q_z$TGC-$N_x$-$S_1S_2S_3S_4$-Pa-$X_1X_2X_3X_4X_5X_6$-$M_y$-3, 5'-$Q_z$ugc-$N_x$-$S_1S_2S_3S_4$-Pa-$X_1X_2X_3X_4X_5X_6$-$M_y$-3, 5'-$Q_z$TIC-$N_x$-$S_1S_2S_3S_4$-Pa-$X_1X_2X_3X_4X_5X_6$-$M_y$-3, or 5'-$Q_z$TTC-$N_x$-$S_1S_2S_3S_4$-Pa-$X_1X_2X_3X_4X_5X_6$-$M_y$-3, wherein each of Q, N, P, $X_1$, $X_2$, $X_3$, $X_4$, and M is a nucleotide or nucleotide analog, a is an integer from 0 to 20, x is an integer from 0 to 50, y is 0 or 1, z is 0, 1 or 2, each of $S_1$, $S_2$, $S_3$, and $S_4$ are G or I, $X_5$ is G or I, and $X_6$ is I or A, upper case letters denote DNA, lower case letters denote 2'-O-methyl RNA, and wherein the polynucleotide does not comprise a CG dinucleotide. In some embodiments, a polynucleotide consisting of a nucleotide sequence of the formula: 5'-$Q_z$TGC-$N_x$-$S_1S_2S_3S_4$-Pa-$X_1X_2X_3X_4X_5X_6$-$M_y$-3, 5'-$Q_z$ugc-$N_x$-$S_1S_2S_3S_4$-Pa-$X_1X_2X_3X_4X_5X_6$-$M_y$-3, 5'-$Q_z$TIC-$N_x$-$S_1S_2S_3S_4$-Pa-$X_1X_2X_3X_4X_5X_6$-$M_y$-3, or 5'-$Q_z$TTC-$N_x$-$S_1S_2S_3S_4$-Pa-$X_1X_2X_3X_4X_5X_6$-$M_y$-3, wherein each of Q, N, P, $X_1$, $X_2$, $X_3$, $X_4$, and M is a nucleotide or nucleotide analog, a is an integer from 0 to 20, x is an integer from 0 to 50, y is 0 or 1, z is 0, 1 or 2, each of $S_1$, $S_2$, $S_3$, and $S_4$ are G or I, $X_5$ is G or I, and $X_6$ is I or A, upper case letters denote DNA, lower case letters denote 2'-O-methyl RNA. In some embodiments, wherein the polynucleotide does not comprise a CG dinucleotide.

As described herein, a is an integer between 0 and 20. This means that a is 0, 1, 2, 3, 4, 5, 6, 7, 8, 9, 10, 11, 12, 13, 14, 15, 16, 17, 18, 19 or 20. In some embodiments, a is greater than 0, 1, 2, 3, 4, 5, 6, 7, 8, 9, 10, 11, 12, 13, 14, 15, 16, 17, 18 or 19, but no greater than 20. In some embodiments, a is less than 21, 20, 19, 18, 17, 16, 15, 14, 13, 12, 11 10, 9, 8, 7, 6, 5, 4, 3, 2, but no less than 1. In some embodiments, a is 0.

As described herein, x is an integer between 0 and 50. This means x is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In some embodiments, x is between 3 to 45, between 3 to 40, between 3 to 35, between 3 to 30, between 3 to 25, between 3 to 20, between 3 to 15, between 3 to 10, or between 3 to 5. In some embodiments, x is greater than 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, but no greater than 50. In some embodiments, x is less than 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11 10, 9, 8, 7, 6, 5, 4, 3, 2, but no less than 1. In some embodiments, x is 0.

In some embodiments, y is 0 or 1. In some embodiments, y is 0 (e.g., the $X_5X_6$ is a nucleotide sequence at the 3'-end of the polynucleotide). In some embodiments, y is 1.

In some embodiments, z is 0, 1, or 2. In some embodiments, z is 0 (e.g., the 5'-TGC-3', 5'-ugc-3', 5'-TIC-3', or 5'-TTC-3' is a nucleotide sequence at the 5' end of the polynucleotide). In some embodiments, z is 1. In some embodiments, z is 2.

Exemplary TLR7/8/9 combination inhibitors, which have TLR7, TLR8 and TLR9 inhibitory motifs, are polynucleotides consisting of one of the following sequences:

```
5'-ugc TGC TCC TTG GGI-3';       (SEQ ID NO: 14)

5'-TIC TCC TTI III-3';           (SEQ ID NO: 64)

5'-TIC TCC TTI GII-3';           (SEQ ID NO: 66)

5'-TGC TCC TGG AGG GGT TIA II-3'; (SEQ ID NO: 113)

5'-TIC TCC TCC TTG GGI AII-3';   (SEQ ID NO: 114)
and

5'-TIC TTC TCC TTG GGI AII-3';   (SEQ ID NO: 115)
``` wherein I=2'-deoxyinosine and upper case letters denote DNA.

Polynucleotide Modifications

The present disclosure further provides TLR inhibitors as described herein (e.g., immunoinhibitory polynucleotides comprising an inhibitory motif for one or more of TLR7, TLR8 and TLR9) comprising at least one modified nucleotide. The modification of at least one nucleotide may be a modified base, a modified sugar, and/or a modified phosphate. In some embodiments, the modification of at least one nucleotide may be a naturally-occurring modification. In some embodiments, the modification of at least one nucleotide may be a synthetic modification. In some embodiments, the modifications may be imparted before or after assembly of the polynucleotide. In some embodiments, the modified nucleotide comprises one or more modified nucleosides. "Modified nucleotide" or "modified nucleoside" as used herein encompass nucleoside or nucleotide "analogs." The term "nucleotide analog" refers to a compound that essentially retains the identity of the nucleotide from which it was derived. For instance, 7-dG is a G analog and N4-ethyl-dC is a C analog. As used herein, "modified nucleotide" or "modified nucleoside" also encompasses compounds that may not retain the identity of the nucleotide or base. That is the term modification encompasses a substitution of a nucleotide or base with a different naturally or non-naturally occurring nucleotide or base. For instance, the term modification encompasses substitution of an A for a G.

In some embodiments, one or more nucleotides of the polynucleotide comprises at least one modification (e.g., nucleotide comprises a modification). In some embodiments, one or more nucleotides of the polynucleotide comprise a modification (e.g., sequence Nx comprises a modification). In some embodiments, the at least one modification is the same modification for each nucleotide that is modified. In some embodiments, every nucleotide of the polynucleotide is modified and the modification is a 2'-O-methyl sugar modification (i.e., nucleotide N consists of a modification and the modification is a 2'-O-methyl sugar modification). In some embodiments, the at least one modification comprises more than one different type of modifications of nucleotides.

In some embodiments, the modification of at least one nucleotide comprises a modified base. Examples of base modifications include, but are not limited to, addition of an electron-withdrawing moiety to C-5 and/or C-6 of a cytosine of a polynucleotide. Preferably, the electron-withdrawing moiety is a halogen, e.g., 5-bromocytosine, 5-chlorocytosine, 5-fluorocytosine, 5-iodocytosine. In some embodiments, the base modifications include, but are not limited to, addition of an electron-withdrawing moiety to C-5 and/or C-6 of a uracil of the immunoinhibitory polynucleotide. Preferably, the electron-withdrawing moiety is a halogen. Such modified uracils can include, but are not limited to, 5-bromouracil, 5-chlorouracil, 5-fluorouracil, 5-iodouracil. In some embodiments, the base modifications include the addition of one or more thiol groups to the base including, but not limited to, 6-thio-guanine, 4-thio-thymine, and 4-thio-uracil. In some embodiments, the base modifications include, but are not limited to, N4-ethylcytosine, 7-deazaguanine, and 5-hydroxycytosine. See, for example, Kandimalla et al. (2001) *Bioorg. Med. Chem.* 9:807-813. In some embodiments, the IIS may include 2'-deoxyuridine and/or 2-amino-2'-deoxyadenosine. In some embodiments, the modified base comprises a methylation modification. In some embodiments, the methylation modification comprises a 5'-methyl-cytosine modification. In some embodiments, a TLR inhibitor comprises multiple base modifications. In some embodiments, the base modifications are the same. In some embodiments, the base modifications are different. In some embodiments, a TLR inhibitor comprises any of about 1, about 2, about 3, about 4, about 5 different base modifications. Base modifications may also be made and combined with any phosphate modification and/or sugar modification in the preparation of a modified TLR inhibitor.

In some embodiments, the modification of at least one nucleotide comprises a modified phosphate. In some embodiments, the modified phosphate is a phosphodiester linkage modification. For example, phosphate modifications may include, but are not limited to, methyl phosphonate, phosphorothioate, phosphoamidates, phosphoramidate (bridging or non-bridging), phosphotriester and phosphorodithioate and may be used in any combination. In some embodiments, the modified phosphate is a 3'-terminal internucleotide phosphodiester linkage modification. For example, the 3'-terminal internucleotide phosphodiester linkage modifications include, but are not limited to, an alkyl or aryl phosphotriester, an alkyl or aryl phosphonate, a hydrogen phosphonate, a phosphoramidate, and/or a phosphoroselenate linkage modification. In some embodiments, the 3'-terminal internucleotide phophodiester linkage modification is a phosphoramidate modification. In some embodiments, the modified phosphate includes, but is not limited to, embodiments wherein the phosphate is replaced by P(O)S ("thioate"), P(S)S ("dithioate"), (O)NR2 ('amidate'), P(O)R, P(R)OR', CO or CH2 ("formacetal"), in which each R or R' is independently H or substituted or unsubstituted alkyl (1-20 C), optionally containing an ether (—O—) linkage, aryl, alkenyl, cycloaklyl, cycloalkenyl, or araldyl.

In some embodiments, a TLR inhibitor may comprise at least one nucleotide comprising at least one phosphorothioate backbone linkage. In some embodiments, polynucleotides of the TLR inhibitor comprise only phosphorothioate backbones. In some embodiments, polynucleotides of the TLR inhibitor comprise one or more phosphorothioate backbones. In some embodiments, polynucleotides of the TLR inhibitor comprise only phosphodiester backbones. In some embodiments, an TLR inhibitor may comprise a combination of phosphate linkages in the phosphate backbone including, but not limited to, a combination of phosphodiester and phosphorothioate linkages.

The TLR inhibitor can contain phosphate-modified polynucleotides, some of which may stabilize the polynucleotide. Accordingly, some embodiments include a stabilized immunoinhibitory polynucleotides. In some embodiments, a TLR inhibitor comprises multiple phosphate modifications. In some embodiments, the phosphate modifications are the same. In some embodiments, the phosphate modifications are different. In some embodiments, the TLR inhibitor comprises any of about 1, about 2, about 3, about 4, about 5 different phosphate modifications. Phosphate modifications may also be made and combined with any base modification and/or sugar modification in the preparation of a modified TLR inhibitor.

In some embodiments, the modification of at least one nucleotide comprises a modified sugar. TLR inhibitors used in the present disclosure may comprise one or more modified sugars or sugar analogs. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. In the TLR inhibitor, the sugar moiety is preferably the furanoside of ribose, deoxyribose, arabinose or 2'-O-alkylribose. In some embodiments, the sugar can be attached to the respective heterocyclic bases either in α or β anomeric configuration. In some embodiments, the sugar is modified by replacing a hydroxyl group ordinarily present. The hydroxyl group ordinarily present in the sugar may be replaced by, for example, but not limited to, phosphonate groups or phosphate groups. The 5' and 3' terminal hydroxyl group can additionally be phosphorylated or substituted with amines or organic capping group moieties of from 1 to 20 carbon atoms. In some embodiments, the modified sugars are 2'-sugar modifications including, but are not limited to, 2'-alkoxy-RNA analogs, 2'-amino-RNA analogs, 2'-fluoro-DNA, and 2'-alkoxy- or amino-RNA/DNA chimeras. In some embodiments, the modified sugars include, but are not limited to, 2'-O-methyl-, 2'-O-allyl, or 2'-azido-sugar modification. In some embodiments, the 2'-modified sugar is 2'-O-methyl sugar modification. In some embodiments, the 2'-modified sugar is 2'-O-methoxyethyl sugar modification. For example, a sugar modification in the IIS includes, but is not limited to, 2'-O-methyl-uridine, 2'-O-methyl-thymidine, 2'-O-methyl-adenine, 2'-O-methyl-guanine, or 2'-O-methyl-cytidine. In some embodiments, the sugar-modified nucleotide comprises one or more sugar modified nucleosides. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example. In some embodiments, a TLR inhibitor comprises multiple sugar modifications. In some embodiments, the sugar modifications are the same. In some embodiments, the sugar modifications are different. In some embodiments, the TLR inhibitor comprises any of about 1, about 2, about 3, about 4, about 5 different sugar modifications. Sugar modifications may also be made and combined with any base modification and/or phosphate modification in the preparation of a modified TLR inhibitor.

Any of the modified polynucleotides described herein may comprise a modification anywhere in the polynucleotide sequence. In some embodiments, the modification is a modification of the nucleotides at or near the 5' end of the polynucleotide sequence. In some embodiments, at the 5' end of the polynucleotide sequence, about any of 1, 2, 3, 4, 5, 6, 7, 8, 9, or 10 nucleotides are modified. In some embodiments, at the 5' end of the polynucleotide sequence, at least about any of 1, 2, 3, 4, 5, 6, 7, 8, 9, or 10 nucleotides are modified. In some embodiments, the modification is a modification of the nucleotides at or near the 3' end of the polynucleotide sequence. In some embodiments, at the 3' end of the polynucleotide sequence, about any of 1, 2, 3, 4, 5, 6, 7, 8, 9, or 10 nucleotides are modified. In some embodiments, at the 3' end of the polynucleotide sequence, at least about any of 1, 2, 3, 4, 5, 6, 7, 8, 9, or 10 nucleotides are modified. In some embodiments, both the nucleotides at or near the 5' end of the polynucleotide sequence and the nucleotides at or near the 3' end of the polynucleotide sequence are modified. In some embodiments, at the 5' end of the polynucleotide sequence and at the 3' end of the polynucleotide sequence, about any of 1, 2, 3, 4, 5, 6, 7, 8, 9, or 10 nucleotides are modified. In some embodiments, at the 5' end of the polynucleotide sequence and at the 3' end of the polynucleotide sequence, at least about any of 1, 2, 3, 4, 5, 6, 7, 8, 9, or 10 nucleotides are modified.

Other examples of polynucleotides effective in suppressing TLR7 and/or TLR9 are found, for example, in PCT/US2005/030494, PCT/US2008/012220 and PCT/US2011/040788, the sequences of which are hereby incorporated by reference in their entirety.

In some embodiments of any of the TLR inhibitors, a uridine (U) nucleoside of the modified TLR inhibitor may be substituted with a thymidine (T) nucleoside. In some embodiments, all uridine (U) nucleoside of the TLR inhibitor may be substituted with a thymidine (T) nucleoside. In some embodiments of any of the TLR inhibitor, a thymidine (T) nucleoside of the modified TLR inhibitor may be substituted with a uridine (U) nucleoside. In some embodiments, all thymidine (T) nucleoside of the TLR inhibitor may be substituted with a uridine (U) nucleoside. In some embodiments, the modified TLR inhibitor may comprise both uridine (U) nucleosides and thymidine (T) nucleosides.

The present disclosure further provides TLR inhibitors as described herein which have immunoinhibitory activity and comprise an inhibitory motif for one or more of TLR7, TLR8 and TLR9 for use in the methods described herein. TLR inhibitors provided herein contain one or more nucleic acid moieties and one or more non-nucleic acid spacer moieties. Compounds conforming to a variety of structural formulas are contemplated for use as TLR inhibitors, including the core structures described in formulas I-VII, below. Formulas I-III show core sequences for "linear TLR inhibitors." Formulas IV-VI show core sequences for "branched TLR inhibitors." Formula VII shows a core structure for "single-spacer TLR inhibitors."

In each formula provided herein, "N" designates a nucleic acid moiety (oriented in either a 5'-3' or 3'-5' orientation) and "Sp" designates a non-nucleic acid spacer moiety. A dash ("-") designates a covalent bond between a nucleic acid moiety and a non-nucleic acid spacer moiety. A double dash ("--") designates covalent bonds between a non-nucleic acid spacer moiety and at least 2 nucleic acid moieties. A triple dash ("---") designates covalent bonds between a non-nucleic acid spacer moiety and multiple (i.e., at least 3) nucleic acid moieties. Subscripts are used to designate differently positioned nucleic acid or non-nucleic acid spacer moieties. However, the use of subscripts to distinguish different nucleic acid moieties is not intended to indicate that the moieties necessarily have a different structure or sequence. Similarly, the use of subscripts to distinguish different spacer moieties is not intended to indicate that the moieties necessarily have different structures. For example, in formula II, infra, the nucleic acid moieties designated $N_1$ and $N_2$ can have the same or different sequences, and the spacer moieties designated $S_1$ and $S_2$ can have the same or different structures. Further, it is contemplated that additional chemical moieties (e.g., phosphate, mononucleotide, additional nucleic acid moieties, alkyl, amino, thiol or disulfide groups or linking groups, and/or spacer moieties) may be covalently bound at the termini of the core structures.

Linear TLR inhibitors have structures in which the non-nucleic acid spacer moieties in the core structure are covalently bound to no more than two nucleic acid moieties.

Exemplary linear TLR inhibitors conform to the following formulas:

$$N_1\text{-}Sp_1\text{-}N_2 \qquad (I)$$

$$N_1\text{-}Sp_1\text{-}N_2\text{-}Sp_2\text{-}N_3 \qquad (II)$$

$$N_1\text{-}Sp_1\text{-}N_2\text{-}Sp_2\text{-}[N_v\text{-}Sp_v]_A \qquad (III)$$

where A is an integer between 1 and about 100 and $[N_v\text{-}Sp_v]$ indicates A additional iterations of nucleic acid moieties conjugated to non-nucleic acid spacer moieties. The subscript "v" indicates that N and Sp are independently selected in each iteration of "$[N_v\text{-}Sp_v]$." "A" is sometimes between 1 and about 10, sometimes between 1 and 3, sometimes exactly 1, 2, 3, 4 or 5. In some embodiments, A is an integer in a range defined by a lower limit of 1, 2, 3, 4, or 5, and an independently selected upper limit of 10, 20, 50 or 100 (e.g., between 3 and 10).

Exemplary linear TLR inhibitors include:

$$N_1\text{-HEG-}N_2\text{—OH} \qquad (Ia)$$

$$N_1\text{-HEG-}N_1\text{—PO}_4 \qquad (Ib)$$

$$N_1\text{-HEG-}N_2\text{-HEG} \qquad (Ic)$$

$$\text{HEG-}N_1\text{-HEG-}N_1\text{-HEG} \qquad (Id)$$

$$N_1\text{-HEG-}N_2\text{-HEG-}N_1 \qquad (Ie)$$

$$N_1\text{-HEG-}N_2\text{-(HEG)}_4\text{-}N_3 \qquad (If)$$

$$(N_1)_2\text{-glycerol-}N_1\text{-HEG-}N_1 \qquad (Ig)$$

$$\text{PO}_4\text{—}N_1\text{-HEG-}N_2 \qquad (Ih)$$

$$N_1\text{-(HEG)}_{15}\text{-T} \qquad (Ii)$$

$$N_1\text{-HEG-T-HEG-T} \qquad (Ik)$$

$$N_1\text{-HEG-}N_2\text{-TEG-}N_3 \qquad (IIa)$$

where HEG refers to hexa-(ethylene glycol). TEG refers to tetra-(ethylene glycol). $N_1$ and $N_2$; and $Sp_1$ and $Sp_2$ are independently selected in examples which do not contain —$[N_v\text{-}Sp_v]_4$. In some embodiments of any of the TLR inhibitors, the TLR inhibitor is a 2'-deoxyribo polynucleotide sequence. In some embodiments of any of the TLR inhibitors, the TLR inhibitor is a 2'deoxyribo polynucleotide and/or the 2'-O-Me sugar polynucleotide chimeric sequence. In some embodiments, the TLR inhibitor has at least one nucleotide comprising a modified phosphate linkage. In some embodiments, TLR inhibitor comprises only phosphorothioate linkages. In some embodiments one or more nucleotides of the polynucleotide comprises a modification. In some embodiments, the modification comprises at least one phosphorothioate backbone modification. In some embodiments, the polynucleotide comprises only phosphorothioate linkages. In some preferred embodiments, the modification comprises a 2'-sugar modification. In a subset of these embodiments, the 2'-sugar modification comprises a 2'-O-methyl sugar modification or a 2'-O-methoxyethyl sugar modification. Branched TLR inhibitors comprise a multivalent spacer moiety ($mS_p$) covalently bound to at least three (3) nucleic acid moieties.

Exemplary branched TLR inhibitors are described according to the following formulas:

$$[N_v]_A\text{---mS}_p \qquad (IV)$$

$$[Sp_v\text{-}N_v]_A\text{---mS}_p \qquad (V)$$

$$(Sp_1\text{-}N_1)\text{-mS}_p\text{--}(N_v\text{-}Sp_v)_A \qquad (VI)$$

where $mS_p$ is a multivalent spacer covalently bonded to the quantity "A" independently selected nucleic acid moieties $N_v$, $Sp_v\text{-}N_v$ (which comprises a spacer moiety covalently bound to a nucleic acid moiety). The terminal iteration of "$[Sp_v\text{-}N_v]$" or "$[N_v\text{-}Sp_v]$" may include only $N_v$. For formulas IV and V, A is at least 3. In various embodiments of formulas IV and V, A is an integer between 3 and 100 (inclusive), although A may be an integer in a range defined by a lower limit of about 3, 5, 10, 50, or 100 and an independently selected upper limit of about 5, 7, 10, 50, 100, 150, 200, 250, or 500, or alternately A may be greater than 500. For formula VI, A is at least 2, an integer in a range defined by a lower limit of 2, 5, 10, 50, or 100 and an independently selected upper limit of 5, 10, 50, 100, 150, 200, 250, or 500, or greater than 500.

Exemplary branched TLR inhibitors include:

$$(N_1)_2\text{-glycerol-}N_1 \qquad (IVa)$$

$$(N_2\text{-HEG})_2\text{-glycerol-}N_1 \qquad (IVb)$$

$$(N_1\text{-HEG-}N_2)_2\text{-glycerol-}N_1 \qquad (IVc)$$

$$[(N_1)_2\text{-glycerol-}N_1]_2\text{-glycerol-}N_1 \qquad (IVd)$$

$$(N_1\text{-HEG})_2\text{-glycerol-HEG-}N_2 \qquad (IVe)$$

$$(N_1\text{-HEG})_2\text{-glycerol-}N_1\text{-TEG-}N_1 \qquad (VIa)$$

wherein HEG refers to hexa-(ethylene glycol). TEG refers to tetra-(ethylene glycol). In some embodiments of any of the TLR inhibitors, the TLR inhibitor is a 2'-deoxyribo polynucleotide sequence. In some embodiments of any of the TLR inhibitors, the TLR inhibitor is a 2'deoxyribo polynucleotide and/or the 2'-O-Me sugar polynucleotide chimeric sequence. In some embodiments, the TLR inhibitor has at least one nucleotide comprising a modified phosphate linkage. In some embodiments, TLR inhibitor comprises only phosphorothioate linkages. Preferred branched TLR inhibitors include (5'-$N_1$-3'-HEG)$_2$-glycerol-HEG-5'-$N_1$-3' and (5'-$N_1$-3'-HEG)$_2$-glycerol-HEG-5'-$N_1$'.

Single spacer TLR inhibitors comprise a structure in which there is a single nucleic acid moiety covalently conjugated to a single spacer moiety, i.e., $$N_1\text{-}Sp_1 \qquad (VII)$$

In a preferred variation $S_1$ has the structure of a multimer comprising smaller units (e.g., HEG, TEG, glycerol, 1'2'-dideoxyribose, C2 alkyl-C12 alkyl subunits, and the like), typically connected by an ester linkage (e.g., phosphodiester or phosphorothioate ester), e.g., as described infra. See, e.g., formula VIIa, infra. The multimer can be heteromeric or homomeric. In one variation, the spacer is a heteromer of monomeric units (e.g., HEG, TEG, glycerol, 1'2'-dideoxyribose, C2 alkyl to C12 alkyl linkers, and the like) linked by an ester linkage (e.g., phosphodiester or phosphorothioate ester). See, e.g., formula VIIb, infra.

Exemplary single spacer TLR inhibitors include:

$N_1\text{-(HEG)}_{15}$  (VIIa)

$N_1\text{-HEG-propyl-HEG-propyl-HEG}$  (VIIb)

wherein HEG refers to hexa-(ethylene glycol). In some embodiments of any of the TLR inhibitors, the TLR inhibitor is a 2'-deoxyribo polynucleotide sequence. In some embodiments of any of the TLR inhibitors, the TLR inhibitor is a 2'deoxyribo polynucleotide and/or the 2'-O-Me sugar polynucleotide chimeric sequence. In some embodiments, the TLR inhibitor has at least one nucleotide comprising a modified phosphate linkage. In some embodiments, TLR inhibitor comprises only phosphorothioate linkages.

In certain embodiments, the terminal structures of the TLR inhibitor are covalently joined (e.g., nucleic acid moiety-to-nucleic acid moiety; spacer moiety-to-spacer moiety, or nucleic acid moiety-to-spacer moiety), resulting in a circular conformation.

TLR inhibitors for use in the immunoinhibitory compositions provided herein include at least one nucleic acid moiety. The term "nucleic acid moiety," as used herein, refers to a nucleotide monomer (i.e., a mononucleotide) or polymer (i.e., comprising at least 2 contiguous nucleotides). As used herein, a nucleotide comprises (1) a purine or pyrimidine base linked to a sugar that is in an ester linkage to a phosphate group, or (2) an analog in which the base and/or sugar and/or phosphate ester are replaced by analogs, e.g., as described infra. In a TLR inhibitor comprising more than one nucleic acid moiety, the nucleic acid moieties may be the same or different.

Nucleic acid moieties used in TLR inhibitors incorporated in the immunoinhibitory compositions may comprise any of the inhibitory motifs disclosed herein and may additionally be sequences of six base pairs or less. It is contemplated that in a TLR inhibitor comprising multiple nucleic acid moieties, the nucleic acid moieties can be the same or different lengths. In some embodiments where the TLR inhibitor comprises more than one nucleic acid moiety, only one of the moieties need comprise the inhibitory motif. It is contemplated that in a TLR inhibitor comprising multiple nucleic acid moieties, the nucleic acid moieties can be the same or different. Accordingly, in various embodiments, TLR inhibitors incorporated into the immunoinhibitory compositions comprise (a) nucleic acid moieties with the same sequence, (b) more than one iteration of a nucleic acid moiety, or (c) two or more different nucleic acid moieties. Additionally, a single nucleic acid moiety may comprise more than one inhibitory motif, which may be adjacent, overlapping, or separated by additional nucleotide bases within the nucleic acid moiety.

The TLR inhibitors comprise one or more non-nucleic acid spacer moieties covalently bound to the nucleic acid moieties. For convenience, non-nucleic acid spacer moieties are sometimes referred to herein simply as "spacers" or "spacer moieties." Spacers are generally of molecular weight about 50 to about 50,000, typically from about 75 to about 5000, most often from about 75 to about 500, which are covalently bound, in various embodiments, to one, two, three, or more than three nucleic acid moieties. A variety of agents are suitable for connecting nucleic acid moieties. For example, a variety of compounds referred to in the scientific literature as "non-nucleic acid linkers," "non-nucleotidic linkers," or "valency platform molecules" may be used as spacers in an IRC. In certain embodiments, a spacer comprises multiple covalently connected subunits and may have a homopolymeric or heteropolymeric structure. It will be appreciated that mononucleotides and polynucleotides are not included in the definition of non-nucleic acid spacers, without which exclusion there would be no difference between nucleic acid moiety and an adjacent non-nucleic acid spacer moiety.

In certain embodiments, a spacer may comprise one or more abasic nucleotides (i.e., lacking a nucleotide base, but having the sugar and phosphate portions). Exemplary abasic nucleotides include 1'2'-dideoxyribose, 1'-deoxyribose, 1'-deoxyarabinose and polymers thereof.

Other suitable spacers comprise optionally substituted alkyl, optionally substituted polyglycol, optionally substituted polyamine, optionally substituted polyalcohol, optionally substituted polyamide, optionally substituted polyether, optionally substituted polyimine, optionally substituted polyphosphodiester (such as poly(1-phospho-3-propanol), and the like. Optional substituents include alcohol, alkoxy (such as methoxy, ethoxy, and propoxy), straight or branched chain alkyl (such as C1-C12 alkyl), amine, aminoalkyl (such as amino C1-C12 alkyl), phosphoramidite, phosphate, thiophosphate, hydrazide, hydrazine, halogen, (such as F, Cl, Br, or I), amide, alkylamide (such as amide C1-C12 alkyl), carboxylic acid, carboxylic ester, carboxylic anhydride, carboxylic acid halide, sulfonyl halide, imidate ester, isocyanate, isothiocyanate, haloformate, carbodiimide adduct, aldehydes, ketone, sulfhydryl, haloacetyl, alkyl halide, alkyl sulfonate, NR1R2 wherein R1R2 is —C(═O) CH═CHC(═O) (maleimide), thioether, cyano, sugar (such as mannose, galactose, and glucose), α,β-unsaturated carbonyl, alkyl mercurial, α,β-unsaturated sulfone.

Suitable spacers may comprise polycyclic molecules, such as those containing phenyl or cyclohexyl rings. The spacer may be a polyether such as polyphosphopropanediol, polyethyleneglycol, polypropylene glycol, a bifunctional polycyclic molecule such as a bifunctional pentalene, indene, naphthalene, azulene, heptalene, biphenylene, asymindacene, sym-indacene, acenaphthylene, fluorene, phenalene, phenanthrene, anthracene, fluoranthene, acephenathrylene, aceanthrylene, triphenylene, pyrene, chrysene, naphthacene, thianthrene, isobenzofuran, chromene, xanthene, phenoxathiin, which may be substituted or modified, or a combination of the polyethers and the polycyclic molecules. The polycyclic molecule may be substituted or polysubstituted with C1-C5 alkyl, C6 alkyl, alkenyl, hydroxyalkyl, halogen or haloalkyl group. Nitrogen-containing polyheterocyclic molecules (e.g., indolizine) are typically not suitable spacers. The spacer may also be a polyalcohol, such as glycerol or pentaerythritol. In one variation, the spacer comprises 1-phosphopropane)$_3$-phosphate or 1-phosphopropane)$_4$-phosphate (also called tetraphosphopropanediol and pentaphosphopropanediol). In one variation, the spacer comprises derivatized 2,2'-ethylenedioxydiethylamine (EDDA).

Specific examples of non-nucleic acid spacers useful in TLR inhibitors include "linkers" described by Cload et al. (1991) *J. Am. Chem. Soc.* 113:6324; Richardson et al. (1991) *J. Am. Chem. Soc.* 113:5109; Ma et al. (1993) *Nucleic Acids Res.* 21:2585; Ma et al. (1993) *Biochemistry* 32:1751; McCurdy et al. (1991) *Nucleosides & Nucleotides* 10:287;

Jaschke et al. (1993) *Tetrahedron Lett.* 34:301; Ono et al. (1991) *Biochemistry* 30:9914; and International Publication No. WO 89/02439.

Other suitable spacers include linkers described by Salunkhe et al. (1992) *J. Am. Chem. Soc.* 114:8768; Nelson et al. (1996) *Biochemistry* 35:5339-5344; Bartley et al. (1997) *Biochemistry* 36:14502-511; Dagneaux et al. (1996) *Nucleic Acids Res.* 24:4506-12; Durand et al. (1990) *Nucleic Acids Res.* 18:6353-59; Reynolds et al. (1996) *Nucleic Acids Res.* 24:760-65; Hendry et al. (1994) *Biochem. Biophys. Acta* 1219:405-12; Altmann et al. (1995) *Nucleic Acids Res.* 23:4827-35. Still other suitable spacers are described in European Pat. No. EP0313219B1 and U.S. Pat. No. 6,117,657.

Exemplary non-nucleic acid spacers comprise oligo-ethylene glycol (e.g., triethylene glycol, tetraethylene glycol, hexaethylene glycol spacers, and other polymers comprising up to about 10, about 20, about 40, about 50, about 100 or about 200 ethylene glycol units), alkyl spacers (e.g., propyl, butyl, hexyl, and other C2-C12 alkyl spacers, e.g., usually C2-C10 alkyl, most often C2-C6 alkyl), abasic nucleotide spacers, symmetric or asymmetric spacers derived from glycerol, pentaerythritol or 1,3,5-trihydroxycyclohexane (e.g., symmetrical doubler and trebler spacer moieties described herein). Spacers can also comprise heteromeric or homomeric oligomers and polymers of the aforementioned compounds (e.g., linked by an amide, ester, ether, thioether, disulfide, phosphodiester, phosphorothioate, phosphoramidate, phosphotriester, phosphorodithioate, methyl phosphonate or other linkage).

Suitable spacer moieties can contribute charge and/or hydrophobicity to the TLR inhibitors, contribute favorable pharmacokinetic properties (e.g., improved stability, longer residence time in blood) to the TLR inhibitor, and/or result in targeting of the TLR inhibitor to particular cells or organs. Spacer moieties can be selected or modified to tailor the TLR inhibitor for desired pharmacokinetic properties or suitability for desired modes of administration (e.g., oral administration). It will be appreciated by the reader that, for convenience, a spacer (or spacer component) is sometimes referred to by the chemical name of the compound from which the spacer component is derived (e.g., hexaethylene glycol), with the understanding that the TLR inhibitor actually comprises the conjugate of the compound and adjacent nucleic acid moieties or other spacer moiety components.

In a TLR inhibitor comprising more than one spacer moiety, the spacers may be the same or different. Thus, in one variation all of the non-nucleic acid spacer moieties in a TLR inhibitor have the same structure. In one variation, a TLR inhibitor comprises non-nucleic acid spacer moieties with at least 2, at least 3, at least 4, at least 5, or at least 6 or more different structures.

In some contemplated embodiments, the spacer moiety of a TLR inhibitor is defined to exclude certain structures. Thus, in some embodiments, a spacer is other than an abasic nucleotide or polymer of abasic nucleotides. In some embodiments, a spacer is other than a oligo(ethyleneglycol) (e.g., HEG, TEG and the like) or poly(ethyleneglycol). In some embodiments a spacer is other than a C3 alkyl spacer. In some embodiments, a spacer is other than a polypeptide. Thus, in some embodiments, an immunogenic molecule, e.g., a protein or polypeptide, is not suitable as a component of spacer moieties. However, as discussed infra, it is contemplated that in certain embodiments, a TLR inhibitor is a "proteinaceous TLR inhibitor" (i.e., comprising a spacer moiety comprising a polypeptide). However, in some embodiments, the spacer moiety is not proteinaceous and/or is not an antigen (i.e., the spacer moiety, if isolated from the TLR inhibitor, is not an antigen).

Generally, suitable spacer moieties do not render the TLR inhibitor of which they are a component insoluble in an aqueous solution (e.g., PBS, pH 7.0). Thus, the definition of spacers excludes microcarriers or nanocarriers. In addition, a spacer moiety that has low solubility, such as a dodecyl spacer (solubility <5 mg/ml when measured as dialcohol precursor 1,12-dihydroxydodecane) is not preferred because it can reduce the hydrophilicity and activity of the IRC. Preferably, spacer moieties have solubility much greater than 5 mg/ml (e.g., ≥20 mg/ml, ≥50 mg/ml or ≥100 mg/ml) when measured as dialcohol precursors.

The charge of a TLR inhibitor may be contributed by phosphate, thiophosphate, or other groups in the nucleic acid moieties as well as groups in non-nucleic acid spacer moieties. In some embodiments, a non-nucleic acid spacer moiety carries a net charge (e.g., a net positive charge or net negative charge when measured at pH 7). In one useful variation, the TLR inhibitor has a net negative charge. In some embodiments, the negative charge of a spacer moiety in a TLR inhibitor is increased by derivatizing a spacer subunit described herein to increase its charge. For example, glycerol can be covalently bound to two nucleic acid moieties and the remaining alcohol can be reacted with an activated phosphoramidite, followed by oxidation or sulfurization to form a phosphate or thiophosphate, respectively. In certain embodiments the negative charge contributed by the non-nucleic acid spacer moieties in a TLR inhibitor (i.e., the sum of the charges when there is more than one spacer) is greater than the negative charge contributed by the nucleic acid moieties of the TLR inhibitor. Charge can be calculated based on molecular formula, or determined experimentally, e.g., by capillary electrophoresis (Li, ed., 1992, *Capillary electrophoresis, Principles, Practice and Application* Elsevier Science Publishers, Amsterdam, The Netherlands, pp202-206).

As is noted supra, suitable spacers can be polymers of smaller non-nucleic acid (e.g., non-nucleotide) compounds, such as those described herein, that are themselves useful as spacers, including compounds commonly referred to as non-nucleotide "linkers." Such polymers (i.e., "multiunit spacers") may be heteromeric or homomeric, and often comprise monomeric units (e.g., HEG, TEG, glycerol, 1'2'-dideoxyribose, and the like) linked by an ester linkage (e.g., phosphodiester or phosphorothioate ester). Thus, in one variation the spacer comprises a polymeric (e.g., heteropolymeric) structure of non-nucleotide units (e.g., from 2 to about 100 units, alternatively 2 to about 50, e.g., 2 to about 5, alternatively e.g., about 5 to about 50, e.g., about 5 to about 20).

In certain embodiments, a spacer moiety is a multivalent non-nucleic acid spacer moiety (i.e., a "multivalent spacer"). As used in this context, a TLR inhibitor containing a multivalent spacer contains a spacer covalently bound to three (3) or more nucleic acid moieties. Multivalent spacers are sometimes referred to in the art as "platform molecules." Multivalent spacers can be polymeric or nonpolymeric. Examples of suitable molecules include glycerol or substituted glycerol (e.g., 2-hydroxymethyl glycerol, levulinylglycerol); tetraaminobenzene, heptaaminobetacyclodextrin, 1,3,5-trihydroxycyclohexane, pentaerythritol and derivatives of pentaerythritol, tetraaminopentaerythritol, 1,4,8,11-tetraazacyclo tetradecane (Cyclam), 1,4,7,10-tetraazacyclododecane (Cyclen), polyethyleneimine, 1,3-diamino-2-propanol and substituted derivatives, propyloxymethyl]ethyl compounds (e.g., "trebler"), polyethylene glycol derivatives such as so-called "Star PEGs" and "bPEG" (see, e.g., Gnanou et al. (1988) *Makromol. Chem.* 189:2885; Rein et al. (1993) *Acta Polymer* 44:225; U.S. Pat. No. 5,171,264), and dendrimers.

Dendrimers are known in the art and are chemically defined globular molecules, generally prepared by stepwise or reiterative reaction of multifunctional monomers to obtain a branched structure (see, e.g., Tomalia et al. (1990) *Angew. Chem. Int. Ed. Engl.* 29:138-75). A variety of dendrimers are known, e.g., amine-terminated polyamidoamine, polyethyleneimine and polypropyleneimine dendrimers. Exemplary dendrimers useful include "dense star" polymers or "starburst" polymers such as those described in U.S. Pat. Nos. 4,587,329; 5,338,532; and 6,177,414, including so-called "poly(amidoamine) ("PAMAM") dendrimers." Still other multimeric spacer molecules suitable for use include chemically-defined, non-polymeric valency platform molecules such as those disclosed in U.S. Pat. No. 5,552,391; and PCT application publications WO 00/75105, WO 96/40197, WO 97/46251, WO 95/07073, and WO 00/34231. Many other suitable multivalent spacers can be used and will be known to those of skill in the art.

Conjugation of a nucleic acid moiety to a platform molecule can be effected in any number of ways, typically involving one or more crosslinking agents and functional groups on the nucleic acid moiety and platform molecule. Linking groups are added to platforms using standard synthetic chemistry techniques. Linking groups can be added to nucleic acid moieties using standard synthetic techniques.

Multivalent spacers with a variety of valencies are useful, and in various embodiments the multivalent spacer of a TLR inhibitor is bound to between about 3 and about 400 nucleic acid moieties, often from 3 to 100, sometimes from 3-50, frequently from 3-10, and sometimes more than 400 nucleic acid moieties. In various embodiments, the multivalent spacer is conjugated to more than 10, more than 25, more than 50, or more than 500 nucleic acid moieties (which may be the same or different). It will be appreciated that, in certain embodiments in which a TLR inhibitor comprises a multivalent spacer, provided herein is a population of TLR inhibitors with slightly different molecular structures. For example, when a TLR inhibitor is prepared using a dendrimer as a high valency the multivalent spacer, a somewhat heterogeneous mixture of molecules is produced, i.e., comprising different numbers (within or predominantly within a determinable range) of nucleic acid moieties joined to each dendrimer molecule.

Polysaccharides derivatized to allow linking to nucleic acid moieties can be used as spacers in TLR inhibitors. Suitable polysaccharides include naturally occurring polysaccharides (e.g., dextran) and synthetic polysaccharides (e.g., FICOLL®). For instance, aminoethylcarboxymethyl-FICOLL® (AECM-FICOLL®) can be prepared by the method of Inman (1975) *J. Imm.* 114:704-709. AECM-FICOLL® can then be reacted with a heterobifunctional crosslinking reagent, such as 6-maleimido caproic acyl N-hydroxysuccinimide ester, and then conjugated to a thiol-derivatized nucleic acid moiety (see Lee et al. (1980) *Mol. Imm.* 17:749-56). Other polysaccharides may be modified similarly.

It will be well within the ability of one of skill, guided by this specification and knowledge in the art, to prepare TLR inhibitors using routine methods. Techniques for making nucleic acid moieties (e.g., oligonucleotides and modified oligonucleotides) are known. Nucleic acid moieties can be synthesized using techniques including, but not limited to, enzymatic methods and chemical methods and combinations of enzymatic and chemical approaches. For example, DNA or RNA containing phosphodiester linkages can be chemically synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Useful solid supports for DNA synthesis include Controlled Pore Glass (Applied Biosystems, Foster City, Calif.), polystyrene bead matrix (Primer Support, Amersham Pharmacia, Piscataway, N.J.) and TentGel (Rapp Polymere GmbH, Tubingen, Germany). Once the desired oligonucleotide sequence has been synthesized, the oligonucleotide is removed from the support, the phosphate triester groups are deprotected to phosphate diesters and the nucleoside bases are deprotected using aqueous ammonia or other bases.

For instance, DNA or RNA or DNA/RNA hybrid polynucleotides (nucleic acid moieties) containing phosphodiester linkages are generally synthesized by repetitive iterations of the following steps: a) removal of the protecting group from the 5'-hydroxyl group of the 3'-solid support-bound nucleoside or nucleic acid, b) coupling of the activated nucleoside phosphoramidite to the 5'-hydroxyl group, c) oxidation of the phosphite triester to the phosphate triester, and d) capping of unreacted 5'-hydroxyl groups. DNA or RNA containing phosphorothioate linkages is prepared as described above, except that the oxidation step is replaced with a sulfurization step. Once the desired oligonucleotide sequence has been synthesized, the oligonucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in PROTOCOLS FOR OLIGONUCLEOTIDES AND ANALOGS, SYNTHESIS AND PROPERTIES (Agrawal, ed.) Humana Press, Totowa, N.J.; Warner et al. (1984) DNA 3:401; Tang et al. (2000) *Org. Process Res. Dev.* 4:194-198; Wyrzykiewica et al. (1994) Bioorg. & Med. Chem. Lett. 4:1519-1522; Radhakrishna et al. (1989) *J. Org. Chem.* 55:4693-4699. and U.S. Pat. No. 4,458,066. Programmable machines that automatically synthesize nucleic acid moieties of specified sequences are widely available. Examples include the Expedite 8909 automated DNA synthesizer (Perseptive Biosystem, Framington Mass.); the ABI 394 (Applied Biosystems, Inc., Foster City, Calif.); and the OligoPilot II (Amersham Pharmacia Biotech, Piscataway, N.J.).

Polynucleotides can be assembled in the 3' to 5' direction, e.g., using base-protected nucleosides (monomers) containing an acid-labile 5'-protecting group and a 3'-phosphoramidite. Examples of such monomers include 5'-O-(4,4'-dimethoxytrityl)-protected nucleoside-3'-O-(N,N-diisopropylamino) 2-cyanoethyl phosphoramidite, where examples of the protected nucleosides include, but are not limited to, N6-benzoyladenosine, N4-benzoylcytidine, N2-isobutryrylguanosine, thymidine, and uridine. In this case, the solid support used contains a 3'-linked protected nucleoside. Alternatively, polynucleotides can be assembled in the 5' to 3' direction using base-protected nucleosides containing an acid-labile 3'-protecting group and a 5'-phosphoramidite. Examples of such monomers include 3'-O-(4,4'-dimethoxytrityl)-protected nucleoside-5'-O-(N,N-diisopropylamino) 2-cyanoethyl phosphoramidite, where examples of the protected nucleosides include, but are not limited to, N6-benzoyladenosine, N4-benzoylcytidine, N2-isobutryrylguanosine, thymidine, and uridine (Glen Research, Sterling, Va.). In this case, the solid support used contains a 5'-linked protected nucleoside. Circular nucleic acid components can be isolated, synthesized through recombinant methods, or chemically synthesized. Chemical synthesis can be performed using any method described in the literature. See, for instance, Gao et al. (1995) *Nucleic Acids Res.* 23:2025-2029 and Wang et al. (1994) *Nucleic Acids Res.* 22:2326-2333.

Addition of non-nucleic acid spacer moieties can be accomplished using routine methods. Methods for addition of particular spacer moieties are known in the art and, for example, are described in the references cited supra. See, e.g., Durand et al. (1990) *Nucleic Acids Res.* 18:6353-6359. The covalent linkage between a spacer moiety and nucleic acid moiety can be any of a number of types, including phosphodiester, phosphorothioate, amide, ester, ether, thioether, disulfide, phosphoramidate, phosphotriester, phosphorodithioate, methyl phosphonate and other linkages. It will often be convenient to combine a spacer moiety(s) and a nucleic acid moiety(s) using the same phosphoramidite-type chemistry used for synthesis of the nucleic acid moiety. For example, IRCs described herein can be conveniently synthesized using an automated DNA synthesizer (e.g., Expedite 8909; Perspective Biosystems, Framington, Mass.) using phosphoramidite chemistry (see, e.g., Beaucage, 1993, supra; *Current Protocols in Nucleic Acid Chemistry*, supra). However, one of skill will understand that the same (or equivalent) synthesis steps carried out by an automated DNA synthesizer can also be carried out manually, if desired. In such a synthesis, typically, one end of the spacer (or spacer subunit for multimeric spacers) is protected with a 4,4'-dimethyoxytrityl group, while the other end contains a phosphoramidite group.

A variety of spacers with the requisite protecting and reacting groups are commercially available, for example:

group protecting groups) can be purchased or can be synthesized using routine methods for use in preparing IRCs disclosed herein. The instrument is programmed according to the manufacturer's instructions to add nucleotide monomers and spacers in the desired order.

Although use of phosphoramidite chemistry is convenient for the preparation of certain TLR inhibitors, it will be appreciated that the TLR inhibitors described herein are not limited to compounds prepared by any particular method of synthesis or preparation.

In one variation, TLR inhibitors with multivalent spacers conjugated to more than one type of nucleic acid moiety are prepared. For instance, platforms containing two maleimide groups (which can react with thiol-containing polynucleotides), and two activated ester groups (which can react with amino-containing nucleic acids) have been described (see, e.g., PCT application publication WO 95/07073). These two activated groups can be reacted independently of each other. This would result in a TLR inhibitor containing a total of 4 nucleic acid moieties, two of each sequence.

TLR inhibitors with multivalent spacers containing two different nucleic acid sequences can also be prepared using the symmetrical branched spacer, described above, and conventional phosphoramidite chemistry (e.g., using manual or automated methods). The symmetrical branched spacer contains a phosphoramidite group and two protecting groups that are the same and are removed simultaneously. In one approach, for example, a first nucleic acid is synthesized and coupled to the symmetrical branched spacer, the protecting groups are removed from the spacer. Then two additional nucleic acids (of the same sequence) are synthesized on the spacer (using double the amount of reagents used for synthesis of a single nucleic acid moiety in each step).

| | |
|---|---|
| triethylene glycol spacer or "TEG spacer" | 9-O-(4,4'-dimethoxytrityl)triethyleneglycol-1-O-[(2-cyanoethyl) N,N-diisopropylphosphoramidite] (Glen Research, Sterling, VA) |
| hexaethylene glycol spacer or "HEG spacer" | 18-O-(4,4'-dimethoxytrityl)hexaethyleneglycol-1-O-[(2-cyanoethyl) N,N-diisopropylphosphoramidite] (Glen Research, Sterling, VA) |
| propyl spacer | 3-(4,4'-dimethoxytrityloxy)propyloxy-1-O-[(2-cyanoethyl) N,N-diisopropylphosphoramidite] (Glen Research, Sterling, VA); |
| butyl spacer | 4-(4,4'-dimethoxytrityloxy)butyloxy-1-O-[(2-cyanoethyl) N,N-diisopropylphosphoramidite] (Chem Genes Corp., Ashland, MA) |
| Hexyl spacer | 6-(4,4'-dimethoxytrityloxy)hexyloxy-1-O-[(2-cyanoethyl) N,N-diisopropylphosphoramidite] |
| 2-(hydroxymethyl)ethyl spacer or "HME spacer" | 1-(4,4'-dimethoxytrityloxy)-3-(levulinyloxy)-propyloxy-2-O-[(2-cyanoethyl) N,N-diisopropylphosphoramidite]; also called "asymmetrical branched" spacer |
| "abasic nucleotide spacer" or "abasic spacer" | 5-O-(4,4'-dimethoxytrityl)-1,2-dideoxyribose-3-O-[(2-cyanoethyl) N,N-diisopropylphosphoramidite] (Glen Research, Sterling, VA) |
| "symmetrical branched spacer" or "glycerol spacer" | 1,3-O,O-bis(4,4'-dimethoxytrityl)glycerol-2-O-[(2-cyanoethyl) N,N-diisopropylphosphoramidite] (Chem Genes Corp., Ashland, MA) |
| "trebler spacer" | 2,2,2-O,O,O-tris[3-O-(4,4'-dimethoxytrityloxy)propyloxymethyl]ethyl-1-O-[(2-cyanoethyl) N,N-diisopropylphosphoramidite] (Glen Research, Sterling, VA) |
| "symmetrical doubler spacer" | 1,3-O,O-bis[5-O-(4,4'-dimethoxytrityloxy)pentylamido]propyl-2-O-[(2-cyanoethyl) N,N-diisopropylphosphoramidite] (Glen Research, Sterling, VA) |
| "dodecyl spacer" | 12-(4,4'-dimethoxytrityloxy)dodecyloxy-1-O-[(2-cyanoethyl) N,N-diisopropylphosphoramidite] (Glen Research, Sterling, VA) |

These and a large variety of other protected spacer moiety precursors (e.g., comprising DMT and phosphoramidite A similar method can be used to connect three different nucleic acid moieties (referred to below as Nucleic acids I, II, and III) to a multivalent platform (e.g., asymmetrical branched spacer). This is most conveniently carried out using an automated DNA synthesizer. In one variation, the asymmetrical branched spacer contains a phosphoramidite group and two orthogonal protecting groups that can be removed independently. First, nucleic acid I is synthesized, then the asymmetrical branched spacer is coupled to nucleic acid I, then nucleic acid II is added after the selective removal of one of the protecting groups. Nucleic acid II is deprotected, and capped, and then the other protecting group on the spacer is removed. Finally, nucleic acid III is synthesized.

In some embodiments, a nucleic acid moiety(s) is synthesized, and a reactive linking group (e.g., amino, carboxylate, thiol, disulfide, and the like) is added using standard synthetic chemistry techniques. The reactive linking group (which is considered to form a portion of the resulting spacer moiety) is conjugated to additional non-nucleic acid compounds to form the spacer moiety. Linking groups are added to nucleic acids using standard methods for nucleic acid synthesis, employing a variety of reagents described in the literature or commercially available. Examples include reagents that contain a protected amino group, carboxylate group, thiol group, or disulfide group and a phosphoramidite group. Once these compounds are incorporated into the nucleic acids, via the activated phosphoramidite group, and are deprotected, they provide nucleic acids with amino, carboxylate, or thiol reactivity.

Hydrophilic linkers of variable lengths are useful, for example to link nucleic acids moieties and platform molecules. A variety of suitable linkers are known. Suitable linkers include, without limitation, linear oligomers or polymers of ethylene glycol. Such linkers include linkers with the formula $R^1S(CH_2CH_2O)_nCH_2CH_2O(CH_2)_mCO_2R^2$ wherein n=0-200, m=1 or 2, $R^1$=H or a protecting group such as trityl, $R^2$=H or alkyl or aryl, e.g., 4-nitrophenyl ester. These linkers are useful in connecting a molecule containing a thiol reactive group such as haloaceyl, maleiamide, etc., via a thioether to a second molecule which contains an amino group via an amide bond. The order of attachment can vary, i.e., the thioether bond can be formed before or after the amide bond is formed. Other useful linkers include Sulfo-SMCC (sulfosuccinimidyl 4-[N-maleimidomethyl]-cyclohexane-1-carboxylate) Pierce Chemical Co. product 22322; Sulfo-EMCS (N-[epsilon-maleimidocaproyloxyl sulfosuccinimide ester) Pierce Chemical Co. product 22307; Sulfo-GMBS (N-[gamma-maleimidobutyryloxy]sulfosuccinimide ester) Pierce Chemical Co. product 22324 (Pierce Chemical Co., Rockford, Ill.), and similar compounds of the general formula maleimido-R—C(O) NHS ester, where R=alkyl, cyclic alkyl, polymers of ethylene glycol, and the like.

Particularly useful methods for covalently joining nucleic acid moieties to multivalent spacers are described in the references cited supra.

In certain embodiments, a polypeptide is used as a multivalent spacer moiety to which a plurality of nucleic acid moieties are covalently conjugated, directly or via linkers, to form a "proteinaceous TLR inhibitor." The polypeptide can be a carrier (e.g., albumin). Typically, a proteinaceous carrier comprises at least one, and usually several or many nucleic acid moieties that (a) are between 2 and 7, more often between 4 and 7 nucleotides in length, alternatively between 2 and 6, 2 and 5, 4 and 6, or 4 and 5 nucleotides in length and/or (b) have inferior isolated immunomodulatory activity as compared to a longer polynucleotide (e.g., at least 8 nucleotides in length) comprising a TLR inhibitory motif.

Methods of making a proteinaceous TLR inhibitor will be apparent to one of skill upon review of the present disclosure. A nucleic acid, for example, can be covalently conjugated to a polypeptide spacer moiety by art known methods including linkages between a 3' or 5' end of a nucleic acid moiety (or at a suitably modified base at an internal position in the a nucleic acid moiety) and a polypeptide with a suitable reactive group (e.g., an N-hydroxysuccinimide ester, which can be reacted directly with the $N^4$ amino group of cytosine residues). As a further example, a polypeptide can be attached to a free 5'-end of a nucleic acid moiety through an amine, thiol, or carboxyl group that has been incorporated into nucleic acid moiety. Alternatively, the polypeptide can be conjugated to a spacer moiety, as described herein. Further, a linking group comprising a protected amine, thiol, or carboxyl at one end, and a phosphoramidite can be covalently attached to a hydroxyl group of a polynucleotide, and, subsequent to deprotection, the functionality can be used to covalently attach the TLR inhibitor to a peptide.

Isolation and Synthesis of Polynucleotides

Provided herein are also methods of making the polynucleotides comprising an inhibitory motif for one or more of TLR7, TLR8 and TLR9 as described herein. In some embodiments, the polynucleotides comprise modified TLR inhibitory motif sequences. In some embodiments, the polynucleotides comprise unmodified TLR inhibitory motif sequences. The methods may be any of those described herein. For example, the method could be synthesizing the TLR inhibitors (for example, using solid state synthesis) and may further comprise any purification step(s). Methods of purification are known in the art.

Also provided are methods for isolating and synthesizing immunoinhibitory polynucleotides comprising an inhibitory motif for one or more of TLR7, TLR8 and TLR9 (TLR inhibitor). In some embodiments, the TLR inhibitor is a modified TLR inhibitor. In some embodiments, the TLR inhibitor is an unmodified TLR inhibitor.

The techniques for making polynucleotides and modified polynucleotides are known in the art. Naturally occurring DNA or RNA, containing phosphodiester linkages, is generally synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Once the desired polynucleotide sequence has been synthesized, the polynucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in Protocols for Oligonucleotides and Analogs, Synthesis and Properties (Agrawal, ed.) Humana Press, Totowa, N.J.; Warner et al. (1984) *DNA* 3:401 and U.S. Pat. No. 4,458,066.

Synthesis of polynucleotides containing modified phosphate linkages or non-phosphate linkages is also known in the art. For a review, see Matteucci (1997) "Oligonucleotide Analogs: an Overview" in Oligonucleotides as Therapeutic Agents, (D. J. Chadwick and G. Cardew, ed.) John Wiley and Sons, New York, N.Y. The phosphorous derivative (or modified phosphate group) which can be attached to the sugar or sugar analog moiety in the polynucleotides can be a monophosphate, diphosphate, triphosphate, alkylphosphonate, phosphorothioate, phosphorodithioate, phosphoramidate or the like. The preparation of the above-noted phosphate analogs, and their incorporation into nucleotides, modified nucleotides and oligonucleotides, per se, is also known and need not be described here in detail. Peyrottes et al. (1996) *Nucleic Acids Res.* 24:1841-1848; Chaturvedi et al. (1996) *Nucleic Acids Res.* 24:2318-2323; and Schultz et al. (1996) *Nucleic Acids Res.* 24:2966-2973. For example, synthesis of phosphorothioate oligonucleotides is similar to that described above for naturally occurring oligonucleotides except that the oxidation step is replaced by a sulfurization step (Zon (1993) "Oligonucleoside Phosphorothioates" in Protocols for Oligonucleotides and Analogs, Synthesis and Properties (Agrawal, ed.) Humana Press, pp. 165-190). Similarly the synthesis of other phosphate analogs, such as phosphotriester (Miller et al. (1971) *JACS* 93:6657-6665), non-bridging phosphoramidates (Jager et al. (1988) *Biochem.* 27:7247-7246), N3' to P5' phosphoramidiates (Nelson et al. (1997) *JOC* 62:7278-7287) and phosphorodithioates (U.S. Pat. No. 5,453,496) has also been described. Other non-phosphorous based modified oligonucleotides can also be used (Stirchak et al. (1989) *Nucleic Acids Res.* 17:6129-6141).

Those skilled in the art will recognize that a large number of "synthetic" non-natural nucleosides comprising various heterocyclic bases and various sugar moieties (and sugar analogs) are available in the art, and that as long as other criteria of the present disclosure are satisfied, the TLR inhibitor can include one or several heterocyclic bases other than the principal five base components of naturally-occurring nucleic acids. Preferably, however, the heterocyclic base in the TLR inhibitor includes, but is not limited to, uracil-5-yl, cytosin-5-yl, adenin-7-yl, adenin-8-yl, guanin-7-yl, guanin-8-yl, 4-aminopyrrolo[2.3-d]pyrimidin-5-yl, 2-amino-4-oxopyrolo[2,3-d]pyrimidin-5-yl, 2-amino-4-oxopyrolo[2.3-d]pyrimidin-3-yl groups, where the purines are attached to the sugar moiety of the TLR inhibitor via the 9-position, the pyrimidines via the 1-position, the pyrrolopyrimidines via the 7-position and the pyrazolopyrimidines via the 1-position.

The preparation of base-modified nucleosides, and the synthesis of modified oligonucleotides using the base-modified nucleosides as precursors, has been described, for example, in U.S. Pat. Nos. 4,910,300, 4,948,882, and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide. Nucleosides modified in their sugar moiety have also been described (including, but not limited to, e.g., U.S. Pat. Nos. 4,849,513, 5,015,733, 5,118,800, 5,118,802) and can be used similarly.

TLR Inhibitor Complexes

TLR inhibitors can be directly administered to the individual or they can be administered in a composition or complex to enhance TLR inhibitor delivery to cells and/or uptake by cells. Compositions or complexes can also be used to enhance co-delivery of two of more different TLR inhibitors to a cell. In some embodiments, a mixture of TLR inhibitors may be complexed so as to deliver at least one TLR inhibitor.

Such delivery compositions or complexes include, but are not limited to, encapsulating complexes and colloidal dispersion systems as described herein and known in the art. Examples of such delivery compositions include oil-in-water emulsions, micelles, and liposomes. Delivery compositions or complexes also include TLR inhibitors linked to a linker molecules, a platform molecule, a nanoparticle or a microparticle, as described herein. Such linkages include both covalent and non-covalent linkages.

In some embodiments, the TLR inhibitor is conjugated with a linker molecule in a variety of ways, including covalent and/or non-covalent interactions.

The link between the portions can be made at the 3' or 5' end of the TLR inhibitor, or at a suitably modified base at an internal position in the TLR inhibitor. If the linker is a peptide and contains a suitable reactive group (e.g., an N-hydroxysuccinimide ester) it can be reacted directly with the $N^4$ amino group of cytosine residues. Depending on the number and location of cytosine residues in the TLR inhibitor, specific coupling at one or more residues can be achieved.

Alternatively, modified oligonucleosides, such as are known in the art, can be incorporated at either terminus, or at internal positions in the TLR inhibitor. These can contain blocked functional groups which, when deblocked, are reactive with a variety of functional groups which can be present on, or attached to, the linker of interest.

Where the linker is a peptide, this portion of the conjugate can be attached to the 3'-end of the TLR inhibitor through solid support chemistry. For example, the TLR inhibitor portion can be added to a peptide portion that has been pre-synthesized on a support. Haralambidis et al. (1990a) *Nucleic Acids Res.* 18:493-499; and Haralambidis et al. (1990b) *Nucleic Acids Res.* 18:501-505. Alternatively, the TLR inhibitor can be synthesized such that it is connected to a solid support through a cleavable linker extending from the 3'-end. Upon chemical cleavage of the TLR inhibitor from the support, a terminal thiol group is left at the 3'-end of the oligonucleotide (Zuckermann et al. (1987) *Nucleic Acids Res.* 15:5305-5321; and Corey et al. (1987) *Science* 238: 1401-1403) or a terminal amino group is left at the 3'-end of the oligonucleotide (Nelson et al. (1989) *Nucleic Acids Res.* 17:1781-1794). Conjugation of the amino-modified TLR inhibitor to amino groups of the peptide can be performed as described in Benoit et al. (1987) *Neuromethods* 6:43-72. Conjugation of the thiol-modified TLR inhibitor to carboxyl groups of the peptide can be performed as described in Sinah et al. (1991) *Oligonucleotide Analogues: A Practical Approach*, IRL Press. Coupling of an oligonucleotide carrying an appended maleimide to the thiol side chain of a cysteine residue of a peptide has also been described. Tung et al. (1991) *Bioconjug. Chem.* 2:464-465.

The peptide linker portion of the conjugate can be attached to the 5'-end of the TLR inhibitor through an amine, thiol, or carboxyl group that has been incorporated into the oligonucleotide during its synthesis. Preferably, while the oligonucleotide is fixed to the solid support, a linking group comprising a protected amine, thiol, or carboxyl at one end, and a phosphoramidite at the other, is covalently attached to the 5'-hydroxyl. Agrawal et al. (1986) *Nucleic Acids Res.* 14:6227-6245; Connolly (1985) *Nucleic Acids Res.* 13:4485-4502; Kremsky et al. (1987) *Nucleic Acids Res.* 15:2891-2909; Connolly (1987) *Nucleic Acids Res.* 15:3131-3139; Bischoff et al. (1987) *Anal. Biochem.* 164: 336-344; Blanks et al. (1988) *Nucleic Acids Res.* 16:10283-10299; and U.S. Pat. Nos. 4,849,513, 5,015,733, 5,118,800, and 5,118,802. Subsequent to deprotection, the amine, thiol, and carboxyl functionalities can be used to covalently attach the oligonucleotide to a peptide. Benoit et al. (1987); and Sinah et al. (1991).

A TLR inhibitor conjugate can also be formed through non-covalent interactions, such as ionic bonds, hydrophobic interactions, hydrogen bonds and/or van der Waals attractions.

Non-covalently linked conjugates can include a non-covalent interaction such as a biotin-streptavidin complex. A biotinyl group can be attached, for example, to a modified base of a TLR inhibitor. Roget et al. (1989) *Nucleic Acids Res.* 17:7643-7651. Incorporation of a streptavidin moiety into the peptide portion allows formation of a non-covalently bound complex of the streptavidin conjugated peptide and the biotinylated oligonucleotide.

Non-covalent associations can also occur through ionic interactions involving a TLR inhibitor through the use of a linker portion comprising charged residues that can interact with an oligonucleotide. For example, non-covalent conjugation can occur between a generally negatively-charged TLR inhibitor and positively-charged amino acid residues of a peptide linker, e.g., polylysine, polyarginine and polyhistidine residues.

The linkage of the TLR inhibitor to a lipid can be formed using standard methods. These methods include, but are not limited to, the synthesis of oligonucleotide-phospholipid conjugates (Yanagawa et al. (1988) *Nucleic Acids Symp. Ser.* 19:189-192), oligonucleotide-fatty acid conjugates (Grabarek et al. (1990) *Anal. Biochem.* 185:131-135; and Staros et al. (1986) *Anal. Biochem.* 156:220-222), and oligonucleotide-sterol conjugates. Boujrad et al. (1993) *Proc. Natl. Acad. Sci. USA* 90:5728-5731.

The linkage of the oligonucleotide to an oligosaccharide can be formed using standard known methods. These methods include, but are not limited to, the synthesis of oligonucleotide-oligosaccharide conjugates, wherein the oligosaccharide is a moiety of an immunoglobulin. O'Shannessy et al. (1985) *J. Applied Biochem.* 7:347-355.

The linkage of a circular TLR inhibitor to a peptide linker can be formed in several ways. Where the circular TLR inhibitor is synthesized using recombinant or chemical methods, a modified nucleoside is suitable. Ruth (1991) in *Oligonucleotides and Analogues: A Practical Approach*, IRL Press. Standard linking technology can then be used to connect the circular TLR inhibitor to the peptide. Goodchild (1990) *Bioconjug. Chem.* 1:165. Where the circular TLR inhibitor is isolated, or synthesized using recombinant or chemical methods, the linkage can be formed by chemically activating, or photoactivating, a reactive group (e.g. carbene, radical) that has been incorporated into the peptide.

Additional methods for the attachment of peptides and other molecules to oligonucleotides can be found in U.S. Pat. No. 5,391,723; Kessler (1992) "Nonradioactive labeling methods for nucleic acids" in Kricka (ed.) *Nonisotopic DNA Probe Techniques*, Academic Press; and Geoghegan et al. (1992) *Bioconjug. Chem.* 3:138-146.

A TLR inhibitor may be proximately associated in other ways. In some embodiments, a TLR inhibitor is proximately associated by encapsulation. In other embodiments, a TLR inhibitor is proximately associated by linkage to a platform molecule. A "platform molecule" (also termed "platform") is a molecule containing sites which allow for attachment of the TLR inhibitor. In other embodiments, a TLR inhibitor is proximately associated by adsorption onto a surface, preferably a carrier particle.

In some embodiments, the methods described herein employ an encapsulating agent in association with the TLR inhibitor. Preferably, the composition comprising TLR inhibitor and encapsulating agent is in the form of adjuvant oil-in-water emulsions, microparticles and/or liposomes. More preferably, adjuvant oil-in-water emulsions, microparticles and/or liposomes encapsulating an TLR inhibitor are in the form of particles from about 0.04 µm to about 100 µm in size, preferably any of the following ranges: from about 0.1 µm to about 20 µm; from about 0.15 µm to about 10 µm; from about 0.05 µm to about 1.00 µm; from about 0.05 µm to about 0.5 µm.

Colloidal dispersion systems, such as microspheres, beads, macromolecular complexes, nanocapsules and lipid-based system, such as oil-in-water emulsions, micelles, mixed micelles and liposomes can provide effective encapsulation of TLR inhibitors-containing compositions.

The encapsulation composition further comprises any of a wide variety of components. These include, but are not limited to, alum, lipids, phospholipids, polyethylene glycol (PEG) and other polymers, such as polypeptides, glycopeptides, and polysaccharides.

Polypeptides suitable for encapsulation components include any known in the art and include, but are not limited to, fatty acid binding proteins. Modified polypeptides contain any of a variety of modifications, including, but not limited to glycosylation, phosphorylation, myristylation, sulfation and hydroxylation. As used herein, a suitable polypeptide is one that will protect a TLR inhibitor-containing composition to preserve the immunoinhibitory activity thereof. Examples of binding proteins include, but are not limited to, albumins such as bovine serum albumin (BSA) and pea albumin.

Other suitable polymers can be any known in the art of pharmaceuticals and include, but are not limited to, naturally-occurring polymers such as dextrans, hydroxyethyl starch, and polysaccharides, and synthetic polymers. Examples of naturally occurring polymers include proteins, glycopeptides, polysaccharides, dextran and lipids. The additional polymer can be a synthetic polymer. Examples of synthetic polymers which are suitable for use include, but are not limited to, polyalkyl glycols (PAG) such as PEG, polyoxyethylated polyols (POP), such as polyoxyethylated glycerol (POG), polytrimethylene glycol (PTG) polypropylene glycol (PPG), polyhydroxyethyl methacrylate, polyvinyl alcohol (PVA), polyacrylic acid, polyethyloxazoline, polyacrylamide, polyvinylpyrrolidone (PVP), polyamino acids, polyurethane and polyphosphazene. The synthetic polymers can also be linear or branched, substituted or unsubstituted, homopolymeric, co-polymers, or block co-polymers of two or more different synthetic monomers.

The PEGs for use in encapsulation compositions are either purchased from chemical suppliers or synthesized using techniques known to those of skill in the art.

An optional colloidal dispersion system is a liposome. As used herein, a "liposome" or "lipid vesicle" is a small vesicle bounded by at least one and possibly more than one bilayer lipid membrane. Liposomes are made artificially from phospholipids, glycolipids, lipids, steroids such as cholesterol, related molecules, or a combination thereof by any technique known in the art, including but not limited to sonication, extrusion, or removal of detergent from lipid-detergent complexes. A liposome can also optionally comprise additional components, such as a tissue targeting component. It is understood that a "lipid membrane" or "lipid bilayer" need not consist exclusively of lipids, but can additionally contain any suitable other components, including, but not limited to, cholesterol and other steroids, lipid-soluble chemicals, proteins of any length, and other amphipathic molecules, providing the general structure of the membrane is a sheet of two hydrophilic surfaces sandwiching a hydrophobic core. For a general discussion of membrane structure, see *The Encyclopedia of Molecular Biology* by J. Kendrew (1994). For suitable lipids see e.g., Lasic (1993) "Liposomes: from Physics to Applications" Elsevier, Amsterdam.

Processes for preparing liposomes containing TLR inhibitor compositions are known in the art. The lipid vesicles can be prepared by any suitable technique known in the art. Methods include, but are not limited to, microencapsulation, microfluidization, LLC method, ethanol injection, freon injection, the "bubble" method, detergent dialysis, hydration, sonication, and reverse-phase evaporation. Reviewed in Watwe et al. (1995) Curr. Sci. 68:715-724. Techniques may be combined in order to provide vesicles with the most desirable attributes.

Provided herein are uses of lipid bilayers such as liposomes containing tissue or cellular targeting components. Such targeting components enhance accumulation at certain tissue or cellular sites in preference to other tissue or cellular sites when administered to an intact animal, organ, or cell culture. A targeting component is generally accessible from outside the liposome, and is therefore preferably either bound to the outer surface or inserted into the outer lipid bilayer. A targeting component can be inter alia a peptide, a region of a larger peptide, an antibody specific for a cell surface molecule or marker, or antigen binding fragment thereof, a nucleic acid, a carbohydrate, a region of a complex carbohydrate, a special lipid, or a small molecule such as a drug, hormone, or hapten, attached to any of the aforementioned molecules. Antibodies with specificity toward cell type-specific cell surface markers are known in the art and are readily prepared by methods known in the art.

The liposomes can be targeted to any cell type toward which a therapeutic treatment is to be directed, e.g., a cell type which can regulate and/or participate in an immune response. Such target cells and organs include, but are not limited to, APCs, such as macrophages, dendritic cells and lymphocytes, lymphatic structures, such as lymph nodes and the spleen, and nonlymphatic structures, particularly those in which dendritic cells are found.

The liposome compositions provided herein can additionally comprise surfactants. Surfactants can be cationic, anionic, amphiphilic, or nonionic. A preferred class of surfactants are nonionic surfactants; particularly preferred are those that are water soluble.

In some embodiments in which an TLR inhibitor are proximately associated by linkage to a platform molecule, the platform may be proteinaceous or non-proteinaceous (i.e., organic). Examples of proteinaceous platforms include, but are not limited to, albumin, gammaglobulin, immunoglobulin (IgG) and ovalbumin. Borel et al. (1990) *Immunol. Methods* 126:159-168; Dumas et al. (1995) *Arch. Dematol. Res.* 287:123-128; Borel et al. (1995) *Int. Arch. Allergy Immunol.* 107:264-267; Borel et al. (1996) *Ann. N.Y. Acad. Sci.* 778:80-87. A platform is multi-valent (i.e., contains more than one binding, or linking, site) to accommodate binding to more than 1 TLR inhibitor. Accordingly, a platform may contain 2 or more, 3 or more, 4 or more, 5 or more, 6 or more, 7 or more, 8 or more, 9 or more, 10 or more binding or linking sites. Other examples of polymeric platforms are dextran, polyacrylamide, FICOLL®, carboxymethylcellulose, polyvinyl alcohol, and poly D-glutamic acid/D-lysine.

In some embodiments, the platform is a polymer platform. In some embodiments, the polymer is dextran, polyacrylamide, FICOLL®, carboxymethylcellulose, polyvinyl alcohol, or poly D-glutamic acid/D-lysine. In some embodiments, the polymeric platform is FICOLL®. In some embodiments, the polymeric platform is FICOLL® 400. In some embodiments, the polymeric platform is FICOLL® 70. In some embodiments, the polymeric platform is FICOLL® PM 70 (Poly(sucrose-co-epichlorhydrin)). In some embodiments, the polymeric platform is FICOLL® PM 400. In some embodiments, any of between about 1 to about 200, about 1 to about 150, about 1 to about 125, about 1 to about 100, about 1 to about 75, about 1 to about 50, or about 1 to about 25 TLR inhibitors are linked to the polymeric platform.

The principles of using platform molecules are well understood in the art. Generally, a platform contains, or is derivatized to contain, appropriate binding sites for TLR inhibitors. In addition, or alternatively, TLR inhibitor is derivatized to provide appropriate linkage groups. For example, a simple platform is a bi-functional linker (i.e., has two binding sites), such as a peptide. Further examples are discussed below.

Platform molecules may be biologically stabilized, i.e., they exhibit an in vivo excretion half-life often of hours to days to months to confer therapeutic efficacy, and are preferably composed of a synthetic single chain of defined composition. They generally have a molecular weight in the range of about 200 to about 1,000,000, preferably any of the following ranges: from about 200 to about 500,000; from about 200 to about 200,000; from about 200 to about 50,000 (or less, such as 30,000). Examples of valency platform molecules are polymers (or are comprised of polymers) such as polyethylene glycol (PEG; preferably having a molecular weight of about 200 to about 8000), poly-D-lysine, polyvinyl alcohol, polyvinylpyrrolidone, D-glutamic acid and D-lysine (in a ratio of 3:2). Other molecules that may be used are albumin and IgG.

Other platform molecules suitable for use are the chemically-defined, non-polymeric valency platform molecules disclosed in U.S. Pat. No. 5,552,391. Other homogeneous chemically-defined valency platform molecules suitable for use are derivatized 2,2'-ethylenedioxydiethylamine (EDDA) and triethylene glycol (TEG).

Additional suitable valency platform molecules include, but are not limited to, tetraaminobenzene, heptaaminobeta-cyclodextrin, tetraaminopentaerythritol, 1,4,8,11-tetraazacyclotetradecane (Cyclam) and 1,4,7,10-tetraazacyclododecane (Cyclen).

In general, these platforms are made by standard chemical synthesis techniques. PEG must be derivatized and made multivalent, which is accomplished using standard techniques. Some substances suitable for conjugate synthesis, such as PEG, albumin, and IgG are available commercially.

Conjugation of a TLR inhibitor to a platform molecule may be effected in any number of ways, typically involving one or more crosslinking agents and functional groups on the TLR inhibitor and platform molecule. Platforms and TLR inhibitor must have appropriate linking groups. Linking groups are added to platforms using standard synthetic chemistry techniques. Linking groups may be added to polypeptide platforms and TLR inhibitor using either standard solid phase synthetic techniques or recombinant techniques. Recombinant approaches may require post-translational modification in order to attach a linker, and such methods are known in the art.

As an example, polypeptides contain amino acid side chain moieties containing functional groups such as amino, carboxyl or sulfhydryl groups that serve as sites for coupling the polypeptide to the platform. Residues that have such functional groups may be added to the polypeptide if the polypeptide does not already contain these groups. Such residues may be incorporated by solid phase synthesis techniques or recombinant techniques, both of which are well known in the peptide synthesis arts. When the polypeptide has a carbohydrate side chain(s) (or if the platform is a carbohydrate), functional amino, sulfhydryl and/or aldehyde groups may be incorporated therein by conventional chemistry. For instance, primary amino groups may be incorporated by reaction of the oxidized sugar with ethylenediamine in the presence of sodium cyanoborohydride, sulfhydryls may be introduced by reaction of cysteamine dihydrochloride followed by reduction with a standard disulfide reducing agent, while aldehyde groups may be generated following periodate oxidation. In a similar fashion, the platform molecule may also be derivatized to contain functional groups if it does not already possess appropriate functional groups.

Hydrophilic linkers of variable lengths are useful for connecting TLR inhibitors to platform molecules. Suitable linkers include linear oligomers or polymers of ethylene glycol. Such linkers include linkers with the formula $R^1S(CH_2CH_2O)_nCH_2CH_2O(CH_2)_mCO_2R^2$ wherein n=0-200, m=1 or 2, $R^1$=H or a protecting group such as trityl, $R^2$=H or alkyl or aryl, e.g., 4-nitrophenyl ester. These linkers are useful in connecting a molecule containing a thiol reactive group such as haloaceyl, maleiamide, etc., via a thioether to a second molecule which contains an amino group via an amide bond. These linkers are flexible with regard to the order of attachment, i.e., the thioether can be formed first or last.

In embodiments in which TLR inhibitors are proximately associated by adsorption onto a surface, the surface may be in the form of a carrier particle (for example, a nanoparticle) made with either an inorganic or organic core. Examples of such nanoparticles include, but are not limited to, nanocrystalline particles, nanoparticles made by the polymerization of alkylcyanoacrylates and nanoparticles made by the polymerization of methylidene malonate. Additional surfaces to which an TLR inhibitor may be adsorbed include, but are not limited to, activated carbon particles and protein-ceramic nanoplates. Other examples of carrier particles are provided herein.

Adsorption of polynucleotides and polypeptides to a surface for the purpose of delivery of the adsorbed molecules to cells is well known in the art. See, for example, Douglas et al. (1987) *Crit. Rev. Ther. Drug. Carrier Syst.* 3:233-261; Hagiwara et al. (1987) *In Vivo* 1:241-252; Bousquet et al. (1999) *Pharm. Res.* 16:141-147; and Kossovsky et al., U.S. Pat. No. 5,460,831. Preferably, the material comprising the adsorbent surface is biodegradable. Adsorption of a TLR inhibitor to a surface may occur through non-covalent interactions, including ionic and/or hydrophobic interactions.

In general, characteristics of carriers such as nanoparticles, such as surface charge, particle size and molecular weight, depend upon polymerization conditions, monomer concentration and the presence of stabilizers during the polymerization process (Douglas et al., 1987). The surface of carrier particles may be modified, for example, with a surface coating, to allow or enhance adsorption of the TLR inhibitor. Carrier particles with adsorbed TLR inhibitor may be further coated with other substances. The addition of such other substances may, for example, prolong the half-life of the particles once administered to the subject and/or may target the particles to a specific cell type or tissue, as described herein.

Nanocrystalline surfaces to which a TLR inhibitor may be adsorbed have been described (see, for example, U.S. Pat. No. 5,460,831). Nanocrystalline core particles (with diameters of 1 μm or less) are coated with a surface energy modifying layer that promotes adsorption of polypeptides, polynucleotides and/or other pharmaceutical agents.

Another adsorbent surface are nanoparticles made by the polymerization of alkylcyanoacrylates. Alkylcyanoacrylates can be polymerized in acidified aqueous media by a process of anionic polymerization. Depending on the polymerization conditions, the small particles tend to have sizes in the range of 20 to 3000 nm, and it is possible to make nanoparticles specific surface characteristics and with specific surface charges (Douglas et al., 1987). For example, oligonucleotides may be adsorbed to polyisobutyl- and polyisohexlcyanoacrylate nanoparticles in the presence of hydrophobic cations such as tetraphenylphosphonium chloride or quaternary ammonium salts, such as cetyltrimethyl ammonium bromide. Oligonucleotide adsorption on these nanoparticles appears to be mediated by the formation of ion pairs between negatively charged phosphate groups of the nucleic acid chain and the hydrophobic cations. See, for example, Lambert et al. (1998) *Biochimie* 80:969-976, Chavany et al. (1994) *Pharm. Res.* 11:1370-1378; Chavany et al. (1992) *Pharm. Res.* 9:441-449. Another adsorbent surface are nanoparticles made by the polymerization of methylidene malonate.

TLR inhibitors may be administered in the form of microcarrier (MC) complexes. Accordingly, provided herein are compositions comprising TLR inhibitor/MC complexes. TLR inhibitor/MC complexes comprise a TLR inhibitor bound to the surface of a microcarrier (i.e., the TLR inhibitor is not encapsulated in the MC), and preferably comprise multiple molecules of TLR inhibitor bound to each microcarrier. In certain embodiments, a mixture of different TLR inhibitors may be complexed with a microcarrier, such that the microcarrier is bound to more than one TLR inhibitor species. The bond between the TLR inhibitor and MC may be covalent or non-covalent. As will be understood by one of skill in the art, the TLR inhibitor may be modified or derivatized and the composition of the microcarrier may be selected and/or modified to accommodate the desired type of binding desired for TLR inhibitor/MC complex formation.

Microcarriers useful are less than about 150, 120 or 100 μm in size, more commonly less than about 50-60 μm in size, preferably less than about 10 μm in size, and are insoluble in pure water. Microcarriers used are preferably biodegradable, although nonbiodegradable microcarriers are acceptable. Microcarriers are commonly solid phase, such as "beads" or other particles, although liquid phase microcarriers such as oil in water emulsions comprising a biodegradable polymers or oils are also contemplated. A wide variety of biodegradable and nonbiodegradable materials acceptable for use as microcarriers are known in the art.

Microcarriers for use in the compositions or methods described herein are generally less than about 10 μm in size (e.g., have an average diameter of less than about 10 μm, or at least about 97% of the particles pass through a 10 μm screen filter), and include nanocarriers (i.e., carriers of less than about 1 μm size). Preferably, microcarriers are selected having sizes within an upper limit of about 9, 7, 5, 2, or 1 μm or 900, 800, 700, 600, 500, 400, 300, 250, 200, or 100 nm and an independently selected lower limit of about 4, 2, or 1 μm or about 800, 600, 500, 400, 300, 250, 200, 150, 100, 50, 25, or 10 nm, where the lower limit is less than the upper limit. In some embodiments, the microcarriers have a size of about 1.0-1.5 μm, about 1.0-2.0 μm or about 0.9-1.6 μm. In certain preferred embodiments, the microcarriers have a size of about 10 nm to about 5 μm or about 25 nm to about 4.5 μm, about 1 μm, about 1.2 μm, about 1.4 μm, about 1.5 μm, about 1.6 μm, about 1.8 μm, about 2.0 μm, about 2.5 μm or about 4.5 μm. When the microcarriers are nanocarriers, preferred embodiments include nanocarriers of about 25 to about 300 nm, 50 to about 200 nm, about 50 nm or about 200 nm.

Solid phase biodegradable microcarriers may be manufactured from biodegradable polymers including, but not limited to: biodegradable polyesters, such as poly(lactic acid), poly(glycolic acid), and copolymers (including block copolymers) thereof, as well as block copolymers of poly (lactic acid) and poly(ethylene glycol); polyorthoesters such as polymers based on 3,9-diethylidene-2,4,8,10-tetraoxaspiro[5.5]undecane (DETOSU); polyanhydrides such as poly (anhydride) polymers based on relatively hydrophilic monomers such as sebacic acid; polyanhydride imides, such as polyanhydride polymers based on sebacic acid-derived monomers incorporating amino acids (i.e., linked to sebacic acid by imide bonds through the amino-terminal nitrogen) such as glycine or alanine; polyanhydride esters; polyphosphazenes, especially poly(phosphazenes) which contain hydrolysis-sensitive ester groups which can catalyze degradation of the polymer backbone through generation of carboxylic acid groups (Schacht et al., (1996) *Biotechnol. Bioeng.* 1996:102); and polyamides such as poly(lactic acid-co-lysine).

A wide variety of nonbiodegradable materials suitable for manufacturing microcarriers are also known, including, but not limited to polystyrene, polypropylene, polyethylene, silica, ceramic, polyacrylamide, dextran, hydroxyapatite, latex, gold, and ferromagnetic or paramagnetic materials. Certain embodiments exclude gold, latex, and/or magnetic beads. In certain embodiments, the microcarriers may be made of a first material (e.g., a magnetic material) encapsulated with a second material (e.g., polystyrene).

Solid phase microspheres are prepared using techniques known in the art. For example, they can be prepared by emulsion-solvent extraction/evaporation technique. Generally, in this technique, biodegradable polymers such as polyanhydrates, poly(alkyl-cyanoacrylates) and poly(hydroxy esters), for example, poly(lactic acid), poly(glycolic acid), poly(D,L-lactic-co-glycolic acid) and poly(caprolactone), are dissolved in a suitable organic solvent, such as methylene chloride, to constitute the dispersed phase (DP) of emulsion. DP is emulsified by high-speed homogenization into excess volume of aqueous continuous phase (CP) that contains a dissolved surfactant, for example, polyvinyl-alcohol (PVA) or polyvinylpirrolidone (PVP). Surfactant in CP is to ensure the formation of discrete and suitably-sized emulsion droplet. The organic solvent is then extracted into the CP and subsequently evaporated by raising the system temperature. The solid microparticles are then separated by centrifugation or filtration, and dried, for example, by lyophilization or application of vacuum, before storing at 4° C.

Physico-chemical characteristics such as mean size, size distribution and surface charge of dried microspheres may be determined. Size characteristics are determined, for example, by dynamic light scattering technique and the surface charge was determined by measuring the zeta potential.

Liquid phase microcarriers include liposomes, micelles, oil droplets and other lipid or oil-based particles which incorporate biodegradable polymers or oils. In certain embodiments, the biodegradable polymer is a surfactant. In other embodiments, the liquid phase microcarriers are biodegradable due to the inclusion of a biodegradable oil such as squalene or a vegetable oil. One preferred liquid phase microcarrier is oil droplets within an oil-in-water emulsion. Preferably, oil-in-water emulsions used as microcarriers comprise biodegradable substituents such as squalene.

Covalently bonded TLR inhibitor/MC complexes may be linked using any covalent crosslinking technology known in the art. Typically, the TLR inhibitor portion will be modified, either to incorporate an additional moiety (e.g., a free amine, carboxyl or sulfhydryl group) or incorporate modified (e.g., phosphorothioate) nucleotide bases to provide a site at which the TLR inhibitor portion may be linked to the microcarrier. The link between the TLR inhibitor and MC portions of the complex can be made at the 3' or 5' end of the TLR inhibitor, or at a suitably modified base at an internal position in the TLR inhibitor. The microcarrier is generally also modified to incorporate moieties through which a covalent link may be formed, although functional groups normally present on the microcarrier may also be utilized. The TLR inhibitor/MC is formed by incubating the TLR inhibitor with a microcarrier under conditions which permit the formation of a covalent complex (e.g., in the presence of a crosslinking agent or by use of an activated microcarrier comprising an activated moiety which will form a covalent bond with the TLR inhibitor).

A wide variety of crosslinking technologies are known in the art, and include crosslinkers reactive with amino, carboxyl and sulfhydryl groups. As will be apparent to one of skill in the art, the selection of a crosslinking agent and crosslinking protocol will depend on the configuration of the TLR inhibitor and the microcarrier as well as the desired final configuration of the TLR inhibitor/MC complex. The crosslinker may be either homobifunctional or heterobifunctional. When a homobifunctional crosslinker is used, the crosslinker exploits the same moiety on the TLR inhibitor and MC (e.g., an aldehyde crosslinker may be used to covalently link an TLR inhibitor and MC where both the TLR inhibitor and MC comprise one or more free amines). Heterobifunctional crosslinkers utilize different moieties on the TLR inhibitor and MC, (e.g., a maleimido-N-hydroxysuccinimide ester may be used to covalently link a free sulfhydryl on the TLR inhibitor and a free amine on the MC), and are preferred to minimize formation of inter-microcarrier bonds. In most cases, it is preferable to crosslink through a first crosslinking moiety on the microcarrier and a second crosslinking moiety on the TLR inhibitor, where the second crosslinking moiety is not present on the microcarrier. One preferred method of producing the TLR inhibitor/MC complex is by 'activating' the microcarrier by incubating with a heterobifunctional crosslinking agent, then forming the TLR inhibitor/MC complex by incubating the TLR inhibitor and activated MC under conditions appropriate for reaction. The crosslinker may incorporate a "spacer" arm between the reactive moieties, or the two reactive moieties in the crosslinker may be directly linked.

In one preferred variation, the TLR inhibitor portion comprises at least one free sulfhydryl (e.g., provided by a 5'-thiol modified base or linker) for crosslinking to the microcarrier, while the microcarrier comprises free amine groups. A heterobifunctional crosslinker reactive with these two groups (e.g., a crosslinker comprising a maleimide group and a NHS-ester), such as succinimidyl 4-(N-maleimidomethyl)cyclohexane-1-carboxylate is used to activate the MC, then covalently crosslink the TLR inhibitor to form the TLR inhibitor/MC complex.

Non-covalent TLR inhibitor/MC complexes may be linked by any non-covalent binding or interaction, including ionic (electrostatic) bonds, hydrophobic interactions, hydrogen bonds, van der Waals attractions, or a combination of two or more different interactions, as is normally the case when a binding pair is to link the TLR inhibitor and MC.

Preferred non-covalent TLR inhibitor/MC complexes are typically complexed by hydrophobic or electrostatic (ionic) interactions, or a combination thereof, (e.g., through base pairing between a TLR inhibitor and a polynucleotide bound to an MC use of a binding pair). Due to the hydrophilic nature of the backbone of polynucleotides, TLR inhibitor/MC complexes which rely on hydrophobic interactions to form the complex generally require modification of the TLR inhibitor portion of the complex to incorporate a highly hydrophobic moiety. Preferably, the hydrophobic moiety is biocompatible, nonimmunogenic, and is naturally occurring in the individual for whom the composition is intended (e.g., is found in mammals, particularly humans). Examples of preferred hydrophobic moieties include lipids, steroids, sterols such as cholesterol, and terpenes. The method of linking the hydrophobic moiety to the TLR inhibitor will, of course, depend on the configuration of the TLR inhibitor and the identity of the hydrophobic moiety. The hydrophobic moiety may be added at any convenient site in the TLR inhibitor, preferably at either the 5' or 3' end; in the case of addition of a cholesterol moiety to a TLR inhibitor, the cholesterol moiety is preferably added to the 5' end of the TLR inhibitor, using conventional chemical reactions (see, for example, Godard et al. (1995) Eur. J. Biochem. 232:404-410). Preferably, microcarriers for use in TLR inhibitor/MC complexes linked by hydrophobic bonding are made from hydrophobic materials, such as oil droplets or hydrophobic polymers, although hydrophilic materials modified to incorporate hydrophobic moieties may be utilized as well. When the microcarrier is a liposome or other liquid phase microcarrier comprising a lumen and the TLR inhibitor is desired to be associated with the outer surface of the MC, the TLR inhibitor/MC complex is formed by mixing the TLR inhibitor and the MC after preparation of the MC, in order to avoid encapsulation of the TLR inhibitor during the MC preparation process.

Non-covalent TLR inhibitor/MC complexes bound by electrostatic binding typically exploit the highly negative charge of the polynucleotide backbone. Accordingly, microcarriers for use in non-covalently bound TLR inhibitor/MC complexes are generally positively charged (cationic) at physiological pH (e.g., about pH 6.8-7.4). The microcarrier may intrinsically possess a positive charge, but microcarriers made from compounds not normally possessing a positive charge may be derivatized or otherwise modified to become positively charged (cationic). For example, the polymer used to make the microcarrier may be derivatized to add positively charged groups, such as primary amines. Alternately, positively charged compounds may be incorporated in the formulation of the microcarrier during manufacture (e.g., positively charged surfactants may be used during the manufacture of poly(lactic acid)/poly(glycolic acid) copolymers to confer a positive charge on the resulting microcarrier particles).

For example, to prepare cationic microspheres, cationic lipids or polymers, for example, 1,2-dioleoyl-1,2,3-trimethylammoniopropane (DOTAP), cetyltrimethylammonium bromide (CTAB) or polylysine, are added either to DP or CP, as per their solubility in these phases.

TLR inhibitor/MC complexes can be preformed by adsorption onto cationic microspheres by incubation of polynucleotide and the particles, preferably in an aqueous admixture. Such incubation may be carried out under any desired conditions, including ambient (room) temperature (e.g., approximately 20° C.) or under refrigeration (e.g., 4° C.). Because cationic microspheres and polynucleotides associate relatively quickly, the incubation may be for any convenient time period, such as 5, 10, 15 minutes or more, including overnight and longer incubations. For example, TLR inhibitors can be adsorbed onto the cationic microspheres by overnight aqueous incubation of polynucleotide and the particles at 4° C. However, because cationic microspheres and polynucleotides spontaneously associate, the TLR inhibitor/MC complex can be formed by simple co-administration of the polynucleotide and the MC. Microspheres may be characterized for size and surface charge before and after polynucleotide association. Selected batches may then be evaluated for activity against suitable controls in, for example, human peripheral blood mononuclear cell (PBMC) and mouse splenocyte assays. The formulations may also be evaluated in suitable animal models.

Non-covalent TLR inhibitor/MC complexes linked by nucleotide base pairing may be produced using conventional methodologies. Generally, base-paired TLR inhibitor/MC complexes are produced using a microcarrier comprising a bound, preferably a covalently bound, polynucleotide (the "capture polynucleotide") that is at least partially complementary to the TLR inhibitor. The segment of complementarity between the TLR inhibitor and the capture nucleotide is preferably at least 6, 8, 10 or 15 contiguous base pairs, more preferably at least 20 contiguous base pairs. The capture nucleotide may be bound to the MC by any method known in the art, and is preferably covalently bound to the TLR inhibitor at the 5' or 3' end.

In other embodiments, a binding pair may be used to link the TLR inhibitor and MC in an TLR inhibitor/MC complex. The binding pair may be a receptor and ligand, an antibody and antigen (or epitope), or any other binding pair which binds at high affinity (e.g., Kd less than about 10-8). One type of preferred binding pair is biotin and streptavidin or biotin and avidin, which form very tight complexes. When using a binding pair to mediate TLR inhibitor/MC complex binding, the TLR inhibitor is derivatized, typically by a covalent linkage, with one member of the binding pair, and the MC is derivatized with the other member of the binding pair. Mixture of the two derivatized compounds results in TLR inhibitor/MC complex formation.

Pharmaceutical Formulations

Pharmaceutical formulations comprising a TLR inhibitor as described herein are also provided. The pharmaceutical formulations comprising the TLR inhibitor may be administered in an effective amount of a composition to an individual to achieve a specific outcome. The pharmaceutical formulations may routinely contain pharmaceutically acceptable concentrations of salt, buffering agents, preservatives, compatible carriers, adjuvants, and optionally other therapeutic ingredients. In some aspects, the pharmaceutical formulations comprise at least one TLR inhibitor.

Pharmaceutical formulations include, for example, aqueous or saline solutions for injection or inhalation, or may be microencapsulated, encochleated, coated onto microscopic gold particles, contained in liposomes, nebulized, aerosols, pellets for implantation into the skin, or dried onto a sharp object to be scratched into the skin. The pharmaceutical formulations also include granules, powders, tablets, coated tablets, (micro)capsules, suppositories, syrups, emulsions, suspensions, creams, drops or preparations with protracted release of active compounds, e.g., in whose preparation excipients and additives and/or auxiliaries such as disintegrants, binders, coating agents, swelling agents, lubricants, flavorings, sweeteners or solubilizers are customarily used as described above. The pharmaceutical formulations are suitable for use in a variety of drug delivery systems. For a brief review of exemplary methods for drug delivery, see Langer, *Science* 249:1527-33 (1990), which is incorporated herein by reference.

In some embodiments, the pharmaceutical formulation comprising the TLR inhibitor further comprises a pharmaceutical acceptable carrier, excipient, or stabilizer. Pharmaceutically acceptable carriers, excipients, or stabilizers are described herein and well known in the art (see, e.g., Remington: The Science and Practice of Pharmacy, 20th edition, Mack Publishing, 2000). Examples of physiologically acceptable carriers, excipients, or stabilizers include, but are not limited to, buffers such as phosphate, citrate, and other organic acids; antioxidants including ascorbic acid; low molecular weight polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®. In some embodiments, the pharmaceutically acceptable carrier is citrate.

In some embodiments, the pharmaceutical formulations comprising the TLR inhibitor is suitable for parenteral administration. Among the acceptable vehicles and solvents are water, Ringer's solution, phosphate buffered saline, and isotonic sodium chloride solution. In addition, sterile, fixed oils are conventionally employed as a solvent or suspending medium. For this purpose any bland fixed mineral or non-mineral oil may be employed including synthetic mono- or diglycerides. In addition, fatty acids such as oleic acid find use in the preparation of injectables. In some embodiments, the pharmaceutical formulations comprising the TLR inhibitor are suitable for subcutaneous, intramuscular, intraperitoneal, or intravenous delivery.

In some embodiments, the pharmaceutical formulation comprising the TLR inhibitor is a time-release, delayed release or sustained release pharmaceutical formulation. Sustained-release pharmaceutical formulations include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Non-polymer pharmaceutical formulation can include: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like.

A pharmaceutical formulation comprising the TLR inhibitor may be suitable for topical application including, but not limited to, physiologically acceptable ointments, creams, rinses, emulsions, lotions, solutions, pastes, and gels.

In some embodiments, the pharmaceutical formulation comprising the TLR inhibitor is a pharmaceutical formulation formulated for transdermal administration. Transdermal administration is accomplished by application of e.g., a cream, rinse, or gel. In some embodiments, the pharmaceutical formulation is a pharmaceutical formulation formulated for gastrointestinal routes of administration. In some embodiments, the pharmaceutical formulation for gastrointestinal routes comprises pharmaceutically acceptable powders, pills or liquids for ingestion and suppositories for rectal administration. In some embodiments, the pharmaceutical formulation is a pharmaceutical formulation formulated for naso-pharyngeal and pulmonary administration. Pharmaceutical formulations suitable for naso-pharyngeal and pulmonary administration include, but not limited to, liquid suspensions for forming aerosols as well as powder forms for dry powder inhalation delivery systems are provided.

IV. Methods of Use

Provided herein are methods of inhibiting an immune response in an individual comprising administering to the individual an effective amount of an inhibitor of TLR7, TLR8, and/or TLR9 (e.g., TLR inhibitor). The TLR inhibitors of the present disclosure are polynucleotides comprising an inhibitory motif for one or more human TLR7, TLR8, and TLR9. In some variations, the TLR inhibitor inhibits a TLR7-dependent immune response. In some variations, the TLR inhibitor inhibits a TLR8-dependent immune response. In some variations, the TLR inhibitor inhibits a TLR7-dependent and a TLR8-dependent immune response. In some variations, the TLR inhibitor inhibits a TLR8-dependent and a TLR9-dependent immune response. In some variations, the TLR inhibitor inhibits a TLR7-dependent, a TLR8-dependent, and a TLR9-dependent immune response. Unless otherwise noted, the term TLR inhibitor refers to any one of the TLR inhibitors disclosed herein. In some preferred embodiments, the individual is a human patient.

Methods of immunoregulation are provided by the present disclosure and include those that suppress and/or inhibit an immune response, including, but not limited to, an immune response. The present disclosure also provides methods for ameliorating symptoms associated with unwanted immune activation, including, but not limited to, symptoms associated with autoimmunity. Immune suppression and/or inhibition according to the methods described herein may be practiced on individuals including those suffering from a disorder associated with an unwanted activation of an immune response. The present disclosure also provides methods for inhibiting a TLR7, TLR8, and/or TLR9 induced response (e.g., in vitro or in vivo). In some variations, the cell is contacted with the TLR inhibitor in an amount effective to inhibit a response from the cell that contributes to an immune response.

Inhibition of TLR7, TLR8, and/or TLR9 may be useful for treating and/or preventing a variety of diseases or disorders that are responsive to cytokines. Conditions for which TLR7, TLR8, and/or TLR9 inhibitors may be used as treatments include, but are not limited to autoimmune diseases and inflammatory disorders. Provided herein are methods of treating or preventing a disease or disorder in an individual comprising administering to the individual an effective amount of an inhibitor of TLR7, TLR8 and/or TLR9. Further, provided are methods for ameliorating symptoms associated with a disease or disorder comprising administering an effective amount of an inhibitor of TLR7, TLR8, and/or TLR9 to an individual having the disease or disorder. Methods are also provided herein for preventing or delaying development of a disease or a disorder, comprising administering an effective amount of an inhibitor of one or more of TLR7, TLR8 and TLR9 to an individual having the disease or the disorder. In some embodiments, the TLR inhibitor is selected from the group consisting of SEQ ID NO:10, SEQ ID NO:14, SEQ ID NO:15, SEQ ID NO:16, SEQ ID NO:17, SEQ ID NO:18, SEQ ID NO:24, SEQ ID NO:26, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:44, SEQ ID NO:46, SEQ ID NO:48, SEQ ID NO:49, SEQ ID NO:50, SEQ ID NO:51, SEQ ID NO:52, SEQ ID NO:53, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:77, SEQ ID NO:78, SEQ ID NO:79, SEQ ID NO:80, SEQ ID NO:81, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, and SEQ ID NO:115. In some embodiments, the TLR inhibitor is a polynucleotide comprising SEQ ID NO:108. In some embodiments, the TLR inhibitor is a polynucleotide comprising SEQ ID NO:109.

Provided herein are methods of inhibiting an immune response in an individual, the method comprising administering to the individual at least one TLR inhibitor as disclosed herein in an amount effective to inhibit the immune response in the individual. In some variations, the immune response is associated with an autoimmune disease. In further aspects, wherein inhibiting the immune response ameliorates one or more symptoms of the autoimmune disease. In still further aspects, wherein inhibiting the immune response treats the autoimmune disease. In yet further aspects, wherein inhibiting the immune response prevents or delays development of the autoimmune disease. In some variations, the TLR inhibitor inhibits a TLR7-dependent immune response. In some variations, the TLR inhibitor inhibits a TLR8-dependent immune response. In some variations, the TLR inhibitor inhibits a TLR7-dependent and a TLR8-dependent immune response. In some variations, the TLR inhibitor inhibits a TLR8-dependent and a TLR9-dependent immune response. In some variations, the TLR inhibitor inhibits a TLR7-dependent, a TLR8-dependent, and a TLR9-dependent immune response. In some aspects, at least one TLR inhibitor is administered in an amount effective to inhibit an immune response in the individual.

Provided herein are also methods of treating or preventing an autoimmune disease in an individual, comprising administering to the individual an effective amount of a TLR7, TLR8, and/or TLR9 inhibitor. In some aspects, the autoimmune disease is characterized by joint pain), antinuclear antibody positivity, malar rash, or discoid rash. In some aspects, the autoimmune disease is associated with the skin, muscle tissue, and/or connective tissue. In some embodiments, the autoimmune disease is not evidenced in the individual by skin, muscle tissue, and/or connective tissue symptoms. In some embodiments, the autoimmune disease is systemic. Autoimmune diseases include, without limitation, rheumatoid arthritis (RA), autoimmune pancreatitis (AIP), systemic lupus erythematosus (SLE), type I diabetes mellitus, multiple sclerosis (MS), antiphospholipid syndrome (APS), sclerosing cholangitis, systemic onset arthritis, irritable bowel disease (IBD), scleroderma, Sjogren's disease, vitiligo, polymyositis, pemphigus vulgaris, pemphigus foliaceus, inflammatory bowel disease including Crohn's disease and ulcerative colitis, autoimmune hepatitis, hypopituitarism, graft-versus-host disease (GvHD), autoimmune skin diseases, uveitis, pernicious anemia, and hypoparathyroidism. Autoimmune diseases may also include, without limitation, polyangiitis overlap syndrome, Kawasaki's disease, sarcoidosis, glomerulonephritis, and cryopathies. These conditions are well known in the medical arts and are described, for example, in Harrison's Principles of Internal Medicine, 14th ed., Fauci et al., eds., New York: McGraw-Hill, 1998. In some aspects, the autoimmune disease is selected from the group consisting of arthritis, pancreatitis, mixed connective tissue disease (MCTD), lupus, antiphospholipid syndrome (APS), systemic onset arthritis, and irritable bowel syndrome. In other aspects, the autoimmune disease is selected from the group consisting of systemic lupus erythematosus (SLE), rheumatoid arthritis, autoimmune skin disease, and multiple sclerosis. In other aspects, the autoimmune disease is selected from the group consisting of pancreatitis, glomerulonephritis, pyelitis, sclerosing cholangitis, and type I diabetes. In some aspects, the autoimmune disease is rheumatoid arthritis. In some aspects, the autoimmune disease is autoimmune pancreatitis (AIP). In some aspects, the autoimmune disease is glomerulonephritis. In some aspects, the autoimmune disease is pyelitis. In some aspects, the autoimmune disease is sclerosing cholangitis. In some aspects the autoimmune disorder is psoriasis. In some aspects, the autoimmune disease is a rheumatoid disease or disorder. In some aspects, the rheumatoid disease or disorder is rheumatoid arthritis. In some aspects, the disease is diabetes and/or diabetic-related disease or disorder. In some aspects, wherein the autoimmune disease is associated with RNA-containing immune complexes. In some aspects, the autoimmune disease is Sjogren's disease.

Provided herein are methods of inhibiting an immune response in an individual, the method comprising administering to the individual at least one TLR inhibitor as disclosed herein in an amount effective to inhibit the immune response in the individual. In some variations, the immune response is associated with an inflammatory disorder. As used herein, the term "inflammatory disorder" encompasses autoimmune diseases, as well as inflammatory conditions without a known autoimmune component (e.g., artherosclerosis, asthma, etc.). In further aspects, inhibiting the immune response ameliorates one or more symptoms of the inflammatory disorder. In still further aspects, inhibiting the immune response treats the inflammatory disorder. In yet further aspects, inhibiting the immune response prevents or delays development of the inflammatory disorder. In some aspects, the inflammatory disorder is selected from the group consisting of non-rheumatoid arthritis, kidney fibrosis, and liver fibrosis. In some aspects, the inflammatory disorder is an interface dermatitis. In some further aspects, the interface dermatitis is selected from the group consisting of lichen planus, lichenoid eruption, lichen planus-like keratosis, lichen striatus, keratosis lichenoides chronica, erythema multiforme, fixed drug eruption, pityriasis lichenoides, phototoxic dermatitis, radiation dermatitis, viral exanthems, dermatomyositis, secondary syphilis, lichen sclerosus et atrophicus, mycosis fungoides, bullous pemphigoid, lichen aureus, porokeratosis, acrodermatitis chronicus atrophicans, and regressing melanoma. In some aspects, the inflammatory condition is a skin disorder such as atopic dermatitis (eczema). In some aspects, the inflammatory disorder is a sterile inflammatory condition such as drug-induced liver and/or pancreas inflammation. In some further aspects, the inflammatory disease is an inflammatory liver disorder. In some other further aspects, the inflammatory disease is an inflammatory pancreatic disorder.

Provided herein are methods of inhibiting an immune response in an individual, the method comprising administering to the individual at least one TLR inhibitor as disclosed herein in an amount effective to inhibit the immune response in the individual. In some variations, the immune response is associated with chronic pathogen stimulation. In some variations, the immune response is associated with infection by HIV. In further aspects, wherein inhibiting the immune response ameliorates one or more symptoms of the viral disease or disorder resulting from infection by HIV. In still further aspects, wherein inhibiting the immune response treats the viral disease or disorder resulting from infection by HIV. In yet further aspects, wherein inhibiting the immune response prevents or delays development of the viral disease or disorder resulting from infection by HIV. Other variations provided herein relate to immunoinhibitory therapy of individuals having been exposed to or infected with HIV. Administration of a TLR inhibitor to an individual having been exposed to or infected with HIV results in suppression of HIV induced cytokine production. In some aspects, at least one TLR inhibitor is administered in an amount effective to suppress HIV induced cytokine production in an individual exposed to or infected with a HIV.

Provided herein are methods for inhibiting a TLR7-, TLR8-, and/or TLR9-dependent immune response in an individual, the method comprising administering to the individual a TLR inhibitor in an amount effective to inhibit the immune response in the individual. In some variations, the immune response is associated with an autoimmune disease. In some aspects, the autoimmune disease is rheumatoid arthritis. In some aspects, the TLR inhibitor is effective in suppressing one or more symptoms of rheumatoid arthritis. In some aspects, the autoimmune disease is multiple sclerosis. In some aspects, the TLR inhibitor is effective in suppressing one or more symptoms of multiple sclerosis. In some aspects, the autoimmune disease is lupus. In some aspects, the TLR inhibitor is effective in suppressing one or more symptoms of lupus. In some aspects, the autoimmune disease is pancreatitis. In some aspects, the TLR inhibitor is effective in suppressing one or more symptoms of pancreatitis. In some aspects, the autoimmune disease is diabetes. In some aspects, the TLR inhibitor is effective in suppressing one or more symptoms of diabetes. In some aspects, the disease is Sjogren's disease. In some aspects, the TLR inhibitor is effective in suppressing one or more symptoms of Sjogren's disease. In some variations, the immune response is associated with an inflammatory disorder. In some aspects, the TLR inhibitor is effective in suppressing one or more symptoms of an inflammatory disorder. In some variations, the immune response is associated with chronic pathogen stimulation. In some aspects, the TLR inhibitor is effective in suppressing one or more symptoms of chronic pathogen stimulation. In some variations, the immune response is associated with viral disease resulting from infection with HIV. In some aspects, the TLR inhibitor is effective in suppressing one or more symptoms of viral disease resulting from infection with HIV. In any variation, the TLR inhibitor is a polynucleotide comprising an inhibitory motif for one or more of TLR7, TLR8, and TLR9.

The methods herein provide prophylactic treatment, therapeutic treatment, or both. Prophylactic treatment as used herein refers to treatment that is initiated prior to observation of symptoms and/or a suspected exposure to a causative agent of the condition (e.g., a pathogen or carcinogen). Generally, prophylactic treatment may reduce (a) the likelihood that an individual receiving the treatment develops the condition and/or (b) the duration and/or severity of symptoms in the event the subject develops the condition. As used herein, therapeutic treatment refers to treatment initiated after observation of symptoms and/or a suspected exposure to a causative agent of the condition. Generally, therapeutic treatment may reduce the severity and/or duration of symptoms associated with the condition.

As demonstrated herein, particular TLR inhibitors comprising an inhibitory motif for one or more of TLR7, TLR8, and/or TLR9 inhibit TLR7-dependent cell responses, TLR8-dependent cell responses, and/or TLR9 dependent cell responses. In some embodiments, certain TLR inhibitors do not inhibit TLR4-dependent cell responses. In some embodiments, certain TLR inhibitors do not inhibit TLR1-dependent, TLR2-dependent, TLR3-dependent, TLR4-dependent, TLR5-dependent, TLR6-dependent, TLR10-dependent, TLR11-dependent, TLR12-dependent and/or TLR13-dependent cell responses. In some embodiments, TLR inhibitors comprising an inhibitory motif for one or more of TLR7, TLR8, and/or TLR9, as described herein, inhibits and/or suppresses a measurable immune response as determined in vitro, in vivo, and/or ex vivo.

As described herein, some TLR inhibitors with newly defined TLR7 inhibitory motifs are particularly effective in suppressing TLR7 dependent cell responses. Such TLR inhibitors include, but are not limited to, SEQ ID NO:36, 38, 44, 46, 48, 50, 55-67, 85-88, 90, 91, 95, 97, 99, 103, 104, 108-111, 114, and 115.

As described herein, some TLR inhibitors with newly defined TLR8 inhibitory motifs are particularly effective in suppressing TLR8 dependent cell responses. Such TLR inhibitors include, but are not limited to, SEQ ID NO:10, 14-18, 20, 24, 26, 30-40, 44, 48-53, 56, 59-73, 77-81, and 84-115.

As described herein, some TLR inhibitors are particularly effective in suppressing TLR7 dependent and TLR8 dependent cell responses. Such TLR inhibitors include, but are not limited to, SEQ ID NO:10, 15-18, 20, 24, 26, 30, 34-36, 38, 40, 44, 48, 50, 56, 59-63, 65, 67, 85-88, 90-95, 97, 99-106, and 108-111.

As described herein, some TLR inhibitors are particularly effective in suppressing TLR8 dependent and TLR9 dependent cell responses. Such TLR inhibitors include, but are not limited to, SEQ ID NO:81, and 112.

As described herein, some TLR inhibitors are particularly effective in suppressing TLR7 dependent, TLR8 dependent and TLR9 dependent cell responses. Such TLR inhibitors include, but are not limited to, SEQ ID NO:14, 64, 66, and 113-115.

In some embodiments of any of the methods involving administration of a TLR inhibitor to an individual (e.g., methods of inhibiting an immune response, treating or preventing an autoimmune disease or inflammatory disorder, etc.) the TLR inhibitor has a therapeutically acceptable safety profile. The TLR inhibitor may for example, have a therapeutically acceptable histological profile including an acceptably low, if any, toxicity of the liver, kidney, pancreas, or other organs. On occasion, polynucleotides have been associated with toxicity to certain organs such as the liver, kidney and pancreas. In some embodiments, the TLR inhibitor has a safety profile that is unexpected and advantageous. In some embodiments, a safety profile includes evaluation of toxicity, histological profile, and/or necrosis (e.g., liver, kidneys and/or heart). In some embodiments, the TLR inhibitor has a therapeutically acceptable level of toxicity. In some embodiments, the TLR inhibitor has a reduced level of toxicity as compared to another TLR inhibitor (e.g., a reference TLR inhibitor such as C954 of SEQ ID NO:7). In some embodiments, the TLR inhibitor induces a therapeutically acceptable reduction in body weight as compared to the initial body weight of a treated individual. In some embodiments, the TLR inhibitor induces less than 5%, 7.5%, 10%, 12.5, or 15% reduction in total body weight. In some embodiments, the TLR inhibitor has a therapeutically acceptable histology profile. In some embodiments, the TLR inhibitor has a better (e.g., lower severity score) histology profile, for example, as compared to a reference TLR inhibitor such as C954 of SEQ ID NO:7. In some embodiments, the TLR inhibitor has a better (e.g., lower severity score) histology profile upon evaluation of the liver, kidneys and/or heart, for example. In some embodiments, the TLR inhibitor has a therapeutically acceptable necrosis score. In some embodiments, the TLR inhibitor has reduced necrosis and/or better (e.g., lower) necrosis score, for example, as compared to a reference TLR inhibitor such as C954 of SEQ ID NO:7. In some embodiments, the average necrosis score is less than or equal to about 3. In some embodiments, the average necrosis score is less than or equal to about 2.0 In some embodiments, the average necrosis score is less than or equal to about 1. In some embodiments, the average necrosis score is less than or equal to about 0. In some embodiments, the TLR inhibitor has reduced renal and/or hepatocellular necrosis and/or a better renal and/or hepatocellular necrosis score, for example, as compared to a reference TLR inhibitor such as C954 of SEQ ID NO:7.

In some embodiments of any of the methods involving administration of a TLR inhibitor to an individual (e.g., methods of inhibiting an immune response, treating or preventing an autoimmune disease or inflammatory disorder, etc.), the TLR inhibitor has therapeutically acceptable pharmacokinetics (PK) or drug metabolism and pharmacokinetics (DMPK). In some embodiments of any of the methods, the TLR inhibitor has a PK profile or PK similar to another TLR inhibitor (e.g., a reference TLR inhibitor such as C954 of SEQ ID NO:7). In some embodiments, the therapeutically acceptable safety profile is determined in mice or rats. In some embodiments, the therapeutically acceptable safety profile is determined in rats.

In some embodiments of any of the methods involving administration of a TLR inhibitor to an individual (e.g., methods of inhibiting an immune response, treating or preventing an autoimmune disease or inflammatory disorder, etc.) the TLR inhibitor induces a therapeutically acceptable level of B-cell activation. In some embodiments, the TLR inhibitor induces a low level of B-cell activation as compared to a positive control polynucleotide (e.g., an immunostimulatory sequence, also referred to as an ISS, comprising an unmethylated CG dinucleotide). In some embodiments, the TLR inhibitor induces a low level of B-cell activation, which is comparable to or not significantly higher than another TLR inhibitor known to have low B-cell activation (e.g., a reference TLR inhibitor such as C954 of SEQ ID NO:7). In some embodiments, the TLR inhibitor induces B-cell activation to levels significantly less than about 1-fold, 1.5-fold, 2-fold, 2.5-fold, or 3-fold as compared a another TLR inhibitor known to have low B-cell activation (e.g., C954 of SEQ ID NO:7). In some embodiments, the TLR inhibitor induces B-cell activation to levels significantly lower than a positive control polynucleotide (e.g., an ISS). In some embodiments, the TLR inhibitor induces B-cell activation in vitro to levels less than about 5%, 10%, 15%, 20%, or 25% as compared to a positive control polynucleotide (e.g., an ISS). In some embodiments, the B-cell activation of the TLR inhibitor is normalized to a positive control polynucleotide (e.g., an ISS). In some embodiments, normalized results of multiple TLR inhibitors are compared. In some embodiments, the TLR inhibitor induces B-cell activation to levels significantly lower than a second TLR inhibitor (e.g., DV185 of SEQ ID NO:116). In some embodiments, the TLR inhibitor does not induce B-cell activation in a cell culture assay to levels significantly higher than media alone or to a reference TLR inhibitor known to have low B-cell activation (e.g., C954 of SEQ ID NO:7). In some embodiments, the TLR inhibitor induces B-cell activation in a cell culture assay to levels significantly less than about 1-fold, 1.5-fold, 2-fold, 2.5-fold, or 3-fold compared a second TLR inhibitor known to have low B-cell activation (e.g., C954 of SEQ ID NO:7). In some embodiments, the TLR inhibitor induces B-cell activation in a cell culture assay to levels significantly less than a positive control polynucleotide (e.g., an ISS). In some embodiments, the TLR inhibitor shows concentration-dependent, B-cell activation, for example over the range of about 4000 nM to about 15 nM. In some embodiments, the TLR inhibitor shows little to no B-cell activation, for example over the range of about 1000 nM to about 15 nM.

Administration of TLR Inhibitors and Assessment of Immune Responses

As with all compositions for inhibition of an immune response, the effective amounts and method of administration of the particular TLR inhibitor formulation can vary based on the individual, what condition is to be treated and other factors evident to one skilled in the art.

In some aspects, the dosage of the TLR inhibitor is sufficient for suppression of a response to a TLR7, TLR8, and/or TLR9 agonists, suppression of a TLR7-dependent immune response, suppression of a TLR8-dependent immune response, suppression of a TLR7-dependent and a TLR8-dependent immune response, suppression of a TLR8-dependent and a TLR9-dependent immune response, suppression of a TLR7-dependent, a TLR8-dependent, and a TLR9-dependent immune response, ameliorating one or more symptoms of an autoimmune disease, ameliorating a symptom of chronic inflammatory disease, decreasing cytokine production in response to HIV, and/or treating and/or preventing one or more symptoms of a disease or disorder mediated by TLR7, TLR8, and/or TLR9. In some aspects, at least one TLR inhibitor is administered in an amount effective to inhibit an immune response in the individual.

A suitable dosage range is one that provides the desired regulation of immune response (e.g., suppression of a TLR7, TLR8, and/or TLR9 agonist or suppression of IFN or other cytokine production in response to a TLR7, TLR8, and/or TLR9 agonist). Generally, dosage is determined by the amount of the TLR inhibitor administered to the individual. Useful dosage ranges of a composition comprising a TLR inhibitor, may be, for example, any of the following: 0.1 to 10 mg/kg, 0.5 to 10 mg/kg, 1 to 10 mg/kg, 0.1 to 20 mg/kg, 0.1 to 20 mg/kg, or 1 to 20 mg/kg. The absolute amount given to each individual depends on pharmacological properties such as bioavailability, clearance rate and route of administration.

For treatment of an individual, depending on activity of the agent, manner of administration, purpose of the administration (i.e., prophylactic or therapeutic), nature and severity of the disorder, age and body weight of the individual, different doses may be necessary. Dosages are generally selected by the physician or other health care professional in accordance with a variety of parameters known in the art, such as severity of symptoms, history of the individual and the like. In some embodiments, an effective amount of the TLR inhibitor may be used in the methods described herein.

The administration of a given dose can be carried out both by single administration in the form of an individual dose unit or else in several smaller dose units. Repeated and multiple administration of doses at specific intervals of days, weeks, or months apart are also contemplated.

The effective amount and method of administration of the particular TLR inhibitor formulation can vary based on the individual patient, desired result and/or type of disorder, the stage of the disease and other factors evident to one skilled in the art. The route(s) of administration useful in a particular application are apparent to one of skill in the art. Routes of administration include but are not limited to topical, dermal, transdermal, transmucosal, epidermal, parenteral, gastrointestinal, and naso-pharyngeal and pulmonary, including transbronchial and transalveolar. A suitable dosage range is one that provides sufficient TLR inhibitor-containing formulation to attain a tissue concentration of about 1-50 $\mu$M as measured by blood levels. The absolute amount given to each patient depends on pharmacological properties such as bioavailability, clearance rate and route of administration.

Any one of the pharmaceutical formulations comprising a TLR inhibitor described herein may be administered by systemic (e.g., parenteral) or local (e.g., topical or intralesional injection) administration. In some embodiments, the pharmaceutical formulation is topically, parenterally, orally, vaginally, intrauterine, intranasal, or by inhalation administered. As described herein, tissues in which unwanted immune activation is occurring or is likely to occur are preferred targets for the TLR inhibitor. Thus, administration of the TLR inhibitor to lymph nodes, spleen, bone marrow, blood, as well as tissue exposed to virus, are preferred sites of administration.

In some embodiments, the pharmaceutical formulation comprising a TLR inhibitor is administered parenterally. Parenteral routes of administration include, but are not limited to, transdermal, transmucosal, nasopharyngeal, pulmonary and direct injection. Parenteral administration by injection may be by any parenteral injection route, including, but not limited to, intravenous (IV), including bolus and infusion (e.g., fast or slow), intraperitoneal (IP), intramuscular (IM), subcutaneous (SC) and intradermal (ID) routes. Transdermal and transmucosal administration may be accomplished by, for example, inclusion of a carrier (e.g., dimethylsulfoxide, DMSO), by application of electrical impulses (e.g., iontophoresis) or a combination thereof. A variety of devices are available for transdermal administration which may be used. Formulations of TLR inhibitors suitable for parenteral administration are generally formulated in USP water or water for injection and may further comprise pH buffers, salts bulking agents, preservatives, and other pharmaceutically acceptable excipients. Immunoinhibitory polynucleotide for parenteral injection may be formulated in pharmaceutically acceptable sterile isotonic solutions such as saline and phosphate buffered saline for injection.

Transdermal administration is accomplished by application of a cream, rinse, gel, etc. capable of allowing the TLR inhibitor to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference. Transdermal transmission may also be accomplished by iontophoresis, for example using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter. Administration via the transdermal and transmucosal routes may be continuous or pulsatile.

Gastrointestinal routes of administration include, but are not limited to, ingestion and rectal routes and can include the use of, for example, pharmaceutically acceptable powders, pills or liquids for ingestion and suppositories for rectal administration.

Naso-pharyngeal and pulmonary administration include are accomplished by inhalation, and include delivery routes such as intranasal, transbronchial and transalveolar routes. Formulations of TLR inhibitors suitable for administration by inhalation including, but not limited to, liquid suspensions for forming aerosols as well as powder forms for dry powder inhalation delivery systems are provided. Devices suitable for administration by inhalation of TLR inhibitor formulations include, but are not limited to, atomizers, vaporizers, nebulizers, and dry powder inhalation delivery devices. Other methods of delivering to respiratory mucosa include delivery of liquid formulations, such as by nose drops. Administration by inhalation is preferably accomplished in discrete doses (e.g., via a metered dose inhaler), although delivery similar to an infusion may be accomplished through use of a nebulizer.

As described herein, tissues in which unwanted immune activation is occurring or is likely to occur are suitable targets for the TLR inhibitors. Thus, administration of the TLR inhibitor composition to lymph nodes, spleen, bone marrow, blood, as well as tissue exposed to virus, are preferred sites of administration.

As is well known in the art, solutions or suspensions used for the routes of administration described herein can include any one or more of the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

As is well known in the art, pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. It may be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

As is well known in the art, sterile injectable solutions can be prepared by incorporating the active compound(s) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In any of the methods described herein a TLR inhibitor may be administered in an amount sufficient to inhibit an immune response. As described herein, the immune response may be humoral and/or cellular, and is measured using standard techniques in the art and as described herein. In some aspects, provided herein are methods for suppressing, reducing, and/or inhibiting TLR7, TLR8, and/or TLR9 dependent cell stimulation (e.g., TLR signaling in a cell expressing the TLR). In some aspects, at least one TLR inhibitor is administered in an amount effective to inhibit an immune response in the individual.

As demonstrated herein, some TLR inhibitors suppress TLR7-dependent, TLR-8-dependent, and/or TLR9 dependent immune responses. In some embodiments, methods are provided for inhibiting a TLR7-dependent, TLR-8-dependent, and/or TLR9 immune response in an individual, comprising administering a TLR inhibitor described herein in an amount sufficient to suppress TLR7-dependent, TLR-8-dependent, and/or TLR9 cytokine production in the individual. In some embodiments, the TLR7-dependent, TLR-8-dependent, and/or TLR9 immune response is an innate immune response. In some embodiments, the TLR7-dependent, TLR-8-dependent, and/or TLR9 immune response is an adaptive immune response.

In some embodiments, the compositions described herein inhibit a response of a monocytes, macrophages, myeloid dendritic cells, regulatory T-cells, B-cells, and neutrophils. In some embodiments, immune responses inhibited by the compositions described herein include inhibition of cytokine production, such as IL-1β and/or TNF, by the cell, inhibition of cell maturation and/or inhibition of cell proliferation. In some embodiments, the compositions described herein inhibit a TLR7-dependent, TLR-8-dependent, and/or TLR9 cell response.

The above-mentioned compositions and methods of administration are meant to describe but not limit the methods of administering the formulations of TLR inhibitors described herein. The methods of producing the various compositions and devices are within the ability of one skilled in the art and therefore are not described in detail here.

Combination Therapy

The TLR inhibitors of the present disclosure can be administered in combination with one or more additional therapeutic agents. As described herein, the TLR inhibitors can be combined with a physiologically acceptable carrier. The methods described herein may be practiced in combination with other therapies that make up the standard of care for the disorder, such as administration of anti-inflammatory agents.

In some embodiments, a TLR inhibitor is administered in combination with a corticosteroid. In some embodiments, the corticosteroid is a glucocorticosteroid. In some embodiments, the corticosteroid is a mineralocorticoid. Corticosteroids include, but are not limited to, corticosterone and derivatives, prodrugs, isomers and analogs thereof, cortisone and derivatives, prodrugs, isomers and analogs thereof (i.e., Cortone), aldosterone and derivatives, prodrugs, isomers and analogs thereof, dexamethasone and derivatives, prodrugs, isomers and analogs thereof (i.e., Decadron), prednisone and derivatives, prodrugs, isomers and analogs thereof (i.e., Prelone), fludrocortisones and derivatives, prodrugs, isomers and analogs thereof (i.e. FLORINEF®), hydrocortisone and derivatives, prodrugs, isomers and analogs thereof (i.e., cortisol or Cortef), hydroxycortisone and derivatives, prodrugs, isomers and analogs thereof, betamethasone and derivatives, prodrugs, isomers and analogs thereof (i.e., Celestone), budesonide and derivatives, prodrugs, isomers and analogs thereof (i.e., Entocort EC), methylprednisolone and derivatives, prodrugs, isomers and analogs thereof (i.e., Medrol), prednisolone and derivatives, prodrugs, isomers and analogs thereof (i.e., Deltasone, Crtan, Meticorten, Orasone, or Sterapred), triamcinolone and derivatives, prodrugs, isomers and analogs thereof (i.e., Kenacort or Kenalog), and the like. In some embodiments, the corticosteroid is fludrocortisone or a derivative, prodrug, isomer or analog thereof. In some embodiments, the corticosteroid is fludrocortisone. In some embodiments, the corticosteroid is hydroxycortisone or a derivative, prodrug, isomer or analog thereof. In some embodiments, the corticosteroid is hydroxycortisone.

In some embodiments, the corticosteroid is administered between about any of 0.001 mg to 1 mg, 0.5 mg to 1 mg, 1 mg to 2 mg, 2 mg to 20 mg, 20 mg to 40 mg, 40 to 80 mg, 80 to 120 mg, 120 mg to 200 mg, 200 mg to 500 mg, or 500 mg to 1000 mg per day. In some embodiments, the corticosteroid is administered between about any of 0.1 mg/kg to 0.5 mg/kg, 0.5 mg/kg to 1 mg/kg, 1 mg/kg to 2 mg/kg, 2 mg/kg to 5 mg/kg, 5 mg/kg to 10 mg/kg, 10 mg/kg to 15 mg/kg, 15 mg/kg to 20 mg/kg, 20 mg/kg to 25 mg/kg, 25 mg/kg to 35 mg/kg, or 35 mg/kg to 50 mg/kg per day.

In some embodiments, the TLR inhibitor used in combination therapy, given in amounts of the TLR inhibitor delivered, may be, for example, from about any of 0.1 to 10 mg/kg, 0.5 to 10 mg/kg, 1 to 10 mg/kg, 0.1 to 20 mg/kg, 0.1 to 20 mg/kg, or 1 to 20 mg/kg.

In some embodiments, the TLR inhibitor is administered simultaneously with one or more additional therapeutic agents including, but not limited to, a corticosteroid (simultaneous administration). In some embodiments, the TLR inhibitor is administered sequentially with an additional therapeutic agent including, but not limited to, a corticosteroid (sequential administration). In some embodiments, sequential administration includes administering the TLR inhibitor or additional therapeutic agent followed within about any of one minutes, five minutes, 30 minutes, one hour, five hours, 24 hours, 48 hours, or a week. In some embodiments, the TLR inhibitor is administered by the same route of administration as the additional therapeutic agent. In some embodiments, the TLR inhibitor is administered by a different route of administration than the additional therapeutic agent. In some embodiments, the additional therapeutic agent is administered parentally (e.g., central venous line, intra-arterial, intravenous, intramuscular, intraperitoneal, intradermal, or subcutaneous injection), orally, gastro-intestinally, topically, naso-pharyngeal and pulmonary (e.g. inhalation or intranasally). In some embodiments, the additional therapeutic agent is a corticosteroid.

In some embodiments, the combination of a TLR inhibitor with one or more additional therapeutic agents reduces the effective amount (including, but not limited to, dosage volume, dosage concentration, and/or total drug dose administered) of the TLR inhibitor and/or the one or more additional therapeutic agents administered to achieve the same result as compared to the effective amount administered when the TLR inhibitor or the additional therapeutic agent is administered alone. In some embodiments, the combination of a TLR inhibitor with a corticosteroid reduces the effective amount of corticosteroid administered as compared to the corticosteroid administered alone. In some embodiments, the combination of a TLR inhibitor with the additional therapeutic agents reduces the frequency of administrations of the therapeutic agent compared to administration of the additional therapeutic agent alone. In some embodiments, the combination of a TLR inhibitor with the additional therapeutic agent reduces the total duration of treatment compared to administration of the additional therapeutic agent alone. In some embodiments, the combination of a TLR inhibitor with the additional therapeutic agent reduces the side effects associated with administration of the additional therapeutic agent alone. In some embodiments, the additional therapeutic agent is a corticosteroid. In some embodiments, the corticosteroid is fludrocortisone or a derivative, prodrug, isomer or analog thereof. In some embodiments, the corticosteroid is fludrocortisone. In some embodiments, the combination of an effective amount of the TLR inhibitor with the additional therapeutic agent is more efficacious compared to an effective amount of the TLR inhibitor or the additional therapeutic agent alone.

TLR inhibitors also may be useful as a vaccine adjuvant for use in conjunction with any material that modulates either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; recombinant proteins; glycoproteins; peptides; and the like. In some aspects, the combination therapy including but not limited to the combination of a TLR inhibitor and a vaccine is used in the treatment of an autoimmune disease or an inflammatory disorder. In some aspects, the combination therapy including but not limited to the combination of a TLR inhibitor and a vaccine is used in the treatment of an infectious disease.

In some embodiments, the combination therapy including but not limited to the combination of a TLR inhibitor and a corticosteroid is used in the treatment of an autoimmune disease or an inflammatory disorder. In some embodiments, the autoimmune disease is selected from but not limited to rheumatoid arthritis, systemic lupus erythematosus, autoimmune skin disease, multiple sclerosis, pancreatitis, glomerulonephritis, pyelitis, Sclerosing cholangitis, and type I diabetes. In some embodiments, the autoimmune disease is Sjogren's disease.

V. Kits, Vials, and Unit Dosage Forms

Also provided herein are kits comprising a TLR inhibitor and instructions for use in the methods of inhibiting a TLR7-, TLR8- and/or TLR9-dependent immune response.

The kits may comprise one or more containers comprising a TLR inhibitor (or a formulation comprising a TLR inhibitor) and a set of instructions, generally written instructions although electronic storage media (e.g., magnetic diskette or optical disk) containing instructions are also acceptable, relating to the use and dosage of the TLR inhibitor or formulation for the intended treatment (e.g., suppression of a response to a TLR7, TLR8, and/or TLR9 agonists, suppression of a TLR7-, TLR8-, and/or TLR9-dependent immune response, ameliorating one or more symptoms of an autoimmune disease, ameliorating a symptom of chronic inflammatory disease, decreasing cytokine production in response to a virus, and/or treating and/or preventing one or more symptoms of a disease or disorder mediated by TLR7, TLR8, and/or TLR9). The instructions included with the kit generally include information as to dosage, dosing schedule, and route of administration for the intended treatment. The containers for the TLR inhibitor (or formulations comprising a TLR inhibitor) may be unit doses, bulk packages (e.g., multi-dose packages) or sub-unit doses. The kits may further comprise a container comprising an adjuvant.

The container of the kits may include at least one vial, test tube, flask, bottle, syringe or other container, into which a component may be placed, and preferably, suitably aliquoted. Where there is more than one component in the kit, the kit may contain a second, third or other additional container into which the additional components may be separately placed. However, various combinations of components may be comprised in a vial. The kits also will typically include a component for containing the containers in close confinement for commercial sale. Such containers may include injection or blow molded plastic containers in which the desired vials are retained.

When the components of the kit are provided in one and/or more liquid solutions, the liquid solution is an aqueous solution, with a sterile aqueous solution being particularly preferred. The components of the kit may also be provided as dried powder(s). When reagents and/or components are provided as a dry powder, the powder can be reconstituted by the addition of a suitable solvent. It is envisioned that the solvent may also be provided in another container means.

The TLR inhibitor formulation component of the kit may be packaged in any convenient, appropriate packaging. For example, if the TLR inhibitor is a freeze-dried formulation, a vial with a resilient stopper is normally used, so that the TLR inhibitor may be easily reconstituted by injecting fluid through the resilient stopper. Ampoules with non-resilient, removable closures (e.g., sealed glass) or resilient stoppers are most conveniently used for injectable forms of TLR inhibitor. Also, prefilled syringes may be used when the kit is supplied with a liquid formulation of the TLR inhibitor. The kit may contain the TLR inhibitor in an ointment for topical formulation in appropriate packaging. Also contemplated are packages for use in combination with a specific device, such as an inhaler, nasal administration device (e.g., an atomizer), transdermal administration device, or an infusion device such as a minipump.

A kit may include instructions for employing the kit components as well as the use of any other reagent(s) not included in the kit. Instructions may include embodiments that can be implemented.

Also provided are vials (e.g., sealed vials) comprising any one of the TLR inhibitor or formulations described herein. In some embodiments, the vials comprising the TLR inhibitor in combination with a vial comprising a therapeutic agent. In some embodiments, wherein the vials are provide in a kit.

Also provided are unit dosage forms for the treatment and/or prevention of a disease or disorder mediated by TLR7, TLR8, and/or TLR9, the dosage forms comprising any one of the TLR inhibitor or formulations described herein. In some embodiments, the unit dosage forms comprising the TLR inhibitor in combination with a unit dosage form of a therapeutic agent. In some embodiments, wherein the dosage forms are provide in a kit.

EXAMPLES

Abbreviations: APS (anti-phospholipid syndrome); CT (threshold cycle); CTRL (control); DNA (deoxyribonucleic acid); ELISA (enzyme-linked immunosorbent assay); FACS (fluorescence activated cell sorter); hTLR8Tg (human Toll-like receptor 8 transgenic); IC50 (half maximal inhibitory concentration); IIS (immunoinhibitory sequence); KO (knock out); mcg or μg (microgram); MCTD (mixed connective tissue disease); MDC (myeloid dendritic cells); MOI (multiplicity of infection); PBMC (peripheral blood mononuclear cells); PDC (plasmacytoid dendritic cells); PN (polynucleotides); RA (rheumatoid arthritis); RNA (ribonucleic acid); SF (synovial fluid); slanDC (6-sulpho LacNAc dendritic cells); TLR (Toll-like receptor); and WT (wild type).

Example 1—TLR8 Expression

TLR8 expression was analyzed in human cellular subsets. Plasmacytoid dendritic cells (pDCs), monocytes, myeloid dendritic cells (mDC), CD4+ T-cells, CD8+ T-cells, and neutrophils were purified by means of magnetic beads (Miltenyi Biotech) according to manufacture instructions. RNA was purified with a micro RNA KIT (Qiagen) according to manufacture instructions. cDNA from RNA was generated with SuperScript First-Strand Synthesis System (Invitrogen). Threshold cycle (CT) values for each gene were normalized to the housekeeping gene Ubiquitin using the formula: relative $CT = 1.8^{(Avg\ CT\ Ubi - CT\ Gene)} * 100{,}000$ where Avg CT Ubi is the mean CT of triplicate housekeeping gene runs, Avg CT Gene is the mean CT of duplicate runs of the gene of interest, and 100,000 is arbitrarily chosen as a factor to bring all values above one. The human TLR8 coding sequence of GENBANK Accession No. NM_138636.4 is set forth as SEQ ID NO:1:

```
ATGGAAAACATGTTCCTTCAGTCGTCAATGCTGACCTGCATTTTCCTGCT

AATATCTGGTTCCTGTGAGTTATGCGCCGAAGAAATTTTTCTAGAAGCT

ATCCTTGTGATGAGAAAAGCAAAATGACTCAGTTATTGCAGAGTGCAGC

AATCGTCGACTACAGGAAGTTCCCCAAACGGTGGGCAAATATGTGACAGA

ACTAGACCTGTCTGATAATTTCATCACACACATAACGAATGAATCATTTC

AAGGGCTGCAAAATCTCACTAAAATAAATCTAAACCACAACCCCAATGTA

-continued
CAGCACCAGAACGGAAATCCCGGTATACAATCAAATGGCTTGAATATCAC

AGACGGGGCATTCCTCAACCTAAAAAACCTAAGGGAGTTACTGCTTGAAG

ACAACCAGTTACCCCAAATACCCTCTGGTTTGCCAGAGTCTTTGACAGAA

CTTAGTCTAATTCAAAACAATATATACAACATAACTAAAGAGGGCATTTC

AAGACTTATAAACTTGAAAAATCTCTATTTGGCCTGGAACTGCTATTTTA

ACAAAGTTTGCGAGAAAACTAACATAGAAGATGGAGTATTTGAAACGCTG

ACAAATTTGGAGTTGCTATCACTATCTTTCAATTCTCTTTCACACGTGCC

ACCCAAACTGCCAAGCTCCCTACGCAAACTTTTTCTGAGCAACACCCAGA

TCAAATACATTAGTGAAGAAGATTTCAAGGGATTGATAAATTTAACATTA

CTAGATTTAAGCGGGAACTGTCCGAGGTGCTTCAATGCCCCATTTCCATG

CGTGCCTTGTGATGGTGGTGCTTCAATTAATATAGATCGTTTTGCTTTTC

AAAACTTGACCCAACTTCGATACCTAAACCTCTCTAGCACTTCCCTCAGG

AAGATTAATGCTGCCTGGTTTAAAAATATGCCTCATCTGAAGGTGCTGGA

TCTTGAATTCAACTATTTAGTGGGAGAAATAGCCTCTGGGGCATTTTTAA

CGATGCTGCCCCGCTTAGAAATACTTGACTTGTCTTTTAACTATATAAAG

GGGAGTTATCCACAGCATATTAATATTTCCAGAAACTTCTCTAAACTTTT

GTCTCTACGGGCATTGCATTTAAGAGGTTATGTGTTCCAGGAACTCAGAG

AAGATGATTTCCAGCCCCTGATGCAGCTTCCAAACTTATCGACTATCAAC

TTGGGTATTAATTTTATTAAGCAAATCGATTTCAAACTTTTCCAAAATTT

CTCCAATCTGGAAATTATTTACTTGTCAGAAAACAGAATATCACCGTTGG

TAAAAGATACCCGGCAGAGTTATGCAAATAGTTCCTCTTTTCAACGTCAT

ATCCGGAAACGACGCTCAACAGATTTTGAGTTTGACCCACATTCGAACTT

TTATCATTTCACCCGTCCTTTAATAAAGCCACAATGTGCTGCTTATGGAA

AAGCCTTAGATTTAAGCCTCAACAGTATTTTCTTCATTGGGCCAAACCAA

TTTGAAAATCTTCCTGACATTGCCTGTTTAAATCTGTCTGCAAATAGCAA

TGCTCAAGTGTTAAGTGGAACTGAATTTTCAGCCATTCCTCATGTCAAAT

ATTTGGATTTGACAAACAATAGACTAGACTTTGATAATGCTAGTGCTCTT

ACTGAATTGTCCGACTTGGAAGTTCTAGATCTCAGCTATAATTCACACTA

TTTCAGAATAGCAGGCGTAACACATCATCTAGAATTTATTCAAAATTTCA

CAAATCTAAAAGTTTTAAACTTGAGCCACAACAACATTTATACTTTAACA

GATAAGTATAACCTGGAAAGCAAGTCCCTGGTAGAATTAGTTTTCAGTGG

CAATCGCCTTGACATTTTGTGGAATGATGATGACAACAGGTATATCTCCA

TTTTCAAAGGTCTCAAGAATCTGACACGTCTGGATTTATCCCTTAATAGG

CTGAAGCACATCCCAAATGAAGCATTCCTTAATTTGCCAGCGAGTCTCAC

TGAACTACATATAAATGATAATATGTTAAAGTTTTTTAACTGGACATTAC

TCCAGCAGTTTCCTCGTCTCGAGTTGCTTGACTTACGTGGAAACAAACTA

CTCTTTTTAACTGATAGCCTATCTGACTTTACATCTTCCCTTCGGACACT

GCTGCTGAGTCATAACAGGATTTCCCACCTACCCTCTGGCTTTCTTTCTG

AAGTCAGTAGTCTGAAGCACCTCGATTTAAGTTCCAATCTGCTAAAAACA

ATCAACAAATCCGCACTTGAAACTAAGACCACCACCAAATTATCTATGTT

GGAACTACACGGAAACCCCTTTGAATGCACCTGTGACATTGGAGATTTCC
```

-continued

```
GAAGATGGATGGATGAACATCTGAATGTCAAAATTCCCAGACTGGTAGAT

GTCATTTGTGCCAGTCCTGGGGATCAAAGAGGGAAGAGTATTGTGAGTCT

GGAGCTAACAACTTGTGTTTCAGATGTCACTGCAGTGATATTATTTTTCT

TCACGTTCTTTATCACCACCATGGTTATGTTGGCTGCCCTGGCTCACCAT

TTGTTTTACTGGGATGTTTGGTTTATATATAATGTGTGTTTAGCTAAGGT

AAAAGGCTACAGGTCTCTTTCCACATCCCAAACTTTCTATGATGCTTACA

TTTCTTATGACACCAAAGATGCCTCTGTTACTGACTGGGTGATAAATGAG

CTGCGCTACCACCTTGAAGAGAGCCGAGACAAAAACGTTCTCCTTTGTCT

AGAGGAGAGGGATTGGGATCCGGGATTGGCCATCATCGACAACCTCATGC

AGAGCATCAACCAAAGCAAGAAAACAGTATTTGTTTTAACCAAAAAATAT

GCAAAAAGCTGGAACTTTAAAACAGCTTTTTACTTGGCTTTGCAGAGGCT

AATGGATGAGAACATGGATGTGATTATATTTATCCTGCTGGAGCCAGTGT

TACAGCATTCTCAGTATTTGAGGCTACGGCAGCGGATCTGTAAGAGCTCC

ATCCTCCAGTGGCCTGACAACCCGAAGGCAGAAGGCTTGTTTTGGCAAAC

TCTGAGAAATGTGGTCTTGACTGAAAATGATTCACGGTATAACAATATGT

ATGTCGATTCCATTAAGCAATACTAA
```

Neutrophils showed the highest level of TLR8 expression, followed by monocytes, mDCs and CD4+ T-cells (e.g., neutrophils>>monocytes>mDCs>CD4+ T-cells). No appreciable TLR8 expression was detected in pDCs and CD8+ T-cells.

Example 2—Activity of TLR7 and TLR8 Using RNA Polynucleotides (PN) in Human and Mouse Cells A PN-based TLR7 ligand stabilized immunomodulatory RNA (5'-URCURCUUCUR-/glycerol/-RUCUUCRUCRU-5' with R=7-deazaguanosine, hereinafter "TLR7 agonist" set forth as SEQ ID NO:2-/glycerol/-SEQ ID NO:117) and a PN-based TLR8 ligand stabilized immunomodulatory RNA (5'-M2UGCUGCUUGUG-/glycerol/-GUGUUCGU-CGUM2-5' with M2=C6-linker, hereinafter ORN8L or "TLR8 agonist" set forth as SEQ ID NO:3-/glycerol/-SEQ ID NO:118) were previously described (Lan et al., PNAS, 104:13750-13755, 2007). The effect of the TLR7- and TLR8-stimulating RNA PN was evaluated by measuring production of IL-6 and TNF-α in human peripheral blood mononuclear cells (PBMCs) and human monocytes. About $5 \times 10^5$ PBMCs or $2 \times 10^5$ monocytes from human healthy donors were stimulated with 20 µg/mL, 100 µg/mL, or 200 µg/mL of either TLR8 agonist or TLR7 agonist. Twenty-four hours later supernatants were assessed for inflammatory cytokines IL-6 and TNF-α by a standard ELISA procedure. TLR7 and TLR8 agonists stimulated production of IL-6 and TNF-α in PBMCs and, to a lesser extent, in monocytes.

The effect of TLR7 and TLR8-stimulating RNA PN were also evaluated in human pDCs, which are TLR8-negative, by measuring production of IL-6, TNF-α, and IFN-α. About $1 \times 10^5$ pDCs from human healthy donors were stimulated with 100 µg/mL of either TLR8 agonist or TLR7 agonist (Lan et al., PNAS, 104:13750-13755, 2007) or medium alone. Twenty-four hours later supernatants were assessed for inflammatory cytokines IL-6, TNF-α, and IFN-α, by a standard ELISA procedure. The TLR7 agonist but not the TLR8 agonist stimulated production of IL-6, TNF-α, and IFN-α by human pDCs. Thus the TLR8 agonist is specific for TLR8.

The effect of TLR7 and TLR8-stimulating RNA PNs was further evaluated in mouse cells by measuring IL-12 and TNF-α production. Mouse splenocytes and PBMCs were prepared from 129S2/SvPasCrl wild type mice (Charles River Laboratories, Wilmington, Mass.) and TLR7KO mice. About $5 \times 10^5$ cells were stimulated with 100 µg/ml of either TLR8 agonist or TLR7 agonist. IL-12 and TNF-α were measured by ELISA using standard techniques. The TLR7 agonist but not the TLR8 agonist stimulated production of IL-12 and TNF-α, by mouse splenocytes and PBMCs.

Example 3—TLR7-, TLR8- and TLR9-Specific Inhibition Screening Assays

The following TLR7-, TLR8- and TLR9-specific screening assays were used to evaluate the inhibitory activity of test polynucleotides (PN). Average results from a minimum of three donors were reported either as cytokine levels or % inhibition. Percent inhibition was calculated as $[1-(Ri/Ro)] \times 100\%$, where $Ri$=cytokine level for test PN+stimulator and $Ro$=cytokine level for stimulator only.

For assays with enough titration points, generally a minimum of about 10 over three orders of magnitude, IC50 values (half maximal inhibitory concentration) were calculated using GraphPad Prizm 5 software. Because these assays use primary cells, there was some donor variation in the response to both the agonist used for stimulation and the TLR inhibitors. Therefore, while qualitative comparisons were made between assays using different donors, quantitative comparisons were made only for PN that were tested with the same set of donors.

TLR7-Specific Inhibition Screening Assay in Human Plasmacytoid Dendritic Cells (PDCs)

Human PDCs stimulated with influenza virus strain PR/8 (ATCC) respond by producing IFN-α. This response is dependent on TLR7 signaling and is independent of TLR8 and TLR9.

Human PDC were isolated using a positive selection kit from Melteni Biotec (Catalog No. 130-090-532) according to the manufacturer's instructions. Primary human PDCs ($3-5 \times 10^4$ cells/well) were stimulated with heat-inactivated influenza at 2 multiplicity of infection (MOI) in complete medium, either alone or in the presence of the test PN, for 18-24 hours at 37° C. Concentrations of the test polynucleotides ranged from 0.002 µM to 1 µM, although not all concentrations were used in all experiments. At 18-24 hours, supernatants were collected and IFN-α production was measured by ELISA.

TLR8-Specific Inhibition Screening Assay in Human Monocytes

Human monocytes stimulated with the TLR8-specific agonist ORN8L respond by producing TNF-α, IL-1β and IL-6. This response is dependent on TLR8 signaling and is independent of TLR7 and TLR9.

Human monocytes were isolated using a negative depletion kit from Stem Cell (Catalog No. 14068) according to the manufacturer's instructions. Primary human monocytes ($5 \times 10^5$ cells/well) were stimulated with 150 µg/mL of ORN8L in complete medium, either alone or in the presence of the test PN, for 16-18 hours at 37° C. Concentrations of the test polynucleotides ranged from 0.002 µM to 1 µM, although not all concentrations were used in all experiments.

At 16-18 hours, supernatants were collected and levels of TNF-α, IL-1β, and IL-6 were measured by ELISA. The inhibitory responses of the PN determined from measuring TNF-α, IL-1β, and IL-6 levels showed the same trend, and therefore not all cytokines were measured for each experiment.

TLR9-Specific Inhibition Screening Assay in Human B Cells and Human PDC

TLR9-specific inhibition screening assays were performed either in human B cells, human PDC, or both. Human B cells stimulated with CpG-containing immunostimulatory sequence (ISS) respond by producing IL-6. This response is dependent on TLR9 signaling and is independent of TLR7 and TLR8. Human PDCs stimulated with CpG-containing immunostimulatory sequence (ISS) respond by producing IFN-α. This response is dependent on TLR9 signaling and is independent of TLR7 and TLR8.

Human B cells were isolated using a positive selection kit from Miltenyi Biotec (Catalog No. 130-050-301) according to the manufacturer's instructions. Primary human B cells ($2\times10^5$ cells/well) were stimulated with 1 µM of TLR9L CpG-ISS 1018 (5'-TGA CTG TGA ACG TTC GAG ATG A-3' set forth as SEQ ID NO:4) in complete medium, either alone or in the presence of the test PN, for 40-48 hours at 37° C. Concentrations of the test polynucleotides ranged from 0.03 µM to 2 µM, although not all concentrations were used in all experiments. At 40-48 hours, supernatants were collected and IL-6 production was measured by ELISA.

Human PDC were isolated using a positive selection kit from Melteni Biotec (Catalog No. 130-090-532) according to the manufacturer's instructions. Primary human PDCs ($3-5\times10^4$ cells/well) were stimulated with 0.5 µM of TLR9L CpG-ISS C274 (5'-TCG TCG AAC GTT CGA GAT GAT-3' set forth as SEQ ID NO:5) in complete medium, either alone or in the presence of the test PN, for 18-24 hours at 37° C. Concentrations of the test polynucleotides ranged from 0.002 µM to 1 µM, although not all concentrations were used in all experiments. At 18-24 hours, supernatants were collected and IFN-α production was measured by ELISA.

Example 4—Polynucleotide (PN) Sequences

Table 4-1 shows the sequences of the PN referred to throughout the present disclosure. Upper case letters represent 2'-deoxyribonucleotides (DNA) and lower case letters represent 2'-O-methyl ribonucleotides (2'-OMe-RNA). Unless otherwise noted, the internucleotide linkages were all phosphorothioate. PN were synthesized using standard solid phase DNA synthesis procedures by TriLink Biotechnologies (San Diego, Calif.). "I" represents to 2'-deoxyinosine.

TABLE 4-1

Polynucleotide Sequences

| SEQ ID NO | PART NO | SEQUENCE |
|---|---|---|
| 6 | C869 | 5'-TCC TGG AGG GGT TGT-3' |
| 7 | C954 | 5'-TGC TCC TGG AGG GGT TGT-3' |
| 8 | DV134 | 5'-ugc TGC TCC TTG AGG GGT Tgu uug u-3' |
| 9 | DV197 | 5'-ugc TGC TCC TTG AGI-3' |
| 10 | DVX1 | 5'-ugc TGC TCC TTG AGA-3' |
| 11 | DVX2 | 5'-ugc TGC TCC TTG AGT-3' |

TABLE 4-1-continued

Polynucleotide Sequences

| SEQ ID NO | PART NO | SEQUENCE |
|---|---|---|
| 12 | DVX3 | 5'-ugc TGC TCC TTG AGG-3' |
| 13 | DVX4 | 5'-ugc TGC TCC TTG AGC-3' |
| 14 | DVX5 | 5'-ugc TGC TCC TTG GGI-3' |
| 15 | DVX6 | 5'-ugC TGC TCC TTG AGI-3' |
| 16 | DVX7 | 5'-uGC TGC TCC TTG AGI-3' |
| 17 | DVX8 | 5'-TGC TGC TCC TTG AGI-3' |
| 18 | DVX9 | 5'-ugc ugc TCC TTG AGI-3' |
| 19 | DVX10 | 5'-ugc TGC TGC TGC TGC-3' |
| 20 | DVX11 | 5'-ugc TGC TCC TTG AGI T-3' |
| 21 | DVX12 | 5'-ugc TGC TCC TTG AGI TT-3' |
| 22 | DVX13 | 5'-ugc TGC TCC TTG AGI TTT-3' |
| 23 | DVX14 | 5'-ugc TGC TCC TTG AG-3' |
| 24 | DVX15 | 5'-ugc TGC TCC TTG A-3' |
| 25 | DVX16 | 5'-ugc TGC TCC TTG-3' |
| 26 | DVX17 | 5'-ugc TIC TCC TTI AII-3' |
| 27 | DVX18 | 5'-ugc TGC TCC TTG AGu-3' |
| 28 | DVX19 | 5'-ugc TGC TCC TTG agu-3' |
| 29 | DVX20 | 5'-UGC UGC UUG UG-3' |
| 30 | DVX21 | 5'-TGC TGC TGG TTG TGI-3' |
| 31 | DVX22 | 5'-ucc TGC TCC TTG AGI-3' |
| 32 | DVX23 | 5'-uuu TGC TCC TTG AGI-3' |
| 33 | DVX24 | 5'-uuu uuu TCC TTG AGI-3' |
| 34 | DVX25 | 5'-ugc ugc ucc uug agI-3' |
| 35 | DVX26 | 5'-TGC TCC TTG AGI-3' |
| 36 | DVX27 | 5'-TIC TGC TCC TTG AGI-3' |
| 37 | DVX28 | 5'-TAC TGC TCC TTG AGI-3' |
| 38 | DVX29 | 5'-TTC TGC TCC TTG AGI-3' |
| 39 | DVX30 | 5'-TCC TGC TCC TTG AGI-3' |
| 40 | DVX31 | 5'-TGC TIC TCC TTI AII-3' |
| 41 | DVX32 | 5'-TGC TAC TCC TTA AAA-3' |
| 42 | DVX33 | 5'-TGC TTC TCC TTT ATT-3' |
| 43 | DVX34 | 5'-TGC TCC TCC TTC ACC-3' |
| 44 | DVX35 | 5'-TIC TIC TCC TTI AII-3' |
| 45 | DVX36 | 5'-TAC TAC TCC TTA AAA-3' |
| 46 | DVX37 | 5'-TTC TTC TCC TTT ATT-3' |
| 47 | DVX38 | 5'-TCC TCC TCC TTC ACC-3' |
| 48 | DVX39 | 5'-TIC TCC TTG AGI-3' |
| 49 | DVX40 | 5'-TAC TCC TTG AGI-3' |

TABLE 4-1-continued

Polynucleotide Sequences

| SEQ ID NO | PART NO | SEQUENCE |
|---|---|---|
| 50 | DVX41 | 5'-TTC TCC TTG AGI-3' |
| 51 | DVX42 | 5'-TCC TCC TTG AGI-3' |
| 52 | DVX43 | 5'-TAC TCC TTI AII-3' |
| 53 | DVX44 | 5'-TAC TCC TTA AII-3' |
| 54 | DVX45 | 5'-TAC TCC TTA AAI-3' |
| 55 | DVX46 | 5'-TIC TCC TTI AAI-3' |
| 56 | DVX47 | 5'-TIC TCC TTI AIA-3' |
| 57 | DVX48 | 5'-TIC TCC TTI AAA-3' |
| 58 | DVX49 | 5'-TIC TCC TTI IAI-3' |
| 59 | DVX50 | 5'-TIC TCC TTA IIA-3' |
| 60 | DVX51 | 5'-TIC AGI TTI AII-3' |
| 61 | DVX52 | 5'-TIC AGI AGI AII-3' |
| 62 | DVX53 | 5'-TIC TIC TII TTI AII-3' |
| 63 | DVX55 | 5'-TIC TCC TTI AII-3' |
| 64 | DVX56 | 5'-TIC TCC TTI III-3' |
| 65 | DVX57 | 5'-TIC TCC TTI CII-3' |
| 66 | DVX58 | 5'-TIC TCC TTI GII-3' |
| 67 | DVX59 | 5'-TIC TCC TTI TII-3' |
| 68 | DVX60 | 5'-TCC TTI AII-3' |
| 69 | DVX61 | 5'-TTI AII-3' |
| 70 | DVX64 | 5'-TAC TCC III AII-3' |
| 71 | DVX65 | 5'-TAC TCC CCI AII-3' |
| 72 | DVX66 | 5'-TAC TCC GGI AII-3' |
| 73 | DVX67 | 5'-TAC TCC AAI AII-3' |
| 74 | DVX68 | 5'-TAC TCC TTI AIG-3' |
| 75 | DVX69 | 5'-TAC TCC TTI AIT-3' |
| 76 | DVX70 | 5'-TAC TCC TTI AIC-3' |
| 77 | DVX71 | 5'-TAC TCC TTC AII-3' |
| 78 | DVX72 | 5'-TAC TCC TTT AII-3' |
| 79 | DVX73 | 5'-TAC TCC TTC CII-3' |
| 80 | DVX74 | 5'-TAC TCC TTT TII-3' |
| 81 | DVX75 | 5'-TAC TCC TTG GII-3' |
| 82 | DVX76 | 5'-TAC TCC TTI ACI-3' |
| 83 | DVX77 | 5'-TAC TCC TTI ATI-3' |
| 84 | DVX78 | 5'-CCC CCC TTI AII-3' |
| 85 | DVX79 | 5'-TIC TIC TCC TII TTI CII-3' |
| 86 | DVX80 | 5'-TIC TCC TCC AGI TTI CII-3' |
| 87 | DVX81 | 5'-TIC TIC TCC TCC TTI CII-3' |
| 88 | DVX82 | 5'-TIC TIC TTG AGI TTI CII-3' |
| 89 | DVX83 | 5'-TCC TIC TCC AGI TTI CII-3' |
| 90 | DVX85 | 5'-TIC TIC TCC TCC TTI CII AII-3' |
| 91 | DVX86 | 5'-TIC TCC TCC TTI CII AII-3' |
| 92 | DVX87 | 5'-TGC TCC TCC TTI CII AII-3' |
| 93 | DVX88 | 5'-TGC TTG TCC TCC TTI CII-3' |
| 94 | DVX89 | 5'-TGC TGC TCC TTI CII-3' |
| 95 | DVX90 | 5'-TIC TIC TCC TTI CII-3' |
| 96 | DVX91 | 5'-TAC TAC TCC TTI CII-3' |
| 97 | DVX92 | 5'-TTC TTC TCC TTI CII-3' |
| 98 | DVX93 | 5'-TCC TCC TCC TTI CII-3' |
| 99 | DVX94 | 5'-TIC TCC TCC TTI CII AII A-3' |
| 100 | DVX95 | 5'-TGC TCC TGG AGG TTI CII-3' |
| 101 | DVX96 | 5'-TGC TCC TGG AGG TTI CII AII-3' |
| 102 | DVX97 | 5'-TGC TCC TGG ATT ICI IAI I-3' |
| 103 | DVX98 | 5'-TIC TIC TTG AGI TTI CII AII-3' |
| 104 | DVX99 | 5'-TIC TTG AGI TTI CII AII-3' |
| 105 | DVX100 | 5'-TGC TIC TTG AGI TTI CII AII-3' |
| 106 | DVX101 | 5'-TGC TTG AGI TTI CII AII-3' |
| 107 | DVX102 | 5'-TCC TCC TTG AGI AII-3' |
| 108 | DVX103 | 5'-TIC TCC TTG AGI AII-3' |
| 109 | DVX104 | 5'-TIC TCC TCC TTG AGI AII-3' |
| 110 | DVX105 | 5'-TIC TTC TCC TTG AGI AII-3' |
| 111 | DVX106 | 5'-TIC TCC TCC TTG IIA II-3' |
| 112 | DVX107 | 5'-TCC TGG AGG GGT TIA II-3' |
| 113 | DVX108 | 5'-TGC TCC TGG AGG GGT TIA II-3' |
| 114 | DVX109 | 5'-TIC TCC TCC TTG GGI AII-3' |
| 115 | DVX110 | 5'-TIC TTC TCC TTG GGI AII-3' |
| 116 | DV185 | 5'-ugc TGC TCC TTG AGI GGT TGT TTG T-3' |

Example 5—TLR7 Inhibitors do not Necessarily Inhibit TLR8

Figure 2:
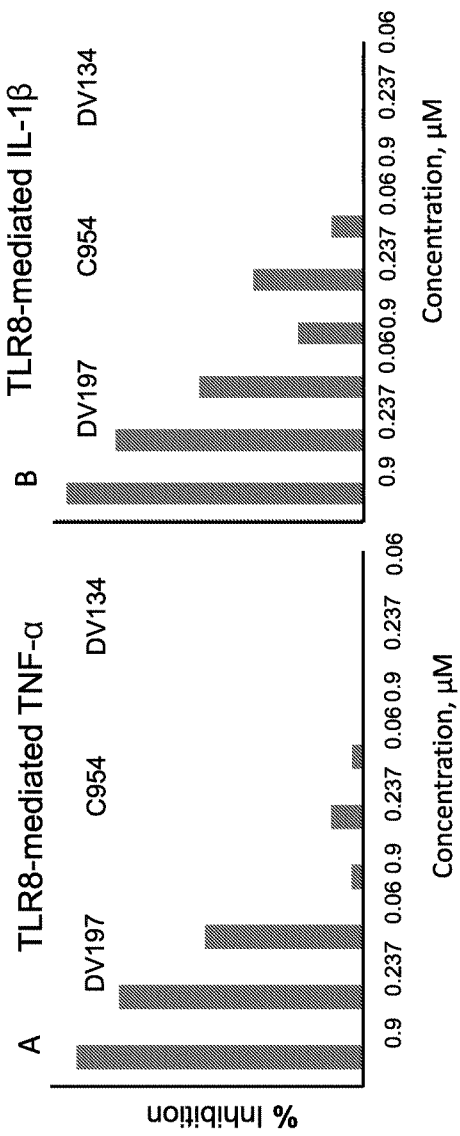
FIGS. 2A and 2B show the percent inhibition of TLR8-mediated TNF-α and IL-1β induction in monocytes stimulated with 150 µg/mL ORN8L by polynucleotides C954, DV197 and DV134 at concentrations of 0.9, 0.237 and 0.06 µM.
Figure 3:
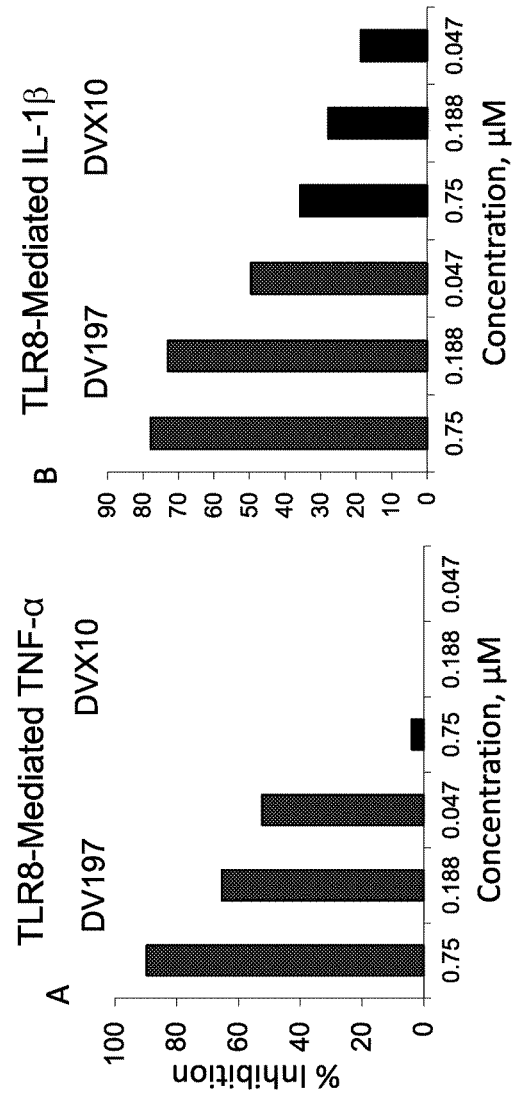
FIGS. 3A and 3B show the percent inhibition of TLR8-mediated TNF-α and IL-1β induction in monocytes stimulated with 150 µg/mL ORN8L by polynucleotides DV197 and DVX10 at concentrations ranging from 0.75 to 0.047 µM.

Known TLR7 inhibitors were tested in the TLR7- and TLR8-specific inhibition assays described in Example 3. As expected, C954, DV197 and DV134 at a concentration of 30 nM all showed good inhibition of TLR7-mediated IFN-α production in PDC stimulated with 2 MOI inactivated influenza virus (FIGS. 1A and 1B). However, only DV197 showed good inhibition of TLR8-mediated TNF-α and IL-1β production in monocytes stimulated with ORN8L (FIGS. 2A and 2B). Previously, 5'-TGC and 5'-ugc were reported to be TLR7/8 inhibitory motifs (see, e.g., U.S. Pub. No. 2007/0238678; and U.S. Pub. No. 2011/0003885). Additionally, 3'-GT and 3'-gu, where G is guanine or 7-deazaguanosine, were previously reported to be TLR8 inhibitory motifs (see, e.g., U.S. Pub. No. 2005/0239733). Thus it was surprising to learn during development of the present disclosure, that these putative TLR8 motifs are not sufficient for TLR8 inhibition. Specifically, DV197, but not C954, DV134 and DVX10, contains a 3'-GI at the 3'-end of the PN. Accordingly, as demonstrated herein, 3'-GT and 3'-gu are not sufficient for TLR8 inhibition. Additionally, although DV197, C954, DV134 and DVX10 all contain a 5'-TGC or 5'-ugc, only DV197 is a potent TLR8 inhibitor (FIGS. 3A and 3B). Accordingly as demonstrated herein, 5'-TGC or 5'-ugc are not sufficient for TLR8 inhibition.

Example 6—DV197 Inhibits TLR8 Activation In Vivo in Human TLR8 Transgenic Mice Human TLR8 transgenic mice were generated as previously described (International App. No. PCT/US2012/031307). Chimeric mice of clone 8, having 1-2 copies of hTLR8 integrated into the genome, were able to breed and pass germline transmission. Therefore, TLR8Tg Clone 8 mice were used for further studies.

Figure 4:
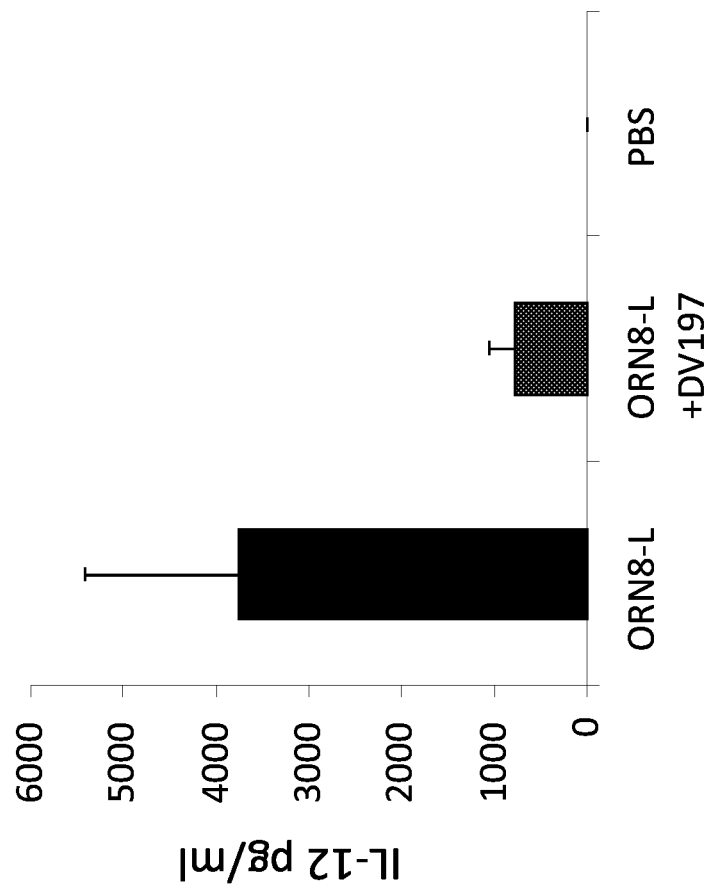
FIG. 4 shows the TLR8-mediated IL-12 induction in hTLR8Tg Clone 8 mice injected with 300 mcg ORN8L given intravenously alone or in combination with DV197 (100 mcg) given subcutaneously.

TLR8Tg Clone 8 mice were injected with 300 mcg of ORN8L (TLR8 agonist) intravenously, alone or in combination with DV197 (100 mcg), which was administered subcutaneously. After 6 hours, mice were bled and IL-12 was measured by ELISA. As shown in FIG. 4, DV197 is able to inhibit TLR8 activation in vivo.

Figure 5:
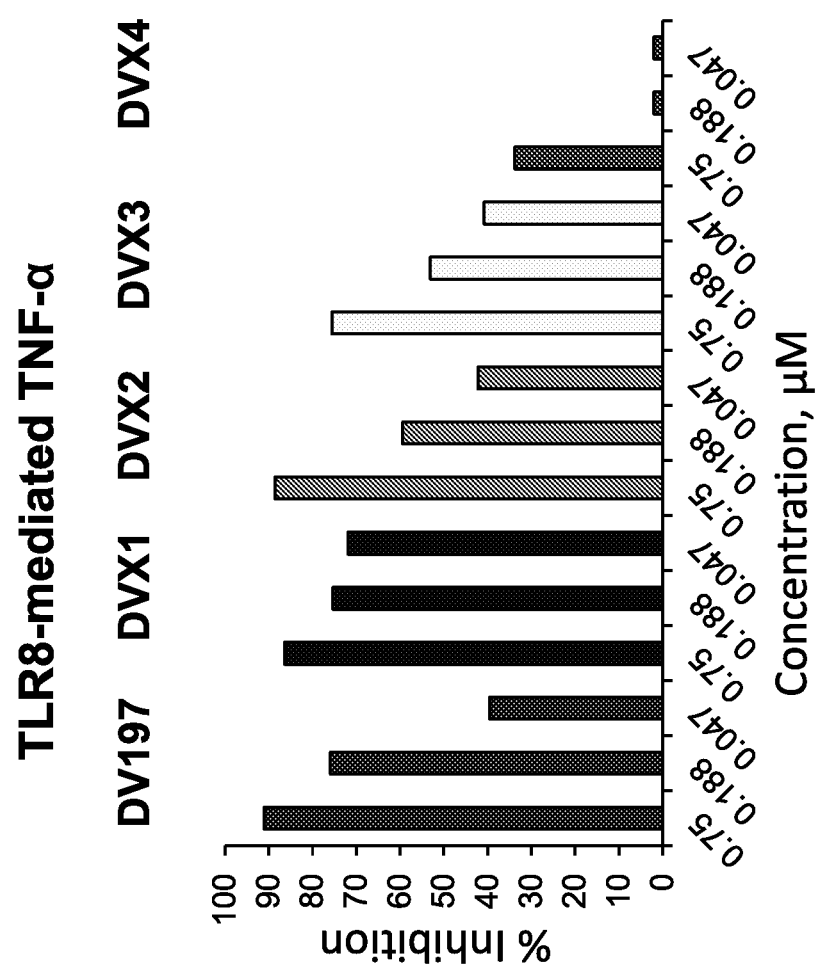
FIG. 5 shows the percent inhibition of TLR8-mediated TNF-α induction in monocytes stimulated with 150 µg/mL ORN8L by polynucleotides DV197, DVX1, DVX2, DVX3 and DVX4 at concentrations ranging from 0.75 to 0.047 µM.

Example 7—Identity of 3'-Nucleotide is Important for TLR8 Inhibitory Activity DV197 analogs containing A, T, G, or C instead of I at the 3'-end (DVX1, DVX2, DVX3 and DVX4, respectively) were tested in the TLR8-specific inhibitory assay described in Example 3. As shown in FIG. 5, the 3'-nucleotide is critical for TLR8 inhibitory activity with 3'-I or 3'-A being the most active. DVX5, which contains GGGI at the 3'-end instead of GAGI like DV197, also retained TLR8 inhibitory activity (~90% inhibition at 0.75 μM).

Figure 6:
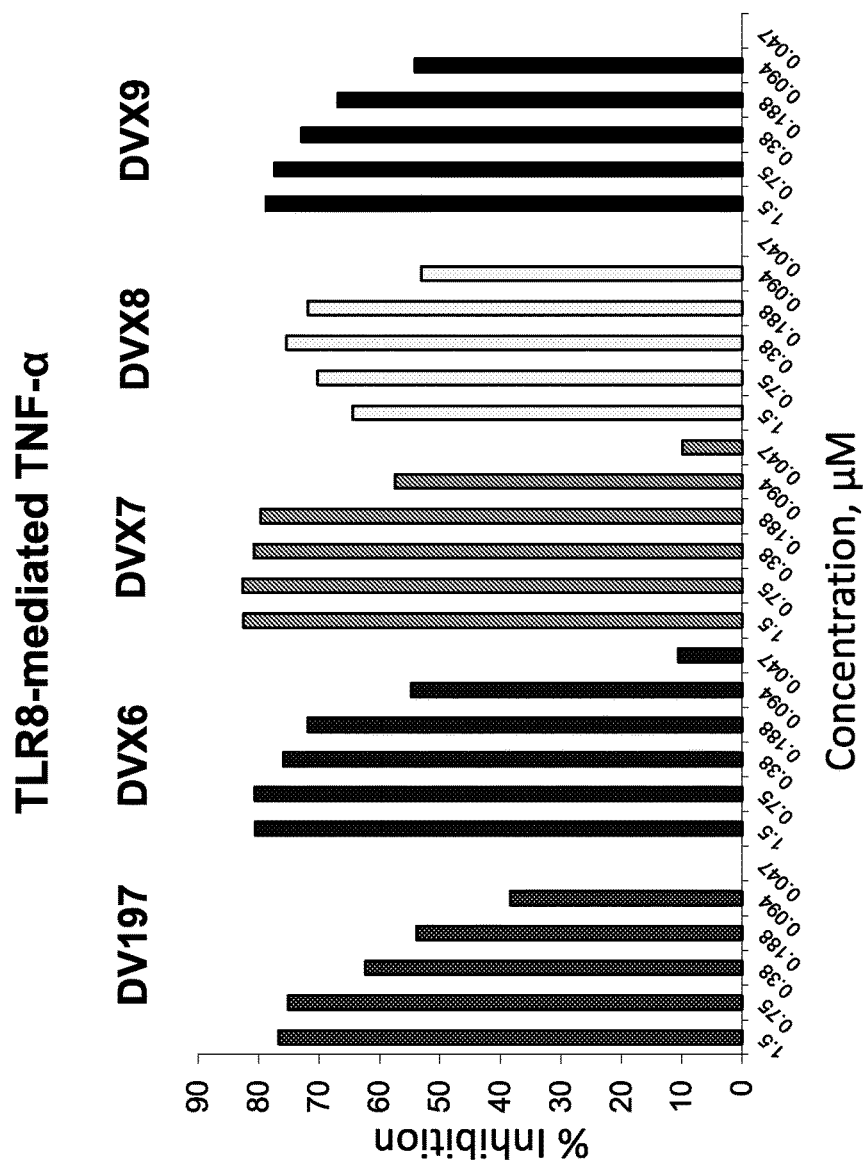
FIG. 6 shows the percent inhibition of TLR8-mediated TNF-α induction in monocytes stimulated with 150 µg/mL ORN8L by polynucleotides DV197, DVX6, DVX7, DVX8 and DVX9 at concentrations ranging from 1.5 to 0.047 µM.
Figure 7:
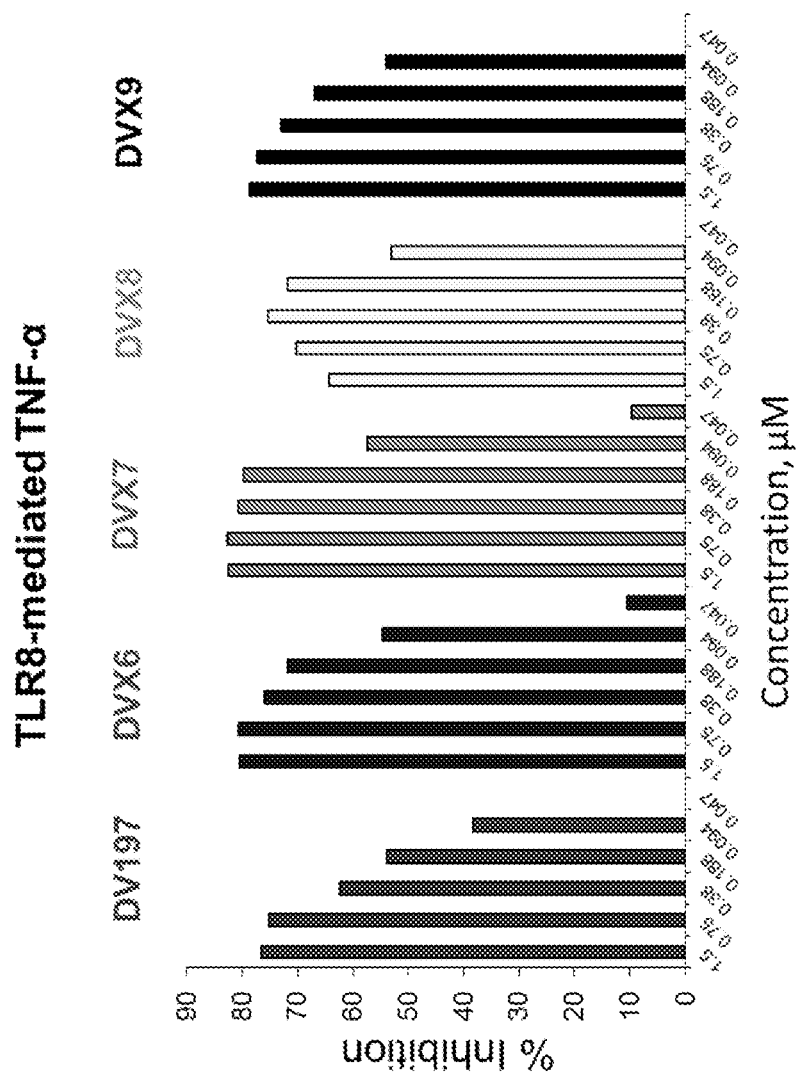
FIG. 7 shows the percent inhibition of TLR8-mediated TNF-α induction in monocytes stimulated with 150 µg/mL ORN8L by polynucleotides DV197, DVX20, DVX21, DVX24, DVX25 and DVX26 at concentrations ranging from 0.75 to 0.047 µM.

Example 8—DNA and Chimeric 2'-O-Methyl RNA/DNA PN have TLR8 Inhibitory Activity DV197 analogs containing different amounts of 2'-O-methyl RNA modifications at the 5'-end (DVX6, DVX7, DVX8, DVX9, DVX24, DVX25 and DVX26) were tested in the TLR8-specific inhibitory assay described in Example 3. As shown in FIG. 6 and FIG. 7, DVX8 and DVX26, which contain only DNA nucleotides, show that 2'-O-methyl RNA is not required for TLR8 inhibitory activity. Additionally, chimeric 2'-O-methyl RNA/DNA PN have TLR8 inhibitory activity, although full modification to 2'-O-methyl RNA, as in DVX25, reduces TLR8 inhibitory activity.

Figure 8:
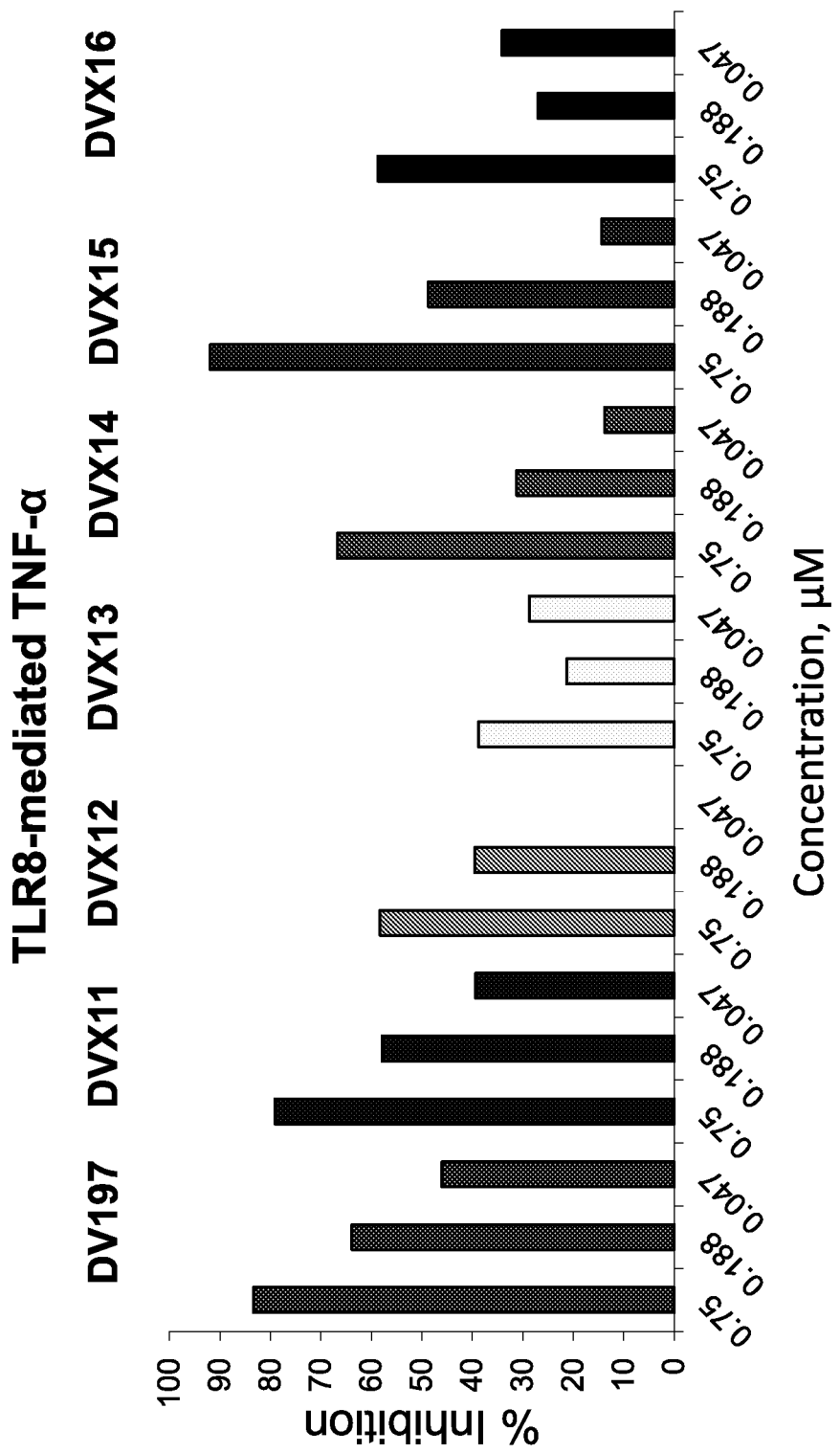
FIG. 8 shows the percent inhibition of TLR8-mediated TNF-α induction in monocytes stimulated with 150 µg/mL ORN8L by polynucleotides DV197, DVX11, DVX12, DVX13, DVX14, DVX15 and DVX16 at concentrations ranging from 0.75 to 0.047 µM.

Example 9—Effect of Additions and Deletions from 3'-End on TLR8 Inhibitory Activity DV197 analogs with 1, 2 or 3 thymidine (T) nucleotides added to the 3'-end (DVX11, DVX12, and DVX13, respectively) or with 1, 2 or 3 nucleotide deletions from the 3'-end (DVX14, DVX15 and DVX16) were tested in the TLR8-specific inhibitory assay described in Example 3. As shown in FIG. 8, one (1) nucleotide may be added to the 3'-end with little loss of TLR8 inhibitory activity. Moreover, the deletion series demonstrates that a 3'-A is preferred over a 3'-G for TLR8 inhibitory activity (FIG. 8). These results confirm the importance of the 3'-end for TLR8 inhibitory activity.

Example 10—Definition of the TLR8 Inhibitory Motif

Additional PNs were designed to define the minimal TLR8 inhibitory motif and polynucleotide length, as well as to identify optimal TLR8 inhibitory sequences. The new PNs were tested in the TLR8-specific inhibitory assay described in Example 3. The results are summarized in Table 10-1.

TABLE 10-1

TLR8 Inhibitory Activity of Polynucleotides

| Experiment | Part No. | TNFα IC50, nM | IL-1β IC50, nM |
|---|---|---|---|
| A | DVX8 | 250 | 300 |
|  | DVX35 | 220 | 227 |
|  | DVX36 | >2000 | >2000 |
|  | DVX37 | >2000 | >2000 |
|  | DVX38 | >2000 | >2000 |
| B | DVX26 | 71 | 137 |
|  | DVX39 | 64 | 151 |
|  | DVX40 | 64 | 73 |
|  | DVX41 | 45 | 94 |
|  | DVX42 | 77 | 92 |
| C | DVX55 | 145 | 145 |
|  | DVX46 | >2000 | >2000 |
|  | DVX47 | 225 | 230 |
|  | DVX48 | >2000 | >2000 |
|  | DVX49 | 1000 | 1000 |
|  | DVX50 | 200 | 200 |
| D | DVX55 | 181 | 143 |
|  | DVX43 | 110 | 175 |
|  | DVX44 | 130 | 160 |
|  | DVX45 | >2000 | >2000 |
| E | DVX43 | 121 | 60 |
|  | DVX68 | 1300 | 1800 |
|  | DVX69 | 550 | 164 |
|  | DVX70 | 1100 | 1400 |
|  | DVX71 | 280 | 41 |
|  | DVX72 | 230 | 51 |
| F | DVX43 | 70 | 300 |
|  | DVX73 | 68 | 140 |
|  | DVX74 | 130 | 200 |
|  | DVX75 | 162 | 45 |
|  | DVX76 | 230 | 1700 |
|  | DVX77 | >2000 | >2000 |
| G | DVX55 | 58 | 92 |
|  | DVX56 | 30 | 58 |
|  | DVX57 | 33 | 36 |
|  | DVX58 | 35 | 63 |
|  | DVX59 | 30 | 44 |
| H | DVX43 | 45 | 70 |
|  | DVX64 | 90 | 63 |
|  | DVX65 | 100 | 77 |
|  | DVX66 | 190 | 96 |
|  | DVX67 | 120 | 100 |
| I | DVX55 | 310 | 45 |
|  | DVX51 | 200 | 36 |
|  | DVX52 | 140 | 37 |
| J | DVX35 | 90 | 67 |
|  | DVX53 | 76 | 75 |
| K | DVX55 | 15 | 42 |
|  | DVX60 | 142 | 152 |
|  | DVX61 | 270 | 102 |
| L | DVX53 | 100 | 40 |
|  | DVX79 | 85 | 50 |
|  | DVX80 | 100 | 46 |

TABLE 10-1-continued

TLR8 Inhibitory Activity of Polynucleotides

| Experiment | Part No. | TNFα IC50, nM | IL-1β IC50, nM |
|---|---|---|---|
|  | DVX81 | 26 | 58 |
|  | DVX82 | 40 | 38 |
|  | DVX83 | 28 | 21 |
| M | DVX89 | 52 | 25 |
|  | DVX90 | 25 | 17 |
|  | DVX91 | 71 | 25 |
|  | DVX92 | 57 | 19 |
|  | DVX93 | 68 | 19 |
| N | DVX81 | 52 | 230 |
|  | DVX82 | 8 | 39 |
|  | DVX86 | 15 | 90 |
|  | DVX95 | 105 | 230 |
|  | DVX96 | 100 | 150 |
|  | DVX97 | 20 | 128 |
| O | DVX82 | 25 | 13 |
|  | DVX98 | 30 | 58 |
|  | DVX99 | 21 | 40 |
|  | DVX100 | 883 | 110 |
|  | DVX101 | 80 | 22 |
| P | DVX102 | 47 | 140 |
|  | DVX103 | 30 | 80 |
|  | DVX104 | 39 | 56 |
|  | DVX105 | 36 | 31 |
|  | DVX106 | 9 | 62 |
| Q | DVX103 | 20 | 25 |
|  | DVX107 | 150 | 55 |
|  | DVX108 | 45 | 17 |
|  | DVX109 | 30 | 10 |

Figure 10:
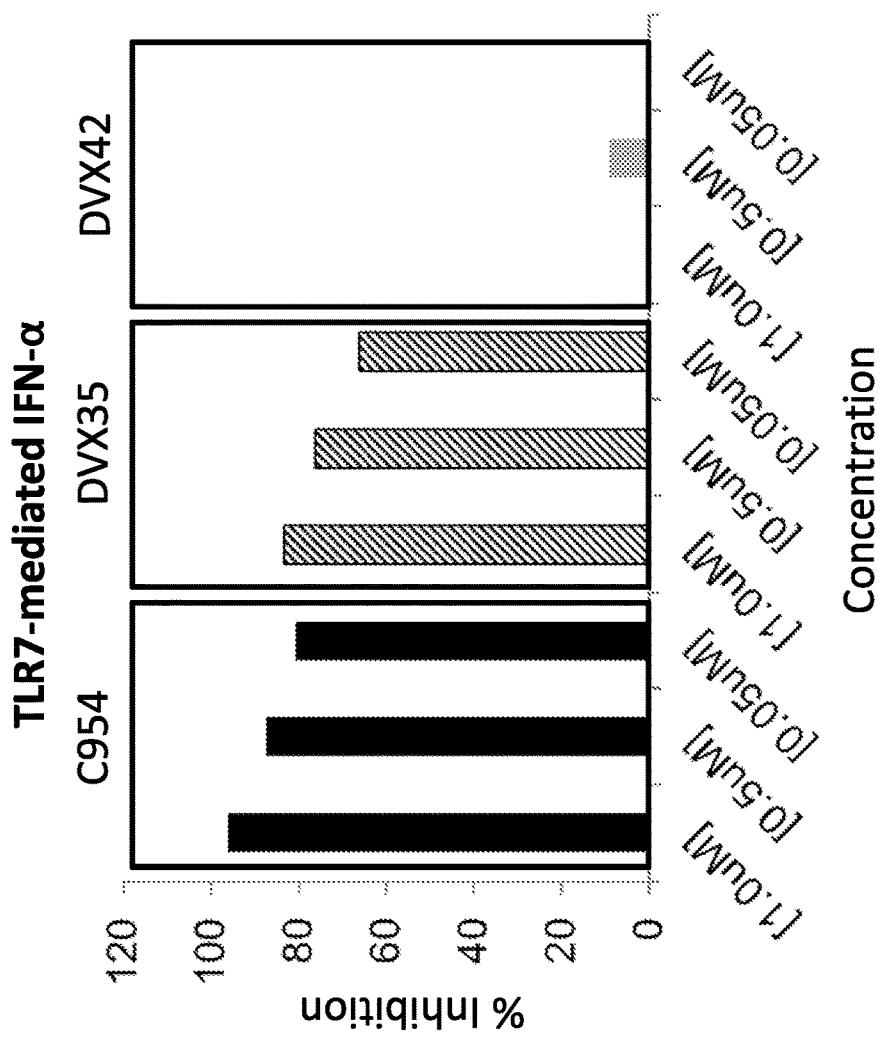
FIG. 10 shows the percent inhibition of TLR7-mediated IFN-α induction in PDC stimulated with 2 MOI inactivated influenza virus by polynucleotides C954, DVX35 and DVX42 at concentrations ranging from 1.0 to 0.05 µM.
Figure 11:
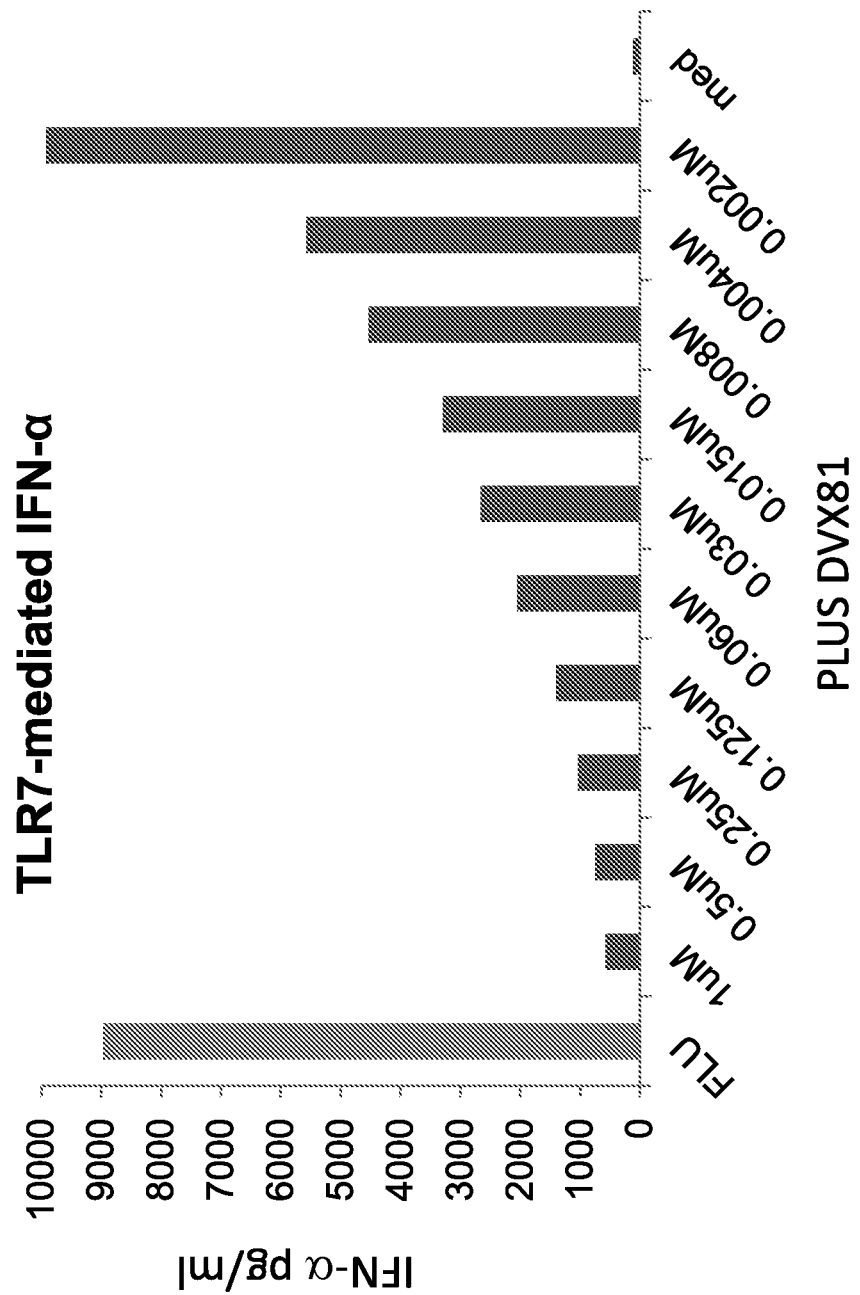
FIG. 11 shows the TLR7-mediated IFN-α induction in PDC stimulated with 2 MOI inactivated influenza virus alone or in combination with DVX81 at concentrations ranging from 1 to 0.002 µM.

Replacement of the G in either the DV197 or DVX8 sequence with I resulted in PN with similar or increased TLR8 inhibitory activity. On the other hand, PN with A, C, or T replacements in the DVX8 sequence were inactive (FIG. 10 and Table 10-1, Experiment A).

DVX26 analogs containing 5'-TIC, 5'-TAC, 5'-TTC, or 5'-TCC instead of a 5'-TGC, all showed similar TLR8 inhibitory activity confirming that 5'-TGC is not required for TLR8 inhibition. These results also confirmed that the 5'-end of the PN is not important for TLR8 inhibitory activity (Table 10-1, Experiment B).

Additionally, Experiments C through G of Table 10-1 evaluated the importance of the four nucleotides at the 3'-end for TLR8 inhibitory activity. These results, in combination with previous observations made during development of the present disclosure, show that PN with an II, IA, GI or GA at the 3'-end had good TLR8 inhibitory activity.

Experiments H through J of Table 10-1 evaluated the importance of the middle nucleotides for TLR8 inhibitory activity, while maintaining an II at the 3'-end of the PN. All PN tested in these experiments had TLR8 inhibitory activity.

Experiment K of Table 10-1 evaluated the minimum length for the PN to maintain TLR8 inhibitory activity. DVX61 is a 6-mer containing an II at the 3'-end, which showed good TLR8 inhibitory activity.

Experiments L, N and O of Table 10-1 evaluated the TLR8 inhibitory activity of a variety of 18-mers to 21-mers containing an II at the 3'-end. All PN tested in this experiment had good TLR8 inhibitory activity. Some differences were observed, however, indicating that the other nucleotides in the PN can have an effect on TLR8 inhibitory activity. Additionally, DVX86, DVX96, DVX97, DVX98, DVX99, DVX100 and DVX101 were designed so that a TLR8 inhibitory motif would be regenerated as the PN is degraded in vivo by 3'-exonucleoases. For instance, each of these PN has the sequence 5'-IIAII-3' at the 3'-end. Sequential degradation by 3'-exonucleases would leave the following sequences at the 3'-end of the PN: 5'-IIAI-3', 5'-IIA-3', and 5'-II-3'. Of these, all except for 5'-IIAI-3' are TLR8 inhibitory motifs. It is expected that the half-life of the TLR8 inhibition for PN that are designed to regenerate a TLR8 inhibitory motif during in vivo degradation by 3'-exonucleases will be longer than for PN that only contain a single TLR8 inhibitory motif.

Experiments P and Q of Table 10-1 evaluated the TLR8 inhibitory activity of additional polynucleotides containing TLR8 inhibitory motifs. DVX102, DVX103, DVX104, DVX105, DVX106, DVX107, DVX108 and DVX109 all showed good TLR8 inhibitory activity.

Example 11—Polynucleotides with TLR7-Only, TLR8-Only or TLR7/8 Inhibitory Activity As determined during development of the present disclosure, the TLR7 and TLR8 inhibitory motifs are different. Therefore, PN can be designed to have TLR7-only, TLR8-only or TLR7/8 inhibitory activity by inclusion or exclusion of unique motifs. To demonstrate this, PN containing only TLR7, only TLR8 or both TLR7 and TLR8 motifs were tested in the TLR7-specific and TLR8-specific inhibitory assays described in Example 3.

Figure 9:
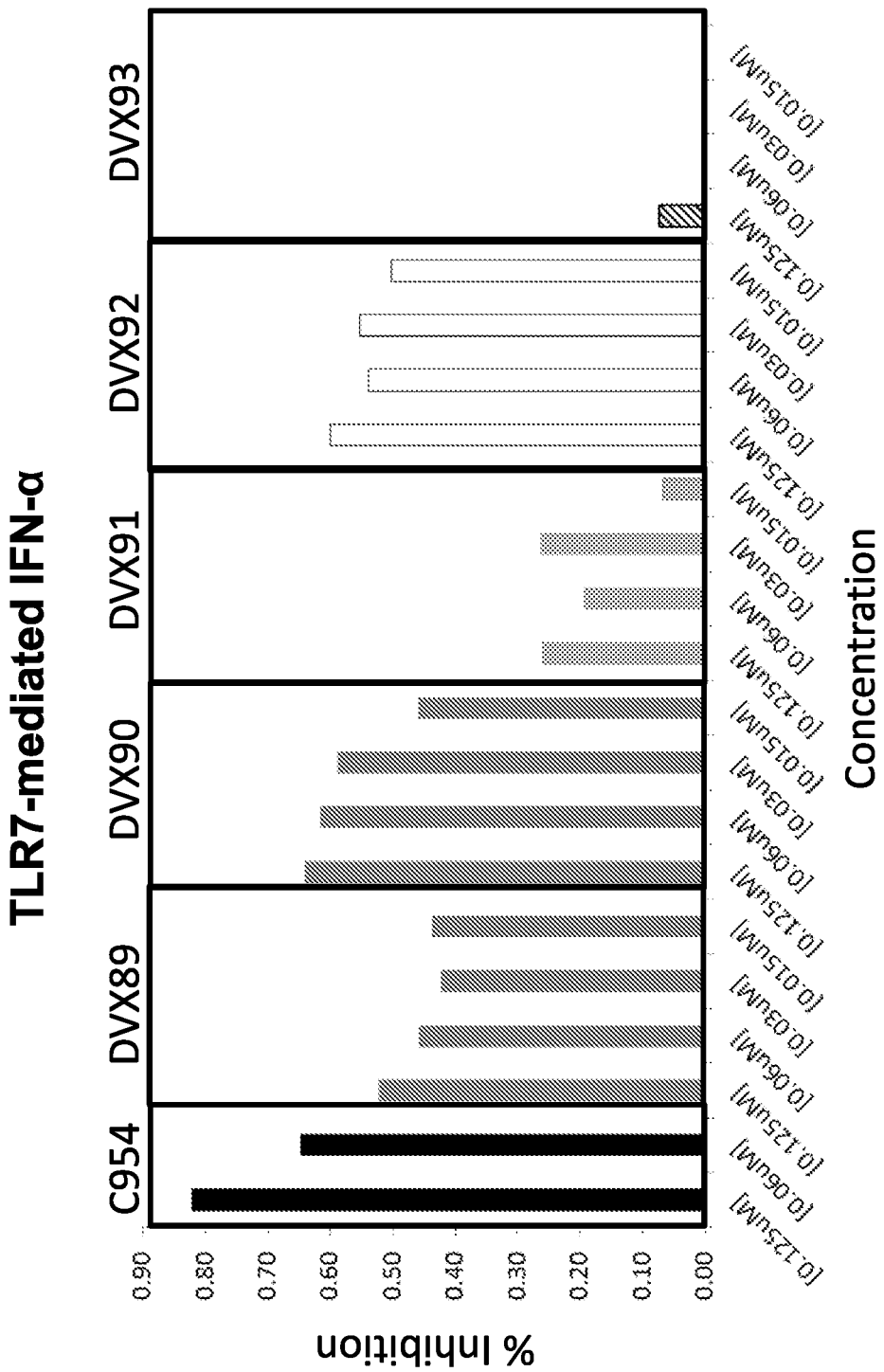
FIG. 9 shows the percent inhibition of TLR7-mediated IFN-α induction in PDC stimulated with 2 MOI inactivated influenza virus by polynucleotides C954, DVX89, DVX90, DVX91, DVX92 and DVX93 at concentrations ranging from 0.125 to 0.015 µM.

As described in Example 5, C954 and DV134, which contain a TLR7 but not a TLR8 inhibitory motif, have only TLR7 inhibitory activity. Experiment M of Table 10-1 and FIG. 9 show that DVX89, DVX90 and DVX92 have TLR7 and TLR8 inhibitory activity, while DVX91 and DVX93 have only TLR8 inhibitory activity. Similarly, Experiments A and B of Table 10-1 and FIG. 10 show that DVX35 has TLR7 and TLR8 inhibitory activity, while DVX42 has only TLR8 inhibitory activity. Retention of TLR8 inhibitory activity was expected because DVX89, DVX90, DVX91, DVX92, DVX93, DVX35 and DVX42 all contained a TLR8 inhibitory motif (II or GI at the 3' end). In contrast, 5'-TIC and 5'-TTC, were found to be TLR7 inhibitory motifs. The latter observation is surprising because previous work had described 5'-TGC, but not 5'-TIC or 5'-TTC as TLR7 inhibitory motifs. Description of two new TLR7 inhibitory motifs was made possible during development of the present disclosure in part through the use of human PBMC stimulated with a selective TLR7 agonist (influenza virus), as opposed to mouse splenocytes stimulated with a non-specific TLR7/8 agonist, R848. This highlights the importance of testing TLR8 inhibitors in cells expressing human TLR8.

Additional PN that contain both TLR7 and TLR8 inhibitory motifs, such as DV197 and DVX81 among many others, were also shown to have TLR7/8 inhibitory activity (FIGS. 1A, 1B, 2A, 2B, 11, 21, 22 and 23, and Table 10-1 Experiments L, N, O, and P). DVX81 had an IC50 of 12 nM in the TLR7 inhibitory assay, and IC50s of 26 nM (TNFα) and 58 nM (IL-1β) respectively in the TLR8-specific inhibitory assays. Further exemplary TLR7/8 inhibitors are: 5'-TIC TCC TTG AGI AII-3' (DVX103; SEQ ID NO:108); 5'-TIC TCC TCC TTG AGI AII-3' (DVX104, SEQ ID NO:109); 5'-TIC TTC TCC TTG AGI AII-3' (DVX105, SEQ ID NO:110); and 5'-TIC TCC TCC TTG IIA II-3' (DVX106, SEQ ID NO:111), as shown in Experiment P of Table 10-1 and FIG. 23.

A further exemplary TLR8-only inhibitor is: 5'-TCC TCC TTG AGI AII-3' (DVX102; SEQ ID NO:107), as shown in Experiment P of Table 10-1 and FIG. 22.

Figure 12:
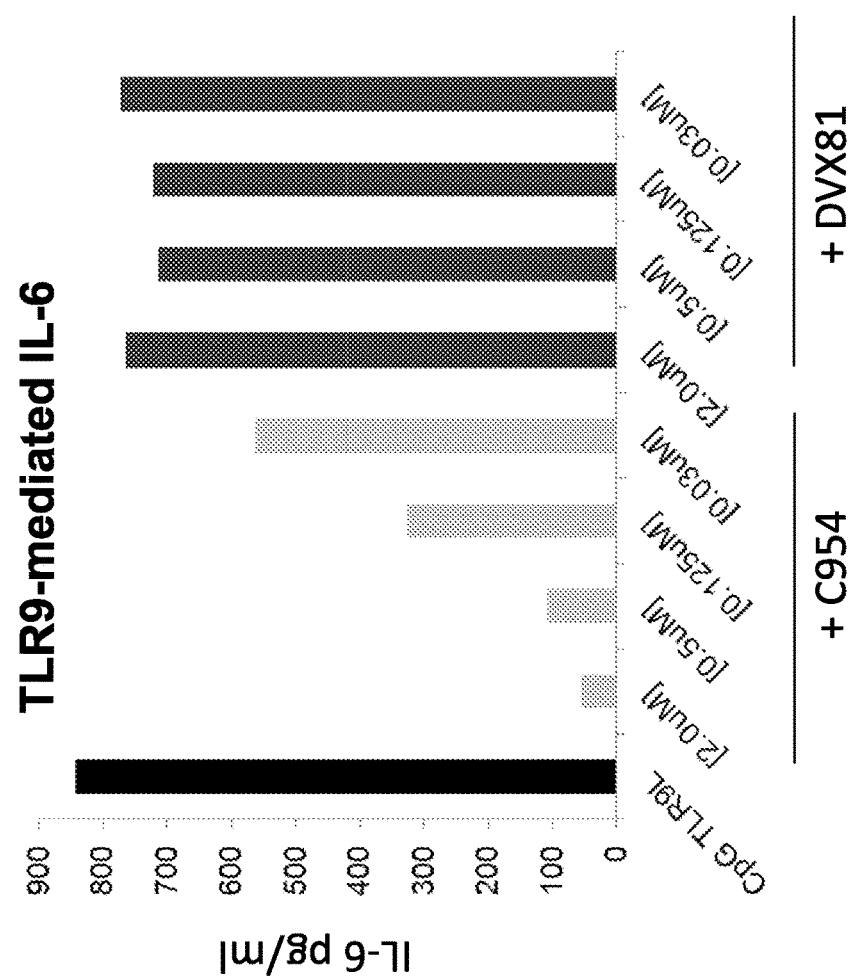
FIG. 12 shows the TLR9-mediated IL-6 induction in B cells stimulated with 1 µM of CpG-TLR9L 1018ISS (SEQ ID NO:4) alone or in combination with C954 or DVX81 at concentrations ranging from 2.0 to 0.03 µM.

The selectivity of the TLR7/8 inhibitory response was demonstrated by evaluation of DVX81 in a TLR9-specific inhibitory assay using B cells, as described in Example 3. DVX81 does not contain a TLR9 inhibitory motif. C954, which contains TLR7 and TLR9 inhibitory motifs, was used as a positive control. As shown in FIG. 12, DVX81 does not inhibit TLR9.

Example 12—Polynucleotides with TLR8/9 or TLR7/8/9 Inhibitory Activity

Since the TLR7, TLR8 and TLR9 inhibitory motifs are different, PNs can also be designed to have TLR8/9 or TLR7/8/9 inhibitory activity by inclusion or exclusion of unique motifs. To demonstrate this, PN containing TLR8 and TLR9 motifs are tested in the TLR8-specific and TLR9-specific inhibitory assays described in Example 3. Additionally, PN containing TLR7, TLR8 and TLR9 motifs are also tested in the TLR7-specific, TLR8-specific, and TLR9-specific inhibitory assays described in Example 3. Exemplary TLR8/9 inhibitors are: 5'-TAC TCC TTG GII-3' (SEQ ID NO:81); and 5'-TCC TGG AGG GGT TIA II-3 (SEQ ID NO:112). Exemplary TLR7/8/9 inhibitors are: 5'-ugc TGC TCC TTG GGI-3' (SEQ ID NO:14); 5'-TIC TCC TTI GII-3' (SEQ ID NO:66); 5'-TGC TCC TGG AGG GGT TIA II-3' (SEQ ID NO:113); 5'-TIC TCC TCC TTG GGI AII-3' (SEQ ID NO:114); and 5'-TIC TTC TCC TTG GGI AII-3' (SEQ ID NO:115).

Figure 37:
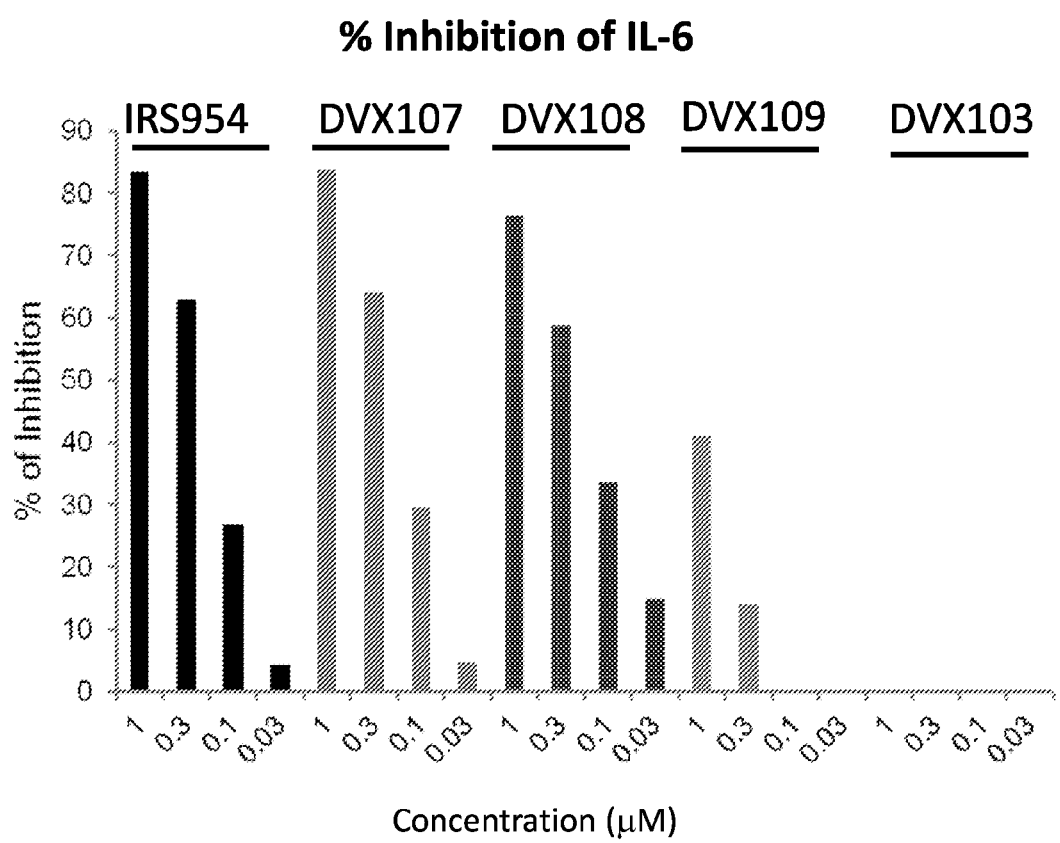
FIG. 37 shows the TLR9-mediated IL-6 induction in B cells stimulated with 1018ISS (SEQ ID NO:4, 1 μM) alone or in combination with C954, DVX107, DVX108, DVX109 or DVX103 at concentrations ranging from 1 μM to 0.03 μM.

DVX107 (SEQ ID NO:112) was designed as a TLR8/9 inhibitor and DVX108 (SEQ ID NO:113) as designed as TLR7/8/9 inhibitor. The PN were tested in the TLR8-specific, and TLR9-specific inhibitory assays described in Example 3. The results in Table 10-1, Experiment Q show that both PNs inhibit TLR8. The results in FIG. 37 show that DVX107 and DVX108 also inhibit TLR9. Moreover, DVX108 contains a 5'-TGC motif, which is known to inhibit TLR7 (see Example 11).

Example 13—Stimulation of Healthy PBMC with RA Patient Plasma is TLR7/8-Dependent About 7×10⁵ PBMC cells from three healthy donors were incubated in 200 µL of medium with 30 µL of plasma from three rheumatoid arthritis (RA) patients or plasma from three normal individuals in absence or presence of a TLR inhibitor at 1 micromolar concentration. Supernatants were evaluated by ELISA for IL-8 concentration after 16-18 hrs. The inhibitors tested were DV197 (TLR 7/8 inhibitor) and DVX42 (TLR8-only inhibitor).

Figure 13:
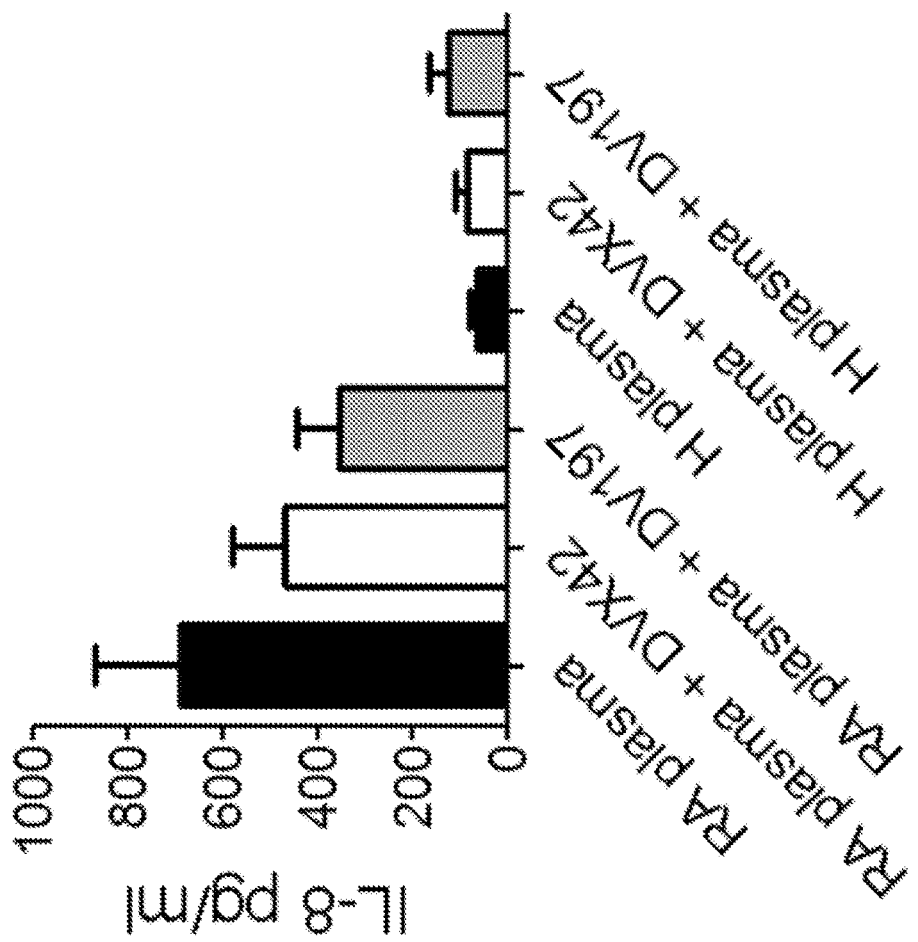
FIG. 13 shows the average IL-8 production by PBMC stimulated with either plasma from three rheumatoid arthritis (RA) patients or plasma from three healthy (H) individuals, alone or in combination with DVX42 or DV197 at a concentration of 1 µM. The PBMC were obtained from three healthy human subjects.

As shown in FIG. 13, plasma from the RA patients stimulates IL-8, while the plasma from normal individuals does not. The IL-8 stimulation by the RA patient plasma was inhibited by both DV197 and DVX42. DV197, which contains both the TLR7 and TLR8 inhibitory motifs, inhibited IL-8 secretion to a greater extent than did DVX42. These results demonstrate that stimulation of healthy PBMC with RA patient plasma is both TLR7 and TLR8-dependent.

Figure 14:
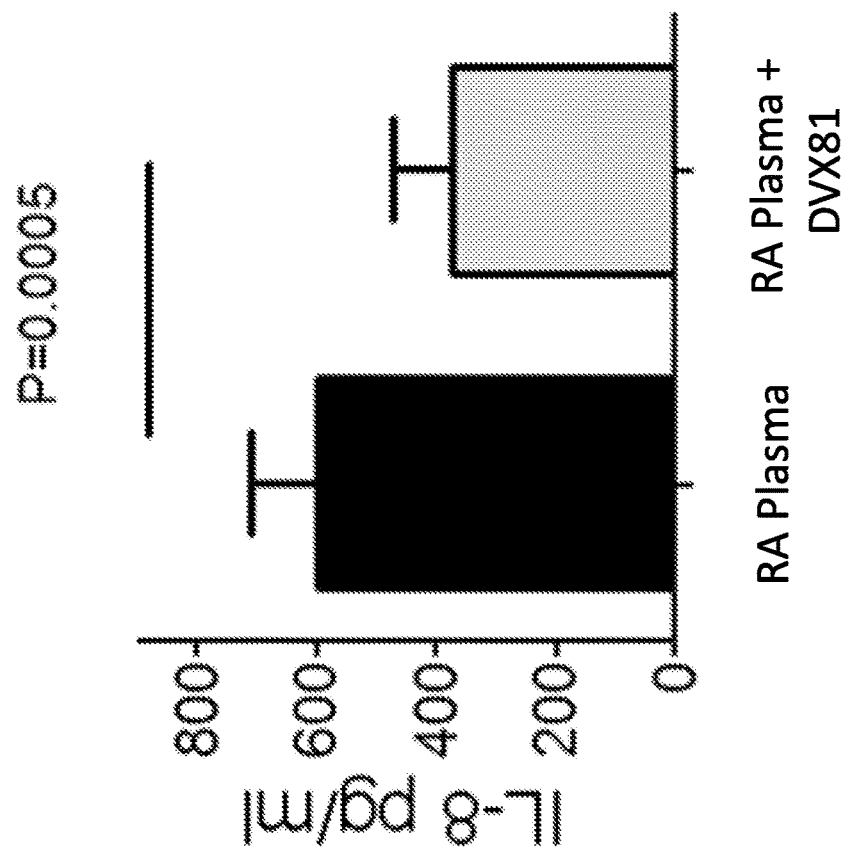
FIG. 14 shows the average IL-8 production by PBMC stimulated with plasma from eight rheumatoid arthritis (RA) patients, alone or in combination with DVX81 at a concentration of 1 µM. The PBMC were obtained from three healthy human subjects.

A second study was performed as described above, except that plasma from eight individual RA patients was used for the stimulation and DVX81 (TLR7/8 inhibitor) was used as the inhibitor. Results were averaged and P values were determined using a Wilcoxon matched-pairs t test. As shown in FIG. 14, the dual TLR7/8 inhibitor DVX81 inhibits RA plasma-stimulated IL-8 secretion by PBMC. Healthy patient plasma did not stimulate IL-8 (data not shown).

Example 14—Stimulation of Human Monocytes with SF from RA Patients is TLR7/8-Dependent Untouched CD14+ monocytes were isolated from Buffy Coats using a negative selection kit (Stem Cell, Catalog No. 14068) according to the manufacturer's instructions. Purity was routinely over 98%. About 3×10⁵ cells were incubated in complete medium (RPMI, 10% FBS) in the presence of 15% synovial fluid (SF) from rheumatoid arthritis (RA) patients alone or in combination with DV197 (1 µM). Synovial fluids were obtained from ProteoGenex (Culver City, Calif.). After 14-16 hours, supernatants were assayed for cytokine levels by Milliplex (Millipore). Data are expressed as percent cytokine level of synovial fluid alone, with the average levels for each cytokine indicated above SF bars. Data are cumulative of seven synovial fluids tested on at least three independent healthy monocytes donors. P values were determined using a Wilcoxon matched-pairs signed rank test.

Figure 15:
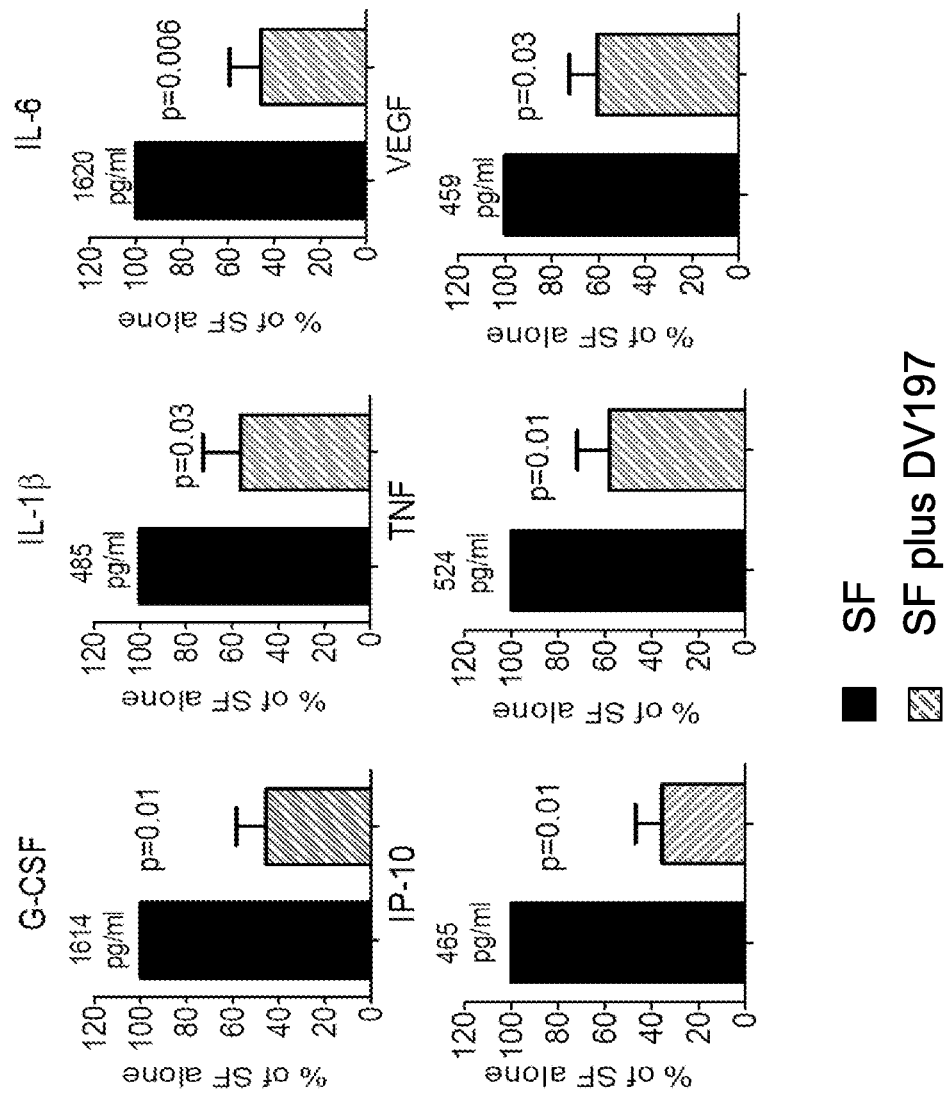
FIG. 15 shows the G-CSF, IL-1β, IL-6, IP-10, TNFα, and VEGF production by purified human monocytes stimulated with 15% synovial fluid (SN) from rheumatoid arthritis patients alone, or in combination with DV197 at a concentration of 1 µM.

As shown in FIG. 15, the SF from the RA patients stimulates G-CSF, IL-1β, IL-6, IP-10, TNF-α, and VEGF production, and SF-stimulated cytokine production can be inhibited by the TLR7/8 inhibitor DV197.

Example 15—DVX81 Inhibits TLR8 Activation In Vivo in Human TLR8 Transgenic Mice

Figure 16:
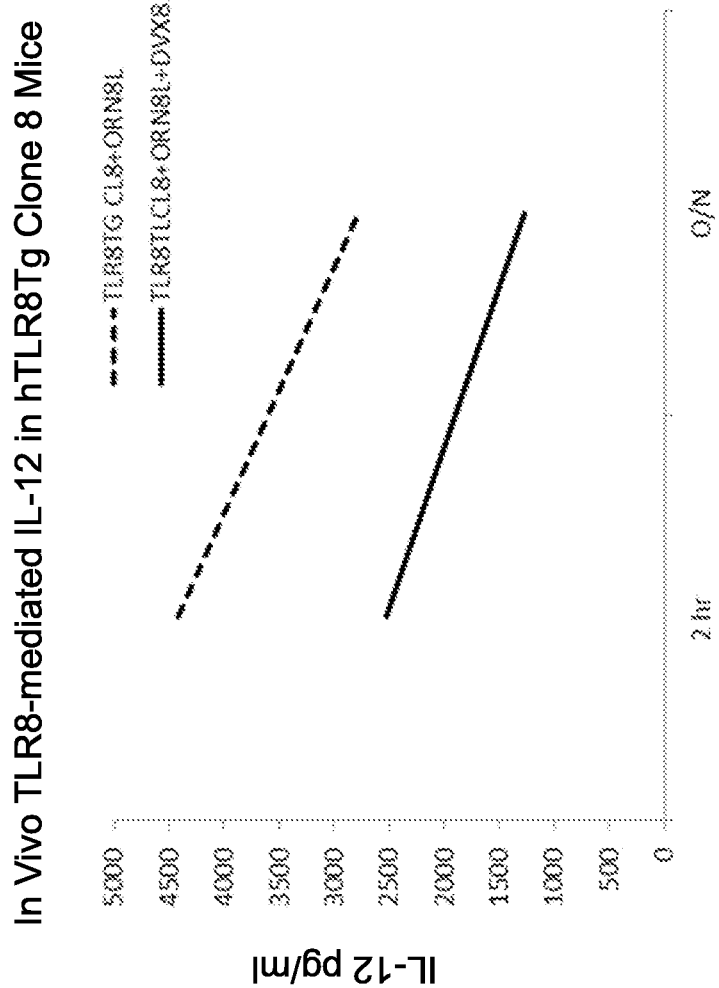
FIG. 16 shows the TLR8-mediated IL-12 induction after 2 hours and overnight (O/N) in hTLR8Tg Clone 8 mice injected with 220 mcg ORN8L given intravenously alone or in combination with 100 mcg DVX81 given intravenously.

The activity of DVX81 was evaluated in vivo in hTLR8Tg Clone 8 mice. hTLR8Tg Clone 8 mice were injected with 220 mcg ORN8L given intravenously alone or in combination with DVX81 (100 mcg), also given intravenously. The effect on TLR8-mediated IL-12 induction was measured by ELISA after 2 hours or overnight (O/N). As shown in FIG. 16, DVX81 is able to inhibit TLR8 activation in vivo.

Example 16—Human B-Cells Cultured in the Presence of Polynucleotides

The effect of polynucleotides on non-specific human B-cell activity was determined by assaying for IL-6. Phosphorothioate-modified oligodeoxynucleotides induce some human B-cell responses in vitro due to the phosphorothioate linkages, but no evidence of B-cell activation has been shown in vivo in primates.

For the human B-cell assay, B-cells were purified from blood cells obtained from healthy donors using magnetic beads (CD19 positive). Cells were resuspended in fresh medium (RPMI 1640 with 10% fetal calf serum, 50 units/mL penicillin, 50 µg/mL streptomycin, and 2 mM glutamine). The cells were then incubated with 0.015 µM to 4.0 µM of the indicated polynucleotides. At 48 hours, supernatants were collected and IL-6 was measured by immunoassay. The polynucleotides tested were C954, DV185, DVX81, DVX82, DVX98, DVX99, DVX42, DVX102 and DVX103. C954 is known to stimulate low levels of IL-6, while DV185 is known to stimulate high levels of IL-6. The amount of IL-6 induced by each polynucleotide was divided by that induced by C954 to determine the magnitude of IL-6 induction relative to C954.

Figure 17:
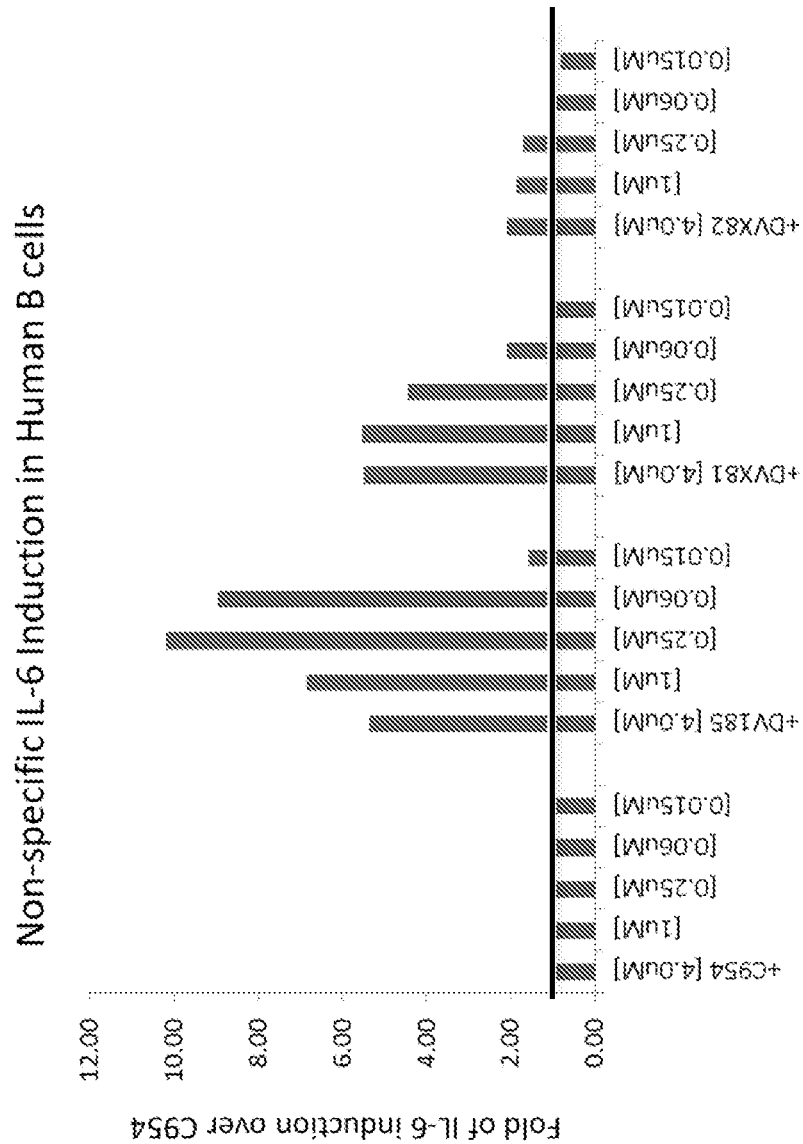
FIG. 17, FIG. 18 and FIG. 19 show the effect of different polynucleotides relative to C954 on non-specific IL-6 production by human B cells.
Figure 18:
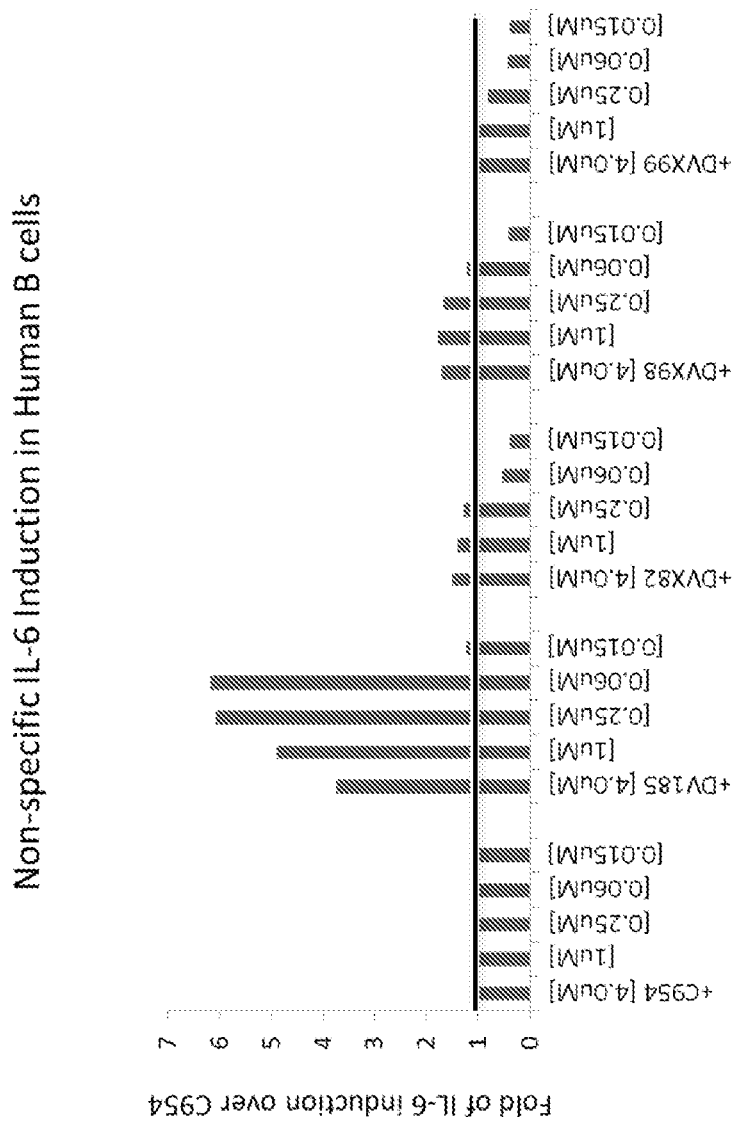
Figure 19:
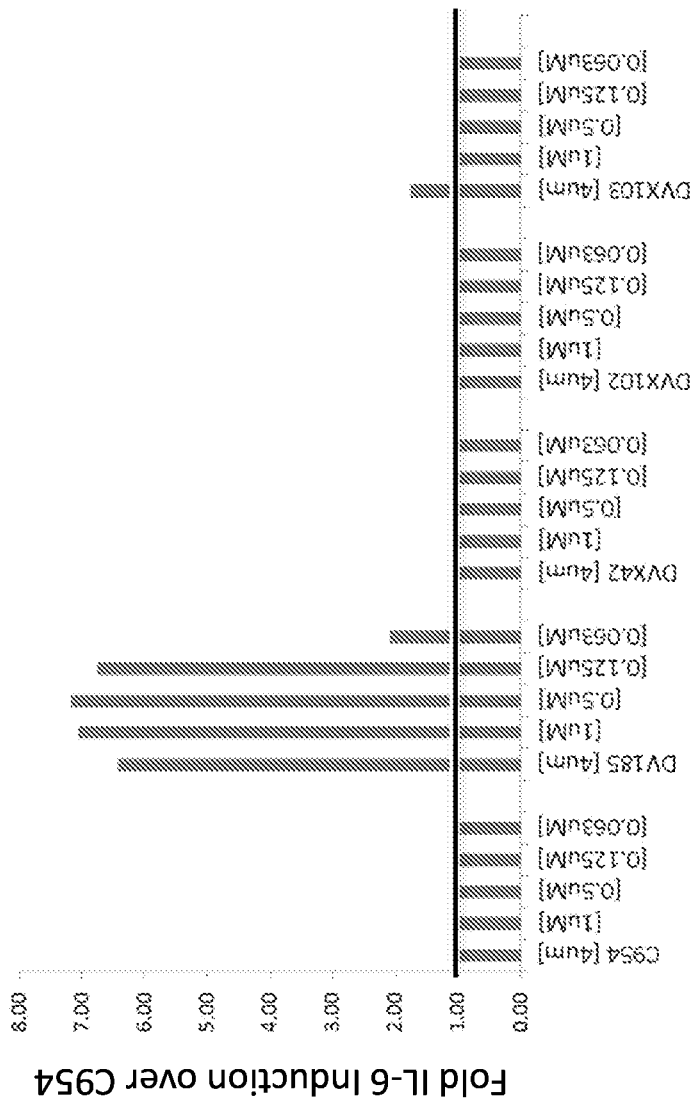

FIG. 17, FIG. 18 and FIG. 19 show that different polynucleotides induce a range of IL-6 responses from human B cells. As expected, DV185 induced significantly more IL-6 than C954. Surprisingly, DVX82 induced significantly less IL-6 than DVX81, despite having the same TLR7/8 motifs, phosphorothioate internucleotide linkages and number of nucleotides. DVX82, DVX98, DVX99, DVX42, DVX102 and DVX103 induced low levels of IL-6 from human B cells. Polynucleotides that only minimally activate human B cells are preferable for inclusion in compositions for inhibiting TLR7, TLR8 and/or TLR9-mediates responses and for inclusion in medicaments for treating or preventing autoimmune diseases or inflammatory disorders.

Example 17—Rat Splenocytes Cultured in the Presence of Polynucleotides

Splenocytes from 8-9 weeks old, female Sprague Dawley rats were harvested and mechanically dispersed by forcing the digested fragments through metal screens. The dispersed splenocytes were pelleted by centrifugation, then resuspended in fresh medium (RPMI 1640 with 10% fetal calf serum, plus 50 units/mL penicillin, 50 µg/mL streptomycin, 2 mM glutamine, and 0.05 mM β-mercaptoethanol). The cells were then incubated with 0.06 µM to 4.0 µM of various polynucleotides. At 48 hours, supernatants were collected and IL-6 was measured by immunoassay. The polynucleotides tested were C954, DV185, DVX81 and DVX82. C954 is known to stimulate low levels of IL-6, while DV185 is known to stimulate high levels of IL-6. The amount of IL-6 induced by each polynucleotide was divided by that induced by C954 to determine the magnitude of IL-6 induction relative to C954.

Figure 20:
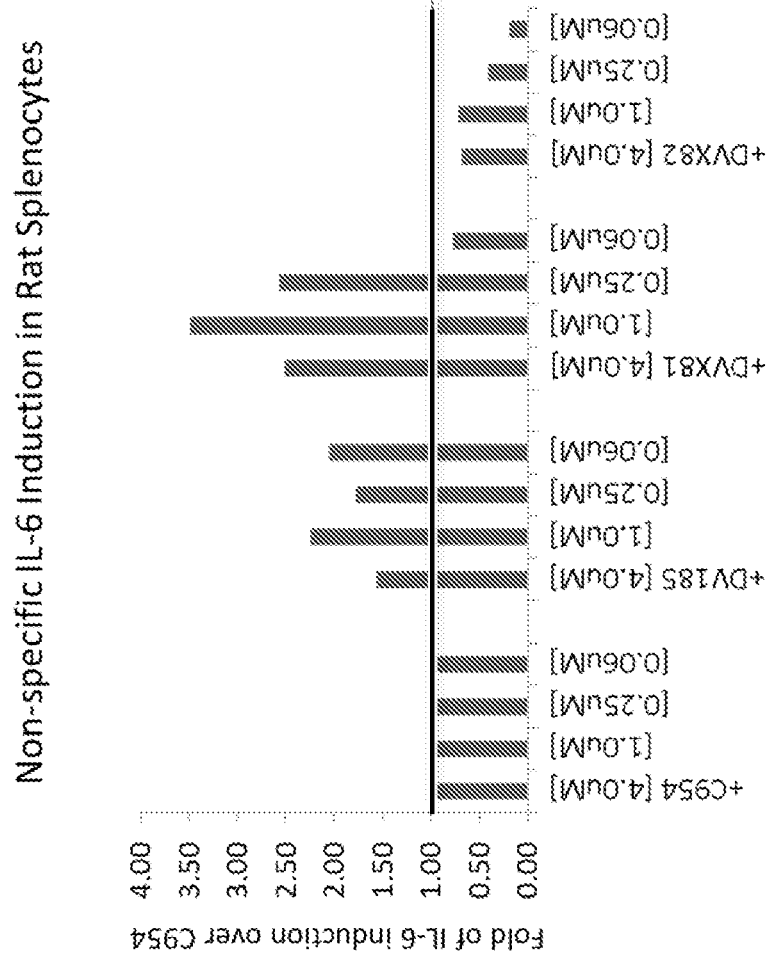
FIG. 20 shows the effect of different polynucleotides relative to C954 on non-specific IL-6 production by rat splenocytes.
Figure 21:
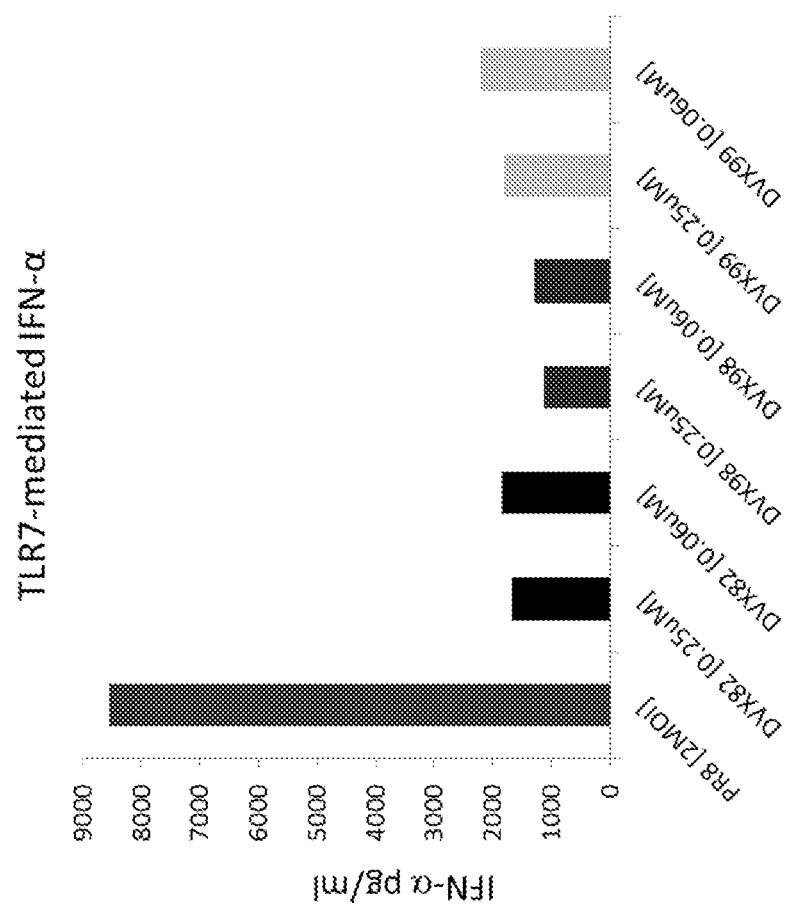
FIG. 21 shows the amount of TLR7-mediated IFN-α induction in PDC stimulated with 2 MOI inactivated influenza virus alone (PR8), or in combination with polynucleotides DVX82, DVX98 or DVX99 at concentrations of 0.25 or 0.06 µM.
Figure 22:
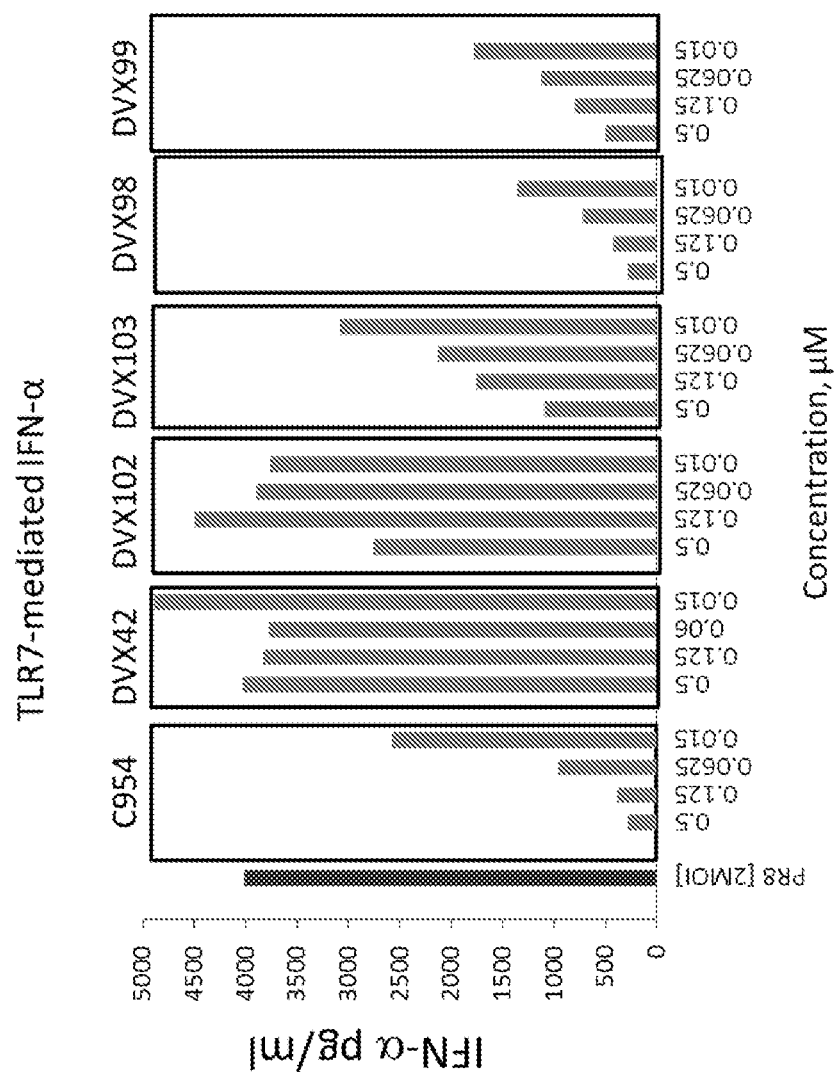
FIG. 22 shows the amount of TLR7-mediated IFN-α induction in PDC stimulated with 2 MOI inactivated influenza virus (PR8) alone, or in combination with polynucleotides C954, DVX42, DVX102, DVX103, DVX98 or DVX99 at concentrations ranging from 0.5 to 0.015 µM.
Figure 23:
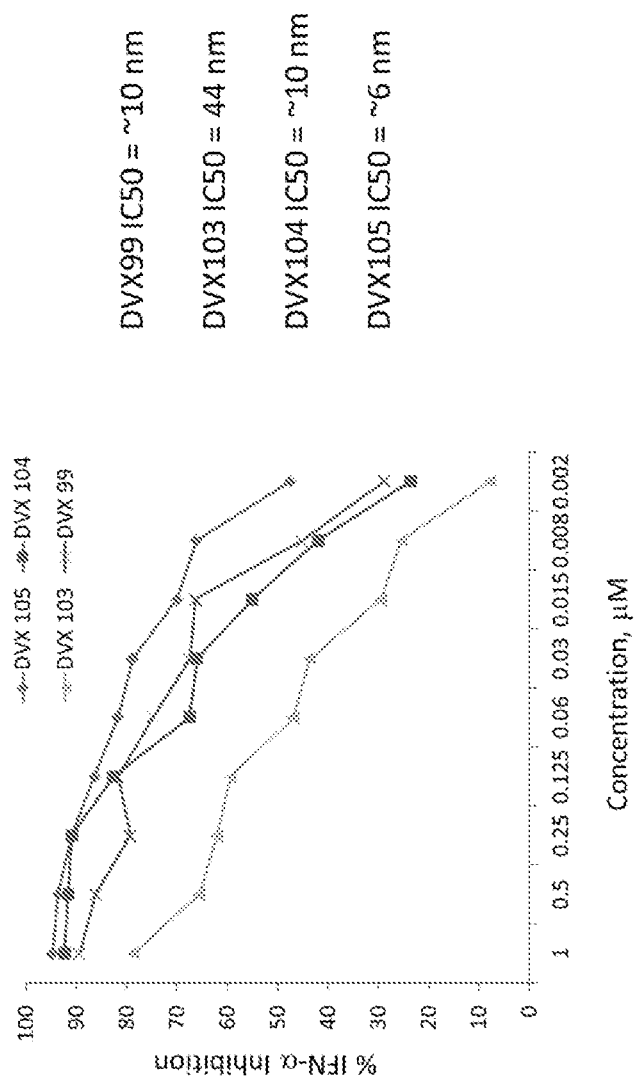
FIG. 23 shows the percent inhibition of TLR7-mediated IFN-α induction in PDC stimulated with 2 MOI inactivated influenza virus (PR8) by polynucleotides DVX99, DVX103, DVX104 and DVX105 at concentrations ranging from 1 to 0.002 µM.

FIG. 20 shows that different polynucleotides induce a range of IL-6 responses from rat splenocytes. The results obtained using rat splenocytes were consistent with the results obtained using human B cells, as. Polynucleotides that only minimally activate rat splenocytes are preferable for inclusion in compositions for inhibiting TLR7, TLR8 and/or TLR9-mediates responses and for inclusion in medicaments for treating or preventing autoimmune diseases or inflammatory disorders.

Figure 24:
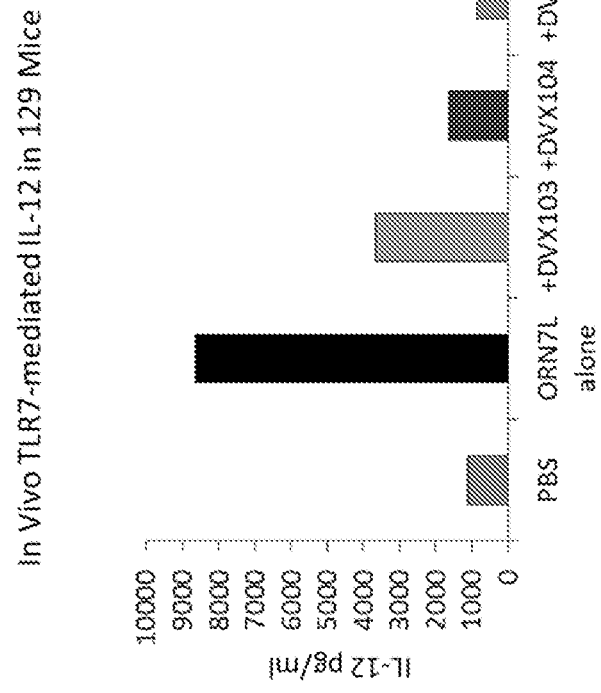
FIG. 24 shows the TLR7-mediated IL-12 induction 2 hours after injection of 129S2/SvPasCrl mice with 250 mcg ORN7L given intravenously, alone or in combination with C954, DVX82, DVX98, or DVX99 (100 mcg) given subcutaneously.

Example 18—Polynucleotides with TLR7 Inhibitory Motifs Inhibit TLR7-Mediated Immune Responses In Vivo in Mice 129S2/SvPasCrl mice were injected with 250 mcg of ORN7 ligand (TLR7 agonist) given intravenously, alone or in combination with C954, DVX82, DVX98 or DVX99 (100 mcg) given subcutaneously. After 2 hours, mice were bled and IL-12 was measured by ELISA. As shown in FIG. 24, C954, DVX82, DVX98 and DVX99 are able to inhibit TLR7-mediated IL-12 induction in vivo.

Figure 25:
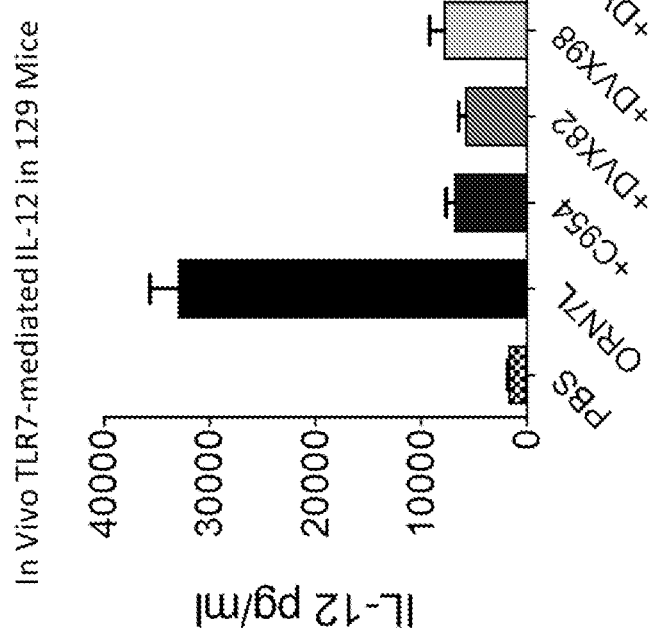
FIG. 25 shows the effect on TLR7-mediated IL-12 induction 6 hours after injection of 129S2/SvPasCrl mice with 250 mcg ORN7L given intravenously, alone or in combination with DVX103, DVX104, or DVX99 (100 mcg) given subcutaneously.

Similarly, 129S2/SvPasCrl mice were injected with 250 mcg of ORN7 ligand (TLR7 agonist) given intravenously, alone or in combination with DVX103, DVX104 or DVX99 (100 mcg) given subcutaneously. After 6 hours, mice were bled and IL-12 was measured by ELISA. As shown in FIG. 25, DVX103, DVX104 and DVX99 are able to inhibit TLR7-mediated IL-12 induction in vivo.

Example 19—Polynucleotides with TLR Inhibitory Motifs do not Exhibit Off-Target Effects Polynucleotides DVX36 (no TLR7, TLR8 or TLR9 motif), DVX98 (TLR7/8 motifs), DVX102 (TLR8 motif), DVX103 (TLR7/8 motifs) and C954 (TLR7/9 motifs) were tested for off-target effects. Human PBMC were isolated from total blood cells obtained from healthy donors using the FICOLL® method. Cells were resuspended in fresh medium (RPMI 1640 with 10% fetal calf serum, 50 units/mL penicillin, 50 µg/mL streptomycin, and 2 mM glutamine).

To test the effect of the polynucleotides on TLR4-signaling, human PBMC were stimulated with 5 µg/ml of lipopolysaccharide (LPS) alone or in combination with either 1 µM or 4 µM of the polynucleotides of interest. At 24 hours, supernatants were collected IL-6 was measured by immunoassay. DVX36, DVX98, DVX102, DVX103 and C954 did not inhibit TLR4-mediated IL-6 production stimulated by LPS.

To test the effect of the polynucleotides on TLR2/1-signaling, human PBMC were stimulated with 0.1 µg/ml of PAM3CSK4 (synthetic triacylated lipoprotein) alone or in combination with either 1 µM or 4 µM of the polynucleotides of interest. At 24 hours, supernatants were collected and IL-6 was measured by immunoassay. DVX36, DVX98, DVX102, DVX103 and C954 did not inhibit TLR2/1-mediated IL-6 production stimulated by PAM3CSK4.

To test the effect of the polynucleotides on TLR5-signaling, human PBMC were stimulated with 1 µg/ml of flagellin alone or in combination with either 1 µM or 4 µM of the polynucleotides of interest. At 24 hours, supernatants were collected and IL-6 was measured by immunoassay. DVX36, DVX98, DVX102, DVX103 and C954 did not inhibit TLR5-mediated IL-6 production stimulated by flagellin.

To test the effect of the polynucleotides on retinoic acid-inducible gene 1 (RIG-I), $3\times10^5$ monocytes were stimulated with a 1 to 100 dilution of Sendai virus (SeV) alone or in combination with either 1 µM or 4 µM of the polynucleotides of interest. At 24 hours, supernatants were collected and IFN-α was measured by immunoassay. DVX36, DVX98, DVX102, DVX103 and C954 did not inhibit RIG-I-mediated IFN-α production stimulated by SeV.

Example 20—Administration of High Dosages of Polynucleotides to Mice

Polynucleotides (C954, DVX82, DVX98, DVX99, DVX102 and DVX103) at high dosages (100 mg/kg) or a control (saline) were subcutaneously administered to BALB/c mice twice a week for two weeks (n=6 per group). Polynucleotides were administered on days 2, 5, 9 and 12. Mice were weighed prior to administration (day 0), and thereafter as indicated in FIGS. 26A and 26B. Organs were harvested at the end of the study, and organ weights were determined. In addition, histological evaluation of the kidney was performed for C954-, DVX99- and DVX103-treated mice.

Figure 26:
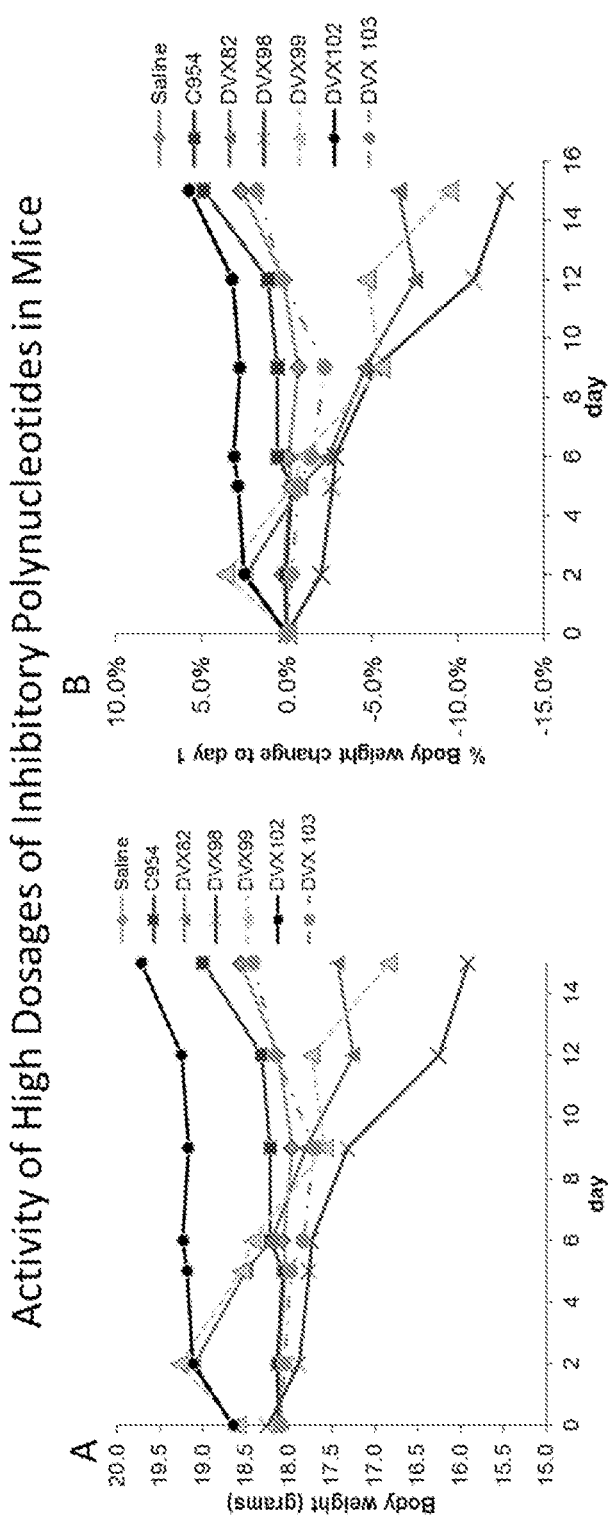
FIG. 26A shows body weight gain/loss over time by mice after administration of saline, or 100 mg/kg C954, DVX82, DVX98, DVX99, DVX102, or DVX103.
FIG. 26B shows body weight percent change (relative to day 1 weight) over time by mice after administration of saline, or 100 mg/kg of C954, DVX82, DVX98, DVX99, DVX102, or DVX103.

Mice treated with DVX102, DVX103 or C954 showed either no change in body weight or a slight increase in body weight, while mice treated with DVX82, DVX98 or DVX99 showed significant loss in body weight during the study (FIG. 26). The mice treated with C954, DVX102 or DVX103 appeared normal, while mice treated with DVX82, DVX98 or DVX99 appeared slightly scruffy at the end of the study, with DVX98-treated mice showing the worst effect. Organ weights of mice of all of the groups did not increase. However, the livers and kidneys of mice treated with DVX82, DVX98 or DVX99 were paler than normal. A summary of the severity score of kidney tubular changes and percent of weight change from Day 15 compared to Day 1 is shown in Table 20-1 for C954-, DVX99- and DVX103-treated mice. Renal changes were noted in all examined animals and were characterized by tubular changes, primarily in subcapsular regions, consisting of: cytoplasmic vacuolation; presence of amorphous eosinophilic material in tubular lumens; slight enlargement of nuclei with slight tinctorial changes of affected cells. Tubular changes were minimal (1.0) in mice receiving saline, and increased slightly in all other groups.

TABLE 20-1

Summary of Kidney Tubular and Body Weight Changes of Polynucleotide-Treated Mice

| Group/Oligo | ID # | Tubular Change | Average | Body Weight Change (%) |
|---|---|---|---|---|
| Saline (None) | 1 | 1 | 1 | +2.65 |
| | 2 | 1 | | |
| | 3 | 1 | | |
| | 4 | 1 | | |
| | 5 | 1 | | |
| | 6 | 1 | | |
| C954 | 1 | 1 | 1.2 | +4.9 |
| | 2 | 1 | | |
| | 3 | 1 | | |
| | 4 | 2 | | |
| | 5 | 1 | | |
| | 6 | 1 | | |
| DVX99 | 1 | 1 | 1.3 | −9.5 |
| | 2 | 2 | | |
| | 3 | 1 | | |
| | 4 | 2 | | |
| | 5 | 1 | | |
| | 6 | 1 | | |
| DVX103 | 1 | 2 | 1.8 | +2.0 |
| | 2 | 2 | | |
| | 3 | 2 | | |
| | 4 | 1 | | |
| | 5 | 2 | | |
| | 6 | 2 | | |

Example 21—Administration of High Dosages of Polynucleotides to Rats

Figure 27:
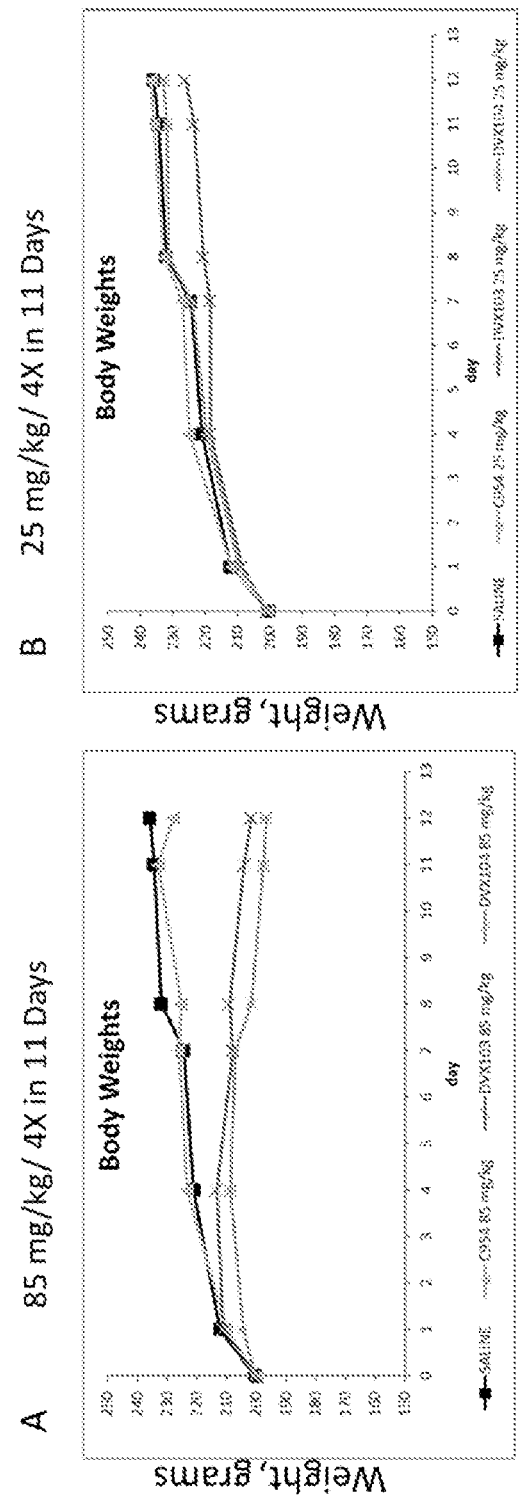
FIG. 27A shows body weight gain/loss over time by rats after administration of saline, or 85 mg/kg of C954, DVX103, and DVX104.
FIG. 27B shows body weight gain/loss over time by rats after administration of saline, or 25 mg/kg of C954, DVX103, or DVX104.

Polynucleotides (C954, DVX103 or DVX104) at a dosage of 85 mg/kg or 25 mg/kg, or a control (saline) were subcutaneously administered to 8-9 week old, female Sprague Dawley rats on days 0, 4, 7, and 11 (n=5 per group). Rats were weighed prior to administration on day 0, and thereafter as indicated in FIGS. 27A and 27B. Organs were harvested at the end of the study, and organ weights were determined. In addition, a histological evaluation of the liver, kidney, and heart was performed.

Figure 28:
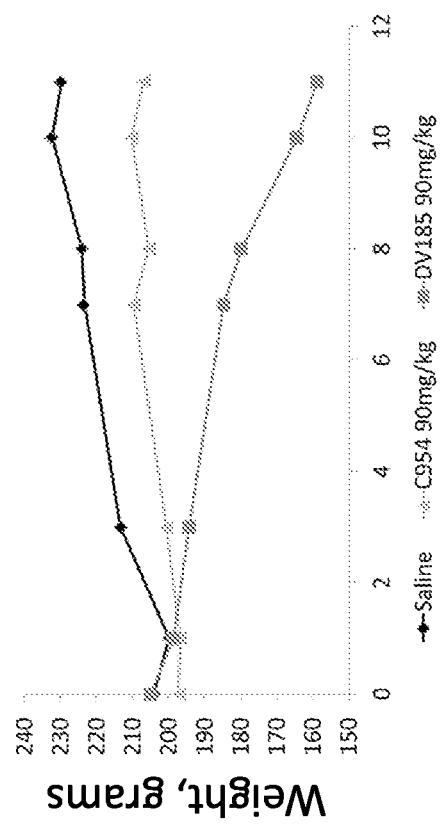
FIG. 28 shows historical body weight gain/loss over time by rats after administration of saline, or 90 mg/kg of C954, or DV185.

There was an increase in body weight observed for the rats treated with 25 mg/kg of C954, DVX103 or DVX104, or 85 mg/kg of C954, or saline. The rats treated with 85 mg/kg of DVX103 or DV104 showed no overall change in body weight. This is in contrast to the significant loss in body weight observed in rats treated with 90 mg/kg of DV185 (FIG. 28). There was no significant difference in organ weight of the liver, kidney, spleen or heart of mice treated with either 25 mg/kg or 85 mg/kg of C954, DVX103 or DVX104.

A summary of the histological evaluation of the liver, kidneys and heart is shown in Table 21-1. The histopathology on the organs confirmed the kidney as the target organ. Mild tubular changes were scored in most groups. C954 at the highest dose historically showed mild changes (severity score 2).

TABLE 21-1

Summary of the Histological Findings in Polynucleotide-Treated Rats

| Group | Saline | C954 | C954 | DVX103 | DVX103 | DVX104 | DVX104 |
|---|---|---|---|---|---|---|---|
| mg/kg | 0 | 85 | 25 | 85 | 25 | 85 | 25 |
| Animals | 5 | 5 | 5 | 5 | 5 | 5 | 5 |
| Kidney: | | | | | | | |
| No changes | 5 | 1 | 4 | 0 | 1 | 0 | 0 |
| Tubular changes | 0 | 4 (1.0) | 0 | 5 (2.8) | 4 (1.0) | 5 (2.6) | 5 (2.0) |
| hydronephorsis | 0 | 0 | 1 (3.0) | 0 | 0 | 0 | 0 |
| Liver: | | | | | | | |
| No changes | 4 | 5 | 4 | 4 | 5 | 5 | 5 |
| Cell Infiltration | 1 (2.0) | 0 | 1 (2.0) | 0 | 0 | 0 | 0 |
| Fatty changes | 0 | 0 | 0 | 1 (2.0) | 0 | 0 | 0 |
| Heart: | | | | | | | |
| No changes | 5 | 5 | 5 | 5 | 5 | 5 | 5 |

( ) = mean severity score;
0 = no change;
1 = minimal;
2 = mild;
3 = moderate;
4 = severe

Figure 29:
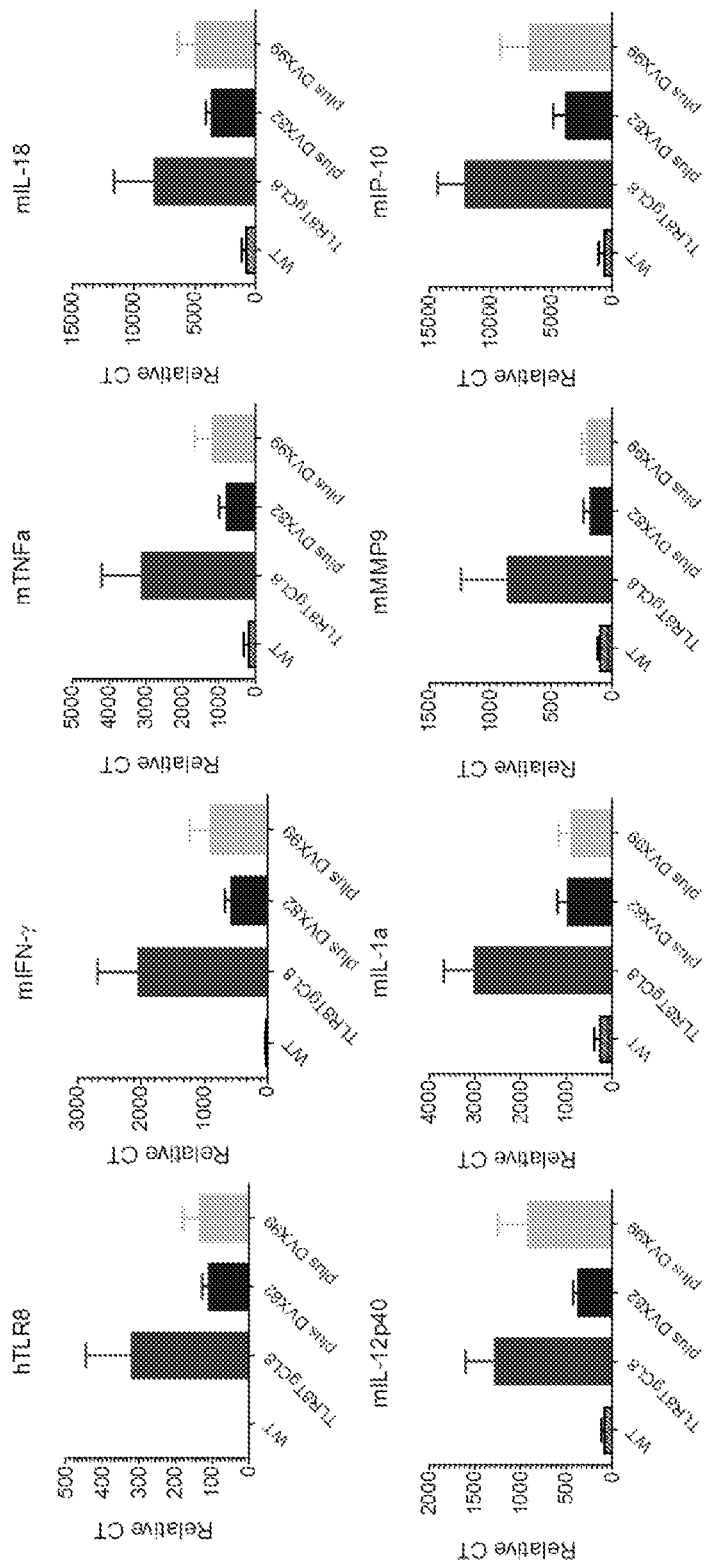
FIG. 29 shows the relative levels of hTLR8, mIFN-γ, mTNF-α, mIL-18, mIL-12p40, mIL-1α, mMMP9 and mIP-10 in the pancreas of human TLR8Tg Clone 8 mice, as compared to wild type mice and to human TLR8Tg Clone 8 mice after treatment with DVX82 or DVX99 (2.2 mg/kg, twice a week for 5 weeks).

Example 22—TLR7/8 Inhibitors Decrease Inflammatory Gene Expression in the Pancreas of Human TLR8 Transgenic Mice The human TLR8Tg Clone 8 mice, described in Example 6, develop pancreatitis, in part as indicated by inflammatory genes expressed at high levels in the pancreas. The pancreas was isolated at necropsy and RNA was isolated with Qiagen Midi Rneasy extraction kit according to the manufacturer's instructions. cDNA was generated from RNA with the SuperScript First-Strand Synthesis System (Invitrogen) and a TAQMAN assay was used to evaluate the gene expression level. FIG. 29 shows the increase in (CT) in hTLR8, mIFN-γ, mTNF-α, mIL-18, mIL-12p40, mIL-1α, mMMP9 and mIP-10 levels in the pancreas from human TLR8Tg Clone 8 mice relative to wild type mice.

Figure 30:
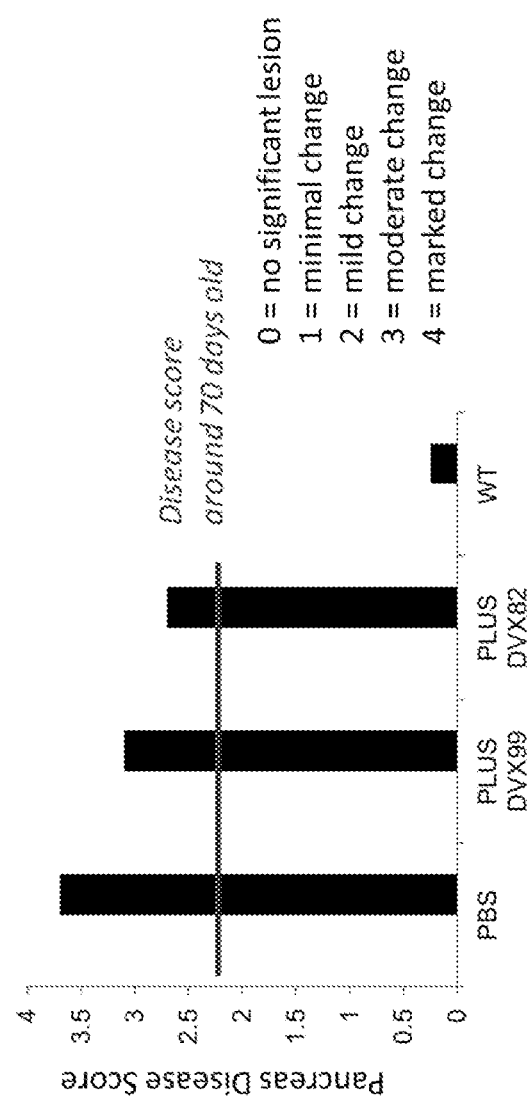
FIG. 30 shows the pancreas disease score of human TLR8Tg Clone 8 mice treated with PBS, DVX82 or DVX99, as compared to wild type (WT) mice.

Human TLR8Tg Clone 8 mice that were 70-80 days old were injected with 2.2 mg/kg of DVX82, DVX99 or PBS twice a week for 5 weeks. As shown in FIG. 29, DVX82 and DVX99 were both able to decrease the levels of inflammatory genes expressed in the pancreas of human TLR8Tg Clone 8 mice. Additionally, the the pancreas from the human TLR8Tg Clone 8 mice treated with DVX82 or DVX99 showed a reduced disease score relative to mice treated with PBS (FIG. 30).

Figure 31:
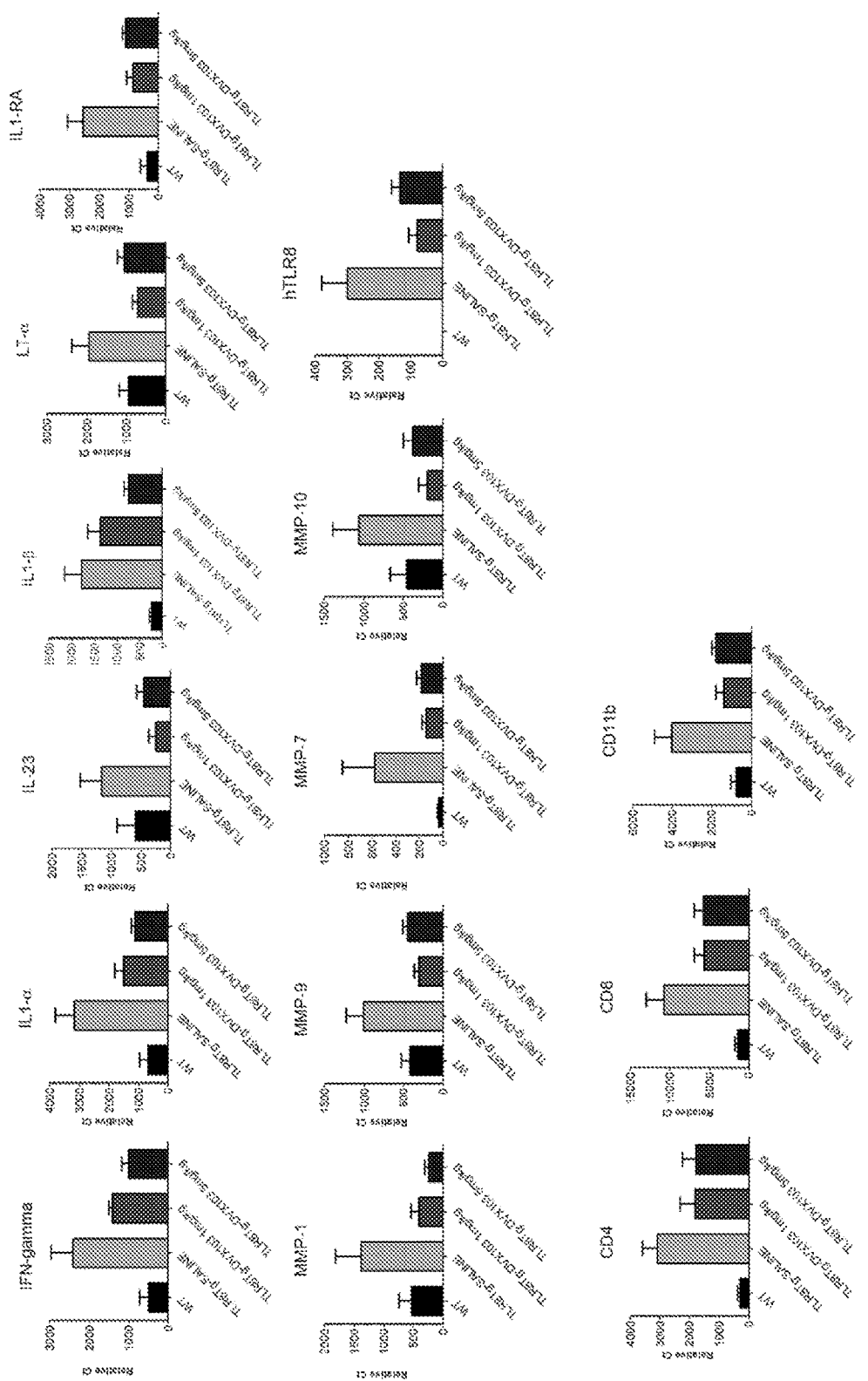
FIG. 31 shows the relative levels of mIFN-γ, mIL-1α, mIL-23, mIL-1β, mLT-α, mIL1-RA, mMMP-1, mMMP-9, mMMP-7, mMMP-10, hTLR8, mCD4, mCD8 and mCD11β in the pancreas of human TLR8Tg Clone 8 mice, as compared to wild type mice and to human TLR8Tg Clone 8 mice after treatment with DVX103 (1 mg/kg or 5 mg/kg, once a week for 10 weeks).

In a second experiment, human TLR8Tg Clone 8 mice that were 60-67 days old were injected with 1 mg/kg or 5 mg/kg of DVX103 or saline once a week for 10 weeks. FIG. 31 shows the relative levels of mIFN-γ, mIL-1α, mIL-23, mIL-1β, mLT-α, mIL1-RA, mMMP-1, mMMP-9, mMMP-7, mMMP-10, hTLR8, mCD4, mCD8 and mCD11β in the pancreas of human TLR8Tg Clone 8 mice, as compared to wild type mice and to human TLR8Tg Clone 8 mice after treatment with DVX103. As shown in FIG. 31, DVX103 was able to decrease the levels of inflammatory genes expressed in the pancreas of human TLR8Tg Clone 8 mice.

Figure 32:
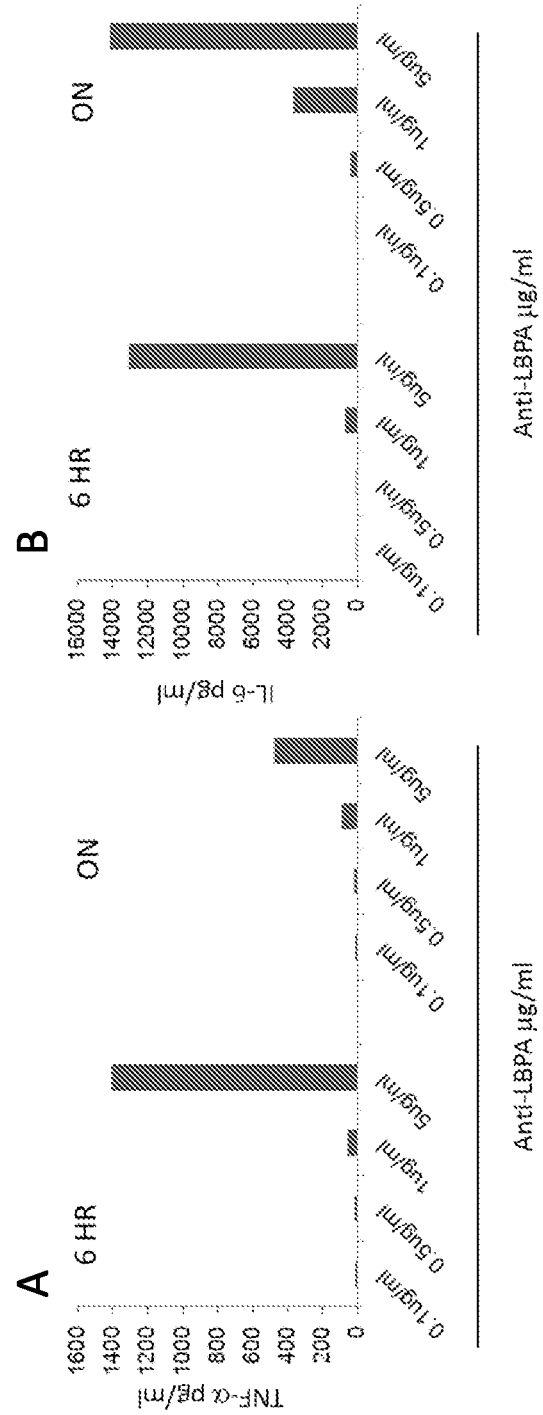
FIGS. 32A and 32B show that anti-LBPA induces the inflammaotry cytokines TNF-α and IL-6 in human monocytes.

Example 23—TLR7/8 Inhibitors Decrease Inflammatory Cytokines Induced by Anti-LBPA in Human Monocytes Anti-phospholipid syndrome (APS) is characterized by anti-phospholipid antibodies, which include antibodies directed against phospholipid-associated proteins such as cardiolipin, β2-glycoprotein-1 and the endosomal lipid lyso-bisphosphatidic acid (LBPA). Primary human monocytes were stimulated with 0.1 µg/mL, 0.5 µg/mL, 1 µg/mL or 5 µg/mL of a commercially available anti-LBPA antibody (clone 6C4; echelon) (Kobayashi et al, Nature, 392:193-197, 1998). After 6 hours or overnight (ON), supernatants were collected and levels of TNF-α and IL-6 were measured by ELISA. FIGS. 32A and 32B show that anti-LBPA induces production of the inflammatory cytokines TNF-α and IL-6 by human monocytes.

Figure 33:
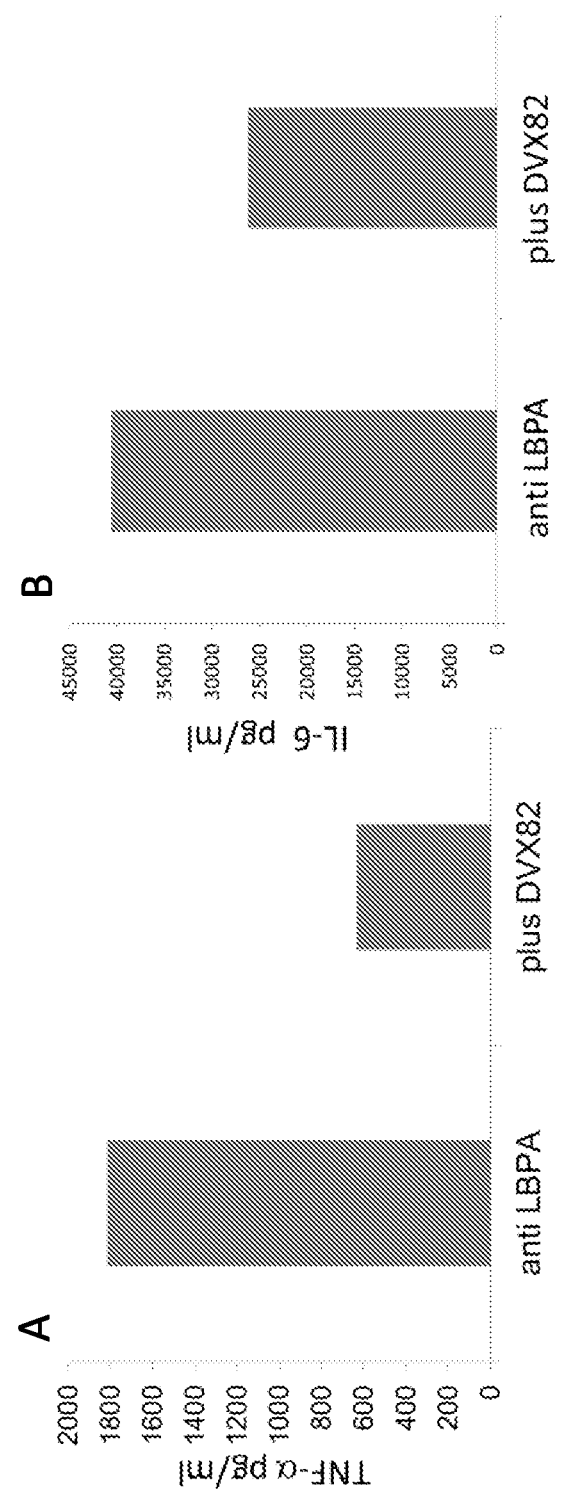
FIGS. 33A and 33B show the TNF-α and IL-6 induction in monocytes stimulated with 1 µg/mL of anti-LBPA, alone or in combination with 1 µM DVX82.

In a second experiment, primary human monocytes were stimulated with 1 µg/mL of the clone 6C4 anti-LBPA antibody alone or in combination with 1 micromolar of DVX82 (exemplary TLR7/8 inhibitor). After overnight incubation, supernatants were collected and levels of TNF-α and IL-6 were measured by ELISA. FIGS. 33A and 33B show that DVX82 reduced IL-6 and TNF levels induced by anti-LBPA in human monocytes. These results show that anti-LBPA stimulation is at least partially TLR7/8 dependent.

Example 24—Stimulation of Healthy PBMC with Serum from Patients with Mixed Connective Tissue Disease Patients with mixed connective tissue disease (MCTD) have high levels of U1-RNP autoantibody, which is a potent activator of TLR7 in PDC and TLR8 in monocytes (Kattah et al., Immunol Rev, 233:126-145, 2010; and Vollmer et al., J Exp Med, 202:1575-1585, 2005).

About $7 \times 10^5$ PBMC cells or $3 \times 10^5$ monocytes from healthy donors are incubated in 200 µL of medium with 30 µL of serum from patients with MCTD or serum from normal individuals in absence or presence of a TLR inhibitor. Supernatants are evaluated by ELISA for IFN-α, TNF-α, IL-6, IL-1β and/or IL-8 concentration(s). It is expected that serum from the MCTD patients will stimulate cytokine production, while the serum from normal individuals will not. It is also expected that the MCTD serum-induced cytokine production will be inhibited by TLR7 and/or TLR8 inhibitors.

Example 25—Stimulation of Healthy PBMC with Plasma or Serum from Patients with Sjogren's Syndrome Sjögren's syndrome is a chronic autoimmune disease characterized by progressive mononuclear cell infiltration within exocrine glands. Dryness of the mouth (xerostomia) and eyes (keratoconjunctivitissicca) are the main organ-related clinical features affecting these patients. Sjögren's syndrome is characterized by the presence of RNP autoantibodies, such as anti-Ro/SSA and anti-La/SSB. There is a clear association of Sjögren's syndrome with TLR7 activation of PDC and with increased Type I IFN produced by infiltrating PDC (Båve et al., Arthritis Rheum 2005, 52:1185-95, 2005; and Gottenberg et al., Proc Natl Acad Sci USA, 103:2770-5, 2006). The anti-Ro/SSA and anti-La/SSB autoantibodies also activate TLR8. In fact, TLR8 is also overexpressed in the salivary glands of these patients.

About $7 \times 10^5$ PBMC cells or $3 \times 10^5$ monocytes from healthy donors are incubated in 200 µL of medium with plasma or serum from patients with Sjogren's syndrome or plasma or serum from normal individuals in absence or presence of a TLR inhibitor. Supernatants are evaluated by ELISA for IFN-α, TNF-α, IL-6 and/or IL-1β and/or IL-8 concentration(s). It is expected that plasma or serum from the patients with Sjogren's syndrome will stimulate cytokine production, while plasma or serum from normal individuals will not. It is also expected that Sjogren's syndrome-associated cytokine production will be inhibited by TLR7 and/or TLR8 inhibitors.

Example 26—Determination of Effect of TLR Inhibitors on TLR8-Mediated Salivary Gland Inflammation, and Pancreas, Kidney and Joint Diseases Human TLR8Tg Clone 12 mice express a high level of human TLR8 and develop spontaneous severe salivary gland inflammation, and pancreas, kidney and joint disease. Human TLR8Tg Clone 8 express a lower level of human TLR8 and still develop spontaneous pancreas and salivary gland inflammation, although other organs are not significantly affected. Human TLR8Tg Clone 12 or Clone 8 are injected with multiple doses of a TLR7 and/or TLR8 and/or TLR9 inhibitor or PBS using a defined treatment schedule. Levels of inflammatory genes in the salivary glands, kidney and/or joints are determined using TAQMAN. Genes that may be monitored include IL-1β, IL-6, IL-10, TNF-α, IL1α, IL12p40, mTLR9, MAC1, TLR7, human TLR8, IP-10, MMP9, IFN-g, MMP3, IL1-RAIL-23, Lta, MIP3a, MIP3B, MIG, MMP8, MMP10CD4, CD8, CCR2, CCR6, MPO, NOS2, MMP12, TLR2, MMP1, and MMP7. TLR inhibitor-treated hTLR8Tg Clone 12 or Clone 8 mice are expected to show a decrease in the levels of inflammatory genes in the target organs compared to the levels found in PBS-treated hTLR8Tg Clone 12 or Clone 8 mice. Additionally, the histopathology on the target organs from the human TLR8Tg Clone 12 or Clone 8 mice treated with a TLR inhibitor are expected to show a reduced disease score relative to those treated with PBS only.

Example 27—Inhibition of TLR7/8-Mediated Stimulation of 6-Sulpho LacNAc Dendritic Cells with TLR7, TLR8 and/or TLR7/8 Inhibitors 6-Sulpho LacNAc dendritic cells (slanDC) account for the majority of dendritic cells (DC) in human blood and are highly pro-inflammatory, as characterized by their capacity to produce TNF-α, IL-23, IL-6, IL-1α and I-1β (Schakel et al., Immunity, 25:767, 2006). slanDC are promptly recruited in inflamed tissue (Hansel et al., J Allergy Clin Immun, 127:787, 2011). SlanDCs infiltrate the dermis of patients with psoriasis vulgaris, atopic dermatitis (AD), cutaneous lupus and in the pannus tissue of rheumatoid arthritis.

SlanDCs co-express both TLR7 and TLR8, while the other type of myeloid DC in human CD1c+DC express only TLR8 (Hansel et al., Autoimmunity, 40:1-8, 2013). SlanDCs become activated via TLR7 and TLR8 by LL37-RNA complexes, which are largely present in psoriatic and cutaneous-lupus skin and produce high level of pro-inflammatory cytokines such as TNF-α, IL-23, IL-6 (Hansel, supra). These LL37-RNA complexes are thought to be central in the pathogenesis of cutaneous disease such as psoriasis and cutaneous lupus (Ganguly et al., J Exp Med, 206:1983, 2009; and Gilliet et al., Nat Rev Immun, 8:594, 2008).

SlanDC purified from healthy donors are stimulated with LL37-RNA complexes alone or in the presence of TLR7, TLR8 and/or TLR7/TLR8 inhibitors. Supernatants are evaluated by ELISA for TNF-α, IL-23 and/or IL-6 concentration(s). It is expected that both TLR7 and TLR8 monofunctional inhibitors will decrease the response to LL37-RNA complexes and the bifunctional TLR7/8 inhibitor will more potently decrease the response than the single combinations.

Example 28—Determination of Contribution of TLR8 to Inflammatory Response in Tape Stripped Mice Tape stripping in mice provokes an inflammatory response that is dependent on TLR7 and TLR9 (Guiducci et al., J Exp Med, 207:2931-2942, 2010). To determine the contribution of human TLR8 in skin inflammation, hTLR8Tg Clone 8 mice are treated with a TLR7, TLR8, and/or TLR9 monofunctional inhibitor, and/or a TLR7/9 and/or TLR7/8 bifunctional inhibitor, and/or aTLR7/8/9 trifunctional inhibitor subcutaneously and immediately after, the mice are tape stripped. A group of mice is left untreated to serve as controls. Skin biopsies are sampled 24 hours after tape stripping and gene expression of Type I IFN regulated genes and inflammatory genes are evaluated by TAQMAN analysis. The contribution of the inflammatory response on TLR8 is determined by comparing the results using the different TLR inhibitors. It is expected that this immune response is at least in part mediated by TLR8 and that administration of a TLR8 inhibitor will cause a reduction expression of the Type I IFN regulated and inflammatory genes.

Example 29—TLR7/8 Inhibitors Decrease Inflammatory Gene Expression in the Kidney of TLR7.6 Mice Mice overexpressing the mouse TLR7 gene (TLR7.6) have been previously described (Deane et. al., Immunity, 27:801-810, 2007). TLR7.6 mice develop autoantibody-mediated glomerulonephritis characterized by increased inflammatory cell infiltration and production of inflammatory cytokines. In addition, TLR7.6 mice develop splenomegaly and increased expansion of myeloid cells.

Figure 34B:
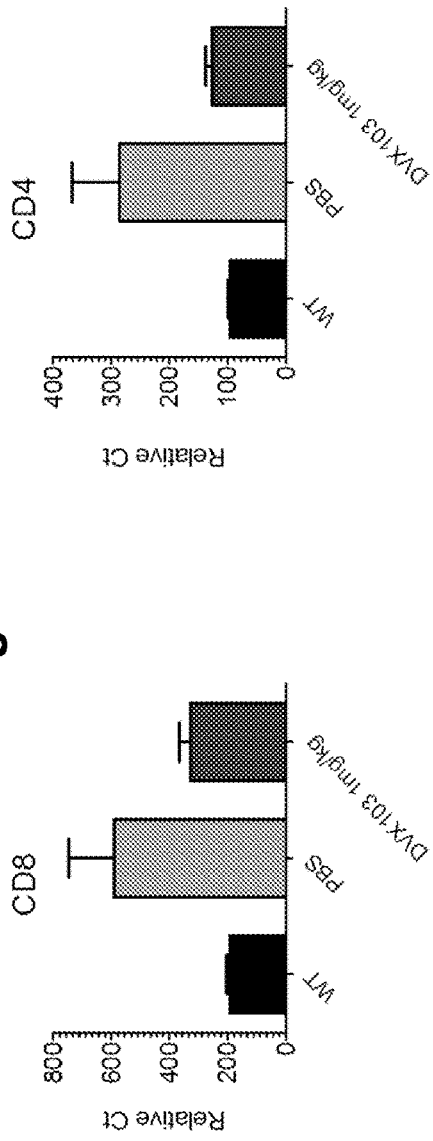
FIG. 34B shows the relative levels of mCD8 and mCD4 in the kidney of mice overexpressing the mouse TLR7 gene (TLR7.6), as compared to wild type (WT) mice and to TLR7.6 mice after treatment with PBS or DVX103 (1 mg/kg, once a week for 15 weeks).

TLR7.6 mice that were 2-3 months old were injected with 1 mg/kg of DVX103 or PBS once a week for 15 weeks. Inflammatory gene expression in the kidney was determined by TAQMAN assay. FIG. 34A and FIG. 34B shows the relative levels of mIL-1α, mIL-1β, mTNF-α, mIFN-γ, mMMP-7, mCD11bβ, mCD8 and mCD4 in the kidney of TLR7.6 mice, as compared to wild type mice and to TLR7.6 mice after treatment with DVX103. DVX103 was able to decrease the levels of inflammatory genes expressed in the kidney of TLR7.6 mice (see, FIG. 34A).

Figure 34C:
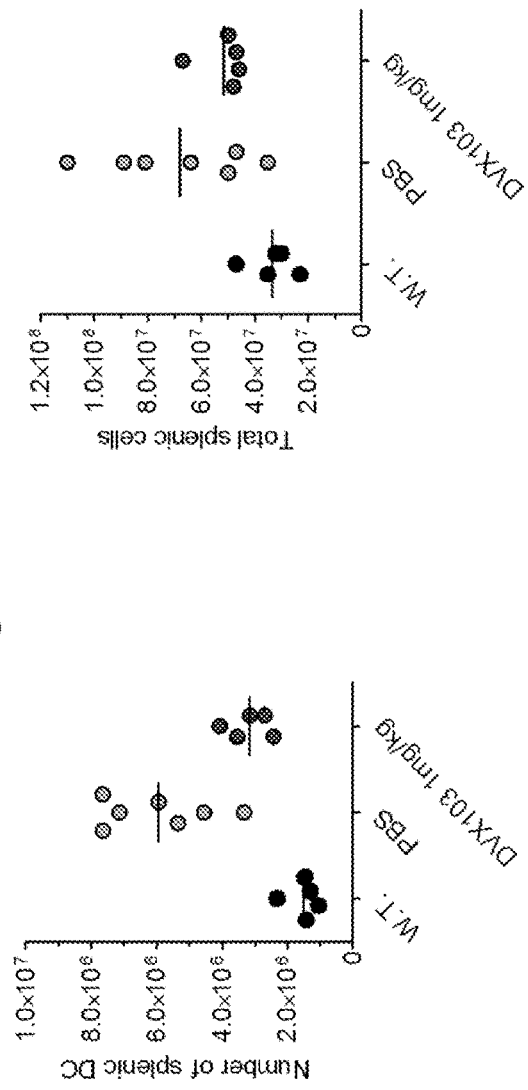
FIG. 34C shows the number of splenic dendritic cells (DC) in wild type mice and in TLR7.6 mice treated with PBS or DVX103 (1 mg/kg, once a week for 15 weeks).

At the end of the experiment, spleens were harvested from the mice. After mechanical disruption, the total number of splenic cells was determined by cell counting. The number of dendritic cells (DC) was determined by flow cytometry using an antibody to label CD11c cells. FIG. 34C shows that treatment of the TLR7.6 mice with DVX103 normalizes the myeloid cell expansion in TLR 7.6 mice.

Figure 35A:
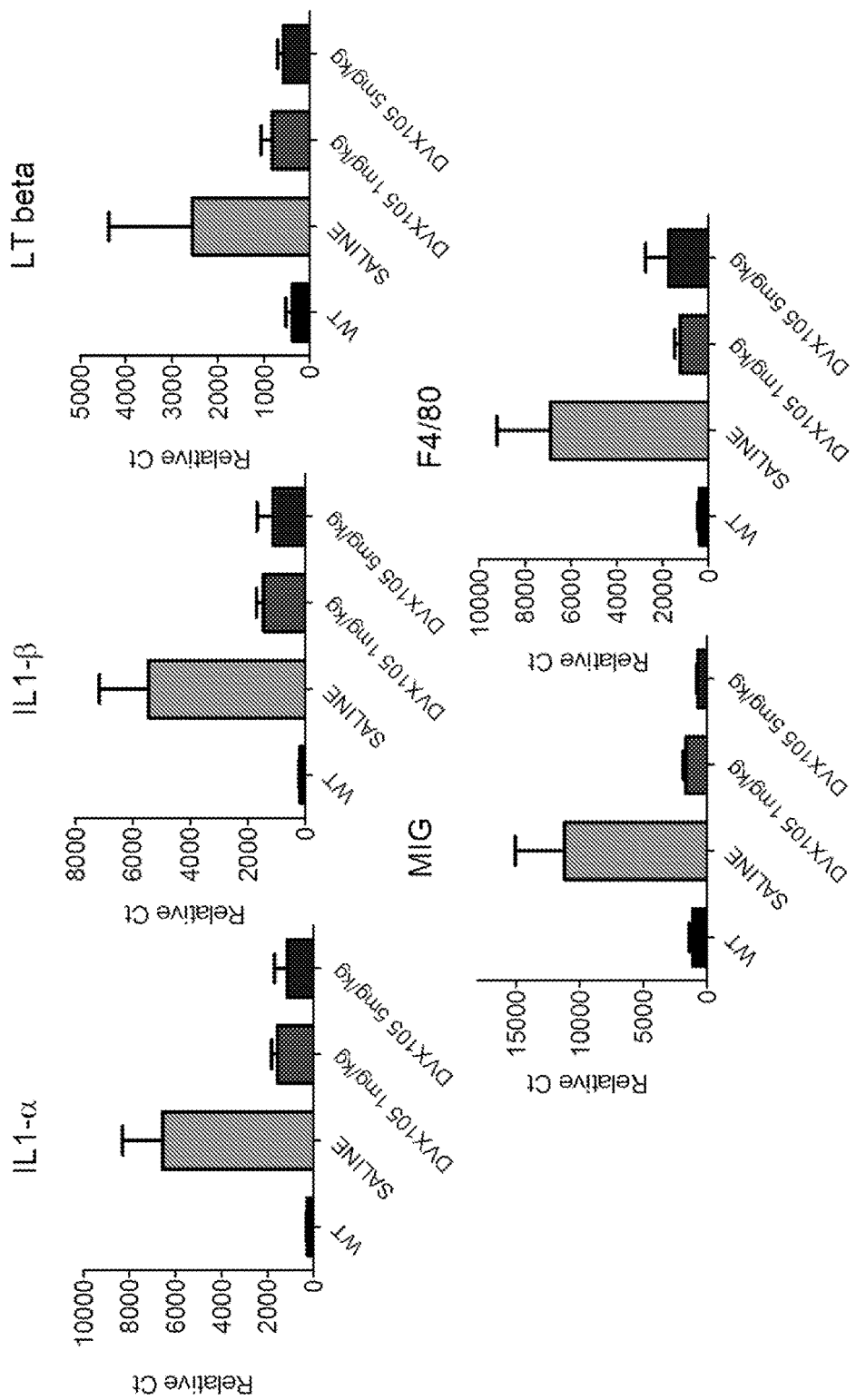
FIG. 35A shows the relative levels of mIL-1α, mIL-1β, mLT-β, mMIG and mF4/80 in the kidney of TLR7.6 mice, as compared to wild type (WT) mice and to TLR7.6 mice after treatment with saline or DVX105 (1 mg/kg or 5 mg/kg, once a week for 8 weeks).

In a second experiment, TLR7.6 mice that were 5-6 months old were injected with 1 mg/kg or 5 mg/kg of DVX105 or saline once a week for 8 weeks. Inflammatory gene expression in the kidney was determined by TAQMAN assay. FIG. 35A shows the relative levels of mIL-1α, mIL-1β, mLT-β, mMIG and mF4/80 in the kidney of TLR7.6 mice, as compared to wild type mice and to TLR7.6 mice after treatment with DVX105. DVX105 was able to decrease the levels of inflammatory genes expressed in the kidney of TLR7.6 mice (see, FIG. 35A).

Figure 35B:
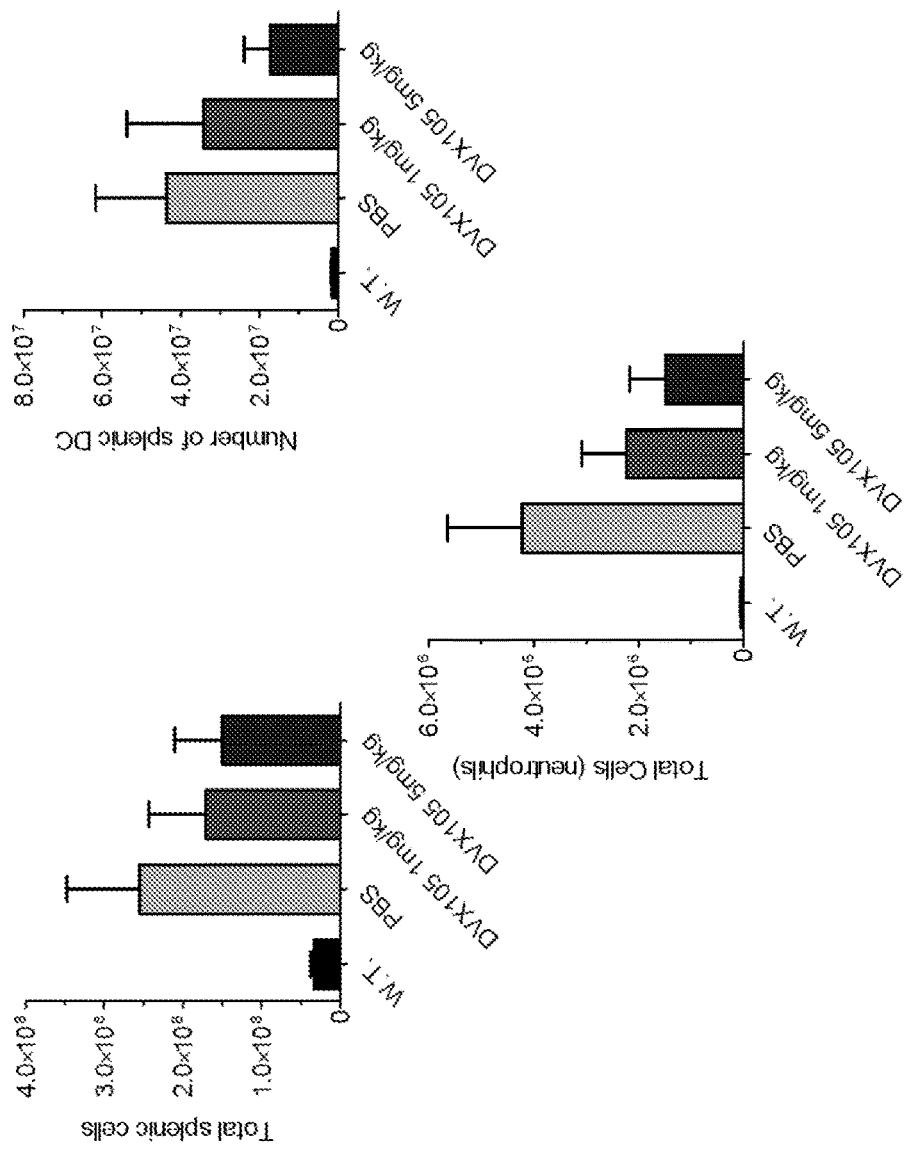
FIG. 35B shows the number of splenic dendritic cells (DC) in wild type mice and in TLR7.6 mice treated with PBS or DVX105 (1 mg/kg or 5 mg/kg, once a week for 8 weeks).

At the end of the experiment, spleens were harvested from the mice. After mechanical disruption, the total number of splenic cells was determined by cell counting. The number of dendritic cells (DC) and neutrophils was determined by flow cytometry using an antibody to label CD11c and LY6G, respectively. FIG. 35B shows that treatment of the TLR7.6 mice with DVX105 normalizes the myeloid cell expansion in TLR 7.6 mice.

Example 30—Activity of High and Low Doses of Inhibitory Polynucleotides in Rats Polynucleotides (C954, DVX103, DVX104, and DVX105) at high dosages (hi=40 mg/kg) or low dosages (lo=10 mg/kg) were subcutaneously administered to Sprague Dawley rats once a week for eight weeks (n=5 per group). Rats were weighed prior to administration (day 0), and thereafter as indicated in Table 30-1. Organs were harvested at the end of the study, and organ weights were determined. In addition, histological evaluation of the liver and kidney was performed. C954 was included in the study as a historical control and is representative of a polynucleotide with a good toxicology profile.

Rats treated with C954, DVX103, DVX104 or DVX105 showed similar increases in body weight. Organ weights of animals of all groups were similar. A summary of the severity scores reflecting changes in the liver and kidney are shown in Table 30-1. The histopathology exam of the organs confirmed the kidney as the target organ. Hepatic extramedullary hematopoiesis is not uncommon in rats. As this was observed in all groups, including the PBS-treated group, it was not considered a significant polynucleotide-related finding. No other significant changes were observed in the liver. In the kidney, mild tubular changes were found in most groups. All of the polynucleotides tested in this chronic setting showed mild changes in the kidney at the high dose (40 mg/kg, severity score about 2), while minimal changes were observed at the low dose (10 mg/kg).

TABLE 30-1

Summary of Histological Findings

| | 1 PBS | 2 C954 hi | 3 C954 lo | 4 DVX103 hi | 5 DVX103 lo |
|---|---|---|---|---|---|
| Liver: | | | | | |
| No lesions | 1 | 1 | 1 | 2 | 2 |
| Hematopoiesis | 4 (1.25) | 3 (1.3) | 3 (1.0) | 2 (1.25) | 3 (1.15) |
| Cell infiltration | 0 | 1 (2.0) | 2 (1.75) | 1 (2.0) | 0 |
| Hepatocyte degeneration | 0 | 0 | 2 (1.25) | 0 | 0 |
| Kidney: | | | | | |
| No lesions | 3 | 1 | 1 | 0 | 0 |
| Mineralization | 2 (1.25) | 0 | 0 | 0 | 0 |
| Tubular changes | 0 | 4 (2.25) | 4 (1.15) | 5 (2.7) | 5 (1.3) |
| Interstitial cell accumulations | 0 | 1 (1.0) | 0 | 1 (2.0) | 0 |

| | 6 DVX104 hi | 7 DVX104 lo | 8 DVX105 hi | 9 DVX105 lo | |
|---|---|---|---|---|---|
| Liver: | | | | | |
| No lesions | 1 | 2 | 1 | 4 | |
| Hematopoiesis | 3 (1.0) | 3 (1.0) | 4 (1.0) | 1 (1.0) | |
| Cell infiltration | 2 (1.5) | 0 | 0 | 0 | |
| Hepatocyte degeneration | 0 | 0 | 0 | 0 | |
| Kidney: | | | | | |
| No lesions | 0 | 0 | 0 | 1 | |
| Mineralization | 1 (2.0) | 0 | 1 (1.0) | 0 | |
| Tubular changes | 5 (2.4) | 5 (1.0) | 5 (2.2) | 4 (1.0) | |
| Interstitial cell accumulations | 0 | 0 | 0 | 0 | |

( ) = mean severity score;
0 = no change;
1 = minimal;
2 = mild;
3 = moderate;
4 = severe.
Data are shown as # animals out of 5 in each group.

Example 31—TLR7/8 Inhibitors Reduce Disease Score in a Collagen-Induced Model of Rheumatoid Arthritis Wild-type (C57BL/6) and TLR8 transgenic mice (TLR8TGCL8 described in WO 2012/135549) were immunized per a published immunization schedule and protocol (Campbell, Eur J Immunol 30:1568-1575, 2000). On day 0 of collagen immunization, collagen (chicken Type II collagen from Chondrex; 2 mg/mL) was emulsified with Complete Freund's Adjuvant (CFA from Chondrex containing 5 mg/mL Mycobacterium tuberculosis H37Ra) as follows:
(i) one volume of CFA was mixed with an equal amount of the collagen solution;
(ii) mixing was continued until a stable, stiff emulsion resulted;
(iii) to ascertain the desired stability of the emulsion, 1 drop of emulsion was added into a water-filled beaker (the emulsion was considered stable if it remained in the water as a solid); and
(iv) 100 μl was injected subcutaneously at the base of the tail.

Figure 36:
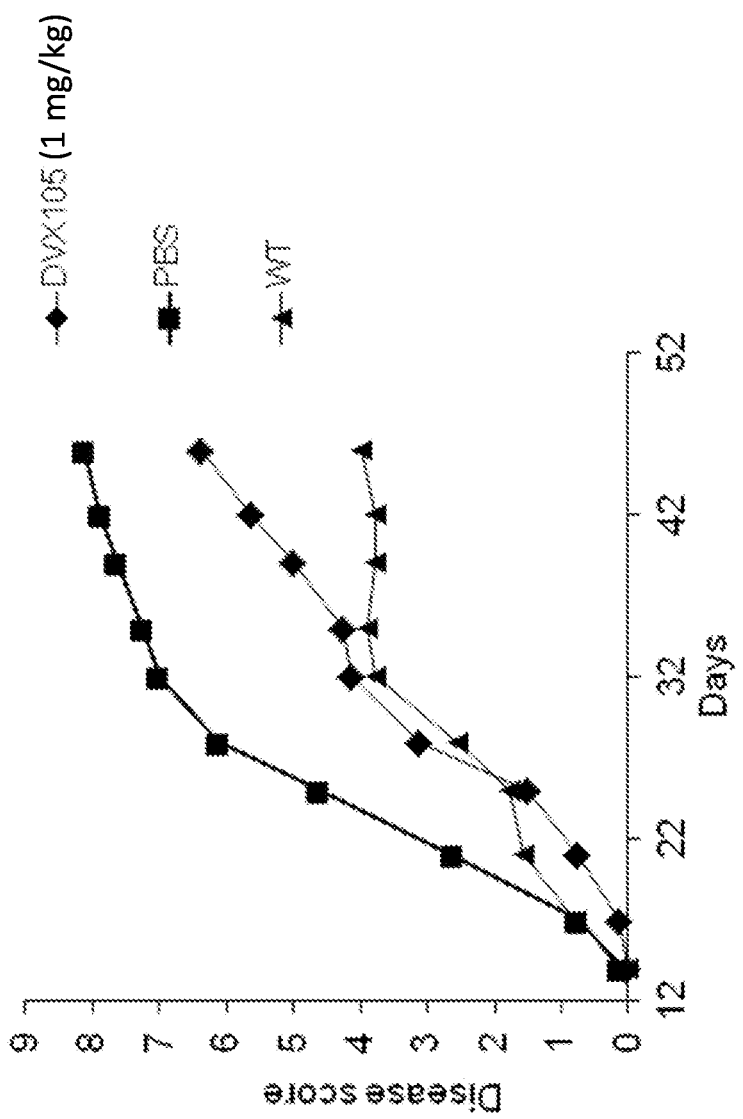
FIG. 36 shows the disease score in a collagen-induced rheumatoid arthritis (CIA) model in wild-type (WT) mice (C57BL/6) and TLR8 transgenic mice (TLR8TGCL8) treated with PBS or DVX105 over time after the first collagen injection. Treatment (PBS or DVX105, 1 mg/kg subcutaneous) was administered on days −1, 7, 14, 20, 24, 28, 31, 35, 42, 49 and 53.

A second injection was administered on day 21. Animals were assessed for redness and swelling of the limbs and the cumulative score of each mouse was the sum of the score obtained for each of the four limbs. The Clinical Score Guidelines were as follows: 0-Normal; 1-Mild, but definite redness and swelling of the ankle or wrist, or apparent redness and swelling limited to individual digits, regardless of the number of affected digits; 2-Moderate redness and swelling of ankle of wrist; 3-Severe redness and swelling of the entire paw including digits; and 4-Maximally inflamed limb with involvement of multiple joints and a clinical score allocated.

hTLR8TgCL8 mice were treated with either PBS or TLR7/8 inhibitor DVX105 (1 mg/kg subcutaneous) on days −1, 7, 14, 20, 24, 28, 31, 35, 42, 49 and 53. As shown in FIG. 36, the disease score in hTLR8TgCL8 mice was greatly exacerbated as compared to that of wild type (WT) mice. Treatment of the hTLR8TgCL8 mice with DVX105 decreased the disease score. This study demonstrates that hTLR8 plays a role in the exacerbation of arthritis and that a TLR7/8 inhibitor decreases arthritis in subjects that express hTLR8.

Figure 38:
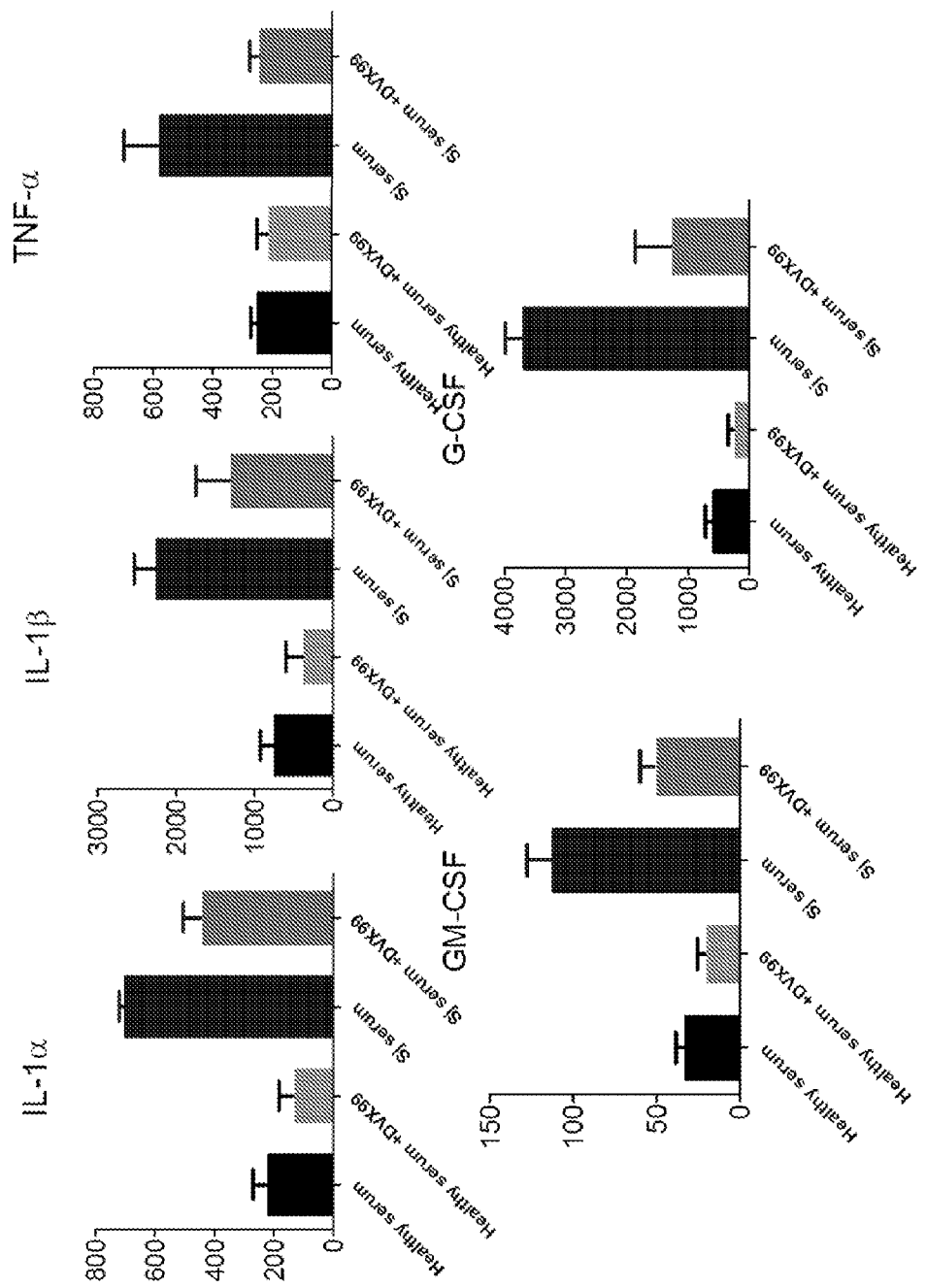
FIG. 38 shows the average hIL-1α, hIL-1β, hTNF-α, hGM-CSF and hG-CSF production by CD14+ monocytes stimulated with either serum from five Sjogren's syndrome (SJ) patients or serum from three healthy individuals, alone or in combination with DVX99 at a concentration of 1 μM. The monocytes were obtained from healthy human subjects. The results shown are representative of three experiments.

Example 33—Stimulation of Human Monocytes with Serum from Sjogren's Syndrome Sjogren's Syndrome Patients is TLR7/8-Dependent CD14+ monocytes were isolated from buffy coats using a negative selection kit (Stem Cell, Catalog No. 14068) according to the manufacturer's instructions. Purity was routinely over 98%. About $3 \times 10^5$ cells were incubated in complete medium (RPMI, 10% FBS), alone or in combination with TLR7/8 inhibitor DVX99 (1 μM), in the presence of 7.5% serum from healthy subjects (n=3) or Sjogren's Syndrome patients with active disease (n=5). Serum from Sjogren's Syndrome patients was obtained from Newcastle University (UK). After 14-16 hours, supernatants were assayed for cytokine levels by Milliplex (Millipore). As shown in FIG. 38, the serum from the Sjogren's Syndrome patients stimulates IL-1α, IL-1β, TNF-α, GM-CSF and G-CSF production, and this cytokines production can be inhibited by the TLR7/8 inhibitor DVX99.

We claim:

1. A polynucleotide consisting of the nucleotide sequence of the formula: 5'-$N_xX_1X_2X_3X_4X_5X_6$-3', wherein each of N, $X_1$, $X_2$, $X_3$ and $X_4$, is a nucleotide or nucleotide analog, $X_5X_6$ is II, x is an integer from 0 to 50, $N_x$ comprises a TTC trinucleotide located at the 5' end of the polynucleotide and the polynucleotide does not comprise a CG dinucleotide.

2. A pharmaceutical composition comprising the polynucleotide of claim 1 and a pharmaceutically acceptable excipient.

3. A method of inhibiting a TLR8-dependent immune response in an individual, the method comprising: administering to the individual the pharmaceutical composition of claim 2 in an amount effective to inhibit the TLR8-dependent immune response in the individual.

4. A method of inhibiting an immune response in an individual, the method comprising: administering to the individual, a pharmaceutical composition in an amount effective to inhibit the immune response in the individual, wherein the pharmaceutical composition comprises a pharmaceutically acceptable excipient and a polynucleotide consisting of the nucleotide sequence of the formula:

5'-$N_xX_1X_2X_3X_4X_5X_6$-3', wherein each of N, $X_1$, $X_2$, $X_3$ and $X_4$, is a nucleotide or nucleotide analog, $X_5X_6$ is II, x is an integer from 0 to 50, $N_x$ comprises a TTC trinucleotide located at the 5' end of the polynucleotide and the polynucleotide does not comprise a CG dinucleotide.

5. The method of claim 4, wherein the immune response is associated with an autoimmune disease.

6. The method of claim 5, wherein inhibiting the immune response ameliorates one or more symptoms of the autoimmune disease.

7. The method of claim 5, wherein the autoimmune disease is selected from the group consisting of rheumatoid arthritis, pancreatitis, mixed tissue connective disease, systemic lupus erythematosus, antiphospholipid syndrome, irritable bowel disease, type I diabetes mellitus, and Sjogren's disease.

8. The method of claim 4, wherein the individual is human.

9. The polynucleotide of claim 1, wherein the polynucleotide is not an antisense sequence or an RNAi molecule.

10. The polynucleotide of claim 1, wherein the polynucleotide does not comprise 5'-GGGG-3'.

11. The polynucleotide of claim 1, wherein the polynucleotide is less than 40 bases or base pairs in length.

12. The polynucleotide of claim 1, wherein the polynucleotide is less than 30 bases or base pairs in length.

13. The polynucleotide of claim 1, wherein at least one internucleotide linkage of the polynucleotide is a phosphate-modified linkage.

14. The polynucleotide of claim 1, wherein all internucleotide linkages of the polynucleotide are phosphorothioate linkages.

15. The polynucleotide of claim 1, wherein the polynucleotide does not comprise 5'-GIGG-3'.

16. The polynucleotide of claim 1, wherein the polynucleotide consists of SEQ ID NO:97.

17. The method of claim 5, wherein the autoimmune disease is selected from the group consisting of dermatomyositis, inflammatory bowel disease, multiple sclerosis and scleroderma.

18. The method of claim 5, wherein the autoimmune disease is associated with RNA-containing immune complexes.

19. The method of claim 4, wherein the immune response is associated with an inflammatory disorder.

20. The method of claim 19, wherein inhibiting the immune response ameliorates one or more symptoms of the inflammatory disorder.

* * * * *

SEQUENCE LISTING

<160> NUMBER OF SEQ ID NOS: 118

<210> SEQ ID NO 1
<211> LENGTH: 3126
<212> TYPE: DNA
<213> ORGANISM: Homo sapiens

<400> SEQUENCE: 1

| | | | | | |
|---|---|---|---|---|---|
| atggaaaaca | tgttccttca | gtcgtcaatg | ctgacctgca | ttttcctgct | aatatctggt | 60 |
| tcctgtgagt | tatgcgccga | agaaaatttt | tctagaagct | atccttgtga | tgagaaaaag | 120 |
| caaaatgact | cagttattgc | agagtgcagc | aatcgtcgac | tacaggaagt | tccccaaacg | 180 |
| gtgggcaaat | atgtgacaga | actagacctg | tctgataatt | tcatcacaca | cataacgaat | 240 |
| gaatcatttc | aagggctgca | aaatctcact | aaaataaatc | taaccacaa | ccccaatgta | 300 |
| cagcaccaga | acggaaatcc | cggtatacaa | tcaaatggct | tgaatatcac | agacggggca | 360 |
| ttcctcaacc | taaaaaacct | aagggagtta | ctgcttgaag | acaaccagtt | accccaaata | 420 |
| ccctctggtt | tgccagagtc | tttgacagaa | cttagtctaa | ttcaaaacaa | tatatacaac | 480 |
| ataactaaag | agggcatttc | aagacttata | aacttgaaaa | atctctattt | ggcctggaac | 540 |
| tgctatttta | acaaagtttg | cgagaaaact | aacatagaag | atggagtatt | tgaaacgctg | 600 |
| acaaatttgg | agttgctatc | actatctttc | aattctcttt | cacacgtgcc | acccaaactg | 660 |
| ccaagctccc | tacgcaaact | ttttctgagc | aacacccaga | tcaaatacat | tagtgaagaa | 720 |
| gatttcaagg | gattgataaa | tttaacatta | ctagatttaa | gcgggaactg | tccgaggtgc | 780 |
| ttcaatgccc | catttccatg | cgtgccttgt | gatggtggtg | cttcaattaa | tatagatcgt | 840 |
| tttgcttttc | aaaacttgac | ccaacttcga | tacctaaacc | tctctagcac | ttccctcagg | 900 |
| aagattaatg | ctgcctggtt | taaaaatatg | cctcatctga | aggtgctgga | tcttgaattc | 960 |
| aactatttag | tgggagaaat | agcctctggg | gcattttaa | cgatgctgcc | ccgcttagaa | 1020 |
| atacttgact | tgtcttttaa | ctatataaag | gggagttatc | cacagcatat | taatatttcc | 1080 |
| agaaacttct | ctaaacttttt | gtctctacgg | gcattgcatt | taagaggtta | tgtgttccag | 1140 |
| gaactcagag | aagatgattt | ccagcccctg | atgcagcttc | aaacttatc | gactatcaac | 1200 |
| ttgggtatta | attttattaa | gcaaatcgat | ttcaaacttt | tccaaaattt | ctccaatctg | 1260 |
| gaaattattt | acttgtcaga | aaacagaata | tcaccgttgg | taaaagatac | ccggcagagt | 1320 |
| tatgcaaata | gttcctcttt | tcaacgtcat | atccggaaac | gacgctcaac | agattttgag | 1380 |
| tttgacccac | attcgaactt | ttatcatttc | acccgtcctt | taataaagcc | acaatgtgct | 1440 |
| gcttatggaa | aagccttaga | tttaagcctc | aacagtattt | tcttcattgg | gccaaaccaa | 1500 |
| tttgaaaatc | ttcctgacat | tgcctgttta | aatctgtctg | caaatagcaa | tgctcaagtg | 1560 |
| ttaagtggaa | ctgaattttc | agccattcct | catgtcaaat | atttggattt | gacaaacaat | 1620 |
| agactagact | tgataatgc | tagtgctctt | actgaattgt | ccgacttgga | agttctagat | 1680 |
| ctcagctata | attcacacta | tttcagaata | gcaggcgtaa | cacatcatct | agaatttatt | 1740 |
| caaaatttca | caaatctaaa | agttttaaac | ttgagccaca | acaacattta | tactttaaca | 1800 |
| gataagtata | acctggaaag | caagtccctg | gtagaattag | ttttcagtgg | caatcgcctt | 1860 |
| gacattttgt | ggaatgatga | tgacaacagg | tatatctcca | ttttcaaagg | tctcaagaat | 1920 |
| ctgacacgtc | tggatttatc | ccttaatagg | ctgaagcaca | tcccaaatga | agcattcctt | 1980 |
| aatttgccag | cgagtctcac | tgaactacat | ataaatgata | atatgttaaa | gtttttaac | 2040 |
| tggacattac | tccagcagtt | tcctcgtctc | gagttgcttg | acttacgtgg | aaacaaacta | 2100 |

```
ctcttttaa ctgatagcct atctgacttt acatcttccc ttcggacact gctgctgagt    2160
cataacagga tttcccacct accctctggc tttctttctg aagtcagtag tctgaagcac    2220
ctcgatttaa gttccaatct gctaaaaaca atcaacaaat ccgcacttga aactaagacc    2280
accaccaaat tatctatgtt ggaactacac ggaaacccct ttgaatgcac ctgtgacatt    2340
ggagatttcc gaagatggat ggatgaacat ctgaatgtca aaattcccag actggtagat    2400
gtcatttgtg ccagtcctgg ggatcaaaga gggaagagta ttgtgagtct ggagctaaca    2460
acttgtgttt cagatgtcac tgcagtgata ttatttttct tcacgttctt tatcaccacc    2520
atggttatgt tggctgccct ggctcaccat ttgtttttact gggatgtttg gtttatatat    2580
aatgtgtgtt tagctaaggt aaaaggctac aggtctcttt ccacatccca aactttctat    2640
gatgcttaca tttcttatga caccaaagat gcctctgtta ctgactgggt gataaatgag    2700
ctgcgctacc accttgaaga gagccgagac aaaaacgttc tcctttgtct agaggagagg    2760
gattgggatc cgggattggc catcatcgac aacctcatgc agagcatcaa ccaaagcaag    2820
aaaacagtat ttgtttaac caaaaaatat gcaaaagct ggaactttaa aacagctttt    2880
tacttggctt tgcagaggct aatggatgag aacatggatg tgattatatt tatcctgctg    2940
gagccagtgt tacagcattc tcagtatttg aggctacggc agcggatctg taagagctcc    3000
atcctccagt ggcctgacaa cccgaaggca gaaggcttgt tttggcaaac tctgagaaat    3060
gtggtcttga ctgaaaatga ttcacggtat aacaatatgt atgtcgattc cattaagcaa    3120
tactaa                                                                3126

<210> SEQ ID NO 2
<211> LENGTH: 11
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 5, 11
<223> OTHER INFORMATION: n = 7-deazaguanosine

<400> SEQUENCE: 2
uncuncuucu n                                                            11

<210> SEQ ID NO 3
<211> LENGTH: 11
<212> TYPE: RNA
<213> ORGANISM: Artificial Sequence
<220> FEATURE:
<223> OTHER INFORMATION: Synthetic Construct

<400> SEQUENCE: 3
ugcugcuugu g                                                            11

<210> SEQ ID NO 4
<211> LENGTH: 22
<212> TYPE: DNA
<213> ORGANISM: Artificial Sequence
<220> FEATURE:
<223> OTHER INFORMATION: Synthetic Construct

<400> SEQUENCE: 4
tgactgtgaa cgttcgagat ga                                                22

<210> SEQ ID NO 5
```

```
<211> LENGTH: 21
<212> TYPE: DNA
<213> ORGANISM: Artificial Sequence
<220> FEATURE:
<223> OTHER INFORMATION: Synthetic Construct

<400> SEQUENCE: 5
tcgtcgaacg ttcgagatga t                                              21

<210> SEQ ID NO 6
<211> LENGTH: 15
<212> TYPE: DNA
<213> ORGANISM: Artificial Sequence
<220> FEATURE:
<223> OTHER INFORMATION: Synthetic Construct

<400> SEQUENCE: 6
tcctggaggg gttgt                                                     15

<210> SEQ ID NO 7
<211> LENGTH: 18
<212> TYPE: DNA
<213> ORGANISM: Artificial Sequence
<220> FEATURE:
<223> OTHER INFORMATION: Synthetic Construct

<400> SEQUENCE: 7
tgctcctgga ggggttgt                                                  18

<210> SEQ ID NO 8
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3,20-25
<223> OTHER INFORMATION: 2'-O-methyl ribonucleotide
<220> FEATURE:
<221> NAME/KEY: misc_feature
<222> LOCATION: 1, 21, 22, 23, 25
<223> OTHER INFORMATION: n = uracil

<400> SEQUENCE: 8
ngctgctcct tgagggggttg nnngn                                         25

<210> SEQ ID NO 9
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: 2'-O-methyl ribonucleotide
<220> FEATURE:
<221> NAME/KEY: misc_feature
<222> LOCATION: 1
<223> OTHER INFORMATION: n = uracil
<220> FEATURE:
<221> NAME/KEY: misc_feature
<222> LOCATION: 15
<223> OTHER INFORMATION: n = 2'-deoxyinosine

<400> SEQUENCE: 9
ngctgctcct tgagn                                                     15
```

```
<210> SEQ ID NO 10
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: 2'-O-methyl ribonucleotide
<220> FEATURE:
<221> NAME/KEY: misc_feature
<222> LOCATION: 1
<223> OTHER INFORMATION: n = uracil

<400> SEQUENCE: 10
ngctgctcct tgaga                                                    15

<210> SEQ ID NO 11
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: 2'-O-methyl ribonucleotide
<220> FEATURE:
<221> NAME/KEY: misc_feature
<222> LOCATION: 1
<223> OTHER INFORMATION: n = uracil

<400> SEQUENCE: 11
ngctgctcct tgagt                                                    15

<210> SEQ ID NO 12
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: 2'-O-methyl ribonucleotide
<220> FEATURE:
<221> NAME/KEY: misc_feature
<222> LOCATION: 1
<223> OTHER INFORMATION: n = uracil

<400> SEQUENCE: 12
ngctgctcct tgagg                                                    15

<210> SEQ ID NO 13
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: 2'-O-methyl ribonucleotide
<220> FEATURE:
<221> NAME/KEY: misc_feature
<222> LOCATION: 1
<223> OTHER INFORMATION: n = uracil

<400> SEQUENCE: 13
ngctgctcct tgagc                                                    15
```

```
<210> SEQ ID NO 14
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: 2'-O-methyl ribonucleotide
<220> FEATURE:
<221> NAME/KEY: misc_feature
<222> LOCATION: 1
<223> OTHER INFORMATION: n = uracil
<220> FEATURE:
<221> NAME/KEY: misc_feature
<222> LOCATION: 15
<223> OTHER INFORMATION: n = 2'-deoxyinosine

<400> SEQUENCE: 14
ngctgctcct tgggn                                                        15

<210> SEQ ID NO 15
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1,2
<223> OTHER INFORMATION: 2'-O-methyl ribonucleotide
<220> FEATURE:
<221> NAME/KEY: misc_feature
<222> LOCATION: 1
<223> OTHER INFORMATION: n = uracil
<220> FEATURE:
<221> NAME/KEY: misc_feature
<222> LOCATION: 15
<223> OTHER INFORMATION: n = 2'-deoxyinosine

<400> SEQUENCE: 15
ngctgctcct tgagn                                                        15

<210> SEQ ID NO 16
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = 2'-O-methyl-uracil
<220> FEATURE:
<221> NAME/KEY: misc_feature
<222> LOCATION: 15
<223> OTHER INFORMATION: n = 2'-deoxyinosine

<400> SEQUENCE: 16
ngctgctcct tgagn                                                        15

<210> SEQ ID NO 17
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15
<223> OTHER INFORMATION: n = 2'-deoxyinosine
```

<400> SEQUENCE: 17
tgctgctcct tgagn                                              15

<210> SEQ ID NO 18
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-6
<223> OTHER INFORMATION: 2'-O-methyl ribonucleotide
<220> FEATURE:
<221> NAME/KEY: misc_feature
<222> LOCATION: 1, 4
<223> OTHER INFORMATION: n = uracil
<220> FEATURE:
<221> NAME/KEY: misc_feature
<222> LOCATION: 15
<223> OTHER INFORMATION: n = 2'-deoxyinosine

<400> SEQUENCE: 18
ngcngctcct tgagn                                              15

<210> SEQ ID NO 19
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: 2'-O-methyl ribonucleotide
<220> FEATURE:
<221> NAME/KEY: misc_feature
<222> LOCATION: 1
<223> OTHER INFORMATION: n = uracil

<400> SEQUENCE: 19
ngctgctgct gctgc                                              15

<210> SEQ ID NO 20
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: 2'-O-methyl ribonucleotide
<220> FEATURE:
<221> NAME/KEY: misc_feature
<222> LOCATION: 1
<223> OTHER INFORMATION: n = uracil
<220> FEATURE:
<221> NAME/KEY: misc_feature
<222> LOCATION: 15
<223> OTHER INFORMATION: n = 2'-deoxyinosine

<400> SEQUENCE: 20
ngctgctcct tgagnt                                             16

<210> SEQ ID NO 21
<211> LENGTH: 17
<212> TYPE: DNA
<213> ORGANISM: Artificial Sequence
<220> FEATURE:

```
<223> OTHER INFORMATION: Synthetic Construct
<220> FEATURE:
<221> NAME/KEY: misc_feature
<222> LOCATION: 1-3
<223> OTHER INFORMATION: 2'-O-methyl ribonucleotide
<220> FEATURE:
<221> NAME/KEY: misc_feature
<222> LOCATION: 1
<223> OTHER INFORMATION: n = uracil
<220> FEATURE:
<221> NAME/KEY: misc_feature
<222> LOCATION: 15
<223> OTHER INFORMATION: n = 2'-deoxyinosine

<400> SEQUENCE: 21
ngctgctcct tgagntt                                                    17

<210> SEQ ID NO 22
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: 2'-O-methyl ribonucleotide
<220> FEATURE:
<221> NAME/KEY: misc_feature
<222> LOCATION: 1
<223> OTHER INFORMATION: n = uracil
<220> FEATURE:
<221> NAME/KEY: misc_feature
<222> LOCATION: 15
<223> OTHER INFORMATION: n = 2'-deoxyinosine

<400> SEQUENCE: 22
ngctgctcct tgagnttt                                                   18

<210> SEQ ID NO 23
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: 2'-O-methyl ribonucleotide
<220> FEATURE:
<221> NAME/KEY: misc_feature
<222> LOCATION: 1
<223> OTHER INFORMATION: n = uracil

<400> SEQUENCE: 23
ngctgctcct tgag                                                       14

<210> SEQ ID NO 24
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: 2'-O-methyl ribonucleotide
<220> FEATURE:
<221> NAME/KEY: misc_feature
<222> LOCATION: 1
<223> OTHER INFORMATION: n = uracil

<400> SEQUENCE: 24
```
ngctgctcct tga                                                      13

<210> SEQ ID NO 25
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: 2'-O-methyl ribonucleotide
<220> FEATURE:
<221> NAME/KEY: misc_feature
<222> LOCATION: 1
<223> OTHER INFORMATION: n = uracil

<400> SEQUENCE: 25
ngctgctcct tg                                                       12

<210> SEQ ID NO 26
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = uracil
<220> FEATURE:
<221> NAME/KEY: misc_feature
<222> LOCATION: 1-3
<223> OTHER INFORMATION: 2'-O-methyl ribonucleotide
<220> FEATURE:
<221> NAME/KEY: misc_feature
<222> LOCATION: 5, 12, 14, 15
<223> OTHER INFORMATION: n = 2'-deoxyinosine

<400> SEQUENCE: 26
ngctnctcct tnann                                                    15

<210> SEQ ID NO 27
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3,15
<223> OTHER INFORMATION: 2'-O-methyl ribonucleotide
<220> FEATURE:
<221> NAME/KEY: misc_feature
<222> LOCATION: 1, 15
<223> OTHER INFORMATION: n = uracil

<400> SEQUENCE: 27
ngctgctcct tgagn                                                    15

<210> SEQ ID NO 28
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3,13-15
<223> OTHER INFORMATION: 2'-O-methyl ribonucleotide
<220> FEATURE:

<221> NAME/KEY: misc_feature
<222> LOCATION: 1, 15
<223> OTHER INFORMATION: n = uracil

<400> SEQUENCE: 28
ngctgctcct tgagn                                                    15

<210> SEQ ID NO 29
<211> LENGTH: 11
<212> TYPE: RNA
<213> ORGANISM: Artificial Sequence
<220> FEATURE:
<223> OTHER INFORMATION: Synthetic Construct

<400> SEQUENCE: 29
ugcugcuugu g                                                        11

<210> SEQ ID NO 30
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15
<223> OTHER INFORMATION: n = 2'-deoxyinosine

<400> SEQUENCE: 30
tgctgctggt tgtgn                                                    15

<210> SEQ ID NO 31
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: 2'-O-methyl ribonucleotide
<220> FEATURE:
<221> NAME/KEY: misc_feature
<222> LOCATION: 1
<223> OTHER INFORMATION: n = uracil
<220> FEATURE:
<221> NAME/KEY: misc_feature
<222> LOCATION: 15
<223> OTHER INFORMATION: n = 2'-deoxyinosine

<400> SEQUENCE: 31
ncctgctcct tgagn                                                    15

<210> SEQ ID NO 32
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: 2'-O-methyl ribonucleotide
<220> FEATURE:
<221> NAME/KEY: misc_feature
<222> LOCATION: 1, 2, 3
<223> OTHER INFORMATION: n = uracil
<220> FEATURE:
<221> NAME/KEY: misc_feature
<222> LOCATION: 15
<223> OTHER INFORMATION: n = 2'-deoxyinosine

<400> SEQUENCE: 32
nnntgctcct tgagn                                                        15

<210> SEQ ID NO 33
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-6
<223> OTHER INFORMATION: 2'-O-methyl ribonucleotide
<220> FEATURE:
<221> NAME/KEY: misc_feature
<222> LOCATION: 1, 2, 3, 4, 5, 6
<223> OTHER INFORMATION: n = uracil
<220> FEATURE:
<221> NAME/KEY: misc_feature
<222> LOCATION: 15
<223> OTHER INFORMATION: n = 2'-deoxyinosine

<400> SEQUENCE: 33
nnnnnntcct tgagn                                                        15

<210> SEQ ID NO 34
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-14
<223> OTHER INFORMATION: 2'-O-methyl ribonucleotide
<220> FEATURE:
<221> NAME/KEY: misc_feature
<222> LOCATION: 1, 4, 7, 10, 11
<223> OTHER INFORMATION: n = uracil
<220> FEATURE:
<221> NAME/KEY: misc_feature
<222> LOCATION: 15
<223> OTHER INFORMATION: n = 2'-deoxyinosine

<400> SEQUENCE: 34
ngcngcnccn ngagn                                                        15

<210> SEQ ID NO 35
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 12
<223> OTHER INFORMATION: n = 2'-deoxyinosine

<400> SEQUENCE: 35
tgctccttga gn                                                           12

<210> SEQ ID NO 36
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 15

```
<223> OTHER INFORMATION: n = 2'-deoxyinosine

<400> SEQUENCE: 36
tnctgctcct tgagn                                                    15

<210> SEQ ID NO 37
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15
<223> OTHER INFORMATION: n = 2'-deoxyinosine

<400> SEQUENCE: 37
tactgctcct tgagn                                                    15

<210> SEQ ID NO 38
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15
<223> OTHER INFORMATION: n = 2'-deoxyinosine

<400> SEQUENCE: 38
ttctgctcct tgagn                                                    15

<210> SEQ ID NO 39
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15
<223> OTHER INFORMATION: n = 2'-deoxyinosine

<400> SEQUENCE: 39
tcctgctcct tgagn                                                    15

<210> SEQ ID NO 40
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5, 12, 14, 15
<223> OTHER INFORMATION: n = 2'-deoxyinosine

<400> SEQUENCE: 40
tgctnctcct tnann                                                    15

<210> SEQ ID NO 41
<211> LENGTH: 15
<212> TYPE: DNA
<213> ORGANISM: Artificial Sequence
<220> FEATURE:
<223> OTHER INFORMATION: Synthetic Construct

<400> SEQUENCE: 41
```
tgctactcct taaaa                                                   15

<210> SEQ ID NO 42
<211> LENGTH: 15
<212> TYPE: DNA
<213> ORGANISM: Artificial Sequence
<220> FEATURE:
<223> OTHER INFORMATION: Synthetic Construct

<400> SEQUENCE: 42
tgcttctcct ttatt                                                   15

<210> SEQ ID NO 43
<211> LENGTH: 15
<212> TYPE: DNA
<213> ORGANISM: Artificial Sequence
<220> FEATURE:
<223> OTHER INFORMATION: Synthetic Construct

<400> SEQUENCE: 43
tgctcctcct tcacc                                                   15

<210> SEQ ID NO 44
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 5, 12, 14, 15
<223> OTHER INFORMATION: n = 2'-deoxyinosine

<400> SEQUENCE: 44
tnctnctcct tnann                                                   15

<210> SEQ ID NO 45
<211> LENGTH: 15
<212> TYPE: DNA
<213> ORGANISM: Artificial Sequence
<220> FEATURE:
<223> OTHER INFORMATION: Synthetic Construct

<400> SEQUENCE: 45
tactactcct taaaa                                                   15

<210> SEQ ID NO 46
<211> LENGTH: 15
<212> TYPE: DNA
<213> ORGANISM: Artificial Sequence
<220> FEATURE:
<223> OTHER INFORMATION: Synthetic Construct

<400> SEQUENCE: 46
ttcttctcct ttatt                                                   15

<210> SEQ ID NO 47
<211> LENGTH: 15
<212> TYPE: DNA
<213> ORGANISM: Artificial Sequence
<220> FEATURE:
<223> OTHER INFORMATION: Synthetic Construct

<400> SEQUENCE: 47
tcctcctcct tcacc                                                   15

<210> SEQ ID NO 48
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 12
<223> OTHER INFORMATION: n = 2'-deoxyinosine

<400> SEQUENCE: 48
tnctccttga gn                                                          12

<210> SEQ ID NO 49
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 12
<223> OTHER INFORMATION: n = 2'-deoxyinosine

<400> SEQUENCE: 49
tactccttga gn                                                          12

<210> SEQ ID NO 50
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 12
<223> OTHER INFORMATION: n = 2'-deoxyinosine

<400> SEQUENCE: 50
ttctccttga gn                                                          12

<210> SEQ ID NO 51
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 12
<223> OTHER INFORMATION: n = 2'-deoxyinosine

<400> SEQUENCE: 51
tcctccttga gn                                                          12

<210> SEQ ID NO 52
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 9, 11, 12
<223> OTHER INFORMATION: n = 2'-deoxyinosine

<400> SEQUENCE: 52 tactcctna nn                                                           12

<210> SEQ ID NO 53
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 11, 12
<223> OTHER INFORMATION: n = 2'-deoxyinosine

<400> SEQUENCE: 53
tactccttaa nn                                                             12

<210> SEQ ID NO 54
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 12
<223> OTHER INFORMATION: n = 2'-deoxyinosine

<400> SEQUENCE: 54
tactccttaa an                                                             12

<210> SEQ ID NO 55
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 9, 12
<223> OTHER INFORMATION: n = 2'-deoxyinosine

<400> SEQUENCE: 55
tnctccttna an                                                             12

<210> SEQ ID NO 56
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 9, 11
<223> OTHER INFORMATION: n = 2'-deoxyinosine

<400> SEQUENCE: 56
tnctccttna na                                                             12

<210> SEQ ID NO 57
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 9
<223> OTHER INFORMATION: n = 2'-deoxyinosine

<400> SEQUENCE: 57
tnctccttna aa    12

<210> SEQ ID NO 58
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 9, 10, 12
<223> OTHER INFORMATION: n = 2'-deoxyinosine

<400> SEQUENCE: 58
tnctccttnn an    12

<210> SEQ ID NO 59
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 10, 11
<223> OTHER INFORMATION: n = 2'-deoxyinosine

<400> SEQUENCE: 59
tnctccttan na    12

<210> SEQ ID NO 60
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 6, 9, 11, 12
<223> OTHER INFORMATION: n = 2'-deoxyinosine

<400> SEQUENCE: 60
tncagnttna nn    12

<210> SEQ ID NO 61
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 6, 9, 11, 12
<223> OTHER INFORMATION: n = 2'-deoxyinosine

<400> SEQUENCE: 61
tncagnagna nn    12

<210> SEQ ID NO 62
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 5, 8, 9, 12, 14, 15
<223> OTHER INFORMATION: n = 2'-deoxyinosine

<400> SEQUENCE: 62
tnctnctnnt tnann     15

<210> SEQ ID NO 63
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 9, 11, 12
<223> OTHER INFORMATION: n = 2'-deoxyinosine

<400> SEQUENCE: 63
tnctccttna nn     12

<210> SEQ ID NO 64
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 9, 10, 11, 12
<223> OTHER INFORMATION: n = 2'-deoxyinosine

<400> SEQUENCE: 64
tnctccttnn nn     12

<210> SEQ ID NO 65
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 9, 11, 12
<223> OTHER INFORMATION: n = 2'-deoxyinosine

<400> SEQUENCE: 65
tnctccttnc nn     12

<210> SEQ ID NO 66
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 9, 11, 12
<223> OTHER INFORMATION: n = 2'-deoxyinosine

<400> SEQUENCE: 66
tnctccttng nn     12

<210> SEQ ID NO 67
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 9, 11, 12
<223> OTHER INFORMATION: n = 2'-deoxyinosine

```
<400> SEQUENCE: 67
tnctccttnt nn                                                         12

<210> SEQ ID NO 68
<211> LENGTH: 9
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 6, 8, 9
<223> OTHER INFORMATION: n = 2'-deoxyinosine

<400> SEQUENCE: 68 tccttnann                                                              9

<210> SEQ ID NO 69
<211> LENGTH: 6
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 3, 5, 6
<223> OTHER INFORMATION: n = 2'-deoxyinosine

<400> SEQUENCE: 69 ttnann                                                                 6

<210> SEQ ID NO 70
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 7, 8, 9, 11, 12
<223> OTHER INFORMATION: n = 2'-deoxyinosine

<400> SEQUENCE: 70
tactccnnna nn                                                         12

<210> SEQ ID NO 71
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 9, 11, 12
<223> OTHER INFORMATION: n = 2'-deoxyinosine

<400> SEQUENCE: 71
tactccccna nn                                                         12

<210> SEQ ID NO 72
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 9, 11, 12
<223> OTHER INFORMATION: n = 2'-deoxyinosine
```

```
<400> SEQUENCE: 72
tactccggna nn                                                      12

<210> SEQ ID NO 73
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 9, 11, 12
<223> OTHER INFORMATION: n = 2'-deoxyinosine

<400> SEQUENCE: 73
tactccaana nn                                                      12

<210> SEQ ID NO 74
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 9, 11
<223> OTHER INFORMATION: n = 2'-deoxyinosine

<400> SEQUENCE: 74
tactccttna ng                                                      12

<210> SEQ ID NO 75
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 9, 11
<223> OTHER INFORMATION: n = 2'-deoxyinosine

<400> SEQUENCE: 75
tactccttna nt                                                      12

<210> SEQ ID NO 76
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 9, 11
<223> OTHER INFORMATION: n = 2'-deoxyinosine

<400> SEQUENCE: 76
tactccttna nc                                                      12

<210> SEQ ID NO 77
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 11, 12
```

<223> OTHER INFORMATION: n = 2'-deoxyinosine

<400> SEQUENCE: 77
tactccttca nn                                                                12

<210> SEQ ID NO 78
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 11, 12
<223> OTHER INFORMATION: n = 2'-deoxyinosine

<400> SEQUENCE: 78
tactccttta nn                                                                12

<210> SEQ ID NO 79
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 11, 12
<223> OTHER INFORMATION: n = 2'-deoxyinosine

<400> SEQUENCE: 79
tactccttcc nn                                                                12

<210> SEQ ID NO 80
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 11, 12
<223> OTHER INFORMATION: n = 2'-deoxyinosine

<400> SEQUENCE: 80 tactccttt nn                                                                 12

<210> SEQ ID NO 81
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 11, 12
<223> OTHER INFORMATION: n = 2'-deoxyinosine

<400> SEQUENCE: 81
tactccttgg nn                                                                12

<210> SEQ ID NO 82
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature

```
<222> LOCATION: 9, 12
<223> OTHER INFORMATION: n = 2'-deoxyinosine

<400> SEQUENCE: 82
tactccttna cn                                                         12

<210> SEQ ID NO 83
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 9, 12
<223> OTHER INFORMATION: n = 2'-deoxyinosine

<400> SEQUENCE: 83
tactccttna tn                                                         12

<210> SEQ ID NO 84
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 9, 11, 12
<223> OTHER INFORMATION: n = 2'-deoxyinosine

<400> SEQUENCE: 84 cccccttna nn                                                          12

<210> SEQ ID NO 85
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 5, 11, 12, 15, 17, 18
<223> OTHER INFORMATION: n = 2'-deoxyinosine

<400> SEQUENCE: 85
tnctnctcct nnttncnn                                                   18

<210> SEQ ID NO 86
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 5, 12, 15, 17, 18
<223> OTHER INFORMATION: n = 2'-deoxyinosine

<400> SEQUENCE: 86
tnctnctcca gnttncnn                                                   18

<210> SEQ ID NO 87
<211> LENGTH: 18
<212> TYPE: DNA
<213> ORGANISM: Artificial Sequence
<220> FEATURE:
<223> OTHER INFORMATION: Synthetic Construct
<220> FEATURE:
```

```
<221> NAME/KEY: misc_feature
<222> LOCATION: 2, 5, 15, 17, 18
<223> OTHER INFORMATION: n = 2'-deoxyinosine

<400> SEQUENCE: 87
tnctnctcct ccttncnn                                                  18

<210> SEQ ID NO 88
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 5, 12, 15, 17, 18
<223> OTHER INFORMATION: n = 2'-deoxyinosine

<400> SEQUENCE: 88
tnctncttga gnttncnn                                                  18

<210> SEQ ID NO 89
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5, 12, 15, 17, 18
<223> OTHER INFORMATION: n = 2'-deoxyinosine

<400> SEQUENCE: 89
tcctnctcca gnttncnn                                                  18

<210> SEQ ID NO 90
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 5, 15, 17, 18, 20, 21
<223> OTHER INFORMATION: n = 2'-deoxyinosine

<400> SEQUENCE: 90
tnctnctcct ccttncnnan n                                              21

<210> SEQ ID NO 91
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 12, 14, 15, 17, 18
<223> OTHER INFORMATION: n = 2'-deoxyinosine

<400> SEQUENCE: 91
tnctcctcct tncnnann                                                  18

<210> SEQ ID NO 92
<211> LENGTH: 18
<212> TYPE: DNA
<213> ORGANISM: Artificial Sequence
<220> FEATURE:
<223> OTHER INFORMATION: Synthetic Construct
```

```
<220> FEATURE:
<221> NAME/KEY: misc_feature
<222> LOCATION: 12, 14, 15, 17, 18
<223> OTHER INFORMATION: n = 2'-deoxyinosine

<400> SEQUENCE: 92
tgctcctcct tncnnann                                                 18

<210> SEQ ID NO 93
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15, 17, 18
<223> OTHER INFORMATION: n = 2'-deoxyinosine

<400> SEQUENCE: 93
tgcttgtcct ccttncnn                                                 18

<210> SEQ ID NO 94
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 12, 14, 15
<223> OTHER INFORMATION: n = 2'-deoxyinosine

<400> SEQUENCE: 94
tgctgctcct tncnn                                                    15

<210> SEQ ID NO 95
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 5, 12, 14, 15
<223> OTHER INFORMATION: n = 2'-deoxyinosine

<400> SEQUENCE: 95
tnctnctcct tncnn                                                    15

<210> SEQ ID NO 96
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 12, 14, 15
<223> OTHER INFORMATION: n = 2'-deoxyinosine

<400> SEQUENCE: 96
tactactcct tncnn                                                    15

<210> SEQ ID NO 97
<211> LENGTH: 15
<212> TYPE: DNA
<213> ORGANISM: Artificial Sequence
<220> FEATURE:
```

```
<223> OTHER INFORMATION: Synthetic Construct
<220> FEATURE:
<221> NAME/KEY: misc_feature
<222> LOCATION: 12, 14, 15
<223> OTHER INFORMATION: n = 2'-deoxyinosine

<400> SEQUENCE: 97
ttcttctcct tncnn                                                15

<210> SEQ ID NO 98
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 12, 14, 15
<223> OTHER INFORMATION: n = 2'-deoxyinosine

<400> SEQUENCE: 98
tcctcctcct tncnn                                                15

<210> SEQ ID NO 99
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 12, 14, 15, 17, 18
<223> OTHER INFORMATION: n = 2'-deoxyinosine

<400> SEQUENCE: 99
tnctcctcct tncnnanna                                            19

<210> SEQ ID NO 100
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15, 17, 18
<223> OTHER INFORMATION: n = 2'-deoxyinosine

<400> SEQUENCE: 100
tgctcctgga ggttncnn                                             18

<210> SEQ ID NO 101
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15, 17, 18, 20, 21
<223> OTHER INFORMATION: n = 2'-deoxyinosine

<400> SEQUENCE: 101
tgctcctgga ggttncnnan n                                         21

<210> SEQ ID NO 102
<211> LENGTH: 19
<212> TYPE: DNA
<213> ORGANISM: Artificial Sequence
```

```
<220> FEATURE:
<223> OTHER INFORMATION: Synthetic Construct
<220> FEATURE:
<221> NAME/KEY: misc_feature
<222> LOCATION: 13, 15, 16, 18, 19
<223> OTHER INFORMATION: n = 2'-deoxyinosine

<400> SEQUENCE: 102
tgctcctgga ttncnnann                                                   19

<210> SEQ ID NO 103
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 5, 12, 15, 17, 18, 20, 21
<223> OTHER INFORMATION: n = 2'-deoxyinosine

<400> SEQUENCE: 103
tnctncttga gnttncnnan n                                                21

<210> SEQ ID NO 104
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 9, 12, 14, 15, 17, 18
<223> OTHER INFORMATION: n = 2'-deoxyinosine

<400> SEQUENCE: 104
tncttgagnt tncnnann                                                    18

<210> SEQ ID NO 105
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5, 12, 15, 17, 18, 20, 21
<223> OTHER INFORMATION: n = 2'-deoxyinosine

<400> SEQUENCE: 105
tgctncttga gnttncnnan n                                                21

<210> SEQ ID NO 106
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 9, 12, 14, 15, 17, 18
<223> OTHER INFORMATION: n = 2'-deoxyinosine

<400> SEQUENCE: 106
tgcttgagnt tncnnann                                                    18

<210> SEQ ID NO 107
<211> LENGTH: 15
<212> TYPE: DNA
```

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 12, 14, 15
<223> OTHER INFORMATION: n = 2'-deoxyinosine

<400> SEQUENCE: 107
tcctccttga gnann                                                   15

<210> SEQ ID NO 108
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 12, 14, 15
<223> OTHER INFORMATION: n = 2'-deoxyinosine

<400> SEQUENCE: 108
tnctccttga gnann                                                   15

<210> SEQ ID NO 109
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 15, 17, 18
<223> OTHER INFORMATION: n = 2'-deoxyinosine

<400> SEQUENCE: 109
tnctcctcct tgagnann                                                18

<210> SEQ ID NO 110
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 15, 17, 18
<223> OTHER INFORMATION: n = 2'-deoxyinosine

<400> SEQUENCE: 110
tncttctcct tgagnann                                                18

<210> SEQ ID NO 111
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 13, 14, 16, 17
<223> OTHER INFORMATION: n = 2'-deoxyinosine

<400> SEQUENCE: 111
tnctcctcct tgnnann                                                 17

<210> SEQ ID NO 112
<211> LENGTH: 17
```

```
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 14, 16, 17
<223> OTHER INFORMATION: n = 2'-deoxyinosine

<400> SEQUENCE: 112
tcctggaggg gttnann                                                17

<210> SEQ ID NO 113
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 17, 19, 20
<223> OTHER INFORMATION: n = 2'-deoxyinosine

<400> SEQUENCE: 113
tgctcctgga ggggttnann                                             20

<210> SEQ ID NO 114
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 15, 17, 18
<223> OTHER INFORMATION: n = 2'-deoxyinosine

<400> SEQUENCE: 114
tnctcctcct tgggnann                                               18

<210> SEQ ID NO 115
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 15, 17, 18
<223> OTHER INFORMATION: n = 2'-deoxyinosine

<400> SEQUENCE: 115
tncttctcct tgggnann                                               18

<210> SEQ ID NO 116
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1-3
<223> OTHER INFORMATION: 2'-O-methyl ribonucleotide
<220> FEATURE:
<221> NAME/KEY: misc_feature
<222> LOCATION: 1
<223> OTHER INFORMATION: n = uracil
<220> FEATURE:
<221> NAME/KEY: misc_feature
<222> LOCATION: 15
```

-continued

```
<223> OTHER INFORMATION: n = 2'-deoxyinosine

<400> SEQUENCE: 116
ngctgctcct tgagnggttg tttgt                                  25

<210> SEQ ID NO 117
<211> LENGTH: 11
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 7, 10
<223> OTHER INFORMATION: n = 7-deazaguanosine

<400> SEQUENCE: 117
nucuucnucn u                                                 11

<210> SEQ ID NO 118
<211> LENGTH: 11
<212> TYPE: RNA
<213> ORGANISM: Artificial Sequence
<220> FEATURE:
<223> OTHER INFORMATION: Synthetic Construct

<400> SEQUENCE: 118
guguucgucg u                                                 11
```